United States Patent
Charrier et al.

(10) Patent No.: US 9,630,956 B2
(45) Date of Patent: Apr. 25, 2017

(54) COMPOUNDS USEFUL AS INHIBITORS OF ATR KINASE

(75) Inventors: Jean-Damien Charrier, Wantage (GB); Hayley Marie Binch, Encinitas, CA (US); Dennis James Hurley, San Marcos, CA (US); Thomas Cleveland, San Diego, CA (US); Pramod Joshi, San Diego, CA (US); Lev Tyler Dewey Fanning, San Marcos, CA (US); Joanne Pinder, Didcot (GB); Michael O'Donnell, Abingdon (GB); Anisa Nizarali Virani, Thatcham (GB); Ronald Marcellus Alphonsus Knegtel, Abingdon (GB); Steven John Durrant, Abingdon (GB); Stephen Clinton Young, Oxford (GB); Pierre-Henri Storck, Abingdon (GB); David Kay, Wiltshire (GB); Philip Michael Reaper, Shillingford (GB); Matthew Paul Grote, New York, NY (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 1127 days.

(21) Appl. No.: 13/106,476

(22) Filed: May 12, 2011

(65) Prior Publication Data

US 2012/0027874 A1     Feb. 2, 2012

Related U.S. Application Data

(60) Provisional application No. 61/470,585, filed on Apr. 1, 2011, provisional application No. 61/333,867, filed on May 12, 2010.

(51) Int. Cl.
| | | |
|---|---|---|
| *A61K 31/497* | (2006.01) | |
| *A61K 33/24* | (2006.01) | |
| *C07D 413/14* | (2006.01) | |
| *C07D 401/14* | (2006.01) | |
| *C07D 241/10* | (2006.01) | |

(52) U.S. Cl.
CPC .................... *C07D 413/14* (2013.01)

(58) Field of Classification Search
CPC .... A61K 31/497; A61K 33/24; C07D 241/10; C07D 401/14; C07D 413/14
USPC ..................... 514/255.05; 544/405
See application file for complete search history.

(56) References Cited

U.S. PATENT DOCUMENTS

| | | | |
|---|---|---|---|
| 4,309,430 A | 1/1982 | Bock et al. | |
| 5,143,824 A | 9/1992 | Yamakawa et al. | |
| 6,469,002 B1 | 10/2002 | Ohshima et al. | |
| 6,660,753 B2 | 12/2003 | Van Wagenen et al. | |
| 6,790,935 B1 | 9/2004 | Mutter et al. | |
| 6,858,600 B2 | 2/2005 | Hamilton et al. | |
| 6,992,087 B2 | 1/2006 | Verhoest et al. | |
| 7,041,672 B2 | 5/2006 | Verhoest et al. | |
| 7,043,079 B2 | 5/2006 | Malvar et al. | |
| 7,145,002 B2 | 12/2006 | Brands et al. | |
| 7,199,123 B2 | 4/2007 | Munchhof | |

(Continued)

FOREIGN PATENT DOCUMENTS

| | | |
|---|---|---|
| CN | 1551869 A | 12/2004 |
| CN | 101001606 A | 7/2007 |

(Continued)

OTHER PUBLICATIONS

Ammar, et al., "3-Ethoxycarbonylmethylenequinoxalin-2-one in Heterocyclic Synthesis. Part 1: Synthesis of New Substituted and Condensed Quinoxalines", Afinidad (2005), 62, pp. 151-160.

(Continued)

*Primary Examiner* — Erich A Leeser
(74) *Attorney, Agent, or Firm* — Wolf, Greenfield & Sacks, P.C.

(57) ABSTRACT

The present invention relates to pyrazine and pyridine compounds useful as inhibitors of ATR protein kinase. The invention also relates to pharmaceutically acceptable compositions comprising the compounds of this invention; methods of treating various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

The compounds of this invention have formula I:

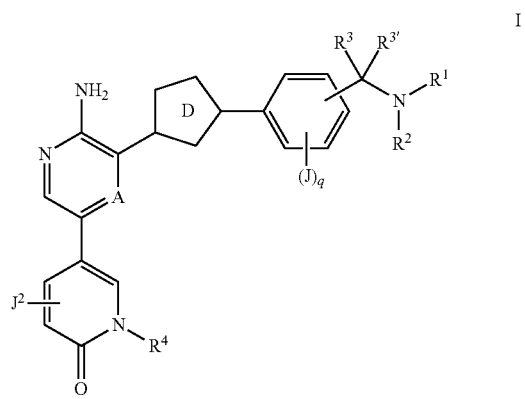

wherein the variables are as defined herein.

36 Claims, No Drawings

(56) References Cited

U.S. PATENT DOCUMENTS

| | | |
|---|---|---|
| 7,277,118 B2 | 10/2007 | Foote |
| 7,385,626 B2 | 6/2008 | Aggarwal et al. |
| 7,394,926 B2 | 7/2008 | Bryll et al. |
| 7,452,993 B2 | 11/2008 | Arnold et al. |
| 7,574,131 B2 | 8/2009 | Chang et al. |
| 7,622,583 B2 | 11/2009 | Ungashe et al. |
| 7,626,021 B2 | 12/2009 | Arnold et al. |
| 7,700,601 B2 | 4/2010 | Chan et al. |
| 7,704,995 B2 | 4/2010 | Buhr et al. |
| 7,829,558 B2 | 11/2010 | Arnold et al. |
| 7,872,031 B2 | 1/2011 | Lauffer et al. |
| 7,902,197 B2 | 3/2011 | Elworthy et al. |
| 7,932,254 B2 | 4/2011 | DuBois et al. |
| 7,939,531 B2 | 5/2011 | Bamberg et al. |
| 7,981,893 B2 | 7/2011 | Mortensen et al. |
| 8,063,032 B2 | 11/2011 | Chytil et al. |
| 8,106,197 B2 | 1/2012 | Cui et al. |
| 8,410,112 B2 | 4/2013 | Charrier et al. |
| 8,492,582 B2 | 7/2013 | Yokotani et al. |
| 8,765,751 B2 | 7/2014 | Charrier et al. |
| 8,841,308 B2 | 9/2014 | Charrier et al. |
| 8,841,337 B2 | 9/2014 | Charrier et al. |
| 8,841,449 B2 | 9/2014 | Charrier et al. |
| 8,841,450 B2 | 9/2014 | Charrier et al. |
| 8,846,686 B2 | 9/2014 | Charrier et al. |
| 8,846,917 B2 | 9/2014 | Charrier et al. |
| 8,846,918 B2 | 9/2014 | Charrier et al. |
| 8,853,217 B2 | 10/2014 | Charrier et al. |
| 8,877,759 B2 | 11/2014 | Charrier et al. |
| 8,912,198 B2 | 12/2014 | Charrier et al. |
| 8,962,631 B2 | 2/2015 | Charrier et al. |
| 8,969,356 B2 | 3/2015 | Charrier et al. |
| 8,999,632 B2 | 4/2015 | Falcon et al. |
| 9,035,053 B2 | 5/2015 | Charrier et al. |
| 9,062,008 B2 | 6/2015 | Charrier et al. |
| 9,096,584 B2 | 8/2015 | Charrier et al. |
| 9,334,244 B2 | 5/2016 | Charrier et al. |
| 9,365,557 B2 | 6/2016 | Charrier et al. |
| 2002/0064314 A1 | 5/2002 | Comaniciu et al. |
| 2002/0158984 A1 | 10/2002 | Brodsky et al. |
| 2002/0180759 A1 | 12/2002 | Park et al. |
| 2002/0195563 A1 | 12/2002 | Iida et al. |
| 2003/0008882 A1 | 1/2003 | Hamilton et al. |
| 2003/0055085 A1 | 3/2003 | Wagenen et al. |
| 2003/0199511 A1 | 10/2003 | Li et al. |
| 2004/0034037 A1 | 2/2004 | Harbeson et al. |
| 2004/0075741 A1 | 4/2004 | Berkey et al. |
| 2004/0100560 A1 | 5/2004 | Stavely et al. |
| 2004/0175042 A1 | 9/2004 | Kroeker et al. |
| 2004/0180905 A1 | 9/2004 | Munchhof |
| 2004/0202382 A1 | 10/2004 | Pilu |
| 2004/0252193 A1 | 12/2004 | Higgins |
| 2004/0264793 A1 | 12/2004 | Okubo |
| 2005/0116968 A1 | 6/2005 | Barrus et al. |
| 2005/0123902 A1 | 6/2005 | Meneses et al. |
| 2005/0207487 A1 | 9/2005 | Monroe |
| 2006/0083440 A1 | 4/2006 | Chen |
| 2006/0211709 A1 | 9/2006 | Buhr et al. |
| 2007/0037794 A1 | 2/2007 | Ungashe et al. |
| 2007/0092245 A1 | 4/2007 | Bazakos et al. |
| 2007/0120954 A1 | 5/2007 | Allen et al. |
| 2007/0149547 A1 | 6/2007 | Bonnefous et al. |
| 2007/0254868 A1 | 11/2007 | Lauffer et al. |
| 2007/0270420 A1 | 11/2007 | Harbeson et al. |
| 2007/0287711 A1 | 12/2007 | Arnold et al. |
| 2008/0132698 A1 | 6/2008 | Fagnou et al. |
| 2009/0001843 A1 | 1/2009 | Enomoto et al. |
| 2009/0005381 A1 | 1/2009 | Brown et al. |
| 2009/0143410 A1 | 6/2009 | Patel |
| 2009/0215724 A1 | 8/2009 | DuBois et al. |
| 2009/0215750 A1 | 8/2009 | Bamberg et al. |
| 2009/0215785 A1 | 8/2009 | DuBois et al. |
| 2009/0215788 A1 | 8/2009 | Elworthy et al. |
| 2009/0306087 A1 | 12/2009 | Ibrahim et al. |
| 2010/0036118 A1 | 2/2010 | Arnold et al. |
| 2010/0168138 A1 | 7/2010 | DeGoey et al. |
| 2010/0204214 A1 | 8/2010 | Chytil et al. |
| 2010/0222318 A1 | 9/2010 | Charrier et al. |
| 2010/0233091 A1 | 9/2010 | Neumann et al. |
| 2010/0249387 A1 | 9/2010 | Inouye |
| 2011/0015231 A1 | 1/2011 | Al-Abed et al. |
| 2011/0275797 A1 | 11/2011 | Yokotani et al. |
| 2011/0288067 A1 | 11/2011 | Hendricks et al. |
| 2011/0288097 A1 | 11/2011 | Hendricks et al. |
| 2012/0025805 A1 | 2/2012 | Matsushita et al. |
| 2012/0027874 A1 | 2/2012 | Charrier et al. |
| 2012/0035407 A1 | 2/2012 | Charrier et al. |
| 2012/0035408 A1 | 2/2012 | Charrier et al. |
| 2012/0040020 A1 | 2/2012 | Charrier et al. |
| 2012/0046295 A1 | 2/2012 | Charrier et al. |
| 2012/0065247 A1 | 3/2012 | Thompson et al. |
| 2012/0115874 A1 | 5/2012 | Wang et al. |
| 2012/0122884 A1 | 5/2012 | Charrier et al. |
| 2012/0177748 A1 | 7/2012 | Charrier et al. |
| 2012/0178756 A1 | 7/2012 | Charrier et al. |
| 2013/0017273 A1 | 1/2013 | Everitt et al. |
| 2013/0018035 A1 | 1/2013 | MacCormick et al. |
| 2013/0034616 A1 | 2/2013 | Storck et al. |
| 2013/0089624 A1 | 4/2013 | Charrier et al. |
| 2013/0089625 A1 | 4/2013 | Charrier et al. |
| 2013/0089626 A1 | 4/2013 | Pollard et al. |
| 2013/0095193 A1 | 4/2013 | Charrier et al. |
| 2013/0096139 A1 | 4/2013 | Charrier et al. |
| 2013/0115310 A1 | 5/2013 | Charrier et al. |
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2013/0115314 A1* | 5/2013 | Charrier et al. ............. 424/649 |
| 2013/0172273 A1 | 7/2013 | Aizpurua Iparraguirre et al. |
| 2013/0184292 A1 | 7/2013 | Charrier et al. |
| 2014/0044802 A1 | 2/2014 | Pollard et al. |
| 2014/0107093 A1 | 4/2014 | Charrier et al. |
| 2014/0113005 A1 | 4/2014 | Charrier et al. |
| 2014/0134596 A1 | 5/2014 | Falcon et al. |
| 2014/0356456 A1 | 12/2014 | Pollard et al. |
| 2015/0031661 A1 | 1/2015 | Charrier et al. |
| 2015/0051187 A1 | 2/2015 | Charrier et al. |
| 2015/0239874 A1 | 8/2015 | Charrier et al. |
| 2015/0247866 A1 | 9/2015 | Falcon et al. |
| 2015/0274710 A1 | 10/2015 | Charrier et al. |
| 2016/0030424 A1 | 2/2016 | Pollard et al. |
| 2016/0271129 A1 | 9/2016 | Charrier et al. |
| 2016/0311809 A1 | 10/2016 | Charrier et al. |

FOREIGN PATENT DOCUMENTS

| | | |
|---|---|---|
| CN | 101479255 A | 7/2009 |
| CN | 101537007 A | 9/2009 |
| CN | 101652354 A | 2/2010 |
| CN | 101671336 A | 3/2010 |
| CN | 103373996 A | 10/2013 |
| EP | 313724 A2 | 5/1989 |
| EP | 1217000 A1 | 6/2002 |
| EP | 2157090 A1 | 2/2010 |
| JP | 62/270623 A2 | 11/1987 |
| JP | 63/208520 A2 | 8/1988 |
| JP | H02-72370 A | 3/1990 |
| JP | H02-72372 A | 3/1990 |
| JP | H03-74370 A | 3/1991 |
| JP | H10-77286 A | 3/1998 |
| JP | 2002/072370 A | 3/2002 |
| JP | 2002/072372 A | 3/2002 |
| JP | 2002/518389 A | 6/2002 |
| JP | 2003/074370 A | 3/2003 |
| JP | 2003/516974 A | 5/2003 |
| JP | 2005/511531 A | 4/2005 |
| JP | 2005/530760 A | 10/2005 |
| JP | 2006/156445 A | 6/2006 |
| JP | 2006/516124 A | 6/2006 |
| JP | 2006/519232 A | 8/2006 |
| JP | 2006/519833 A | 8/2006 |
| JP | 2006/520794 A | 9/2006 |
| JP | 2006/521357 A | 9/2006 |
| JP | 2007/524682 A | 8/2007 |

(56) References Cited

FOREIGN PATENT DOCUMENTS

| | | |
|---|---|---|
| JP | 2008/510790 A | 4/2008 |
| JP | 2008/510792 A | 4/2008 |
| JP | 2008/517945 A | 5/2008 |
| JP | 2008/525453 A | 7/2008 |
| JP | 2008/543754 A | 12/2008 |
| JP | 2009/503103 A | 1/2009 |
| JP | 2009/027904 A | 2/2009 |
| JP | 2009/530233 A | 8/2009 |
| JP | 2009/532356 A | 9/2009 |
| JP | 2009/533327 A | 9/2009 |
| JP | 2009/541247 A | 11/2009 |
| JP | 2009/541268 A | 11/2009 |
| JP | 2010/506934 A | 3/2010 |
| JP | 2010/509356 A | 3/2010 |
| JP | 2010/077286 A | 4/2010 |
| JP | 2010/513433 A | 4/2010 |
| JP | 2010/180180 A | 8/2010 |
| JP | 2011/500778 A | 1/2011 |
| JP | 2011/042639 A | 3/2011 |
| JP | 2012/508260 A | 4/2012 |
| JP | 2012/513398 A | 6/2012 |
| JP | 2012/533248 A | 12/2012 |
| JP | 2013/501720 A | 1/2013 |
| JP | 2013/505900 A | 2/2013 |
| JP | 2013/517264 A | 5/2013 |
| JP | 2013/525476 A | 6/2013 |
| JP | 2014/510072 A | 4/2014 |
| JP | 2014/518545 A | 7/2014 |
| JP | 2014/165380 A | 9/2014 |
| NZ | 593316 A | 6/2013 |
| NZ | 593969 A | 11/2013 |
| WO | 97/43267 | 11/1997 |
| WO | 9842701 A1 | 10/1998 |
| WO | WO 99/44609 A1 | 9/1999 |
| WO | 0004014 A1 | 1/2000 |
| WO | WO 00/76982 A1 | 12/2000 |
| WO | 0144206 A1 | 6/2001 |
| WO | 0209648 A2 | 2/2002 |
| WO | WO 02/080899 A2 | 10/2002 |
| WO | 03004472 A1 | 1/2003 |
| WO | 03004475 A1 | 1/2003 |
| WO | WO 03/004472 * 1/2003 ........... C07D 213/73 | |
| WO | WO 03/032971 A1 | 4/2003 |
| WO | 03045924 A1 | 6/2003 |
| WO | 03076422 A1 | 9/2003 |
| WO | 03080610 A1 | 10/2003 |
| WO | 03087057 A1 | 10/2003 |
| WO | 03092686 A1 | 11/2003 |
| WO | 03093297 A2 | 11/2003 |
| WO | 03101968 A1 | 12/2003 |
| WO | 2004000318 A2 | 12/2003 |
| WO | WO 2004/000820 A2 | 12/2003 |
| WO | 2004033431 A2 | 4/2004 |
| WO | 2004055005 A1 | 7/2004 |
| WO | 2004055006 A1 | 7/2004 |
| WO | 2004/080982 | 9/2004 |
| WO | WO 2004/076412 A2 | 9/2004 |
| WO | 2004084813 A2 | 10/2004 |
| WO | 2004084824 A2 | 10/2004 |
| WO | 2004085409 A2 | 10/2004 |
| WO | 2004103279 A2 | 12/2004 |
| WO | WO 2004/103369 A1 | 12/2004 |
| WO | WO 2004/103991 A1 | 12/2004 |
| WO | 2005028475 A2 | 3/2005 |
| WO | WO 2005/058876 A1 | 6/2005 |
| WO | 2005079802 A1 | 9/2005 |
| WO | 2005123672 A2 | 12/2005 |
| WO | 2006015124 A2 | 2/2006 |
| WO | WO 2006/021886 A1 | 3/2006 |
| WO | 2006053342 A2 | 5/2006 |
| WO | WO 2006/047504 A1 | 5/2006 |
| WO | 2006058074 A1 | 6/2006 |
| WO | 2006067462 A1 | 6/2006 |
| WO | 2006071548 A2 | 7/2006 |
| WO | 2006075152 A1 | 7/2006 |
| WO | 2006088837 A2 | 8/2006 |
| WO | 2006114180 A1 | 11/2006 |
| WO | 2006120573 A2 | 11/2006 |
| WO | WO 2006/124874 A2 | 11/2006 |
| WO | WO 2006/135604 A2 | 12/2006 |
| WO | 2007015632 A1 | 2/2007 |
| WO | WO 2007/016674 A2 | 2/2007 |
| WO | 2007058850 A2 | 5/2007 |
| WO | 2007063012 A1 | 6/2007 |
| WO | 2007066805 A1 | 6/2007 |
| WO | 2007076360 A1 | 7/2007 |
| WO | 2007096151 A2 | 8/2007 |
| WO | 2007096764 A2 | 8/2007 |
| WO | 2007096765 A1 | 8/2007 |
| WO | WO 2007/095588 A1 | 8/2007 |
| WO | 2007102770 A1 | 9/2007 |
| WO | 2007111904 A2 | 10/2007 |
| WO | 2007126964 A2 | 11/2007 |
| WO | 2007147874 A1 | 12/2007 |
| WO | WO 2007/147746 A1 | 12/2007 |
| WO | WO 2008/025820 A1 | 3/2008 |
| WO | 2008037477 A1 | 4/2008 |
| WO | 2008038010 A1 | 4/2008 |
| WO | 2008040651 A1 | 4/2008 |
| WO | 2008060907 A2 | 5/2008 |
| WO | WO 2008/051493 A2 | 5/2008 |
| WO | 2008071456 A2 | 6/2008 |
| WO | 2008074997 A1 | 6/2008 |
| WO | 2008079291 A2 | 7/2008 |
| WO | 2008079903 A1 | 7/2008 |
| WO | 2008079906 A1 | 7/2008 |
| WO | 2008103277 A2 | 8/2008 |
| WO | 2008106692 A1 | 9/2008 |
| WO | 2008122375 A2 | 10/2008 |
| WO | 2008124850 A1 | 10/2008 |
| WO | 2008141065 A1 | 11/2008 |
| WO | 2008144463 A1 | 11/2008 |
| WO | 2008144464 A1 | 11/2008 |
| WO | 2008157191 A2 | 12/2008 |
| WO | WO 2008/156174 A1 | 12/2008 |
| WO | 2009007390 A2 | 1/2009 |
| WO | 2009012482 A2 | 1/2009 |
| WO | 2009014637 A2 | 1/2009 |
| WO | WO 2009/005638 A1 | 1/2009 |
| WO | 2009016460 A2 | 2/2009 |
| WO | 2009024825 A1 | 2/2009 |
| WO | 2009037247 A1 | 3/2009 |
| WO | 2009053737 A2 | 4/2009 |
| WO | WO 2009/099982 A1 | 8/2009 |
| WO | 2009106885 A1 | 9/2009 |
| WO | WO 2009/111280 A1 | 9/2009 |
| WO | WO 2009/115517 A2 | 9/2009 |
| WO | 2010015803 A1 | 2/2010 |
| WO | WO 2010/016005 A1 | 2/2010 |
| WO | WO 2010/017055 A2 | 2/2010 |
| WO | 2010048131 A1 | 4/2010 |
| WO | 2010054398 A1 | 5/2010 |
| WO | 2010063634 A1 | 6/2010 |
| WO | 2010068483 A2 | 6/2010 |
| WO | 2010071837 A1 | 6/2010 |
| WO | WO 2010/073034 A1 | 7/2010 |
| WO | WO 2010/075200 A1 | 7/2010 |
| WO | 2011008830 A1 | 1/2011 |
| WO | WO 2011/017513 A1 | 2/2011 |
| WO | WO 2011/035855 A1 | 3/2011 |
| WO | WO 2011/044157 A1 | 4/2011 |
| WO | WO 2011/086531 A2 | 7/2011 |
| WO | 2011117145 A2 | 9/2011 |
| WO | 2011124998 A1 | 10/2011 |
| WO | 2011130689 A1 | 10/2011 |
| WO | 2011143399 A1 | 11/2011 |
| WO | 2011143419 A1 | 11/2011 |
| WO | 2011143422 A1 | 11/2011 |
| WO | 2011143423 A2 | 11/2011 |
| WO | 2011143425 A2 | 11/2011 |
| WO | 2011143426 A1 | 11/2011 |
| WO | 2011144584 A1 | 11/2011 |
| WO | 2011144585 A1 | 11/2011 |
| WO | WO 2011/138751 A2 | 11/2011 |

(56) References Cited

FOREIGN PATENT DOCUMENTS

| WO | 2012158785 A1 | 11/2012 |
|---|---|---|
| WO | 2013049726 A2 | 4/2013 |
| WO | WO 2013/049722 A1 | 4/2013 |
| WO | WO 2013/049859 A1 | 4/2013 |

OTHER PUBLICATIONS

Charrier, et al, "Discovery of Potent and Selective Inhibitors of Ataxia Telangiesctasia Mutated and Rad3 Related (ATR) Protein Kinase as Potential Anticancer Agents" J. Med. Chem. (Apr. 14, 2011) 54(7), pp. 2320-2330.
El-Emary, "Synthesis and Biological Activity of Some New Pyrazolo[3,4-b]pyrazines", J. Chin. Chem. Soc. (2006), 53, pp. 391-401.
Fernandes, et al., "Synthesis and Biological Activity of Heterocyclic Derivatives derived from Ethyl-2-hydroxy-guinoxaline-3-carboxylate", J. Indian Chem. Soc. (1986), 63, pp. 427-429.
Hickson, et al., "Identification and Characterization of a Novel and Specific Inhibitor of the Ataxia-Telangiectasia Mutated Kinase ATM", Cancer Research (2004), 64, pp. 9152-9159.
Hilton, et al., "Identification and characterisation of 2-aminopyridine inhibitors of checkpoint kinase 2", Bioorg. Med. Chem., (2010) 18, pp. 707-718.
Klicnar, et al., "Studien in der Chinoxalinreihe III. Syntheses, Reaktionen and ir-spektren einiger 3-hydroxy-2-carboxymethylchinoxalin-derivative", Collection Czechoslav. Chem. Commun. (1965), 30, pp. 3092-3101.
Kim, et al., "Substrate Specificities and Identification of Putative Substrates of ATM Kinase Family Members", J. Biol. Chem. (1999) 274, pp. 37538-37543.
Kurasawa, et al., "Revised Structure for the Product from the Reaction of 3-Hydrazinocarbonylmethylene-2-oxo-1,2,3,4-tetrahydroquinoxaline with Nitrous Acid", Chem. Pharm. Bull. (1984), 32(10), pp. 4140-4143.
Reaper, et al, "Selective Killing of ATM- or p53-deficient cancer cells through inhibition of ATR" Nature Communications (2011), 7, pp. 428-430.
Sarkaria, et al., "Inhibition of ATM and ATR Kinase Activities by the Radiosensitizing Agent, Caffeine", Cancer Research (1999) 59, pp. 4375-4382.
Sugimoto, et al., "Imidazopteridines. I. Synthesis of Imidazo[1,2-c]pteridine and Its Alkyl Derivatives", Bull. Chem. Soc. Japan (1977) 50(10), pp. 2744-2747.
Ward and Chen, "Histone H2AX is Phosphorylated in an ATR-dependent Manner in Response to Replicational Stress", J. Biol. Chem. (2001), 51, pp. 47759-47762.
Abdel-Magid, A., "Inhibitors of ATR Kinase for Treatment on Cancer", ACS Medicinal Chemistry Letters, 4(8), (2013), pp. 688-689.
Charrier, J.D., "Discovery of potent and selective inhibitors of Ataxia Telangiectasia mutated and Rad3 related (ATR) protein kinase as potential anticancer agents", Presentation, ACS Denver 2011, Aug. 28, 2011.
Charrier, J.D., et al., "Discovery of Potent and Selective Inhibitors of ATR (Ataxia Telangiectasia Mutated and Rad3 Related) as Potential Anticancer Agents", Supplementary Information, Apr. 14, 2011.
Clark, B.A.J., et al., "Mass Spectrometry of Pyrroloä2,3-Büpyrazines and Pyrazinoä2,3-Büindole", Organic Mass Spectrometry, 12(7), (1997), pp. 421-423.
Curtin, N.J., "Inhibiting the DNA damage response as a therapeutic manoeuvre in cancer", British Journal of Pharmacology, (2013), pp. 1-52.
Finlay, M.R., et al., "Modulation of DNA repair by pharmacological inhibitors of the PIKK protein kinase family", Bioorg. Med. Chem. Letters, 22(17) (2012), pp. 5352-5359.
Fokas, E., et al., "Targeting ATR in vivo using the novel inhibitor VE-822 results in selective sensitization of pancreatic tumors to radiation", Cell Death and Disease, 3 (2012), pp. 1-5 (DOI: 10.1038/cddis.2012.181).
Fokas, E., et al., "Targeting ATR in DNA damage response and cancer therapeutics", Cancer Treatment Reviews (2013), (DOI: 10.1016/j.ctrv.2013.03.002).
Gentili, F., et al., "Alpha2-Adrenoreceptors Profile Modulation. 4. From Antagonist to Agonist Behavior", J. Med. Chem., 51(14), Jun. 25, 2008), pp. 4289-4299.
Hall-Jackson, C.A., et al., "ATR is a caffeine-sensitive, DNA-activated protein kinase with a substrate specificity distinct from DNA-PK", Oncogene, 18(48) (1999), pp. 6707-6713.
Jiang, B., et al., "Synthesis and cytotoxicity evaluation of novel indolylpyrimidiens and indolylpyrazines as potential antitummor agents", Bioorganic & Medicinal Chemistry, 9 (2001), pp. 1149-1154.
Luo, et al., "Molecular dynamics-based self-organizing molecular field analysis on 3-amino-6-arypyrazines as the ataxia telangiectasia mutated and Rad3 related (ATR) protein kinase inhibitors", Medicinal Chemistry Research, (2013), pp. 1-12.
McKenna, G., et al., "Evaluation of the first potent and highly selective inhibitor of ATR kinase: an approach to selectively sensitize cancer cells to ionizing radiation and hypoxia", Abstract, Mar. 31, 2012.
McKenna, G., et al., "Evaluation of the first potent and highly selective inhibitor of ATR inhibitor, VE-821: an approach to selectively sensitize cancer cells to ionizing radiation and hypoxia", Poster, Mar. 31, 2012.
Middleton, F. and Curtin, N.J., "ATR as a Therapeutic Target", Advances in DNA Repair in Cancer, Northern Institute for Cancer Research, Newcastle University (2013), pp. 211-228.
Nakamura, H., et al., "Bimodal chemiluminescence of 8-chlorostyryl-6-phenylethynylimidazopyrazinone: Large bathochromic shift caused by a styryl group at 8-position", Tetrahedron Letters, 39, (1998), pp. 301-304.
Pires, I.M., et al., "Targeting radiation-resisitant hypoxic tumour cells thorugh ATR inhibition", British Journal of Cancer, Jun. 19, 2012, pp. 1-9.
Pollard, J., "Inhibition of the DNA Damage Response Kinase, ATR, as a Promising Anti-Cancer Approach", Presentation, Mar. 8, 2012.
Qi, et al., "Chemi- and bio-luminescence of coelenterazine analogs with phenyl homologs at the C-2 position", Journal of the Chemical Society, Perkin Transactions 1: Organic and Bio-Organic Chemistry,13, (1992), pp. 1607-1611.
Reaper, P.M., et al., "Selective Killing of ATM- or p53-deficient cancer cells through inhibition of ATR", Supplementary Information, Apr. 13, 2011.
Reaper, P.M., et al., "Selective Killing of ATM- or p53-deficient cancer cells through inhibition of ATR", Presentation, Nov. 21, 2011.
Reaper, P.M., et al., "Selective Killing of ATM- or p53-deficient cancer cells through inhibition of ATR", Presentation, Nov. 29, 2011.
Reaper, P.M., et al., "Evaluation of a potent and highly selective inhibitor of ATR kinase: an approach to selectively sensitize cancer cells to genotoxic drugs", Abstract, Mar. 31, 2012.
Reaper, P.M., et al., "Evaluation of a Potent and Highly Selective Inhibitor of ATR Kinase: An Approach to Selectively Sensitize Cancer Cells to Genotoxic Drugs", Poster, Mar. 31, 2012.
Katritzky, A.R., et al., "Efficient synthesis of 3,5-functionalized isoxazoles and isoxazolines via 1,3-dipolar cycloaddition reactions of 1-propargyl- and 1-allylbenzotriazoles", J. Heterocyclic Chem., 37(6), (2000), pp. 1505-1510.
Kumpaty, H.J., et al., "Synthesis of N-Methyl Secondary Amines", Synth. Commun., 33(8), (2003), pp. 1411-1416.
March, J., March's Advanced Organic Chemistry, 2007, John Wiley and Sons, Chapter 16.
Saito, R., et al., "Synthesis and in vitro evaluation of botryllazine B analogues as a new class of inhibitor against human aldose reductase", Tetrahedron, 65 (2009), pp. 3019-3026.
Wuts, P.G.M., Greene's Protective Groups in Organic Synthesis, 4th Edition, 2006, John Wiley and Sons, Chapter 4.

(56) References Cited

OTHER PUBLICATIONS

Wuts, P.G.M., Greene's Protective Groups in Organic Synthesis, 4th Edition, 2006, John Wiley and Sons, Chapter 7.
Non-Final Office Action dated Sep. 28, 2013 in U.S. Appl. No. 13/631,727.
Non-Final Office Action dated Sep. 28, 2013 in U.S. Appl. No. 13/631,732.
International Search Report and Written Opinion for Application No. PCT/US2011/036246, mailed Jul. 19, 2011.
International Search Report and Written Opinion for Application No. PCT/US2013/035466, mailed Aug. 23, 2013.
International Search Report and Written Opinion for Application No. PCT/US2012/058127, mailed Apr. 23, 2013.
International Search Report and Written Opinion for Application No. PCT/US2011/036243, mailed Jan. 11, 2012.
International Search Report and Written Opinion for Application No. PCT/US2011/036239, mailed Oct. 12, 2011.
International Search Report and Written Opinion for Application No. PCT/US2013/063254, mailed Dec. 20, 2013.
International Search Report and Written Opinion for Application No. PCT/US2011/036245, mailed Dec. 28, 2011.
International Search Report and Written Opinion for Application No. PCT/US2012/058374, mailed Jan. 8, 2013.
International Search Report and Written Opinion for Application No. PCT/US2011/036242, mailed Jun. 28, 2011.
International Search Report and Written Opinion for Application No. PCT/US2009/068827, mailed Mar. 4, 2010.
International Search Report and Written Opinion for Application No. PCT/US2009/063922, mailed Mar. 15, 2010.
International Search Report and Written Opinion for Application No. PCT/US2012/058117, mailed Jan. 30, 2013.
International Search Report and Written Opinion for Application No. PCT/US2012/064421, mailed Feb. 15, 2013.
International Search Report and Written Opinion for Application No. PCT/US2011/036214, mailed Jun. 17, 2011.
International Search Report and Written Opinion for Application No. PCT/US2012/032438, mailed Aug. 10, 2012.
International Search Report and Written Opinion for Application No. PCT/US2012/058121, mailed Nov. 12, 2012.
International Search Report and Written Opinion for Application No. PCT/US2012/058119, mailed Nov. 12, 2012.
International Search Report and Written Opinion for Application No. PCT/US2012/064426, mailed Feb. 1, 2013.
International Search Report and Written Opinion for Application No. PCT/US2012/064430, mailed Feb. 1, 2013.
International Search Report and Written Opinion for Application No. PCT/US2012/064433, mailed Feb. 26, 2013.
International Search Report and Written Opinion for Application No. PCT/US2012/064435, mailed Jan. 30, 2013.
International Search Report and Written Opinion for Application No. PCT/US2013/064920, mailed Feb. 27, 2014.
Adamczyk et al., Synthesis of 3,7-dihydroimidazo[1,2a]pyrazine-3-ones and their chemiluminescent properties. Tetrahedron. 2003;59(41):8129-42.
Bastin et al., Salt Selection and Optimisation Procedures for Pharmaceutical New Chemical Entities. Organic Process Research and Development. American Chemical Society. 2000;4(5):42735.
Biss et al., Selective tumor killing based on specific Dna-damage response deficiencies. Cancer Biology & Therapy. Mar. 2012; 239-46.
Bracher et al., Total Synthesis of the Indolizidinium Alkaloid Ficuseptine. Eur J Org Chem. 2002:2288-91.
Buscemi et al., Dna damage-induced cell cycle regulation and function of novel Chk2 phosphoresidues. Mol Cell Biol. Nov. 2006;26(21):7832-45. Epub Aug. 28, 2006.
Caira, Crystalline Polymorphism of Organic Compounds. Topics in Current Chemistry. Design of Organic Solids. 1998;198:163-208.
Campone et al., Phase I and pharmacokinetic trial of AP5346, a DACH-platinum-polymer conjugate, administered weekly for three out of every 4 weeks to advanced solid tumor patients. Cancer Chemother Pharmacol. Sep. 2007;60(4):523-33. Epub Feb. 17, 2007.
Chen et al., Development of biomarker of ATR activity in surrogate human tissues. Newcastle University. Poster. Nov. 2012. 1 page.
Chen et al., Targeting the S and G2 checkpoint to treat cancer. Drug Discov Today. Mar. 2012;17(5-6):194-202. doi: 10.1016/j.drudis. 2011.12.009. Epub Dec. 15, 2011.
Darabantu et al., Synthesis of new polyaza heterocycles. Part 42: Diazines. Tetrahedron. 2005;61(11):2897-905.
De Wergifosse et al., Coelenterazine: a two-stage antioxidant in lipid micelles. Free Radical Biol Med. 2004;36(3):278-87.
Dias et al., Synthesis of 2,6-diphenylpyrazine derivatives and their DNA binding and cytotoxic properties. Eur J Med Chem. 2005;40:1206-13.
Erickson et al., Structure-guided expansion of kinase fragment libraries driven by support vector machine models. Biochim Biophys Acta. Mar. 2010;1804(3):642-52. doi: 10.1016/j.bbapap. 2009.12.002. Epub Dec. 11, 2009.
Goto et al.,Squid bioluminescence I. Structure of watasenia oxyluciferin, a possible light-emitter in the bioluminescence of watasenia scintillans Tetrahedron Lett. 1974;15(26):2321-4.
Hart et al., Renilla Reinformis Bioluminescence: Luciferase-Catalyzed Production of Nonradiating Excited States from Luciferin Analogues and Elucidation of the Excited State Species Involved in Energy Transfer to Renilla Green Fluorescent Protein. Biochemistry. 1979;18:2204-10.
Hilfiker et al., Relevance of Solid-state Properties for Pharmaceutical Products. Polymorphism: in the Pharmaceutical Industry. 2006;1-19.
Hirano et al., Bioluminescent properties of fluorinated semi-synthetic aequorins. Tetrahedron Lett. 1998;39(31):5541-4.
Jia et al., A Facile Preparation of 2,6-Diarylpyrazines. Heteroatom Chemistry. 1998;9(3):341-5.
Jones et al., A Suzuki Coupling Approach to Pyrazines Related to Coelenterazine. Synlett. 1996;(6):509-10.
Kao et al , Inhibition of γ-H2AX after ionizing radiation as a biological surrogate of impaired upstream DNA damage signaling and radiosensitivity. J Cancer Mol. 2010;5(2):49-54.
Kumar et al., Salt selection in drug development. Pharmaceutical Technology. 2008;32(3):128-46.
Lima et al., Bioisosterism: a useful strategy for molecular modification and drug design. Curr Med Chem. 2005;12(1):23-49.
Ling et al., Mechanism of Cell Cycle G2/M Arrest in Human Gastric Cancer BGC823 Cells Induced by Diallyl Disulfide. Chinese J Clin Oncol. Feb. 28, 2010;(3):121-5.
Liu et al., Chemical Biology Foundation. Science Press. Sep. 30, 2010;213-8.
Middleton et al., ATR as a Therapeutic Target. Cancer Drug Discovery and Development. 2013. Author's Proof. 20 pages.
Middleton et al., Chemosensitisation by, and Single Agent Activity of, ATR Inhibitor VE-821 in Human Breast Cancer Cells. Eur J Canc. Nov. 1, 2012;85-6.
Muslimovic et al., An optimized method for measurement of gamma-H2AX in blood mononuclear and cultured cells. Nat Protoc. 2008;3(7):1187-93. doi: 10.1038/nprot.2008.93.
Nowotnik et al., ProLindac (AP5346): a review of the development of an HPMA DACH platinum Polymer Therapeutic. Adv Drug Deliv Rev. Nov. 12, 2009;61(13):1214-9. doi:.10.1016/j.addr.2009. 06.004. Epub Aug. 9, 2009. Review.
Patani et al., Bioisosterism: A Rational Approach in Drug Design. Chem Rev. Dec. 19, 1996;96(8):3147-76.
Peasland et al., Identification and evaluation of a potent novel ATR inhibitor, NU6027, in breast and ovarian cancer cell lines. British Journal of Cancer. Jul. 2011; 105(3):372-81.
Prevo et al., The novel ATR inhibitor VE-821 increases sensitivity of pancreatic cancer cells to radiation and chemotherapy. Cancer Biol Ther. Sep. 2012;13(11):1072-81. doi: 10.4161/cbt.21093. Epub Jul. 24, 2012.
Reaper, et al., Selective killing of ATM- or p53-deficient cancer cells through inhibition of ATR. Nat Chem Biol. Apr. 13, 2011;7(7):428-30. doi: 10.1038/nchembio.573. Supplementary Information.

(56) References Cited

OTHER PUBLICATIONS

Redon et al., γ-H2AX as a biomarker of DNA damage induced by ionizing radiation in human peripheral blood lymphocytes and artificial skin. Adv Space Res. 2009;43(8):1171-8.
Registry (STN), RN 726138-31-4. 2004. 9 pages.
Richards et al., An Autoinhibitory Tyrosine Motif in the Cell-Cycle-Regulated Nek7 Kinase is Released through Binding of Nek9. Molec Cell. 2009;36:560-70.
Schultheiss et al., Facile Synthesis of Diarylpyrazines Using Suzuki Coupling of Dichloropyrazines with Aryl Boronic Acids. Heterocycles. 2003;60(8):1891-7.
Serajuddin, Salt formation to improve drug solubility. Advanced Drug Delivery Reviews. 2007; 59(7):603-16.
Sevilla et al., Microwave-assisted synthesis of 1,3-dihydro-[1,2,5]thiadiazolo [3,4-b]pyrazine-2,2-dioxides. Tetrahedron Letters. 2006;47(48):8603-6.
Shimomura et al., Semi-synthetic aequorins with improved sensitivity to Ca2+ ions. Biochem J. Aug. 1, 1989;261(3):913-20.
Teranishi et al., Synthesis and Chemiluminescence of Coelenterazine (Oplophorus Luciferin) Analogues . Bulletin Chem Soc Japan. 1990;63(11):3132-40.
Tutin, Cclvii.—Syntheses in the epinephrine series. Part II. The formation and properties of some 2 : 5- and 2 : 6-substituted pyrazines and their conversion into amino-ketones and imino-diketones. J Chem Soc Trans. 1910;97:2495-524.
Vicent, Polymer Anticancer Drug Conjugates: Use as Single Agents and as Combination Therapy. 2007 AACR Annual Meeting. Apr. 14-18, 2007:56-62.
Wu et al., Chemi- and bioluminescence of coelenterazine analogues with a conjugated group at the C-8 position. Tetrahedron Lett. 2001;42(16):2997-3000.
Brittain, editor. Polymorphism in pharmaceutical solids. CRC Press; 2009, Chapters 7 (p. 233-281) and 12 (p. 436-480).
Hancock et al., Characteristics and significance of the amorphous state in pharmaceutical systems. J Pharm Sci. Jan. 1997;86(1):1-12.
Pollard et al. Defining optimal dose schedules for ATR inhibitors in combination with DNA damaging drugs: Informing clinical studies of VX-970, the first-in-class ATR inhibitor. Proceedings: AACR Annual Meeting. Apr. 16-20, 2016. Abstract.
U.S. Appl. No. 13/857,658, filed Apr. 5, 2013, Pollard et al.
U.S. Appl. No. 13/631,759, filed Sep. 28, 2012, Charrier et al.
U.S. Appl. No. 13/106,337, filed May 12, 2011, Charrier et al.
U.S. Appl. No. 13/106,173, filed May 12, 2011, Charrier et al.
U.S. Appl. No. 14/045,373, filed Oct. 3, 2013, Falcon et al.
U.S. Appl. No. 13/106,184, filed May 12, 2011, Charrier et al.
U.S. Appl. No. 13/633,114, filed Oct. 1, 2012, Pollard et al.
U.S. Appl. No. 13/106,178, filed May 12, 2011, Charrier et al.
U.S. Appl. No. 12/642,447, filed Dec. 18, 2009, Charrier et al.
U.S. Appl. No. 14/223,109, filed Mar. 24, 2014, Charrier et al.
U.S. Appl. No. 13/104,291, filed Oct. 27, 2011, Charrier et al.
U.S. Appl. No. 13/742,948, filed Jan. 16, 2013, Charrier et al.
U.S. Appl. No. 13/631,730, filed Sep. 28, 2012, Charrier et al.
U.S. Appl. No. 13/672,937, filed Nov. 9, 2012, Charrier et al.
U.S. Appl. No. 13/106,167, filed May 12, 2011, Charrier et al.
U.S. Appl. No. 13/440,981, filed Sep. 4, 2012, Charrier et al.
U.S. Appl. No. 13/631,732, filed Sep. 28, 2012, Charrier et al.
U.S. Appl. No. 13/631,727, filed Sep. 28, 2012, Charrier et al.
U.S. Appl. No. 13/672,944, filed Nov. 9, 2012, Charrier et al.
U.S. Appl. No. 13/672,949, filed Nov. 9, 2012, Charrier et al.
U.S. Appl. No. 13/672,954, filed Nov. 9, 2012, Charrier et al.
U.S. Appl. No. 13/672,958, filed Nov. 9, 2012, Charrier et al.
U.S. Appl. No. 14/053,737, filed Oct. 15, 2013, Charrier et al.

* cited by examiner

COMPOUNDS USEFUL AS INHIBITORS OF ATR KINASE

CROSS REFERENCE TO RELATED APPLICATIONS

This present application claims the benefit, under 35 U.S.C. §119, to U.S. Provisional Application No. 61/333,867, filed on May 12, 2010, and U.S. Provisional Application No. 61/470,585, filed Apr. 1, 2011, the entire contents of which are incorporated herein by reference.

BACKGROUND OF THE INVENTION

ATR ("ATM and Rad3 related") kinase is a protein kinase involved in cellular responses to DNA damage. ATR kinase acts with ATM ("ataxia telangiectasia mutated") kinase and many other proteins to regulate a cell's response to DNA damage, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinase ATR. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells.

In fact, disruption of ATR function (e.g. by gene deletion) has been shown to promote cancer cell death both in the absence and presence of DNA damaging agents. This suggests that ATR inhibitors may be effective both as single agents and as potent sensitizers to radiotherapy or genotoxic chemotherapy.

ATR peptide can be expressed and isolated using a variety of methods known in the literature (see e.g., Ünsal-Kaçmaz et al, *PNAS* 99: 10, pp 6673-6678, May 14, 2002; see also Kumagai et al. *Cell* 124, pp 943-955, Mar. 10, 2006; Unsal-Kacmaz et al. *Molecular and Cellular Biology*, February 2004, p 1292-1300; and Hall-Jackson et al. *Oncogene* 1999, 18, 6707-6713).

For all of these reasons, there is a need for the development of potent and selective ATR inhibitors for the treatment of cancer, either as single agents or as combination therapies with radiotherapy or genotoxic chemotherapy.

SUMMARY OF THE INVENTION

The present invention relates to pyrazine and pyridine compounds useful as inhibitors of ATR protein kinase. The invention also relates to pharmaceutically acceptable compositions comprising the compounds of this invention; methods of treating various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors. These compounds have an unexpected ability to treat cancer as single agents. These compounds also show surprising synergy with other cancer agents, such as cisplatin, in combination therapies.

DETAILED DESCRIPTION OF THE INVENTION

One aspect of the invention provides a compound of formula I:

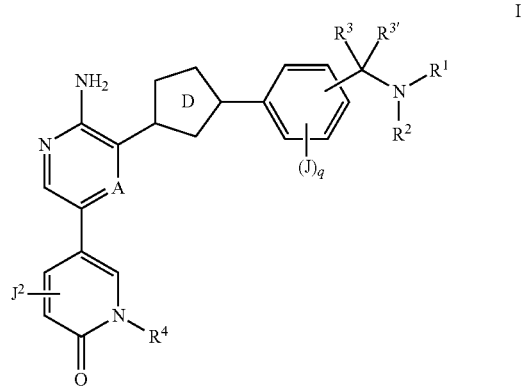

or a pharmaceutically acceptable salt thereof, wherein
A is C or N;
Ring D is isoxazolyl or oxadiazolyl;
J is —$C_{1-3}$alkyl, —O($C_{1-3}$alkyl), halo, or CN;
q is 0 or 1;
$R^1$ is H, $C_{1-6}$aliphatic, phenyl, or tetrahydrofuranyl, wherein said $C_{1-6}$aliphatic is optionally substituted with one occurrence of OH and up to two occurrences of F;
$R^2$ is H or $C_{1-3}$alkyl;
or $R^1$ and $R^2$, together with the nitrogen atom to which they are attached, optionally form a 4-6 membered monocyclic heterocyclyl ring having 1-2 heteroatoms selected from the group consisting of O, N, and S;
$R^3$ is H or $C_{1-3}$alkyl, wherein said alkyl is optionally substituted with up to three occurrences of F;
$R^{3'}$ is H or $C_{1-3}$alkyl;
or $R^3$ and $R^{3'}$, together with the carbon atom to which they are attached, form a 3-4 membered monocyclic saturated carbocyclic ring;
$R^4$ is Q, —($C_{1-2}$alkyl)-Q, or a $C_{1-10}$aliphatic wherein up to two methylene units of said $C_{1-10}$aliphatic are optionally replaced with O, NR', S, or CO; and wherein one methylene unit of the $C_{1-2}$alkyl can optionally be replaced with C(=O);
$R^4$ is optionally substituted with 1-3 occurrences of halo, CN, NRR', OR, or $C_{1-3}$aliphatic wherein said $C_{1-3}$aliphatic is optionally substituted with up to 1 occurrence of CN and up to 4 occurrences of F;

Q is 3-6 membered saturated, partially unsaturated, or aromatic monocyclic ring having 0-2 heteroatoms selected from the group consisting of oxygen, nitrogen, and sulfur; Q is optionally substituted with 1-3 occurrences of halo, CN, NRR', OR, or $C_{1-3}$aliphatic wherein said $C_{1-3}$aliphatic is optionally substituted with up to 4 occurrences of F;

R' is H or $C_{1-4}$alkyl;

R is H or $C_{1-4}$alkyl;

or R and R', together with the nitrogen to which they are attached, optionally form a 3-6 membered heterocyclic ring having 1-2 heteroatoms selected from the group consisting of O, N, and S;

$J^2$ is H, $C_{1-6}$aliphatic, halo, phenyl, or CN, wherein said $C_{1-6}$aliphatic is optionally substituted with 1-2 occurrences of halo, OH, CN, or OR.

In some embodiments, $R^1$ is H, $C_{1-6}$aliphatic, or tetrahydrofuranyl, wherein said $C_{1-6}$aliphatic is optionally substituted with one occurrence of OH and up to two occurrences of F; $R^{3'}$ is H;

$R^4$ is Q, —($C_{1-2}$alkyl)-Q, or a $C_{1-10}$aliphatic wherein up to two methylene units of said $C_{1-10}$aliphatic are optionally replaced with O, NR', S, or CO;

Q is 3-6 membered saturated or partially unsaturated monocyclic ring having 0-2 heteroatoms selected from the group consisting of oxygen, nitrogen, and sulfur; Q is optionally substituted with 1-3 occurrences of halo, CN, NRR', OR, or $C_{1-3}$aliphatic wherein said $C_{1-3}$aliphatic is optionally substituted with up to 4 occurrences of F;

$J^2$ is H.

In some embodiments A is N. In other embodiments, $R^2$ is H.

In some embodiments, Ring D is isoxazolyl. In other embodiments, Ring D is oxadiazolyl.

Another embodiment provides compounds wherein

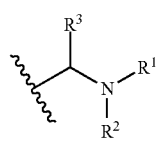

is bonded at the meta or para position of the phenyl ring as shown in Formula Ia and Ib below:

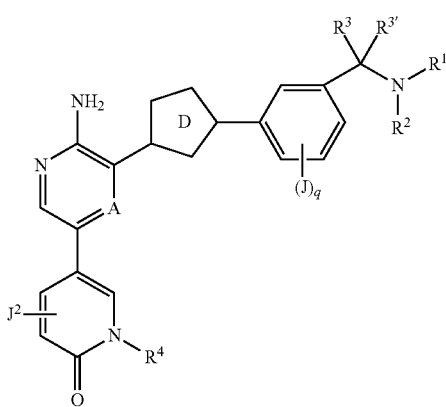

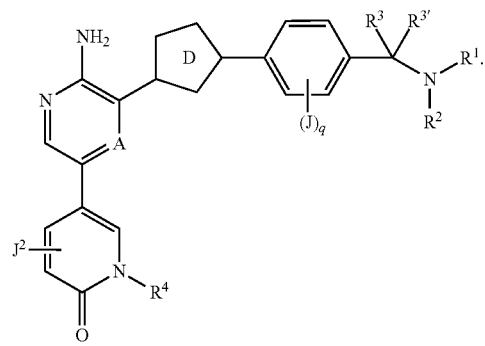

In some embodiments, $R^3$ is H or methyl. In other embodiments, $R^3$ is H.

In some embodiments, $R^1$ is $C_{1-6}$aliphatic, phenyl, or tetrahydrofuranyl. In other embodiments, $R^1$ is $C_{1-6}$aliphatic or tetrahydrofuranyl. In yet other embodiments, $R^1$ is $C_{1-4}$alkyl or tetrahydrofuranyl. In some embodiments, $R^1$ is $C_{1-4}$alkyl. In other embodiments, $R^1$ is methyl, isopropyl, tert-butyl, or tetrahydrofuranyl.

Another embodiment provides compounds wherein the $C_{1-6}$alkyl of $R^1$ is optionally substituted with 1-2 occurrences of OH or fluoro. In some embodiments, q is 1.

Another embodiment provides compounds wherein J is bonded at the ortho position of the phenyl ring as shown in Formula Ic:

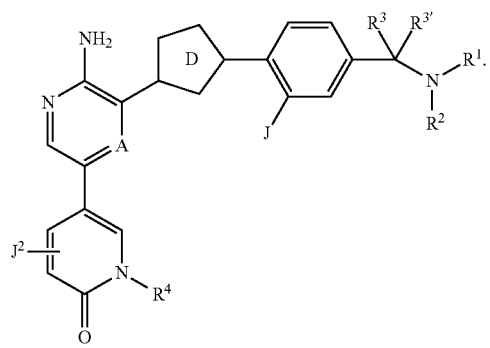

In some embodiments, J is fluoro, $C_{1-3}$alkyl, O($C_{1-3}$alkyl), or CN. In some embodiments, the $C_{1-3}$alkyl is methyl or isopropyl. In other embodiments, J is fluoro, $CH_3$, $OCH_3$, or CN.

Another aspect provides compounds wherein q is 0. In some embodiments, $R^4$ is Q, —($C_{1-2}$alkyl)-Q, or a $C_{1-10}$aliphatic wherein up to two methylene units of said $C_{1-10}$aliphatic are optionally replaced with O, NR', or CO; and wherein one methylene unit of the $C_{1-2}$alkyl can optionally be replaced with C(=O). In some embodiments, Q is a 5 membered heteroaryl having 1-2 heteroatoms selected from O, N, or S; 4-6 membered heterocyclyl having 1 heteroatoms selected from O or N; or a 3-6 membered cycloalkyl. In other embodiments, Q is furanyl, thiazoyl, imidazolyl, oxetanyl, tetrahydrofuranyl, tetrahydropyranyl, pyrrolidinonyl, or 3-6 membered cycloalkyl.

In some embodiments, $R^4$ is $C_{1-10}$aliphatic, —($C_{1-4}$alkyl)-$CF_3$, —($C_{1-4}$alkyl)-($C_3$-$C_6$cycloaliphatic), —($C_{1-4}$alkyl)-N($C_{1-3}$alkyl)$_2$, —($C_{1-4}$alkyl)-O($C_{1-3}$alkyl), $C_3$-$C_6$cycloaliphatic, or tetrahydrofuranyl, wherein said alkyl group is optionally substituted. In other embodiments, R⁴ is $C_{1-6}$alkyl, —($C_{1-4}$alkyl)-CF₃, —($C_{1-4}$alkyl)-($C_3$-$C_6$cycloaliphatic), $C_3$-$C_6$cycloaliphatic, or tetrahydrofuranyl. In yet other embodiments, R⁴ is methyl, ethyl, isopropyl, sec-butyl, isobutyl, CH(CH₃)C≡CCH₃, CH(CH₃)COOH, CH₂CONH₂, CH(CH₃)CONH₂, CH(CH₃)CONHCH₃, CH(CH₃)CONCH₂CH₃)₂, cyclobutyl, cyclopentyl, methylcyclopentyl, CH(CH₃)(cyclopropyl), CH₂(cyclopropyl), CH₂CH₂(cyclopropyl), CH₂CH₂(cyclopentyl), CH(CH₃)CH₂F, CH(CH₃)CF₃, CH₂CF₃, C(CH₃)₂CN, C(CH₂CH₃)₂CN, CH(CH₃)CN, CH₂CN, CH₂CH(CH₃)CH₂CH₃, CH(CH₂CH₃)₂ CH(CH₂OH)₂ CH(CH₃)CH₂OH, CH(CH₃)CH₂OCH₃, CH₂CH₂OH, CH₂CH₂OCH₃, CH₂CH₂N(CH₃)₂, CH₂CH₂CH₂NH₂, tetrahydrofuranyl, tetrohydropyranyl, CH₂(furanyl), CH₂(thiazolyl), CH₂(imidazolyl), CH₂CH₂CN, CH₂CH(OCH₃) CH₂CH₃, CH₂CH₂CH(CH₃)CH₂CH₃,

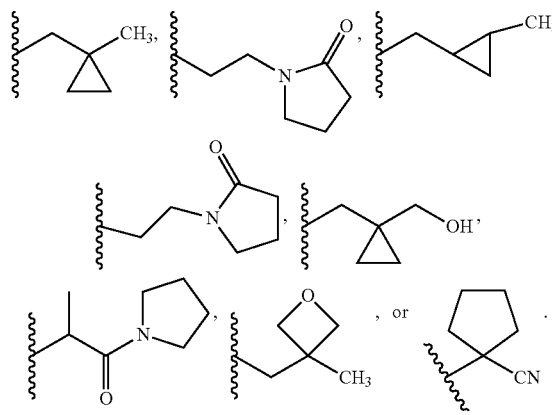

According to another embodiment, R⁴ is methyl, ethyl, isopropyl, sec-butyl, isobutyl, CH(CH₃)C≡CCH₃, CH(CH₃)COOH, cyclobutyl, cyclopentyl, CH(CH₃)(cyclopropyl), CH(CH₃)CH₂F, CH(CH₃)CF₃, CH₂CF₃, CH(CH₃) CN, CH₂CN, CH(CH₃)CH₂OH, CH₂CH₂OH, CH₂CH₂OCH₃, CH₂CH₂N(CH₃)₂, CH₂CH₂CH₂NH₂, CH(CH₃)CH₂OCH₃, or tetrahydrofuranyl.

According to yet another embodiment, R⁴ is methyl, ethyl, isopropyl, sec-butyl, isobutyl, CH(CH₃)C≡CCH₃, cyclobutyl, cyclopentyl, CH(CH₃)(cyclopropyl), CH(CH₃) CH₂F, CH(CH₃)CF₃, CH₂CF₃, CH(CH₃)CN, CH₂CN, or tetrahydrofuranyl.

In some embodiments, J² is H, CN, F, Cl, Br, CH=CH₂, methyl, ethyl, isopropyl, CH₂OH, CH(CH₂CH₃) CH₂CH₂CH₃, CH(CH₂CH₃)₂, cyclopentyl, cyclohexyl, cyclohexenyl, or phenyl.

According to another embodiment,
A is N;
J² is H;
R¹ is methyl;
R² is H;
R³ is H; and
R⁴ is $C_{1-10}$aliphatic, —($C_{1-4}$alkyl)-CF₃, —($C_{1-4}$alkyl)-($C_3$-$C_6$cycloaliphatic), —($C_{1-4}$alkyl)-N($C_{1-3}$alkyl)₂, —($C_{1-4}$alkyl)-O($C_{1-3}$alkyl), $C_3$-$C_6$cycloaliphatic, or tetrahydrofuranyl, wherein said alkyl group is optionally substituted.

In some embodiments, R⁴ is $C_{1-10}$aliphatic, —($C_{1-4}$alkyl)-CF₃—($C_{1-4}$alkyl)-($C_3$-$C_6$cycloaliphatic), $C_3$-$C_6$cycloaliphatic, or tetrahydrofuranyl. In other embodiments, said alkyl group is optionally substituted with CH₃, OH, OCH₃, NH₂, CN, or tetrahydrofuranyl.

Another aspect of this invention provides a compound of Formula I:

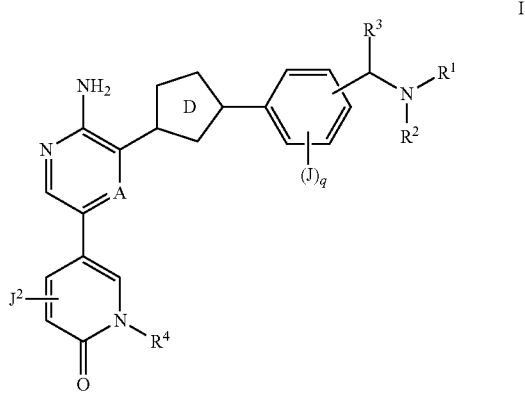

I or a pharmaceutically acceptable salt thereof, wherein
A is C or N;
Ring D is isoxazolyl or oxadiazolyl;
J is —$C_{1-3}$alkyl, —O($C_{1-3}$alkyl), halo, or CN;
q is 0 or 1;
R¹ is H, $C_{1-6}$aliphatic, or tetrahydrofuranyl, wherein said $C_{1-6}$aliphatic is optionally substituted with one occurrence of OH and up to two occurrences of F;
R² is H or $C_{1-3}$alkyl;
or R¹ and R², together with the nitrogen atom to which they are attached, optionally form a 4-6 membered monocyclic heterocyclyl ring having 1-2 heteroatoms selected from the group consisting of O, N, and S;
R³ is H or $C_{1-3}$alkyl, wherein said alkyl is optionally substituted with up to three occurrences of F;
R⁴ is Q, —($C_{1-2}$alkyl)-Q, or a $C_{1-10}$aliphatic wherein up to two methylene units of said $C_{1-10}$aliphatic are optionally replaced with O, NR', S, or CO; R⁴ is optionally substituted with 1-3 occurrences of halo, CN, NRR', OR, or $C_{1-3}$aliphatic wherein said $C_{1-3}$aliphatic is optionally substituted with up to 1 occurrence of CN and up to 4 occurrences of F;
Q is 3-6 membered saturated or partially unsaturated monocyclic ring having 0-2 heteroatoms selected from the group consisting of oxygen, nitrogen, and sulfur; Q is optionally substituted with 1-3 occurrences of halo, CN, NRR', OR, or $C_{1-3}$aliphatic wherein said $C_{1-3}$aliphatic is optionally substituted with up to 4 occurrences of F;
R' is H or $C_{1-4}$alkyl;
R is H or $C_{1-4}$alkyl;
or R and R', together with the nitrogen to which they are attached, optionally form a 3-6 membered heterocyclic ring having 1-2 heteroatoms selected from the group consisting of O, N, and S;
J² is H.

In some embodiments, A is N. In some embodiments, R² is H.

In some embodiments, Ring D is isoxazolyl. In other embodiments, Ring D is oxadiazolyl. In some embodiments, J² is H.

One embodiment provides compounds wherein

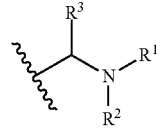

is bonded at the meta or para position of the phenyl ring as shown in Formula Ia and Ib below:

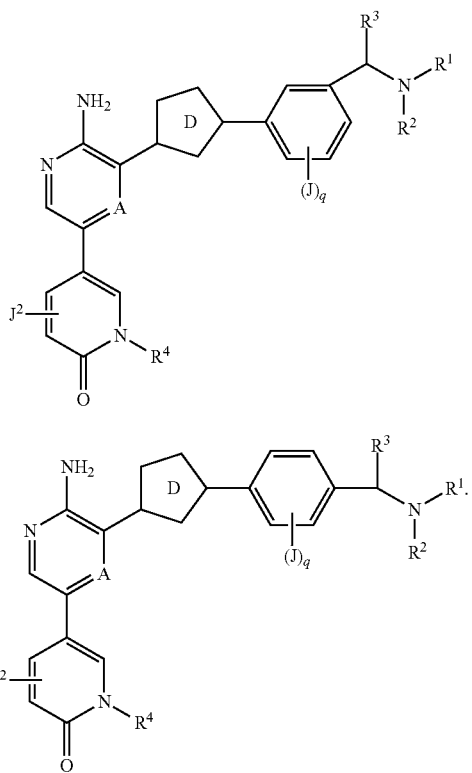

In some embodiments, the compounds have formula Ib. In some embodiments, $R^3$ is H or methyl. In other embodiments, $R^3$ is H. In certain embodiments, $R^1$ is $C_{1-6}$aliphatic or tetrahydrofuranyl. In other embodiments, $R^1$ is $C_{1-4}$alkyl or tetrahydrofuranyl. In some embodiments, $R^1$ is $C_{1-6}$aliphatic. In other embodiments, $R^1$ is $C_{1-4}$alkyl. In yet other embodiments, $R^1$ is methyl, isopropyl, tert-butyl, or tetrahydrofuranyl.

Another embodiment provides compounds wherein q is 1. In some embodiments, J is bonded at the ortho position of the phenyl ring as shown in Formula Ic:

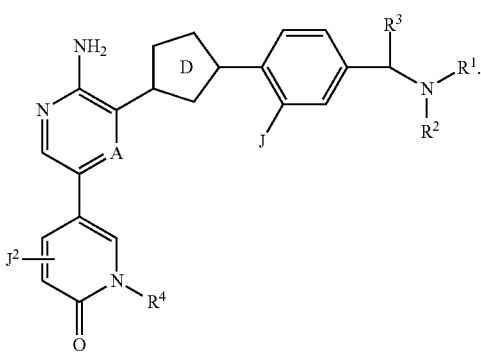

In some embodiments, J is fluoro, $CH_3$, $OCH_3$, or CN.
Another embodiment provides compounds wherein q is 0.
In another embodiment, $R^4$ is $C_{1-10}$aliphatic, —($C_{1-4}$alkyl)-$CF_3$, —($C_{1-4}$alkyl)-($C_3$-$C_6$cycloaliphatic), —($C_{1-4}$alkyl)-N($C_{1-3}$alkyl)$_2$, —($C_{1-4}$alkyl)-O($C_{1-3}$alkyl), $C_3$-$C_6$cycloaliphatic, or tetrahydrofuranyl, wherein said alkyl group is optionally substituted. In some embodiments, $R^4$ is $C_{1-6}$alkyl, —($C_{1-4}$alkyl)-$CF_3$, —($C_{1-4}$alkyl)-($C_3$-$C_6$cycloaliphatic), $C_3$-$C_6$cycloaliphatic, or tetrahydrofuranyl. In yet other embodiments, $R^4$ is methyl, ethyl, isopropyl, sec-butyl, isobutyl, $CH(CH_3)C \equiv CCH_3$, $CH(CH_3)COOH$, cyclobutyl, cyclopentyl, $CH(CH_3)$(cyclopropyl), $CH(CH_3)CH_2F$, $CH(CH_3)CF_3$, $CH_2CF_3$, $CH(CH_3)CN$, $CH_2CN$, $CH(CH_3)CH_2OH$, $CH_2CH_2OH$, $CH_2CH_2OCH_3$, $CH_2CH_2N(CH_3)_2$, $CH_2CH_2CH_2NH_2$, $CH(CH_3)CH_2OCH_3$, or tetrahydrofuranyl. In yet other embodiments, $R^4$ is methyl, ethyl, isopropyl, sec-butyl, isobutyl, $CH(CH_3)C \equiv CCH_3$, cyclobutyl, cyclopentyl, $CH(CH_3)$(cyclopropyl), $CH(CH_3)CH_2F$, $CH(CH_3)CF_3$, $CH_2CF_3$, $CH(CH_3)CN$, $CH_2CN$, or tetrahydrofuranyl.

Another embodiment provides compounds wherein
A is N;
$J^2$ is H;
$R^1$ is methyl;
$R^2$ is H;
$R^3$ is H; and
$R^4$ is $C_{1-10}$aliphatic, —($C_{1-4}$alkyl)-$CF_3$, —($C_{1-4}$alkyl)-($C_3$-$C_6$cycloaliphatic), —($C_{1-4}$alkyl)-N($C_{1-3}$alkyl)$_2$, —($C_{1-4}$alkyl)-O($C_{1-3}$alkyl), $C_3$-$C_6$cycloaliphatic, or tetrahydrofuranyl, wherein said alkyl group is optionally substituted.

In some embodiments, $R^4$ is $C_{1-10}$aliphatic, —($C_{1-4}$alkyl)-$CF_3$, —($C_{1-4}$alkyl)-($C_3$-$C_6$cycloaliphatic), $C_3$-$C_6$cycloaliphatic, or tetrahydrofuranyl.

Another embodiment provides a compound selected from the following table:

TABLE 1

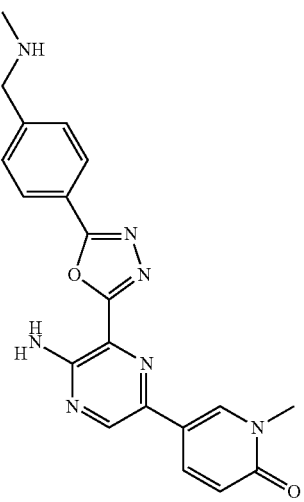

I-1

TABLE 1-continued
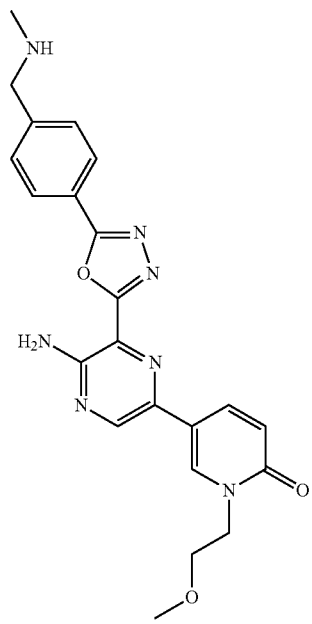 [SMILES: CNCc1ccc(-c2nnc(-c3nc(-c4ccc(=O)n(CCOC)c4)cnc3N)o2)cc1]
I-2
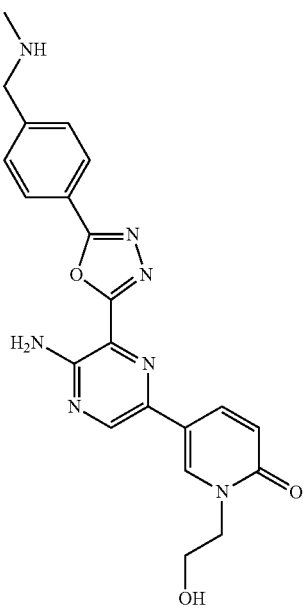
I-4
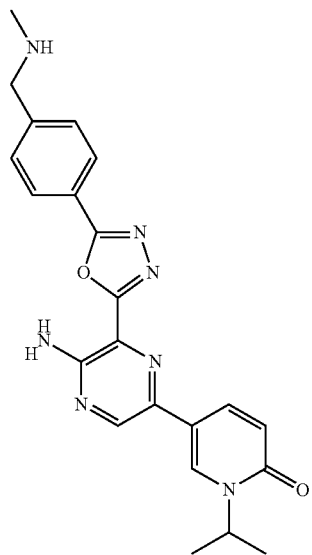
I-3
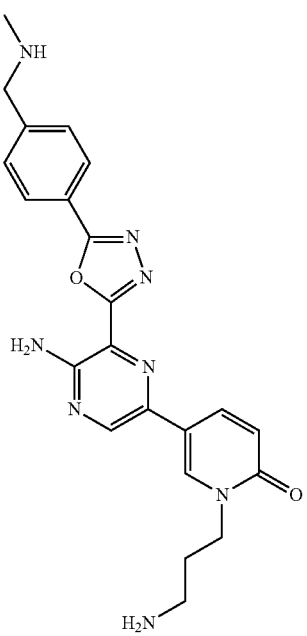 [SMILES: CNCc1ccc(-c2nnc(-c3nc(-c4ccc(=O)n(CCCN)c4)cnc3N)o2)cc1]
I-5

TABLE 1-continued
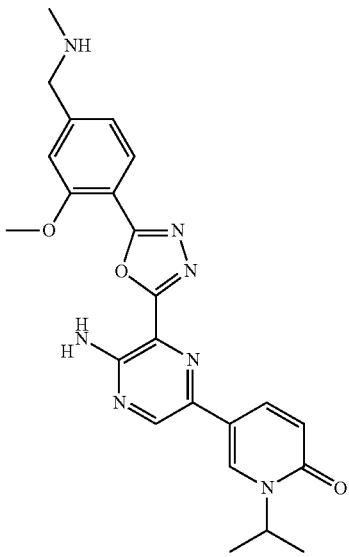
I-6
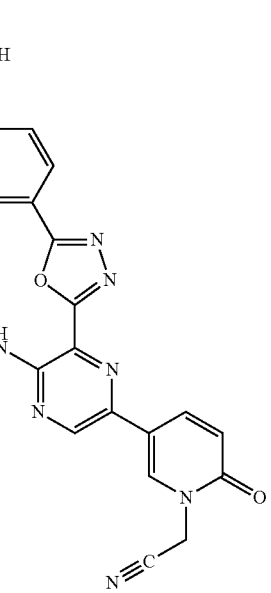
I-7
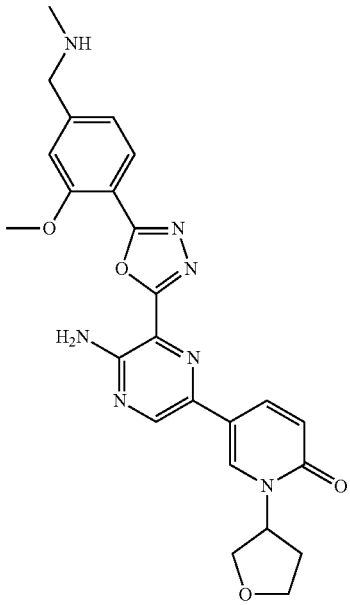 [SMILES: CNCc1ccc(-c2nnc(-c3nc(-c4ccc(=O)n(C5CCOC5)c4)cnc3N)o2)c(OC)c1]
I-8
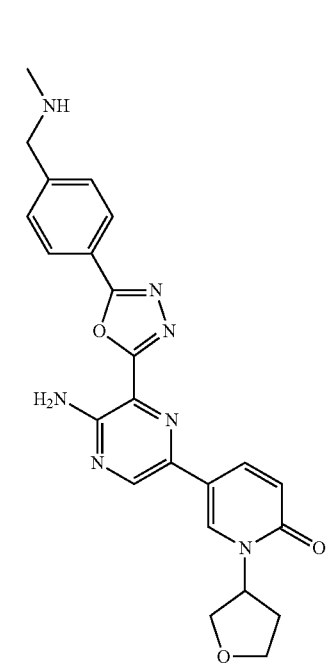 [SMILES: CNCc1ccc(-c2nnc(-c3nc(-c4ccc(=O)n(C5CCOC5)c4)cnc3N)o2)cc1]
I-9

TABLE 1-continued
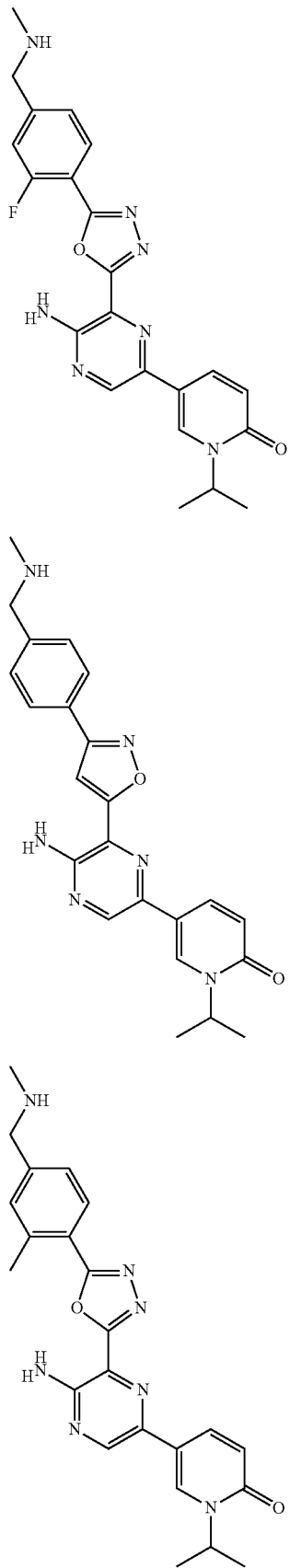
I-10
I-11
I-12
TABLE 1-continued
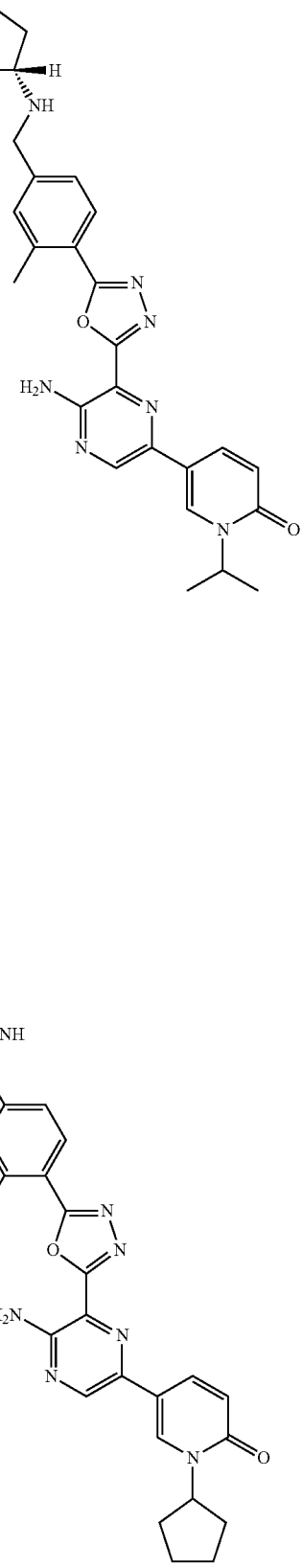
I-13
I-14

TABLE 1-continued
I-15
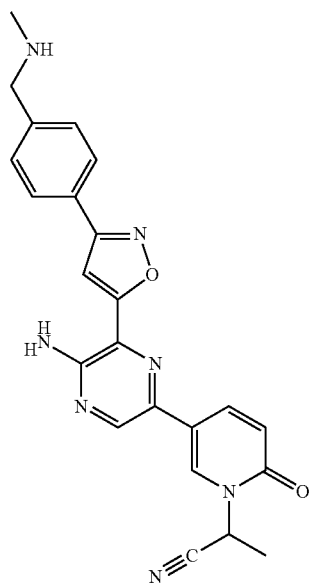
I-16
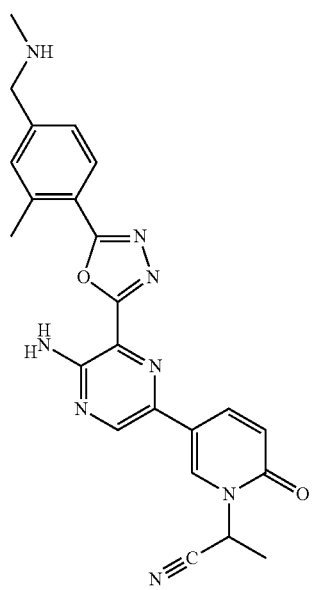
TABLE 1-continued
I-17
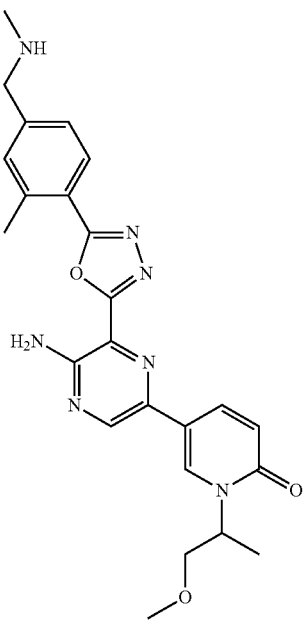 [SMILES: CNCc1ccc(-c2nnc(-c3nc(-c4ccc(=O)n(C(C)COC)c4)cnc3N)o2)c(C)c1]
I-18
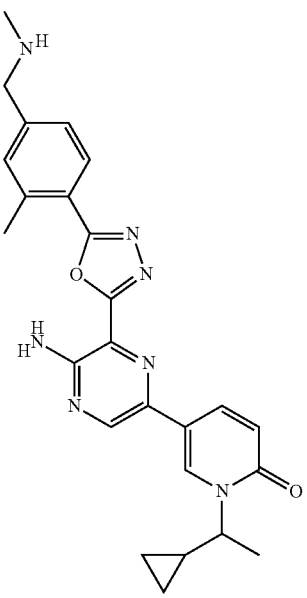

TABLE 1-continued
I-19
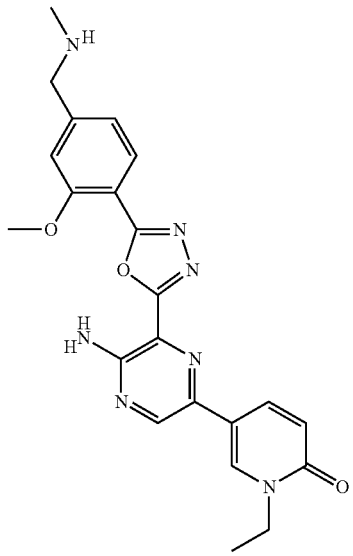
I-21
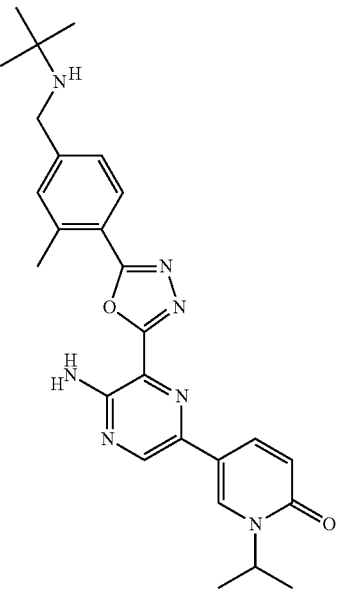
I-20
I-22
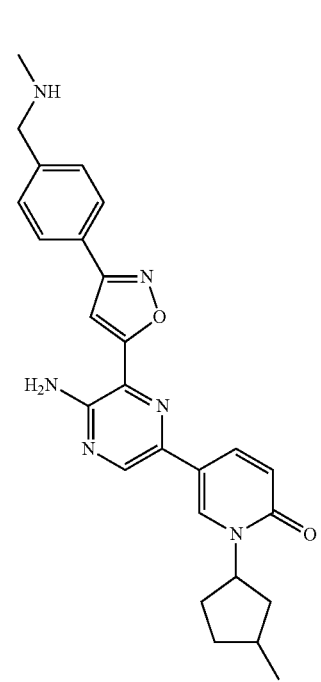 [SMILES: CNCc1ccc(-c2cc(-c3nc(-c4ccc(=O)n(C5CCC(C)C5)c4)cnc3N)on2)cc1]

TABLE 1-continued
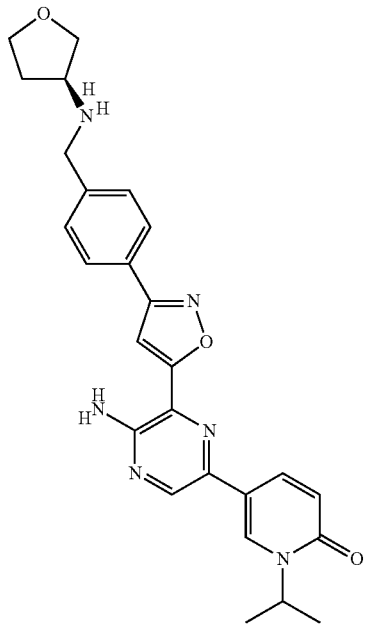
I-23
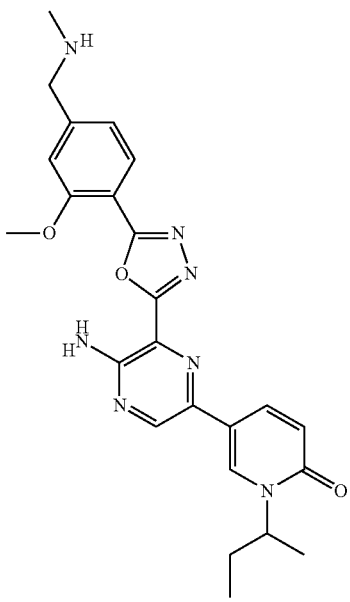
I-25
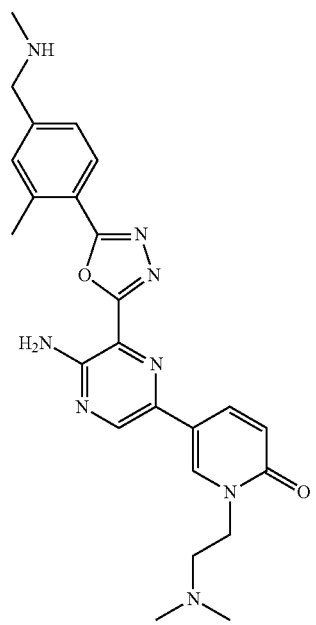 [SMILES: CNCc1ccc(-c2nnc(-c3nc(-c4ccc(=O)n(CCN(C)C)c4)cnc3N)o2)c(C)c1]
I-24
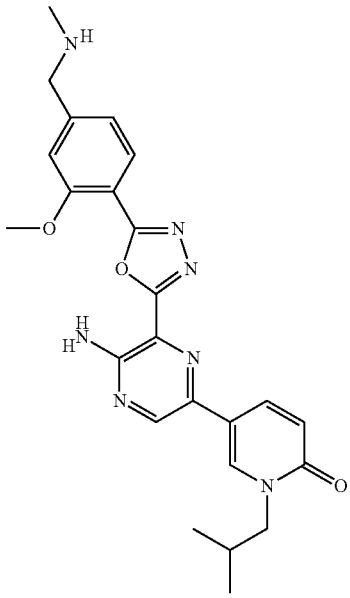
I-26

TABLE 1-continued
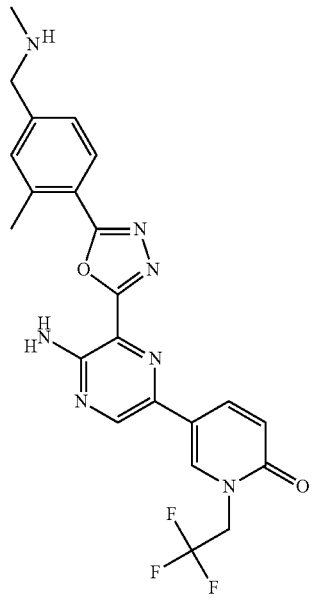
I-27
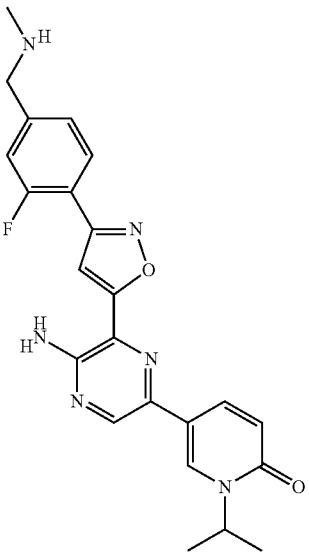
I-29
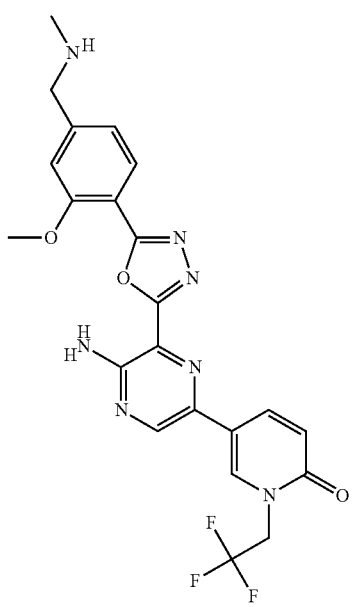
I-28
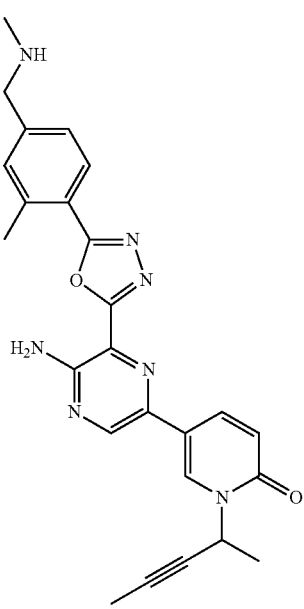 [SMILES: CC#CC(C)n1cc(-c2cnc(N)c(-c3nnc(-c4ccc(CNC)cc4C)o3)n2)ccc1=O]
I-30

TABLE 1-continued
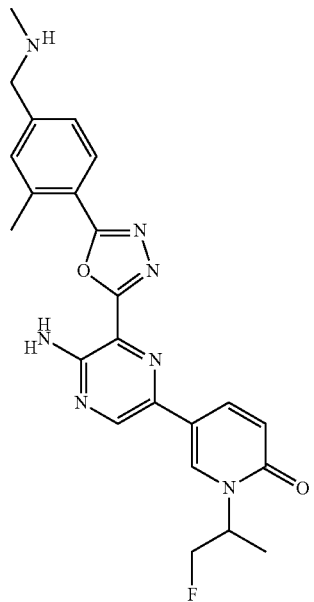
I-31
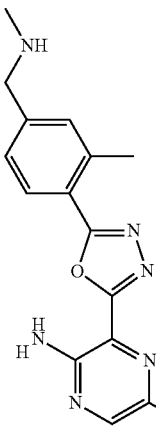
I-33
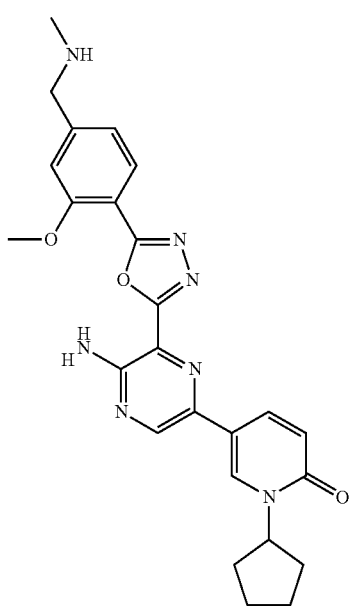
I-32
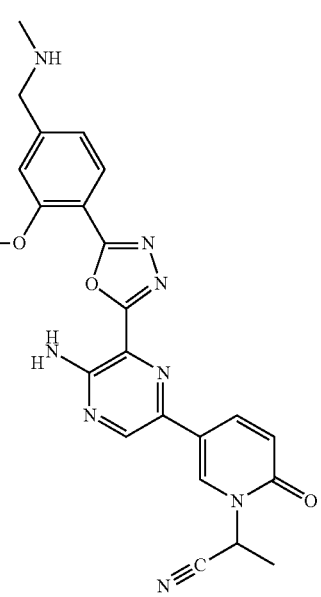
I-34

TABLE 1-continued
I-35
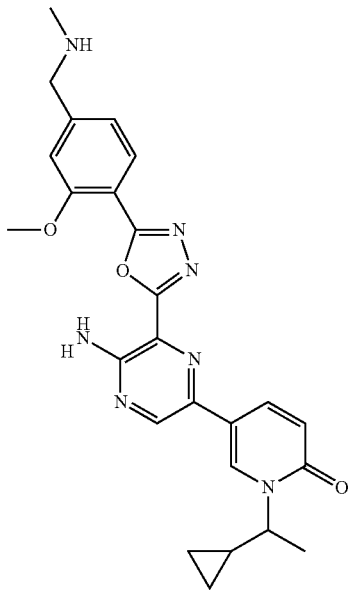
I-37
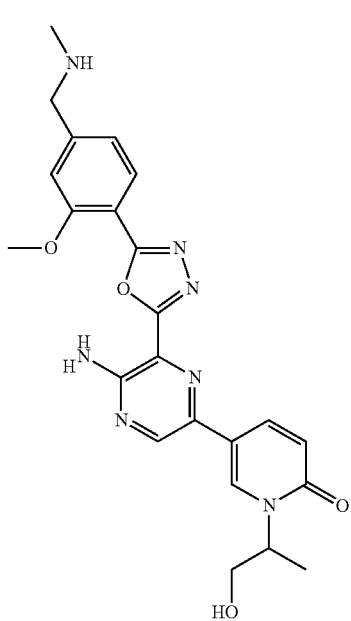
I-36
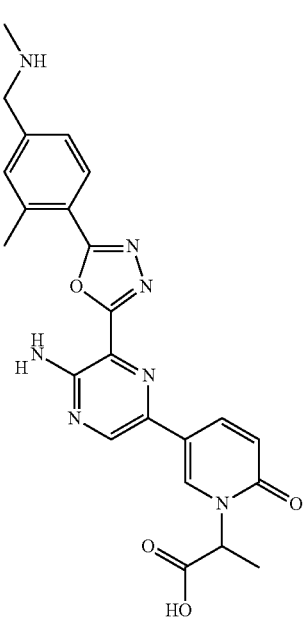
I-38

TABLE 1-continued
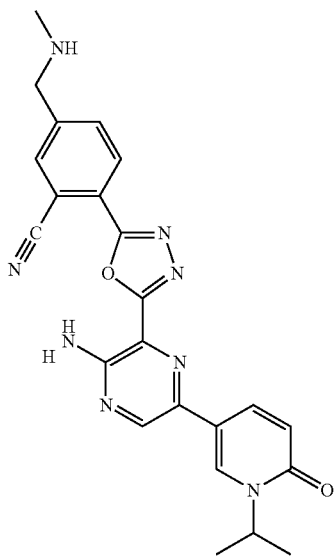
I-39
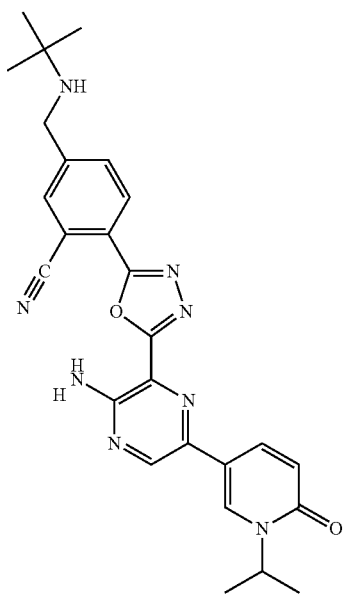
I-40
TABLE 1-continued
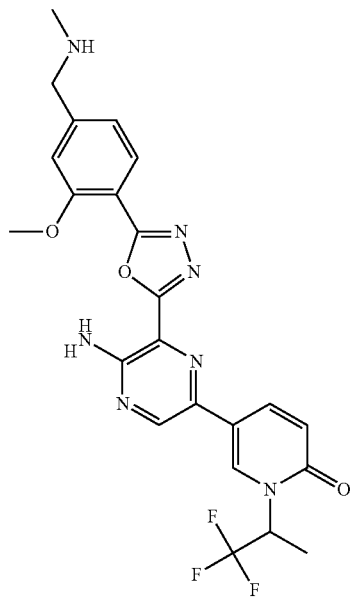
I-41
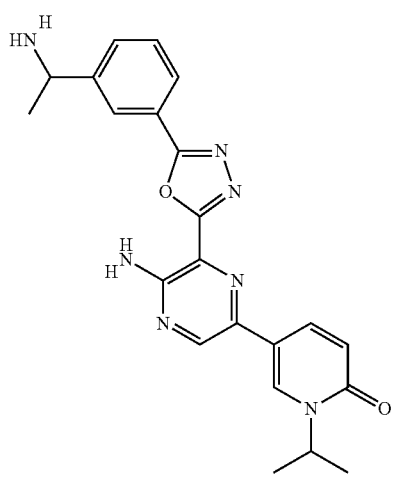
I-42
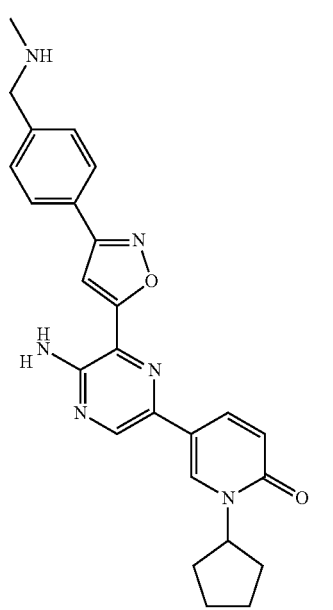
I-43

TABLE 1-continued
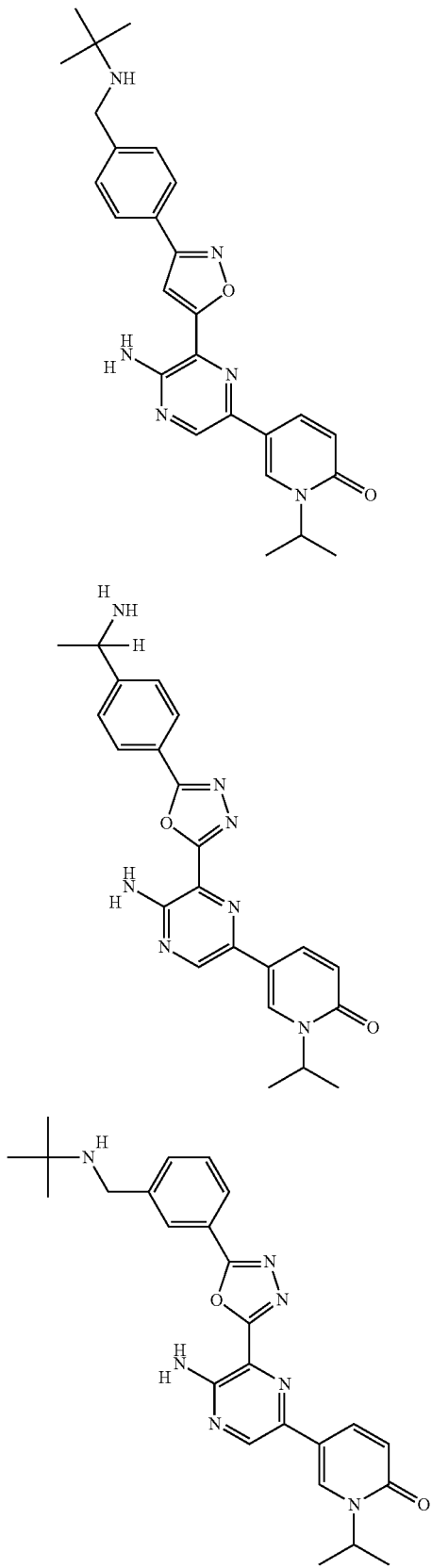
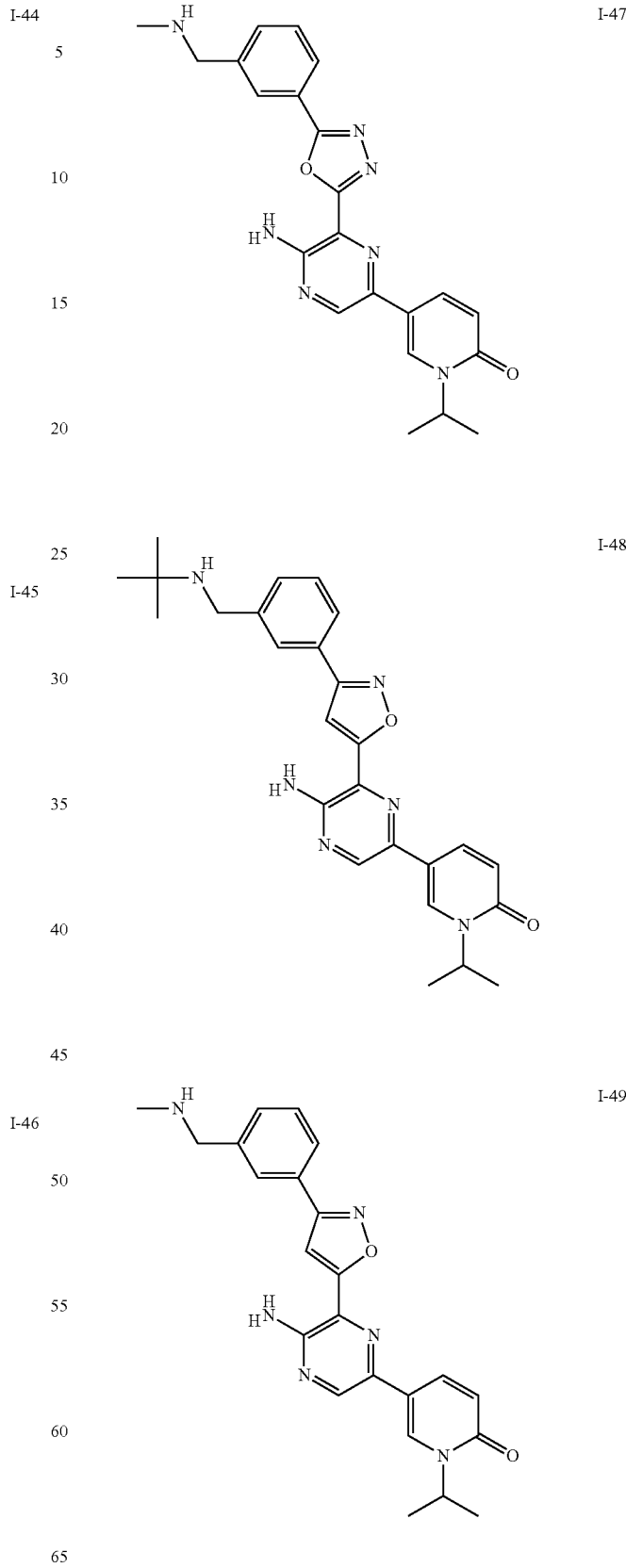

TABLE 1-continued
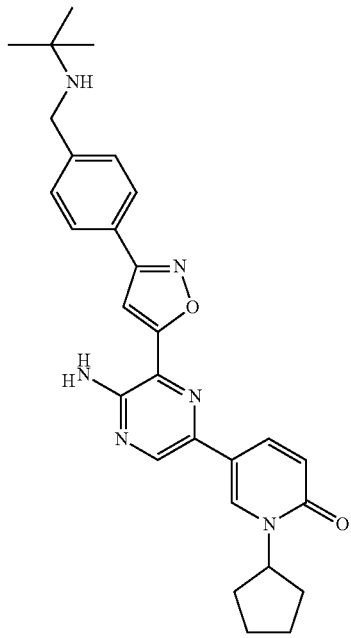
I-50
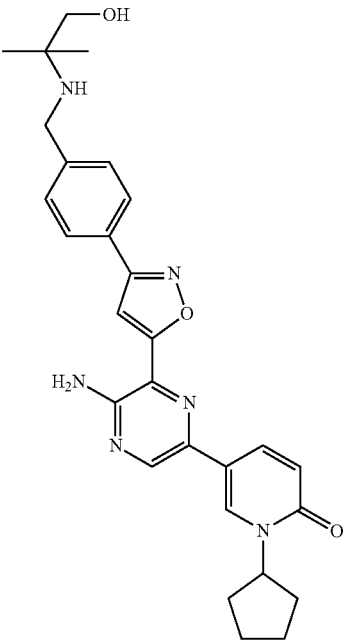
I-52
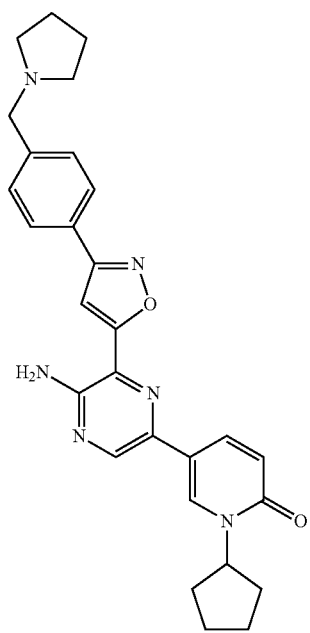 [SMILES: Nc1ncc(-c2ccc(=O)n(C3CCCC3)c2)nc1-c1cc(-c2ccc(CN3CCCC3)cc2)no1]
I-51
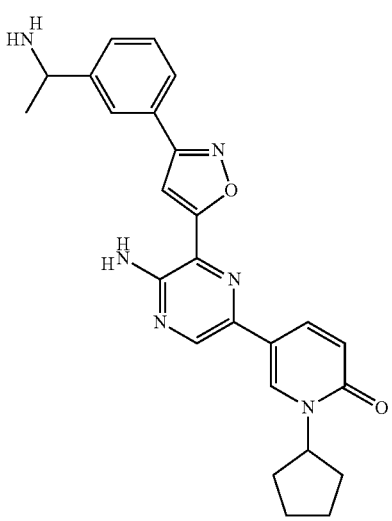
I-53

TABLE 1-continued
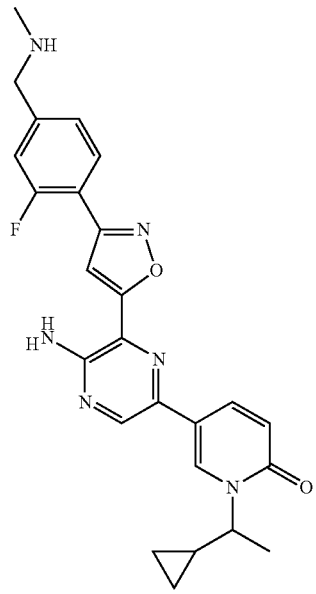
I-54
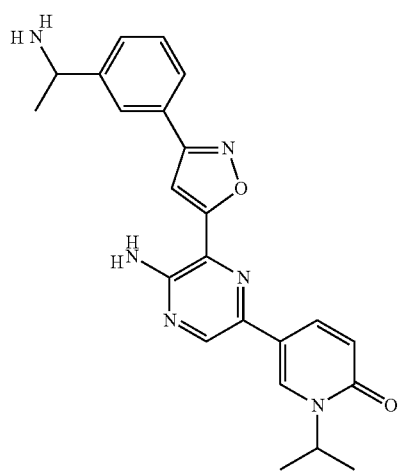
I-55
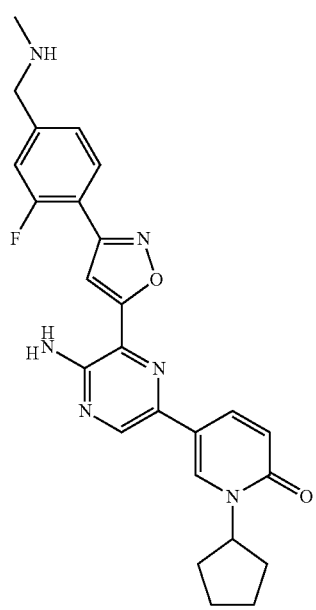
I-56
TABLE 1-continued
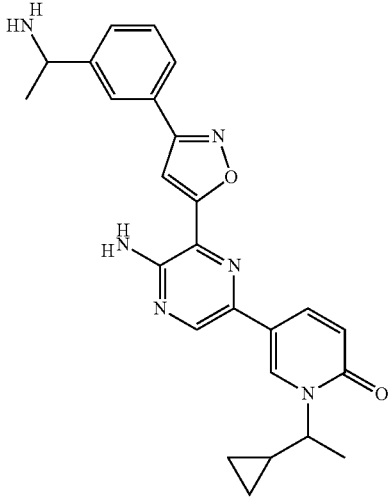
I-57
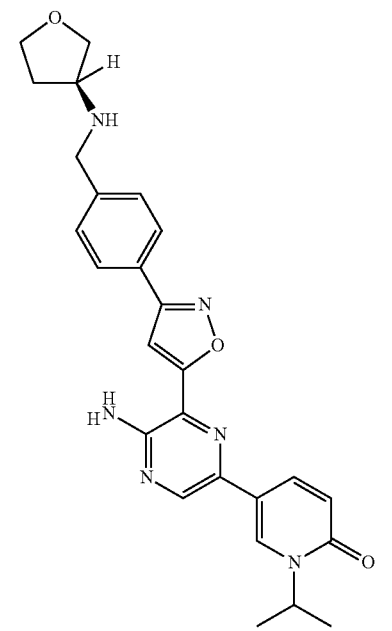
I-58

TABLE 1-continued
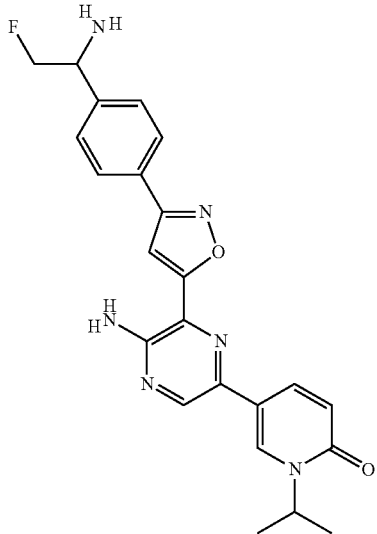
I-59
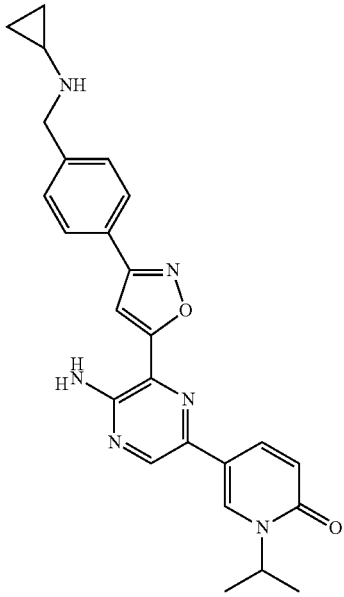
I-61
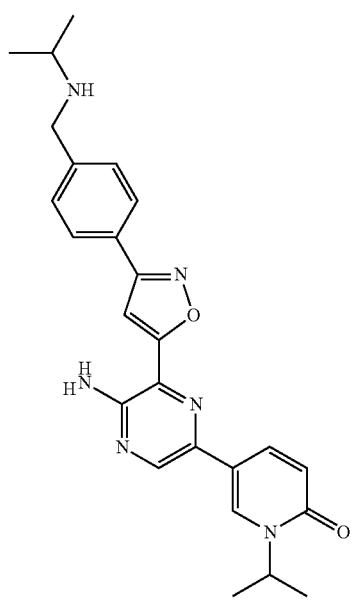
I-60
I-62

TABLE 1-continued
I-63
I-64
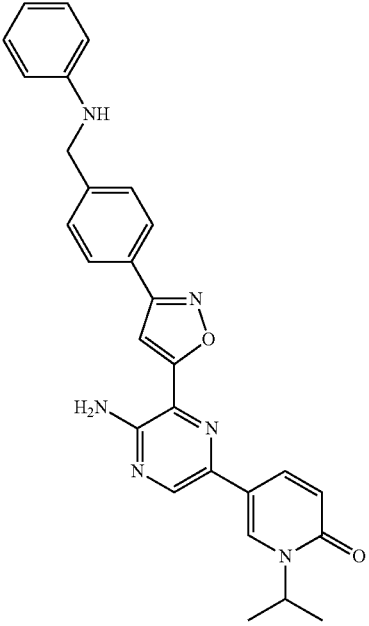 [SMILES: CC(C)n1cc(-c2cnc(N)c(-c3cc(-c4ccc(CNc5ccccc5)cc4)no3)n2)ccc1=O]
I-65
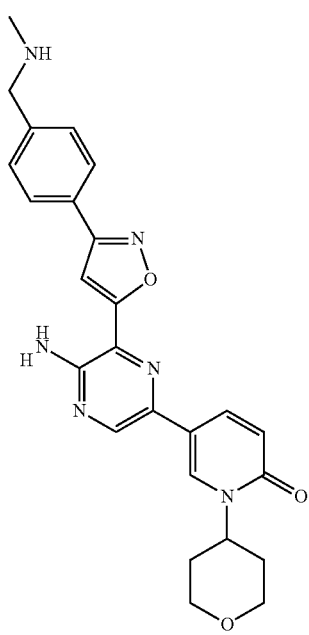
I-66
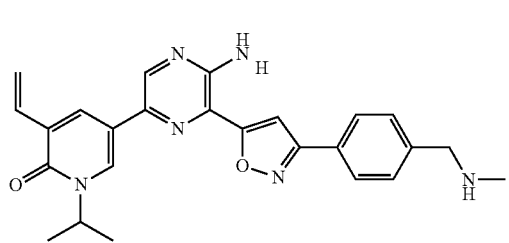
I-67

TABLE 1-continued
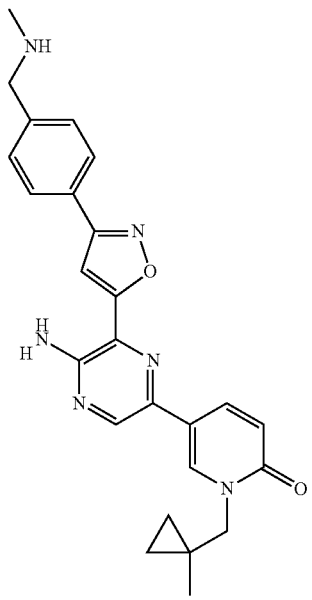
I-68
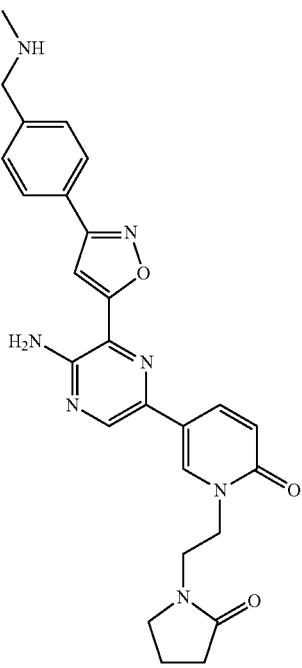
I-70
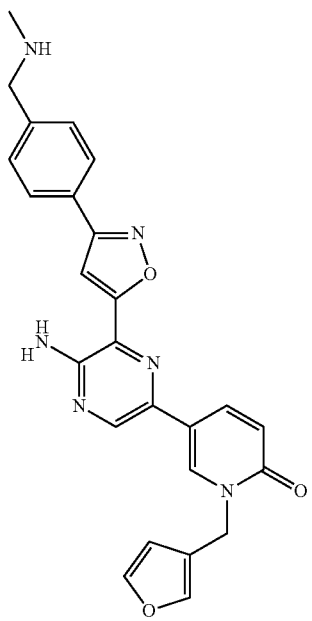
I-69
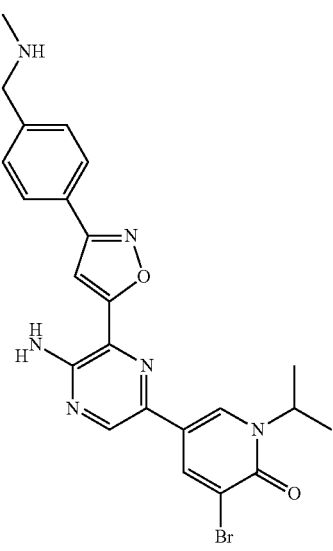
I-71

TABLE 1-continued
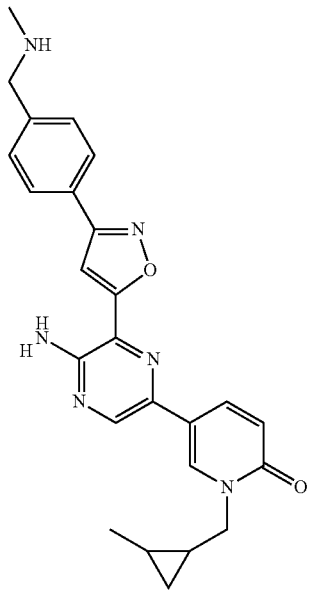
I-72
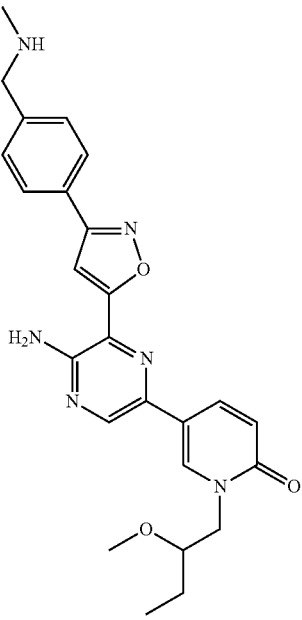
I-74
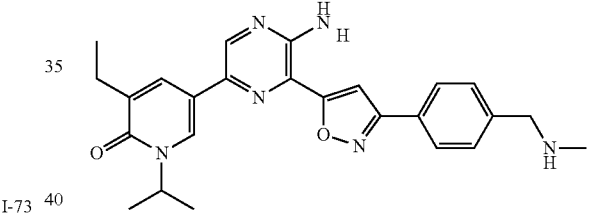
I-75
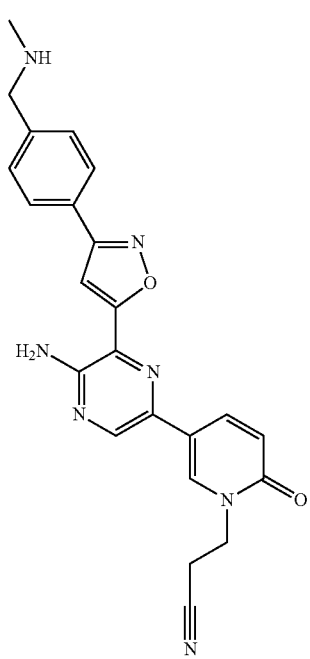 [SMILES: CNCc1ccc(-c2cc(-c3nc(-c4ccc(=O)n(CCC#N)c4)cnc3N)on2)cc1]
I-73
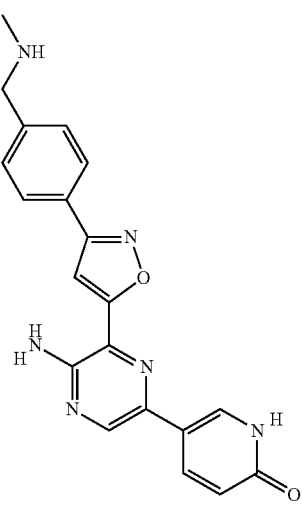
I-76

TABLE 1-continued
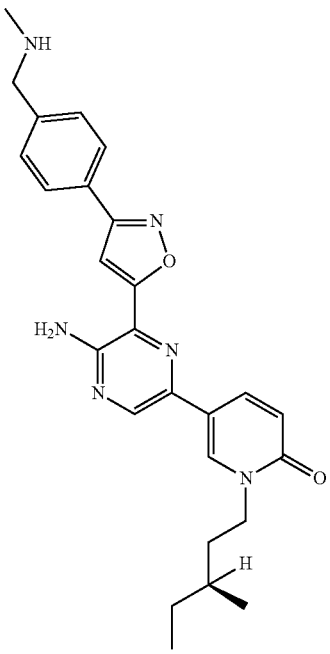 [SMILES: CC[C@H](C)CCn1cc(-c2cnc(N)c(-c3cc(-c4ccc(CNC)cc4)no3)n2)ccc1=O]
I-77
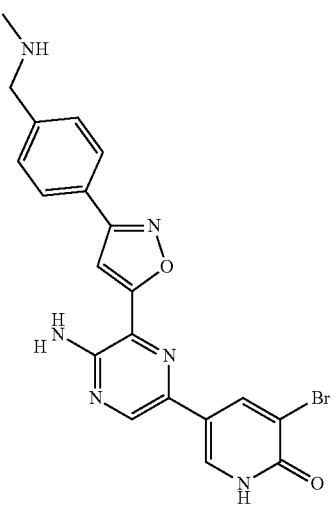
I-78
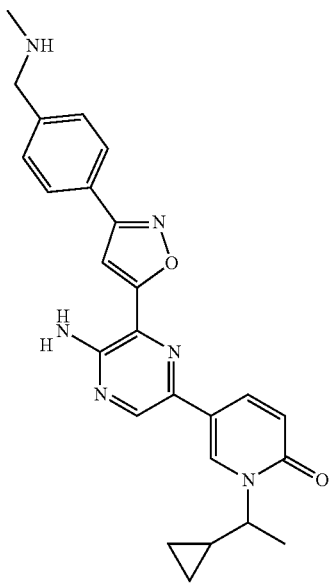
I-79
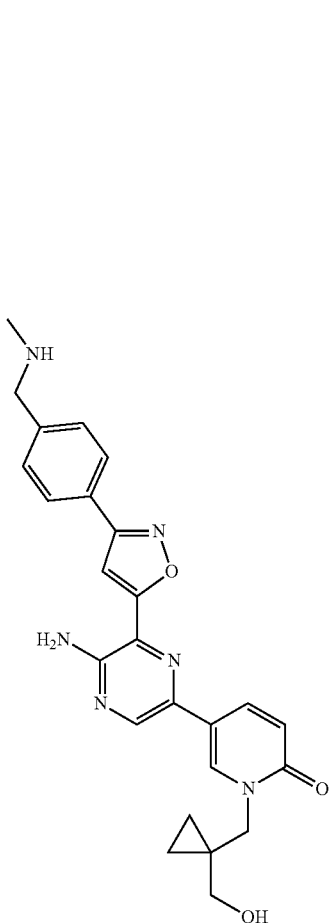 [SMILES: CNCc1ccc(-c2cc(-c3nc(-c4ccc(=O)n(CC5(CO)CC5)c4)cnc3N)on2)cc1]
I-80

TABLE 1-continued
I-81
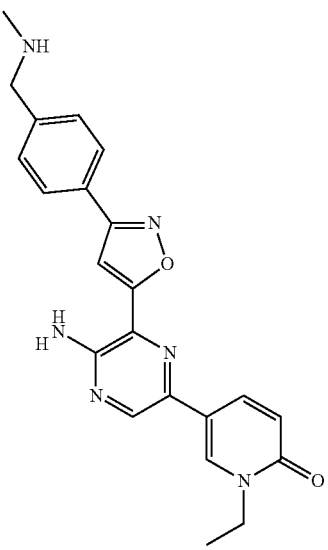
I-82
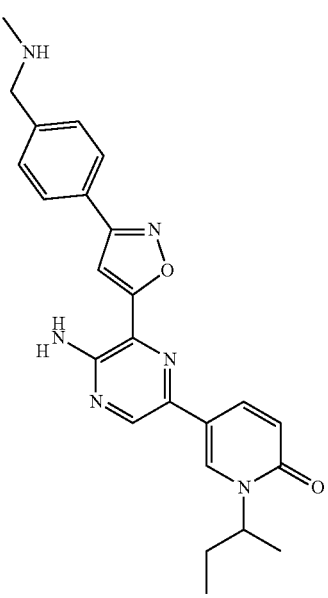
TABLE 1-continued
I-83
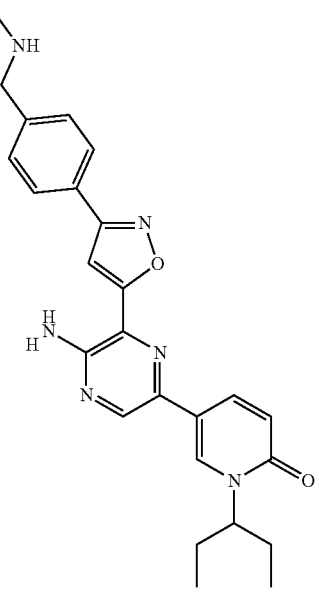
I-84
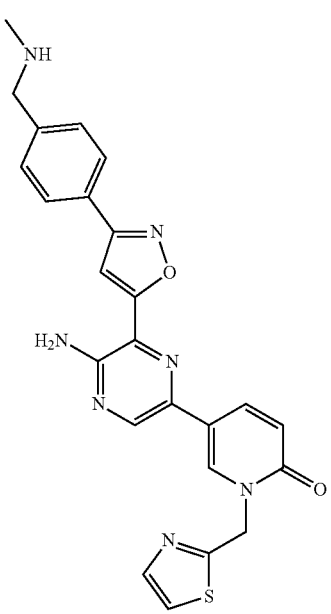 [SMILES: CNCc1ccc(-c2cc(-c3nc(-c4ccc(=O)n(Cc5nccs5)c4)cnc3N)on2)cc1]

TABLE 1-continued

I-85
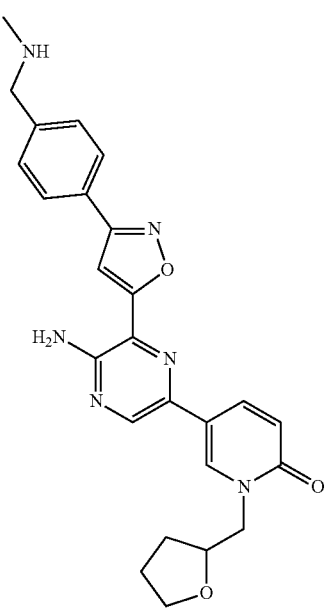 [SMILES: CNCc1ccc(-c2cc(-c3nc(-c4ccc(=O)n(CC5CCCO5)c4)cnc3N)on2)cc1]
I-86
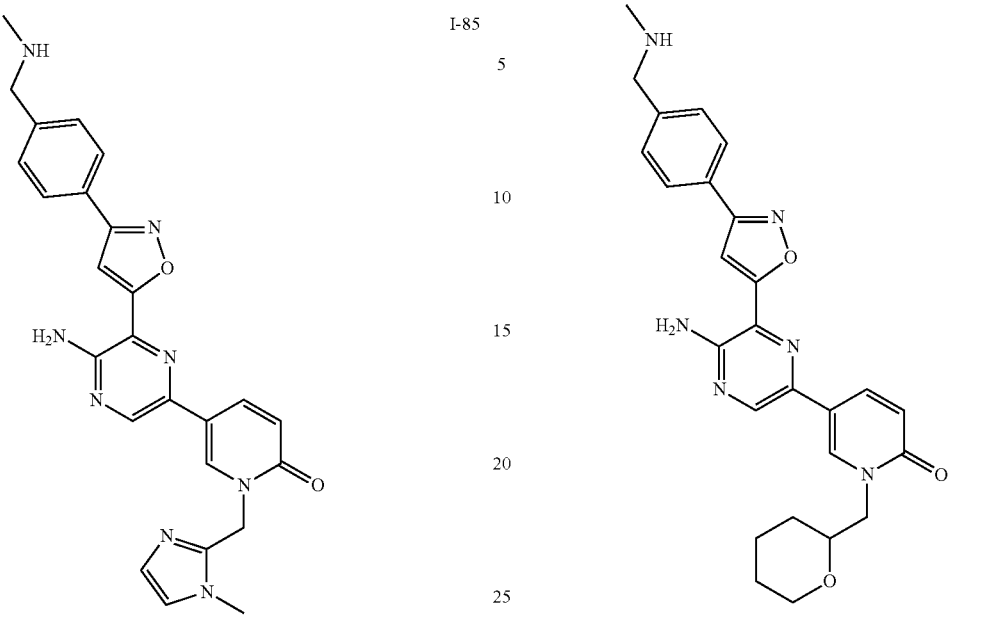
I-87
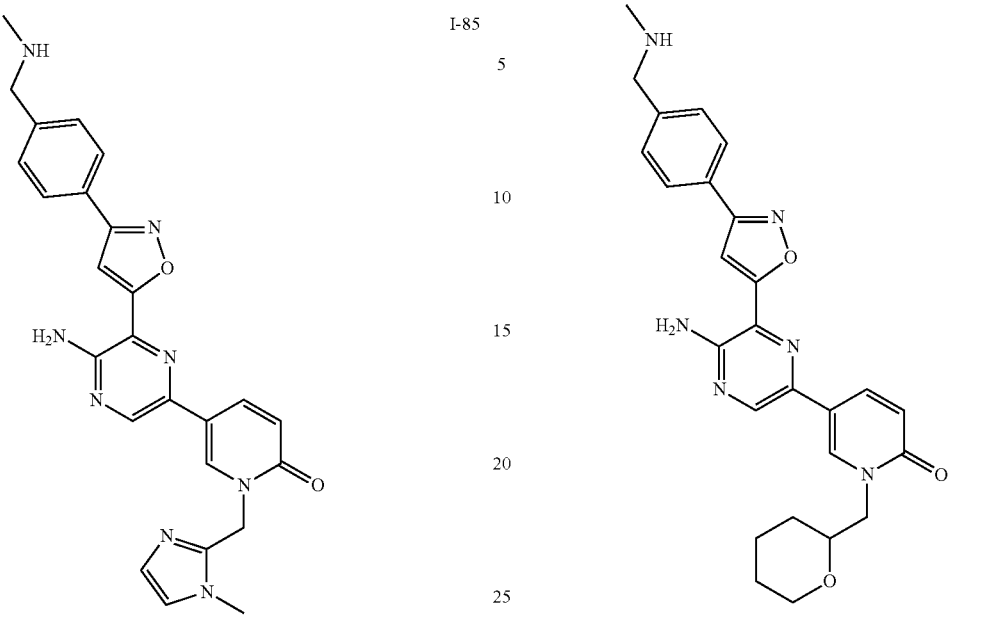
I-88
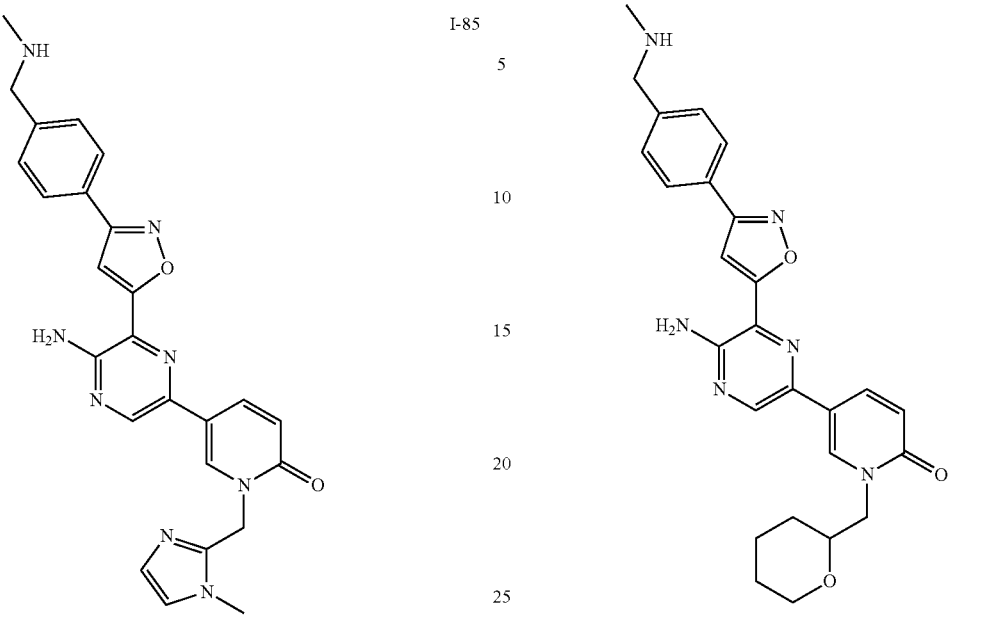
I-89

TABLE 1-continued
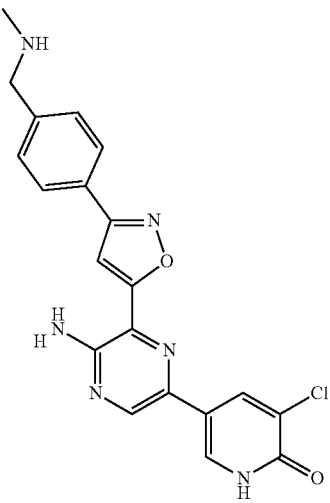
I-90
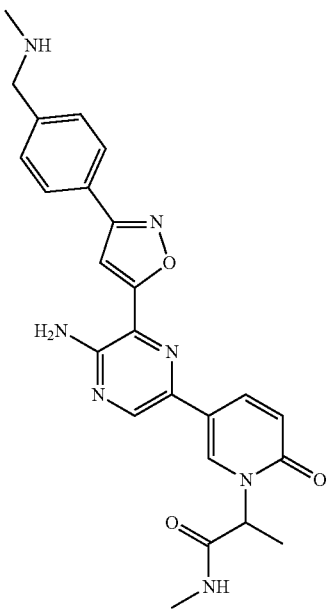 [SMILES: CNCc1ccc(-c2cc(-c3nc(-c4ccc(=O)n(C(C)C(=O)NC)c4)cnc3N)on2)cc1]
I-91
TABLE 1-continued
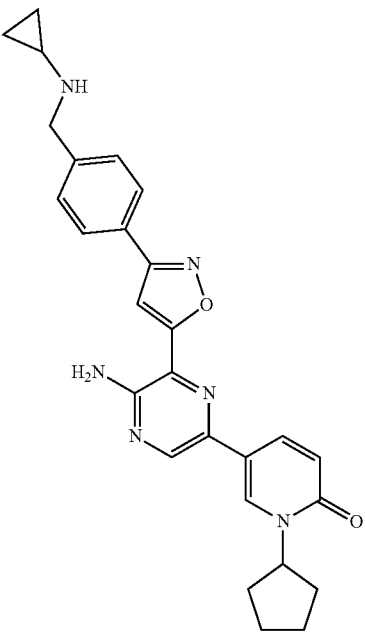 [SMILES: Nc1ncc(-c2ccc(=O)n(C3CCCC3)c2)nc1-c1cc(-c2ccc(CNC3CC3)cc2)no1]
I-92
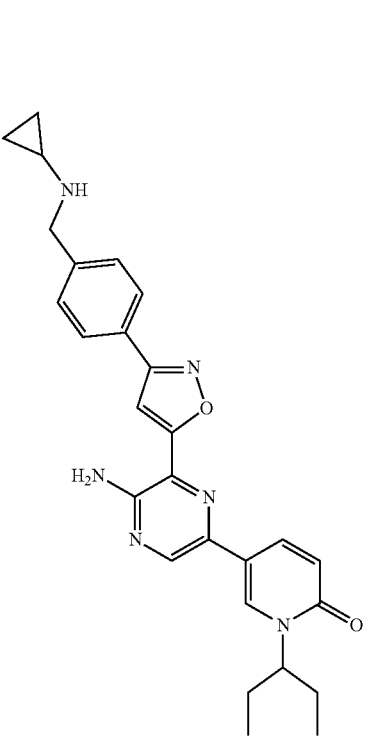 [SMILES: CCC(CC)n1cc(-c2cnc(N)c(-c3cc(-c4ccc(CNC5CC5)cc4)no3)n2)ccc1=O]
I-93

TABLE 1-continued
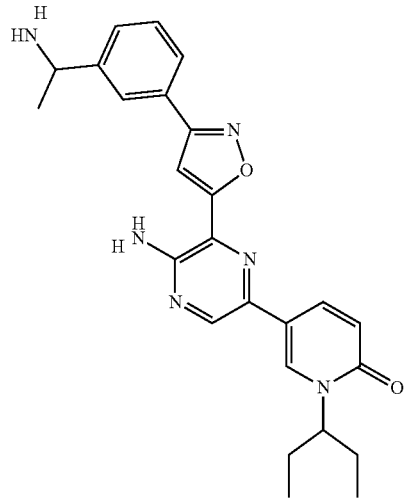
I-94
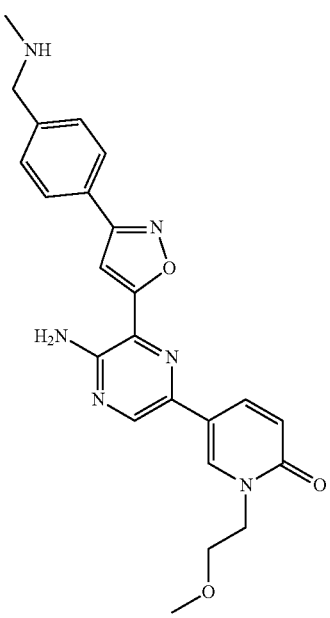 [SMILES: CNCc1ccc(-c2cc(-c3nc(-c4ccc(=O)n(CCOC)c4)cnc3N)on2)cc1]
I-95
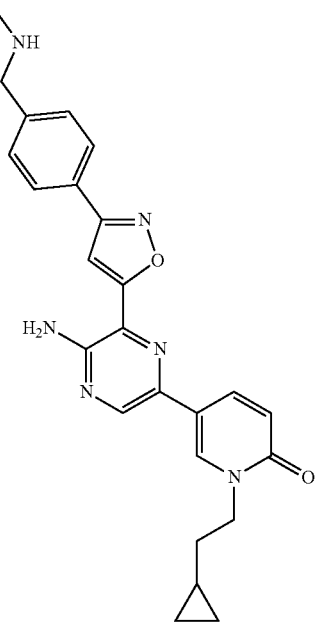
I-96
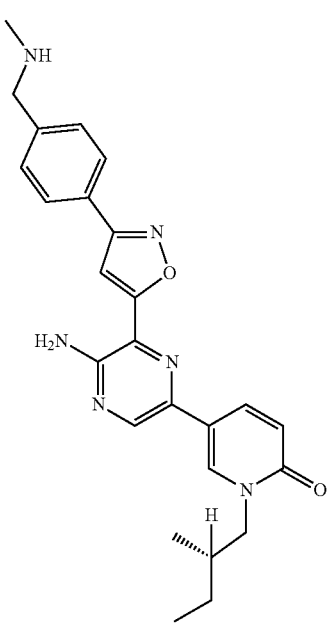 [SMILES: CC[C@H](C)Cn1cc(-c2cnc(N)c(-c3cc(-c4ccc(CNC)cc4)no3)n2)ccc1=O]
I-97

TABLE 1-continued
I-98
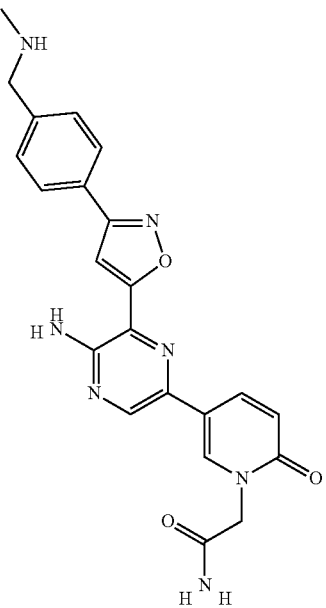
I-100
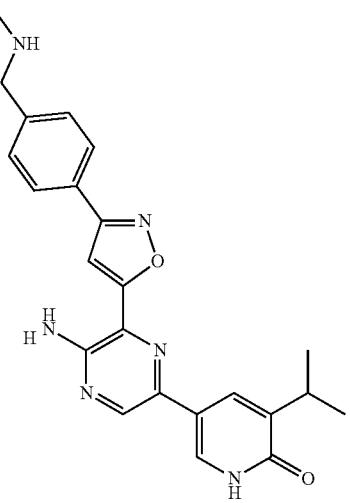
I-99
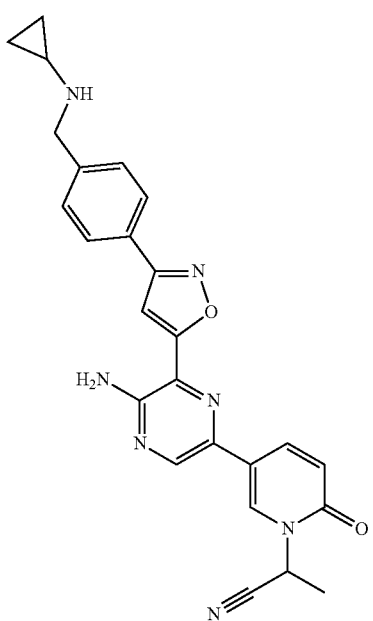 [SMILES: CC(C#N)n1cc(-c2cnc(N)c(-c3cc(-c4ccc(CNC5CC5)cc4)no3)n2)ccc1=O]
I-101

TABLE 1-continued
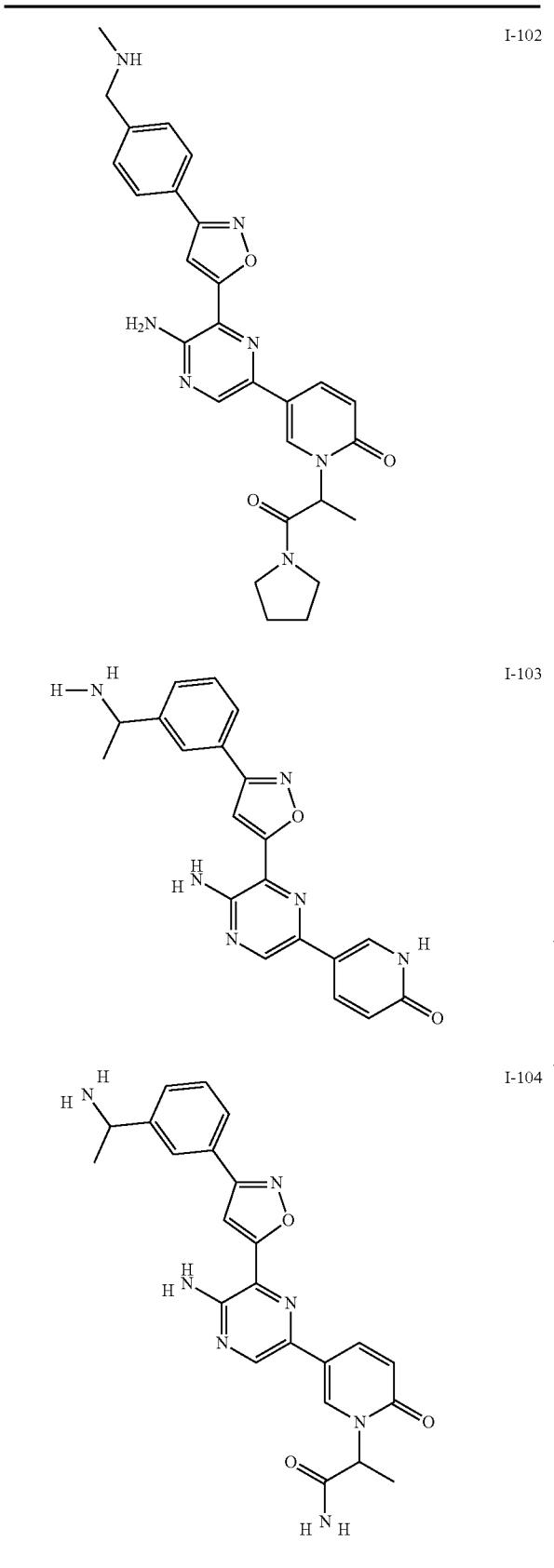
I-102
I-103
I-104
TABLE 1-continued
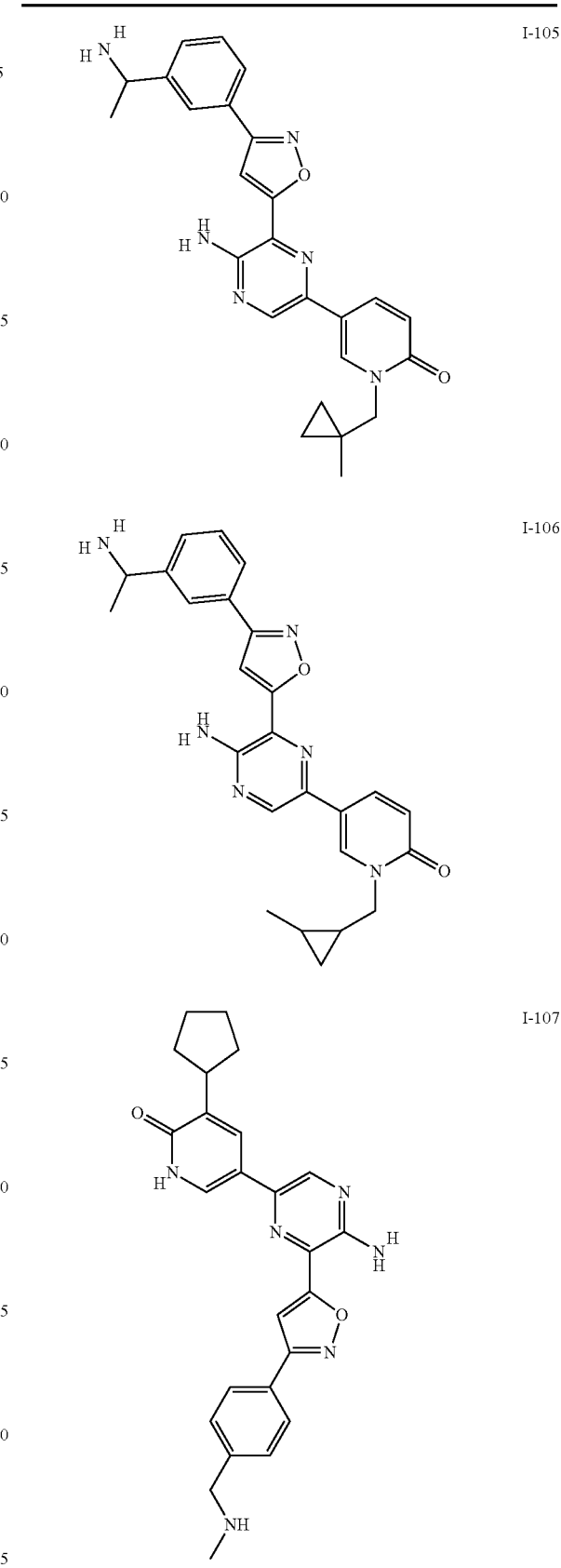
I-105
I-106
I-107

TABLE 1-continued
I-108
I-109
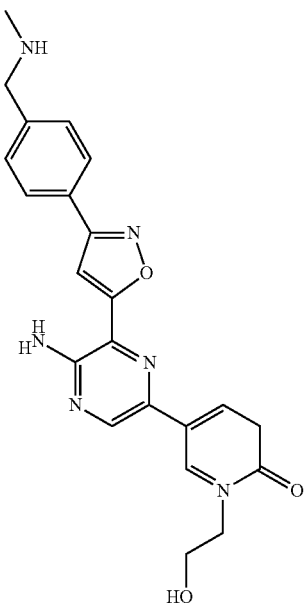
I-110
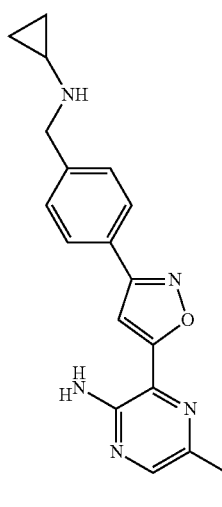
I-111
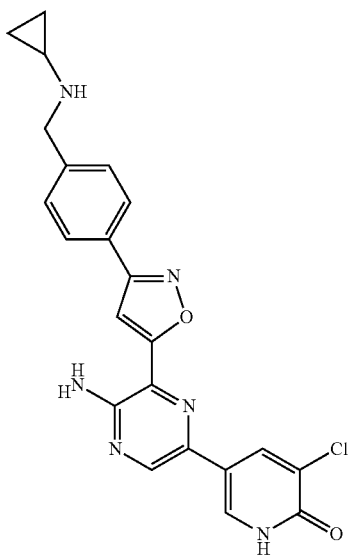
I-112

TABLE 1-continued
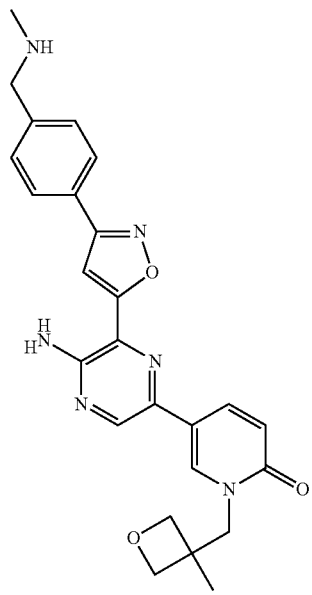
I-113
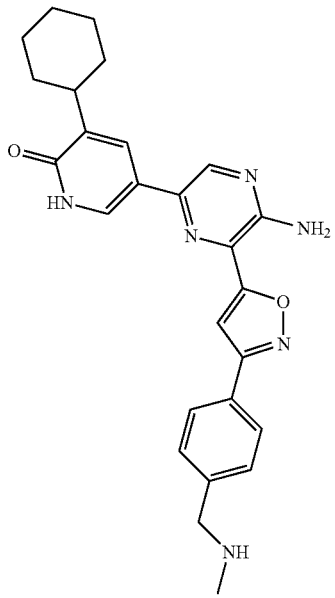 [SMILES: CNCc1ccc(-c2cc(-c3nc(-c4c[nH]c(=O)c(C5CCCCC5)c4)cnc3N)on2)cc1]
I-115
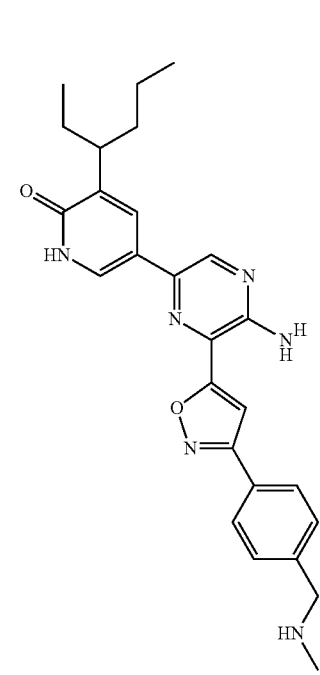
I-116
I-114

TABLE 1-continued
I-117
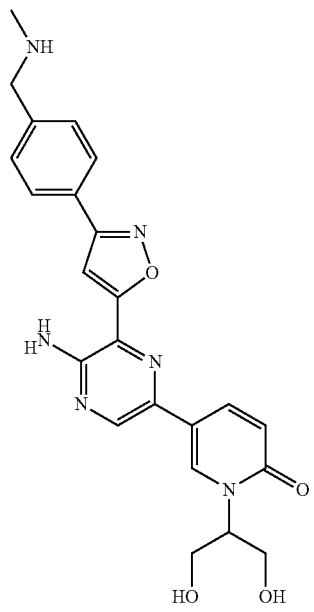
I-118
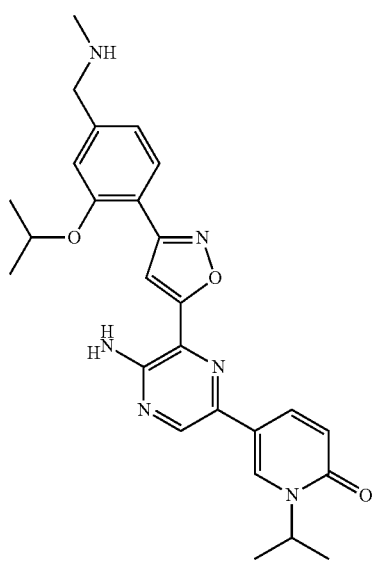
TABLE 1-continued
I-119
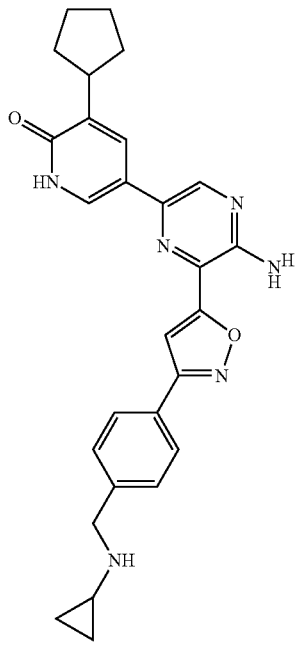
I-120
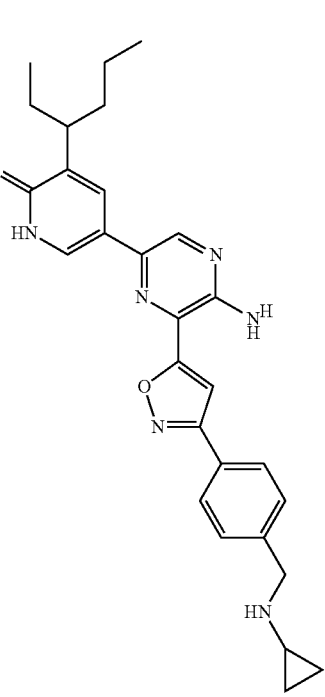

TABLE 1-continued
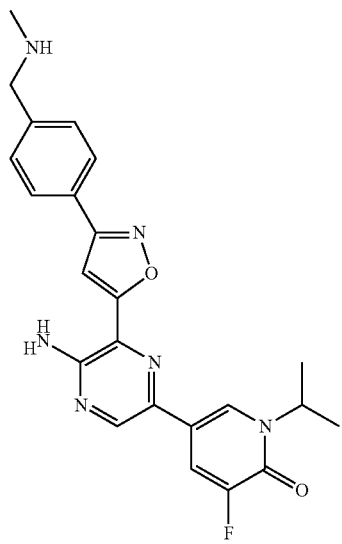
I-121
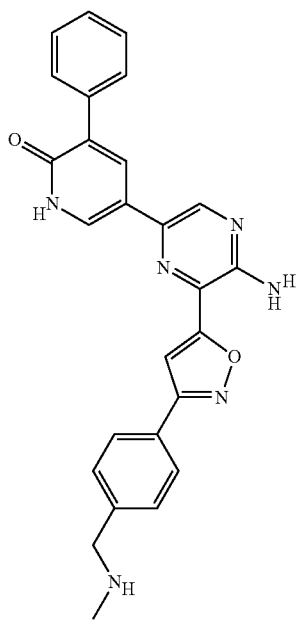
I-123
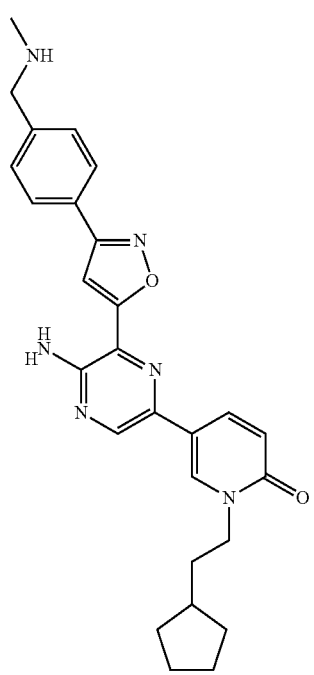
I-122
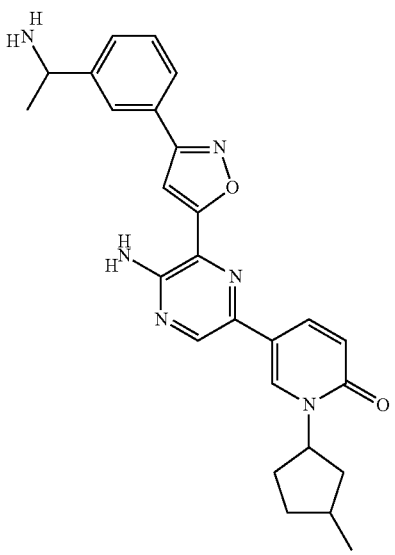
I-124

TABLE 1-continued
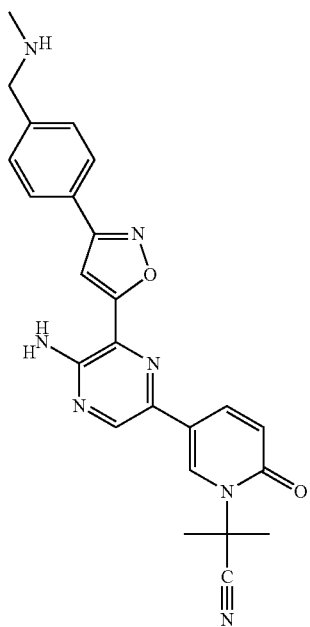
I-125
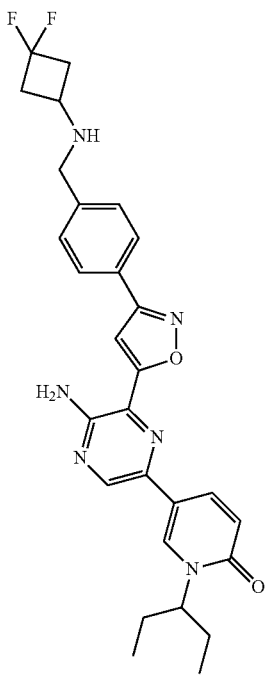
I-127
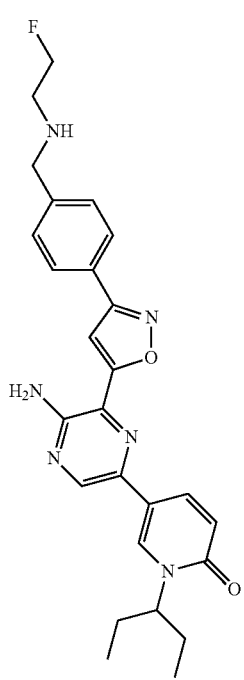 [SMILES: CCC(CC)n1cc(-c2cnc(N)c(-c3cc(-c4ccc(CNCCF)cc4)no3)n2)ccc1=O]
I-126
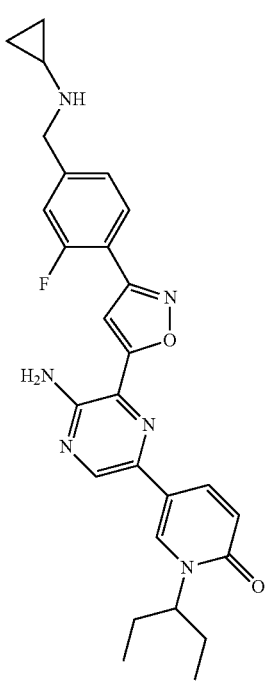 [SMILES: CCC(CC)n1cc(-c2cnc(N)c(-c3cc(-c4ccc(CNC5CC5)cc4F)no3)n2)ccc1=O]
I-128

TABLE 1-continued
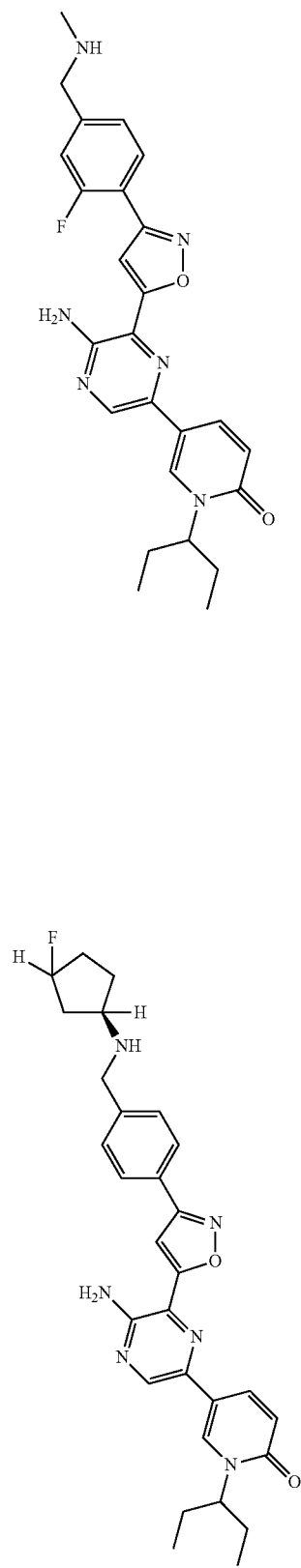
I-129
I-130
TABLE 1-continued
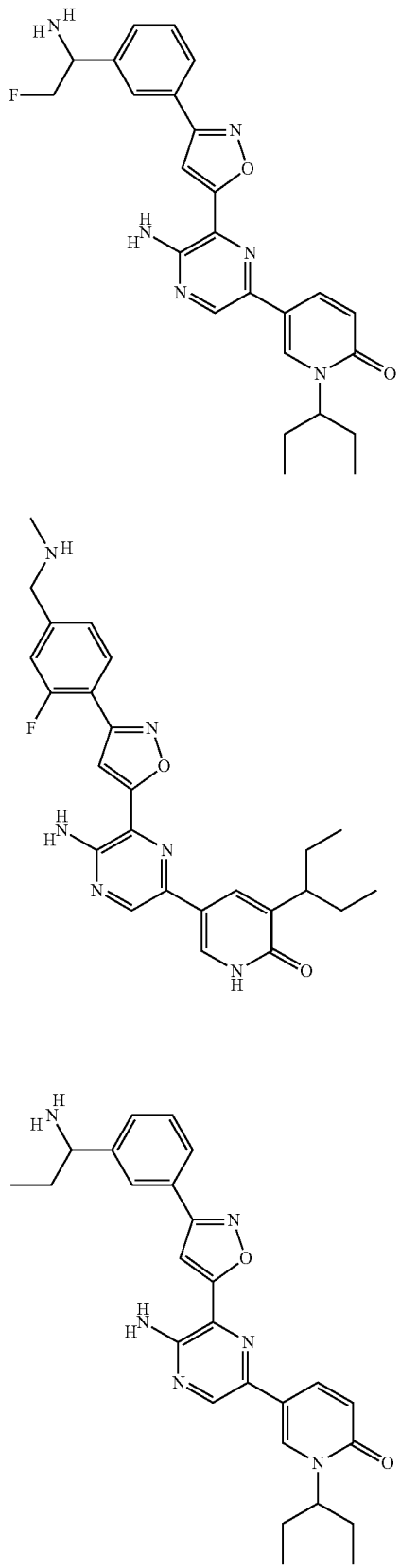
I-131
I-132
I-133

TABLE 1-continued
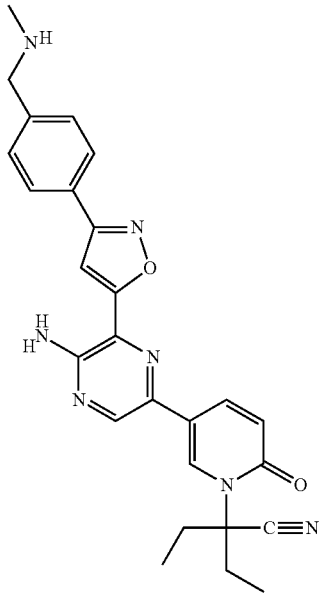
I-134
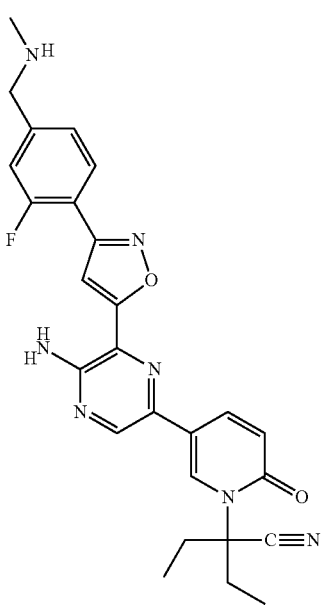
I-135
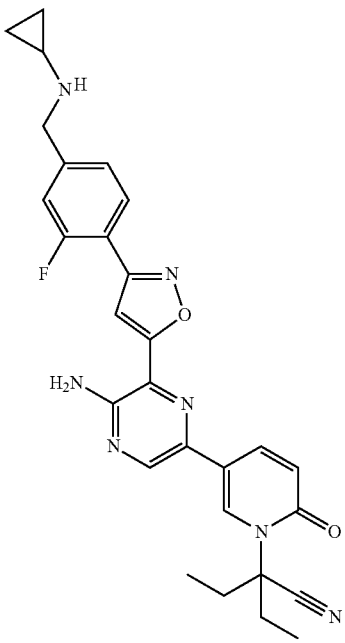
I-136
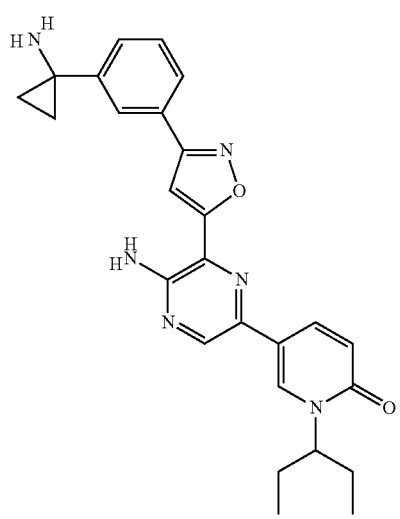
I-137
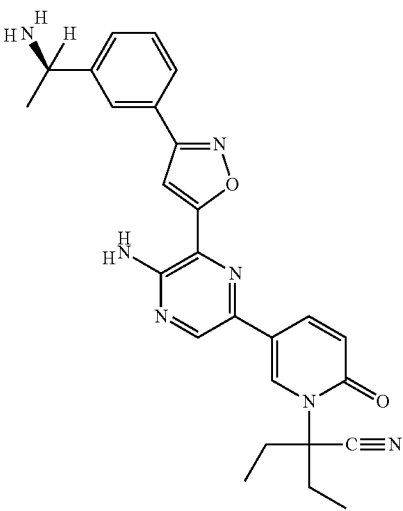
I-138

TABLE 1-continued
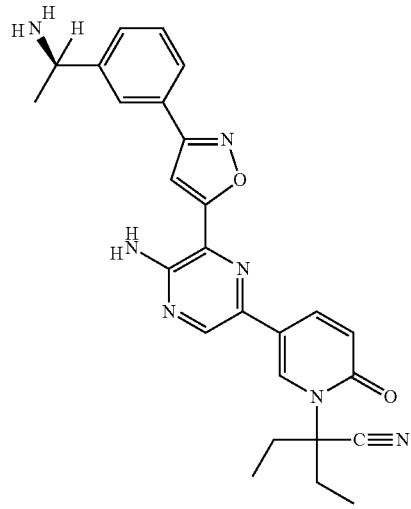
I-139
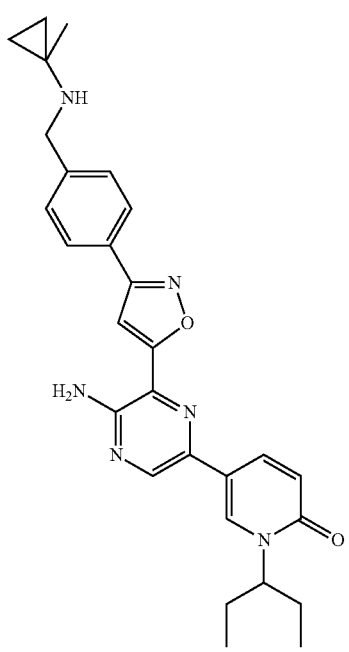 [SMILES: CCC(CC)n1cc(-c2cnc(N)c(-c3cc(-c4ccc(CNC5(C)CC5)cc4)no3)n2)ccc1=O]
I-140
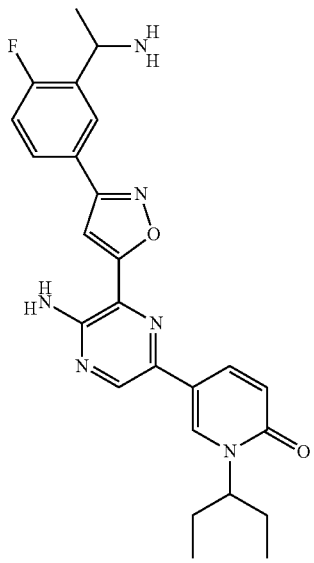
I-141
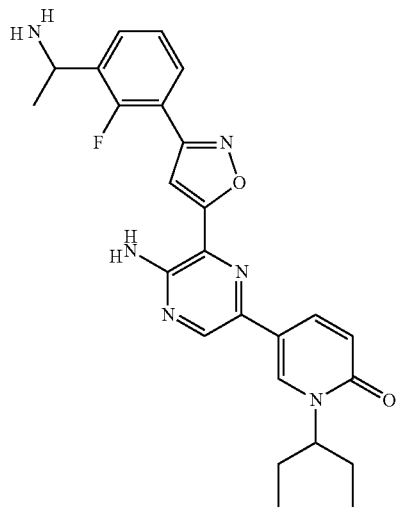
I-142
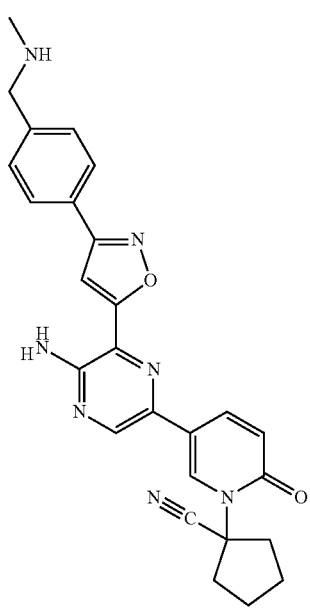
I-143

TABLE 1-continued
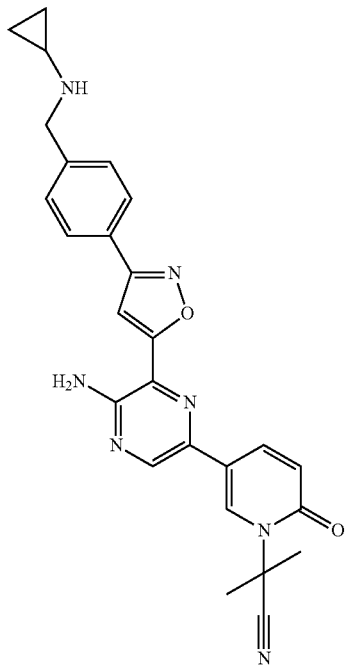 [SMILES: CC(C)(C#N)n1cc(-c2cnc(N)c(-c3cc(-c4ccc(CNC5CC5)cc4)no3)n2)ccc1=O]
I-144
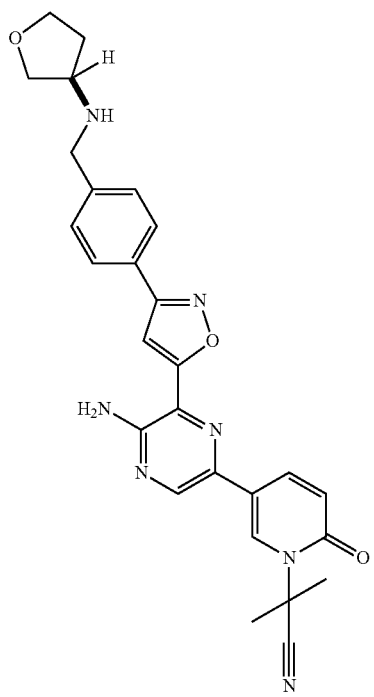
I-145
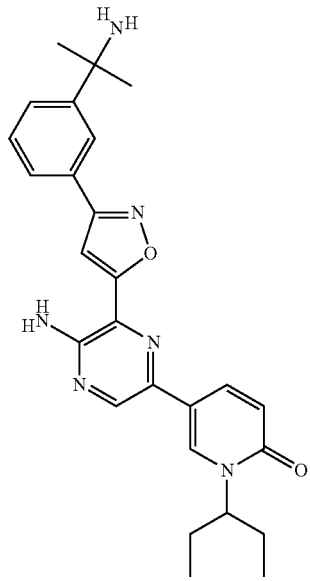
I-146
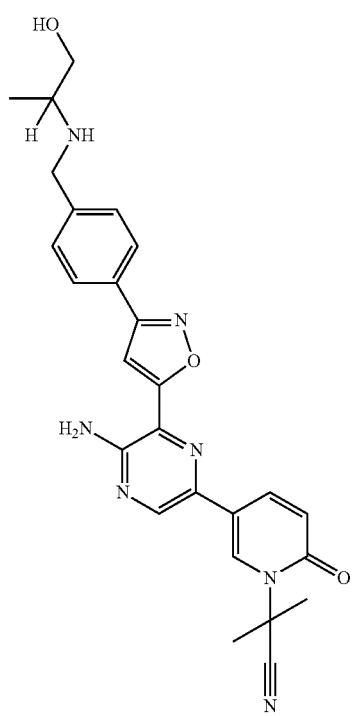 [SMILES: CC(CO)NCc1ccc(-c2cc(-c3nc(-c4ccc(=O)n(C(C)(C)C#N)c4)cnc3N)on2)cc1]
I-147

TABLE 1-continued

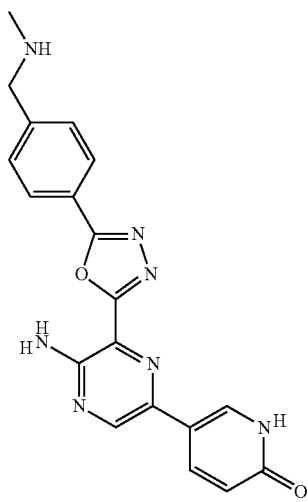

I-148

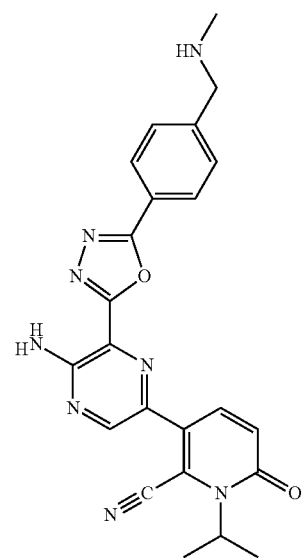

I-149

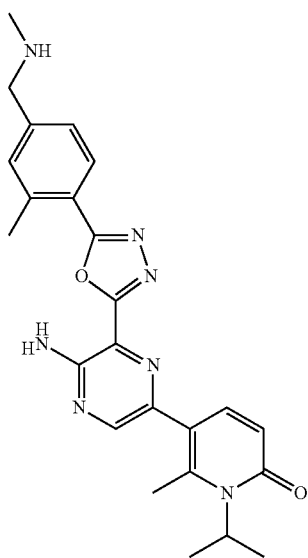

I-150

TABLE 1-continued

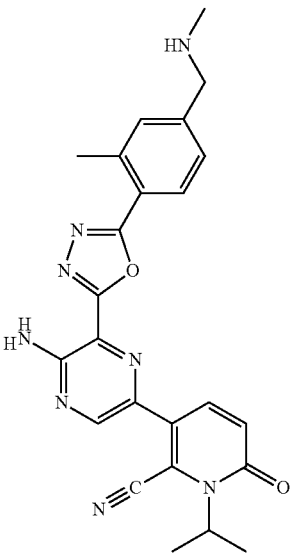

I-151

In some embodiments, the variables are as depicted in the compounds of the disclosure including compounds in the tables above.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, J$^1$ can be bonded to any position on the pyridyl ring. For bicyclic rings, a bond drawn through both rings indicates that the substituent can be bonded from any position of the bicyclic ring. In example ii below, for instance, J¹ can be bonded to the 5-membered ring (on the nitrogen atom, for instance), and to the 6-membered ring.

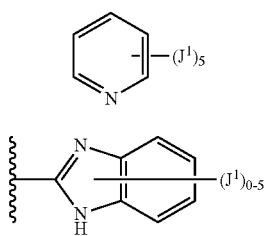

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —CH$_2$-cyclopropyl, CH$_2$CH$_2$CH(CH$_3$)-cyclohexyl.

The term "cycloaliphatic" (or "carbocycle" or "carbocyclyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

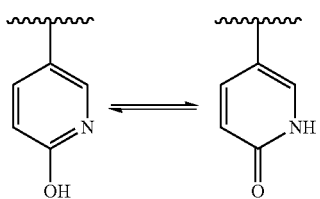 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O) CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N≡N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. It should be understood that if the terminal atom does not contain any free valence electrons, then a hydrogen atom is not required at the terminal end (e.g., —CH$_2$CH$_2$CH=O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

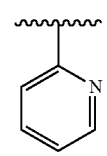 [SMILES: *c1ccccn1]

also represents

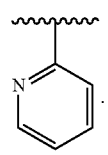

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

Pharmaceutically Acceptable Salts

The compounds of this invention can exist in free form for treatment, or where appropriate, as a pharmaceutically acceptable salt.

A "pharmaceutically acceptable salt" means any nontoxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of the ATR protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

Abbreviations

The following abbreviations are used:

| | |
|---|---|
| DMSO | dimethyl sulfoxide |
| ATP | adenosine triphosphate |
| $^1$HNMR | proton nuclear magnetic resonance |
| HPLC | high performance liquid chromatography |
| LCMS | liquid chromatography-mass spectrometry |
| TLC | thin layer chromatography |
| Rt | retention time |

Compound Uses

One aspect of this invention provides compounds that are inhibitors of ATR kinase, and thus are useful for treating or lessening the severity of a disease, condition, or disorder where ATR is implicated in the disease, condition, or disorder.

Another aspect of this invention provides compounds that are useful for the treatment of diseases, disorders, and conditions characterized by excessive or abnormal cell proliferation. Such diseases include, a proliferative or hyperproliferative disease. Examples of proliferative and hyperproliferative diseases include, without limitation, cancer and myeloproliferative disorders.

In some embodiments, said compounds are selected from the group consisting of a compound of formula I. The term "cancer" includes, but is not limited to the following cancers. Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

Thus, the term "cancerous cell" as provided herein, includes a cell afflicted by any one of the above-identified conditions. In some embodiments, the cancer is selected from colorectal, thyroid, or breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Pharmaceutically Acceptable Derivatives or Prodrugs

In addition to the compounds of this invention, pharmaceutically acceptable derivatives or prodrugs of the compounds of this invention may also be employed in compositions to treat or prevent the herein identified disorders.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" means any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutical Compositions

The present invention also provides compounds and compositions that are useful as inhibitors of ATR kinase.

One aspect of this invention provides pharmaceutically acceptable compositions that comprise any of the compounds as described herein, and optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Combination Therapies

Another aspect of this invention is directed towards a method of treating cancer in a subject in need thereof, comprising administration of a compound of this invention or a pharmaceutically acceptable salt thereof, and an additional therapeutic agent. In some embodiments, said method comprises the sequential or co-administration of the compound or a pharmaceutically acceptable salt thereof, and the additional therapeutic agent.

In some embodiments, said additional therapeutic agent is an anti-cancer agent. In other embodiments, said additional therapeutic agent is a DNA-damaging agent. In yet other embodiments, said additional therapeutic agent is selected from radiation therapy, chemotherapy, or other agents typically used in combination with radiation therapy or chemotherapy, such as radiosensitizers and chemosensitizers.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

Examples of DNA-damaging agents that may be used in combination with compounds of this invention include, but are not limited to Platinating agents, such as Carboplatin, Nedaplatin, Satraplatin and other derivatives; Topo I inhibitors, such as Topotecan, irinotecan/SN38, rubitecan and other derivatives; Antimetabolites, such as Folic family (Methotrexate, Pemetrexed and relatives); Purine antagonists and Pyrimidine antagonists (Thioguanine, Fludarabine, Cladribine, Cytarabine, Gemcitabine, 6-Mercaptopurine, 5-Fluorouracil (5FU) and relatives); Alkylating agents, such as Nitrogen mustards (Cyclophosphamide, Melphalan, Chlorambucil, mechlorethamine, Ifosfamide and relatives); nitrosoureas (eg Carmustine); Triazenes (Dacarbazine, temozolomide); Alkyl sulphonates (eg Busulfan); Procarbazine and Aziridines; Antibiotics, such as Hydroxyurea, Anthracyclines (doxorubicin, daunorubicin, epirubicin and other derivatives); Anthracenediones (Mitoxantrone and relatives); Streptomyces family (Bleomycin, Mitomycin C, actinomycin); and Ultraviolet light.

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topotecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (dromostanolone®); dromostanolone propionate (masterone injection®); Elliott's B Solution (Elliott's B Solution®); epirubicin (Ellence®); Epoetin alfa (epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrel in acetate (Histrelin implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Compositions for Administration into a Subject

The ATR kinase inhibitors or pharmaceutical salts thereof may be formulated into pharmaceutical compositions for administration to animals or humans. These pharmaceutical compositions, which comprise an amount of the ATR inhibitor effective to treat or prevent the diseases or conditions described herein and a pharmaceutically acceptable carrier, are another embodiment of the present invention.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, these compositions optionally further comprise one or more additional therapeutic agents. For example, chemotherapeutic agents or other anti-proliferative agents may be combined with the compounds of this invention to treat proliferative diseases and cancer. Examples of known agents with which these compositions can be combined are listed above under the "Combination Therapies" section and also throughout the specification. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar--agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Administering with Another Agent

Depending upon the particular protein kinase-mediated conditions to be treated or prevented, additional drugs, which are normally administered to treat or prevent that condition, may be administered together with the compounds of this invention.

Those additional agents may be administered separately, as part of a multiple dosage regimen, from the protein kinase inhibitor-containing compound or composition.

Alternatively, those agents may be part of a single dosage form, mixed together with the protein kinase inhibitor in a single composition.

Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from Platinating agents, such as Cisplatin, Oxaliplatin, Carboplatin, Nedaplatin, or Satraplatin and other derivatives; Topo I inhibitors, such as Camptothecin, Topotecan, irinotecan/SN38, rubitecan and other derivatives; Antimetabolites, such as Folic family (Methotrexate, Pemetrexed and relatives); Purine family (Thioguanine, Fludarabine, Cladribine, 6-Mercaptopurine and relatives); Pyrimidine family (Cytarabine, Gemcitabine, 5-Fluorouracil and relatives); Alkylating agents, such as Nitrogen mustards (Cyclophosphamide, Melphalan, Chlorambucil, mechlorethamine, Ifosfamide, and relatives); nitrosoureas (e.g. Carmustine); Triazenes (Dacarbazine, temozolomide); Alkyl sulphonates (e.g. Busulfan); Procarbazine and Aziridines; Antibiotics, such as Hydroxyurea; Anthracyclines (doxorubicin, daunorubicin, epirubicin and other derivatives); Anthracenediones (Mitoxantrone and relatives); Streptomyces family (Bleomycin, Mitomycin C, actinomycin) and Ultraviolet light.

Biological Samples

As inhibitors of ATR kinase, the compounds and compositions of this invention are also useful in biological samples. One aspect of the invention relates to inhibiting ATR kinase activity in a biological sample, which method comprises contacting said biological sample with a compound described herein or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. The term "compounds described herein" includes compounds of formula I.

Inhibition of ATR kinase activity in a biological sample is useful for a variety of purposes that are known to one of skill in the art. Examples of such purposes include, but are not limited to, blood transfusion, organ-transplantation, and biological specimen storage.

Study of Protein Kinases

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of ATR is set forth in the Examples below.

Another aspect of the invention provides a method for modulating enzyme activity by contacting a compound described herein with ATR kinase.

Methods of Treatment

In one aspect, the present invention provides a method for treating or lessening the severity of a disease, condition, or disorder where ATR kinase is implicated in the disease state. In another aspect, the present invention provides a method for treating or lessening the severity of an ATR kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the ATR kinase. Another aspect provides a method for treating or lessening the severity of a kinase disease, condition, or disorder by inhibiting enzymatic activity of ATR kinase with an ATR kinase inhibitor.

One aspect of the invention relates to a method of inhibiting ATR kinase activity in a patient, which method comprises administering to the patient a compound described herein, or a composition comprising said compound. In some embodiments, said method is used to treat or prevent a condition selected from proliferative and hyperproliferative diseases, such as cancer.

Another aspect of this invention provides a method for treating, preventing, or lessening the severity of proliferative or hyperproliferative diseases comprising administering an effective amount of a compound, or a pharmaceutically acceptable composition comprising a compound, to a subject in need thereof. In some embodiments, said subject is a patient. The term "patient", as used herein, means an animal, preferably a human.

In some embodiments, said method is used to treat or prevent cancer. In some embodiments, said method is used to treat or prevent a type of cancer with solid tumors. In yet another embodiment, said cancer is selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from the cancers described herein. In some embodiments, said cancer is lung cancer, head and neck cancer, pancreatic cancer, gastric cancer, or brain cancer.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

One aspect provides a method for inhibiting ATR in a patient comprising administering a compound described herein as described herein. Another embodiment provides a method of treating cancer comprising administering to a patient a compound described herein, wherein the variables are as defined herein.

Some embodiments comprising administering to said patient an additional therapeutic agent selected from a DNA-damaging agent; wherein said additional therapeutic agent is appropriate for the disease being treated; and said additional therapeutic agent is administered together with said compound as a single dosage form or separately from said compound as part of a multiple dosage form.

In some embodiments, said DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonates, an antimetabolite, or an antibiotic. In other embodiments, said DNA-damaging agent is selected from ionizing radiation, a platinating agent, a Topo I inhibitor, a Topo II inhibitor, or an antibiotic.

Examples of Platinating agents include Cisplatin, Oxaliplatin, Carboplatin, Nedaplatin, Satraplatin and other derivatives. Other platinating agents include Lobaplatin, and Triplatin. Other platinating agents include Tetranitrate, Picoplatin, Satraplatin, ProLindac and Aroplatin.

Examples of Topo I inhibitor include Camptothecin, Topotecan, irinotecan/SN38, rubitecan and other derivatives. Other Topo I inhibitors include Belotecan.

Examples of Topo II inhibitors include Etoposide, Daunorubicin, Doxorubicin, Aclarubicin, Epirubicin, Idarubicin, Amrubicin, Pirarubicin, Valrubicin, Zorubicin and Teniposide.

Examples of Antimetabolites include members of the Folic family, Purine family (purine antagonists), or Pyrimidine family (pyrimidine antagonists). Examples of the Folic family include methotrexate, pemetrexed and relatives; examples of the Purine family include Thioguanine, Fludarabine, Cladribine, 6-Mercaptopurine, and relatives;

examples of the Pyrimidine family include Cytarabine, gemcitabine, 5-Fluorouracil (5FU) and relatives.

Some other specific examples of antimetabolites include Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea.

Examples of alkylating agents include Nitrogen mustards, Triazenes, alkyl sulphonates, Procarbazine and Aziridines. Examples of Nitrogen mustards include Cyclophosphamide, Melphalan, Chlorambucil and relatives; examples of nitrosoureas include Carmustine; examples of triazenes include Dacarbazine and temozolomide; examples of alkyl sulphonates include Busulfan.

Other specific examples of alkylating agents include Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

Examples of antibiotics include Mitomycin, Hydroxyurea; Anthracyclines, Anthracenediones, Streptomyces family. Examples of Anthracyclines include doxorubicin, daunorubicin, epirubicin and other derivatives; examples of Anthracenediones include Mitoxantrone and relatives; examples of Streptomyces family include Bleomycin, Mitomycin C, and actinomycin.

In certain embodiments, said platinating agent is Cisplatin or Oxaliplatin; said Topo I inhibitor is Camptothecin; said Topo II inhibitor is Etoposide; and said antibiotic is Mitomycin. In other embodiments, said platinating agent is selected from Cisplatin, Oxaliplatin, Carboplatin, Nedaplatin, or Satraplatin; said Topo I inhibitor is selected from Camptothecin, Topotecan, irinotecan/SN38, rubitecan; said Topo II inhibitor is selected from Etoposide; said antimetabolite is selected from a member of the Folic Family, the Purine Family, or the Pyrimidine Family; said alkylating agent is selected from nitrogen mustards, nitrosoureas, triazenes, alkyl sulfonates, Procarbazine, or aziridines; and said antibiotic is selected from Hydroxyurea, Anthracyclines, Anthracenediones, or Streptomyces family.

Another embodiment provides a method of promoting cell death in cancer cells comprising administering to a patient a compound described herein, or a composition comprising said compound.

Yet another embodiment provides a method of preventing cell repair of DNA damage in cancer cells comprising administering to a patient a compound described herein, or a composition comprising said compound. Yet another embodiment provides a method of preventing cell repair caused by of DNA damage in cancer cells comprising administering to a patient a compound of formula I, or composition comprising said compound.

Another embodiment provides a method of sensitizing cells to DNA damaging agents comprising administering to a patient a compound described herein, or a composition comprising said compound.

In some embodiments, the method is used on a cancer cell having defects in the ATM signaling cascade. In some embodiments, said defect is altered expression or activity of one or more of the following: ATM, p53, CHK2, MRE11, RAD50, NBS1, 53BP1, MDC1 or H2AX. In another embodiment, the cell is a cancer cell expressing DNA damaging oncogenes. In some embodiments, said cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

Yet another embodiment provides use of a compound described herein as a radio-sensitizer or a chemo-sensitizer.

Yet other embodiment provides use of a compound of formula I as a single agent (monotherapy) for treating cancer. In some embodiments, the compounds of formula I are used for treating patients having cancer with a DNA-damage response (DDR) defect. In other embodiments, said defect is a mutation or loss of ATM, p53, CHK2, MRE11, RAD50, NBS1, 53BP1, MDC1, or H2AX.

SCHEMES AND EXAMPLES

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear magnetic resonance). The following generic schemes and examples illustrate how to prepare the compounds of the present disclosure. The examples are for the purpose of illustration only and are not to be construed as limiting the scope of the invention in any way. $^1$H-NMR spectra were recorded at 400 MHz using a Bruker DPX 400 instrument. Mass spec. samples were analyzed on a MicroMass Quattro Micro mass spectrometer operated in single MS mode with electrospray ionization.

Scheme A-1

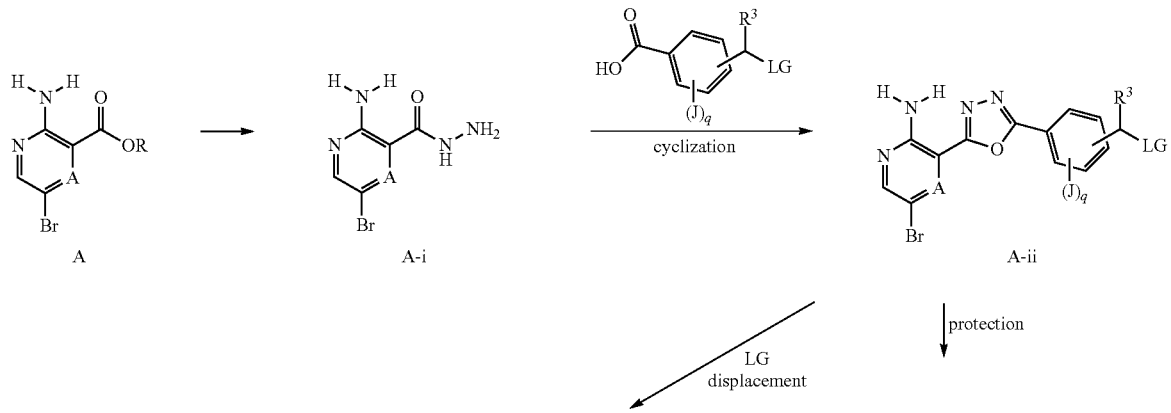

97
-continued
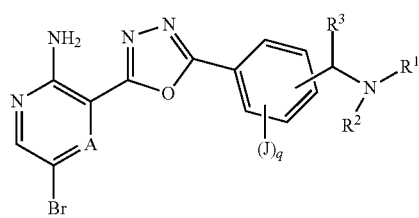
A-iii
↓ protection
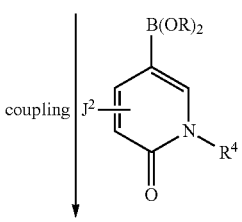
A-iv
↓ coupling (B(OR)₂ / J² / N-R⁴ / =O)
A-v
98
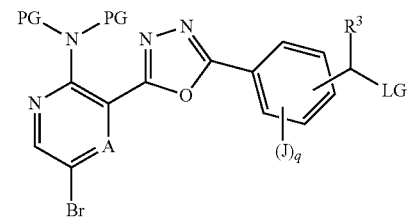
A-vi
↓ coupling (B(OR)₂ / J² / N-R⁴ / =O)
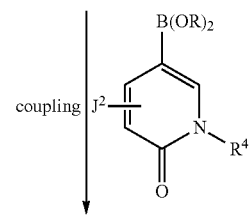
A-vii
↙ LG displacement     ↓ deprotection
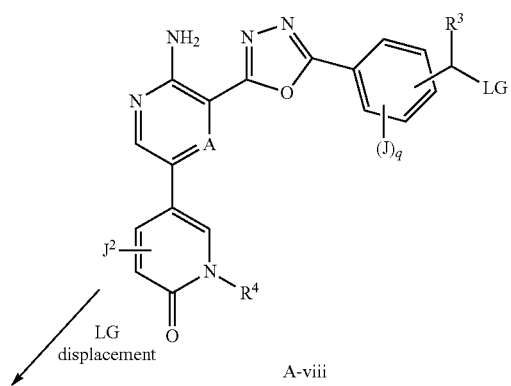
A-viii
↙ LG displacement

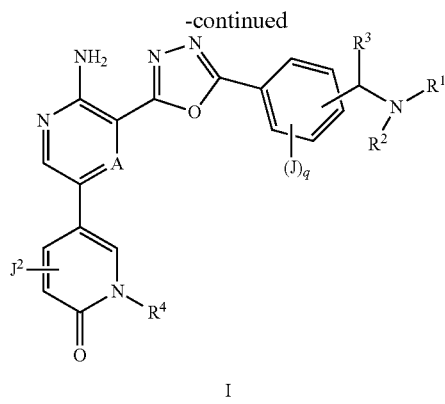

I

Scheme A-1 depicts a general method for making compounds of Formula I in which Ring D is oxadiazole. Compound A, preferably the methyl ester, is reacted with hydrazine to form the acyl hydrazide A-i. From compounds of Formula A-i and an appropriately substituted benzoic acid, the corresponding 1,3,4-oxadiazole A-ii can be obtained using reagents such as, but not limited to, $PPh_3Br_2$ and a base. Alternatively, compounds of Formula A-ii can be obtained from the step-wise condensation of the acyl hydrazide A-i with the appropriate acid, followed by cyclo-dehydration using but not limited to reagents such as $PPh_3Br_2$, $POCl_3$, or T3P®. The leaving group LG of compound A-ii consists of a group which may be displaced by an amine of formula $NHR^1R^2$ resulting in compounds of Formula A-iii, and includes but is not limited to chlorine and bromine. Compounds of Formula A-iii are then protected with a suitable amine protecting group PG such as, but not limited to BOC (ᵗButyl Carbamate), to give compounds of Formula A-iv (if $R^2$=H in A-iii, then $R^2$ is protected as PG).

The pyridone ring system is introduced under metal-mediated coupling conditions, including but not limited to Suzuki coupling with an appropriate boronic ester or boronic acid to provide compounds of Formula A-v. Removal of the nitrogen protecting groups PG from compounds of Formula A-v takes place under standard conditions known to those skilled in the art such as, but not limited to, treatment with HCl or TFA to provide compounds of Formula I in which Ring D is oxadiazole. Protection, coupling, leaving group displacement, and deprotection reactions for the generation of compounds of Formula A-vi through A-viii are analogous to those described above. In addition, substituents $R^4$ on Formula I can undergo further functionalization by reactions known to those skilled in the art such as, but not limited to hydrolysis, nucleophilic displacement reactions, acylation reactions, amide bond formation reactions, or further deprotection to reveal additional functionality.

Scheme A-2

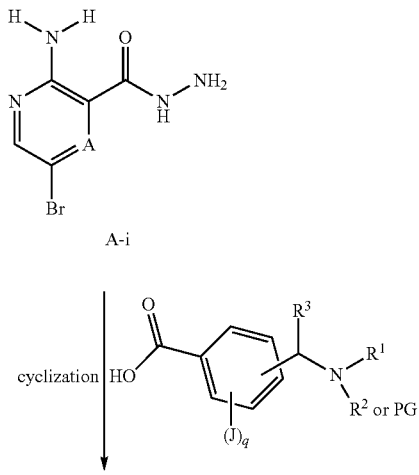

101

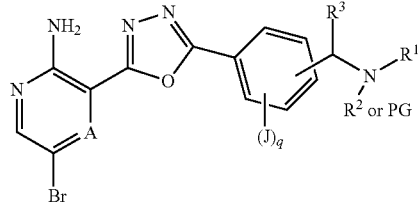

A-iii

102

-continued

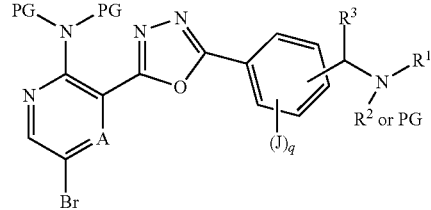

A-iv

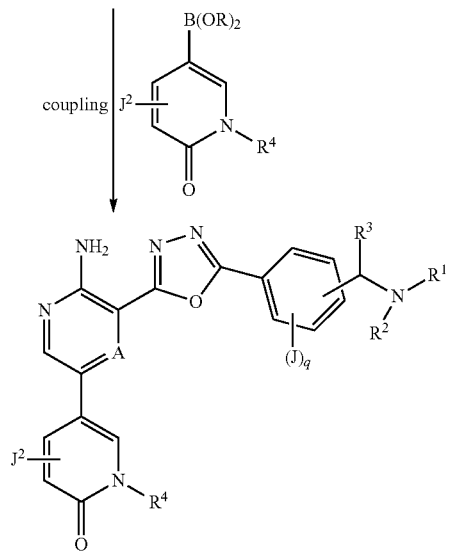

I

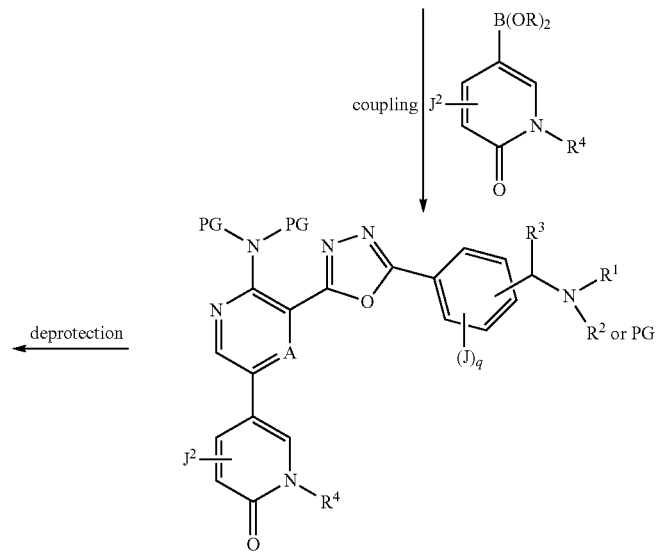

A-v

Scheme A-2 depicts a general method for making compounds of Formula I which Ring D is oxadiazole. From compounds of formula A-i and the appropriate benzoic acid substituted by an amine of formula —NR$^1$R$^2$ (protected as PG if R$^2$=H), the corresponding 1,3,4-oxadiazole A-iii can be obtained using reagents such as, but not limited to, PPh$_3$Br$_2$ and a base. Alternatively, compounds of Formula A-iii can be obtained from the step-wise condensation of the acyl hydrazide A-i with the substituted benzoic acid, followed by cyclodehydration using but not limited to reagents such as PPh$_3$Br$_2$, POCl$_3$, or T3P®. Compounds of Formula A-iii may be protected with a suitable amine protecting group PG such as, but not limited to BOC (Butyl Carbamate), to give compounds of Formula A-iv. The pyridone ring system is introduced under metal-mediated coupling conditions, including but not limited to Suzuki coupling of A-iv with an appropriate boronic ester or boronic acid to provide compounds of Formula A-v. Removal of the nitrogen protecting groups PG from compounds of Formula A-v takes place under standard conditions known to those skilled in the art such as, but not limited to, treatment with HCl or TFA to provide compounds of Formula I in which Ring D is oxadiazole. Alternatively, compounds of Formula I in which Ring D is oxadiazole may be accessed directly from A-iii utilizing the metal-mediated coupling conditions described above. In addition, substituents R$^4$ on Formula I can undergo further functionalization by reactions known to those skilled in the art such as, but not limited to, hydrolysis, nucleophilic displacement reactions, acylation reactions, amide bond formation reactions, or further deprotection to reveal additional functionality. Preparations 1-7 relate to Scheme A1 and A2.

Preparation 1

Synthesis of 5-bromo-3-(5-(4-(bromomethyl)phenyl)-1,3,4-oxadiazol-2-yl)pyrazin-2-amine

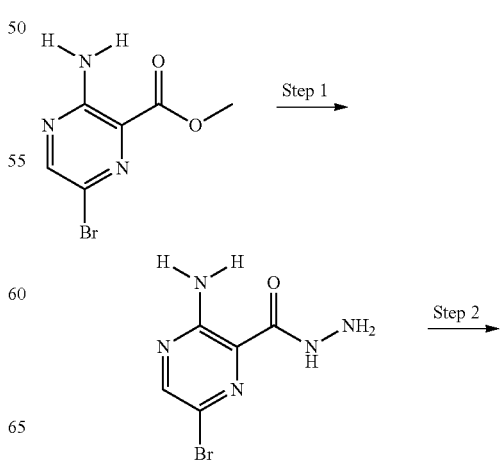

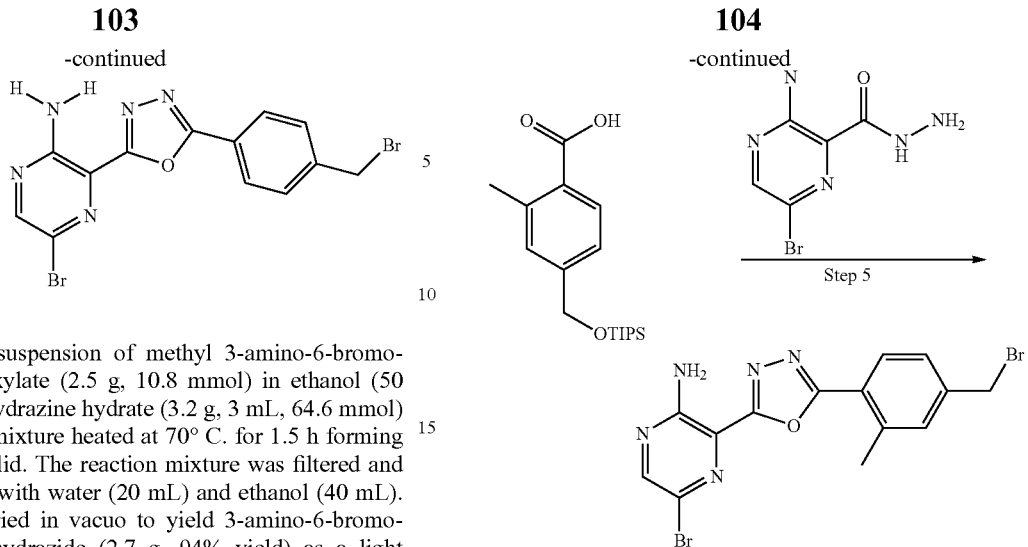

Step 1: To a suspension of methyl 3-amino-6-bromo-pyrazine-2-carboxylate (2.5 g, 10.8 mmol) in ethanol (50 mL) was added hydrazine hydrate (3.2 g, 3 mL, 64.6 mmol) and the reaction mixture heated at 70° C. for 1.5 h forming a thick yellow solid. The reaction mixture was filtered and the solid washed with water (20 mL) and ethanol (40 mL). The solid was dried in vacuo to yield 3-amino-6-bromo-pyrazine-2-carbohydrazide (2.7 g, 94% yield) as a light yellow solid. LC/MS m/z 233.1 [M+H]$^+$. $^1$H NMR (400 MHz, DMSO-d$_6$) δ 9.78 (s, 1H), 8.31 (s, 1H), 7.62 (s, 2H), 4.53 (d, J=3.5 Hz, 2H).

Step 2: Dibromo(triphenyl)phosphorane (1.746 g, 4.137 mmol) was added to a suspension of 3-amino-6-bromo-pyrazine-2-carbohydrazide (200 mg, 0.862 mmol) and 4-(bromomethyl)benzoic acid (185 mg, 0.862 mmol) in acetonitrile (4 mL) at room temperature and the resulting suspension stirred for 1 h. The reaction mixture was diluted with acetonitrile (2 mL), treated dropwise with DIEA (900 μL, 5.171 mmol) and stirred for 16 h. The suspension was filtered, washed with acetonitrile and hexane, and dried to provide 5-bromo-3-(5-(4-(bromomethyl)phenyl)-1,3,4-oxadiazol-2-yl)pyrazin-2-amine (354 mg, 68% yield) as a yellow solid. LC/MS m/z 412.1 [M+H]$^+$. $^1$H NMR (400 MHz, DMSO-d6) δ 8.45 (s, 1H), 8.11 (d, J=8.1 Hz, 2H), 7.80 (s, 2H), 7.72 (d, J=8.2 Hz, 2H), 4.82 (s, 2H).

Preparation 2

Synthesis of 5-bromo-3-(5-(4-(bromomethyl)-2-methylphenyl)-1,3,4-oxadiazol-2-yl)pyrazin-2-amine

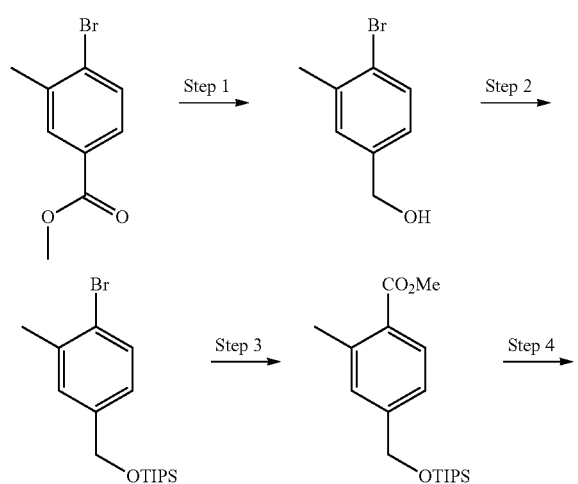

Step 1: To a solution of methyl 4-bromo-3-methylbenzoate (50 g, 219 mmol) in THF (500 mL) at 0° C. was added lithium aluminum hydride (262 mL of 1 M solution in THF, 262 mmol) over 15 min. After stirring for 20 min, water (50 mL) was added dropwise, followed by 1 M NaOH (50 mL), and water (50 mL). The reaction mixture was filtered through Celite and concentrated in vacuo. The resulting residue was azeotroped once with toluene, then dissolved in DCM, dried over Na$_2$SO$_4$, filtered and the solvent removed in vacuo to provide (4-bromo-3-methylphenyl)methanol as a colorless solid (42 g, 96% yield).
$^1$H NMR (400 MHz, DMSO-d$_6$) δ 7.51 (d, J=8.1 Hz, 1H), 7.29 (s, 1H), 7.07 (d, J=8.1 Hz, 1H), 5.23 (t, J=5.7 Hz, 1H), 4.44 (d, J=5.7 Hz, 2H), 2.33 (s, 3H).

Step 2: A solution of (4-bromo-3-methylphenyl)methanol (5.0 g, 24.87 mmol) and imidazole (5.1 g, 74.61 mmol) in THF (50 mL) was cooled to 0° C. and treated with chloro(triisopropyl)silane (7. 2 g, 7.9 mL, 37.30 mmol), then allowed to warm to room temperature and stirred for 16 h. The reaction mixture was diluted with water and DCM. The organic layer was washed with brine, dried over Na$_2$SO$_4$, filtered, and concentrated in vacuo to yield (4-bromo-3-methylbenzyloxy)triisopropylsilane as a colorless oil, (8.8 g, 97% yield). $^1$H NMR (400 MHz, CDCl$_3$) δ 7.47 (d, J=8.2 Hz, 1H), 7.21 (s, 1H), 7.04 (d, J=8.1. Hz, 1H), 4.75 (s, 2H), 2.39 (s, 3H), 1.22-1.14 (m, 3H), 1.09 (d, J=6.5 Hz, 18H).

Step 3: A solution of (4-bromo-3-methylbenzyloxy)triisopropylsilane (6.8 g, 19.03 mmol), Pd(OAc)$_2$ (427 mg, 1.90 mmol), 3-diphenylphosphanylpropyl(diphenyl)phosphane (785 mg, 1.90 mmol), and triethylamine (8.5 mL, 60.90 mmol) in DMF (38 mL) and MeOH (23 mL) was treated with CO gas at 40 psi and heated at 80° C. for 14 h. The reaction mixture was cooled to room temperature and depressurized. The reaction was concentrated and partitioned between ethyl acetate and water. The organic layer was washed with brine, dried over Na$_2$SO$_4$, filtered and concentrated in vacuo. The residue was purified by silica gel column chromatography (0-50% ethyl acetate/hexanes) to provide methyl 2-methyl-4-((triisopropylsilyloxy)methyl)benzoate as a colorless oil (6.0 g, 94% yield). $^1$H NMR (400 MHz, CDCl$_3$) δ 7.90 (d, J=7.9 Hz, 1H), 7.23 (d, J=9.0 Hz, 2H), 4.84 (s, 2H), 3.88 (s, 3H), 2.60 (s, 3H), 1.22-1.12 (m, 3H), 1.09 (d, J=6.6 Hz, 18H).

Step 4: Methyl 2-methyl-4-(triisopropylsilyloxymethyl)benzoate (6.0 g, 17.83 mmol) in THF (35 mL) was treated with lithium hydroxide (2.6 g, 107.0 mmol) in water (18 mL) followed by MeOH (18 mL) and the reaction mixture was heated to 60° C. for 2 h. The solvent was removed in vacuo, and the resulting residue was diluted with ethyl acetate and quenched with 1N HCl to pH 2. The resulting layers were separated and the organic phase was washed with brine and dried over Na$_2$SO$_4$. The solvent was removed in vacuo to yield 2-methyl-4-(triisopropylsilyloxymethyl) benzoic acid as a colorless solid (5.4 g, 94% yield). LC/MS m/z 321.5 [M]−. $^1$H NMR (400 MHz, DMSO-d$_6$) δ 12.70 (s, 1H), 7.82 (d, J=8.1 Hz, 1H), 7.25 (m, 2H), 4.82 (s, 2H), 2.52 (s, 3H), 1.22-1.11 (m, 3H), 1.05 (d, J=7.0 Hz. 18H).

Step 5: Dibromo(triphenyl)phosphorane (25.0 g, 56.9 mmol) was added to a suspension of 3-amino-6-bromo-pyrazine-2-carbohydrazide (3.0 g, 12.9 mmol) and 2-methyl-4-(triisopropylsilyloxymethyl)benzoic acid (4.2 g, 12.9 mmol) in anhydrous acetonitrile (100 mL). The reaction mixture was stirred for 2 h at room temperature and then cooled to 0° C. DIEA (10.0 g, 14 mL, 77.6 mmol) was added dropwise and the reaction stirred for 1.5 h. Water (50 mL) was added dropwise to the stirring solution and the resulting suspension stirred for 20 min. The precipitate was collected by filtration and the solid was washed with a 10% aqueous acetonitrile until the dark color disappeared. The solid was then dried to yield 5-bromo-3-(5-(4-(bromomethyl)-2-methylphenyl)-1,3,4-oxadiazol-2-yl)pyrazin-2-amine as a yellow solid (3.4 g, 62% yield). $^1$H NMR (400 MHz, DMSO-d$_6$) δ 8.45 (s, 1H), 8.00 (d, J=8.0 Hz, 1H), 7.91 (d, J=67.6 Hz, 2H), 7.69-7.45 (m, 2H), 4.77 (s, 2H), 2.70 (s, 3H).

Preparation 3

Synthesis of 5-bromo-3-(5-(4-(bromomethyl)-2-fluorophenyl)-1,3,4-oxadiazol-2-yl)pyrazin-2-amine

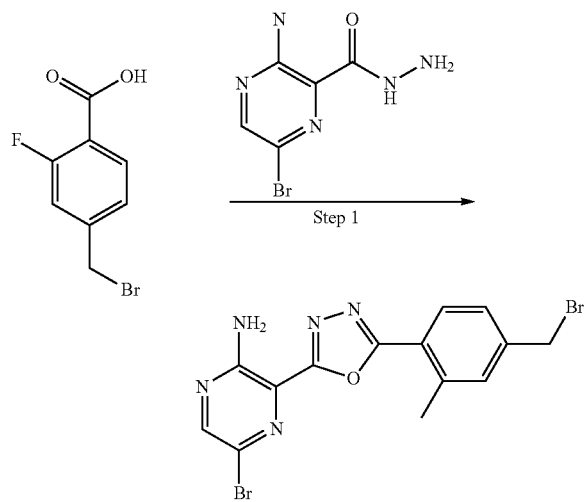

Step 1: 4-(Bromomethyl)-2-fluorobenzoic acid was prepared as described in the *Journal of Fluorine Chemistry*, 2002, 116, 173-179. Dibromo(triphenyl)phosphorane (18.40 g, 43.60 mmol) was added to a suspension of 4-(bromomethyl)-2-fluorobenzoic acid (2.54 g, 10.90 mmol) and 3-amino-6-bromo-pyrazine-2-carbohydrazide (2.53 g, 10.90 mmol) in acetonitrile (75 mL). The reaction mixture was stirred for 30 min at room temperature, then cooled to 0° C. and treated with DIEA (11.0 mL, 65.4 mmol). The reaction mixture was then stirred at room temperature for 3 h and filtered. The resulting solid was washed with 20% water/ CH$_3$CN and dried to give 5-bromo-3-(5-(4-(bromomethyl)-2-fluorophenyl)-1,3,4-oxadiazol-2-yl)pyrazin-2-amine as a yellow solid (1.69 g, 36% yield). LC/MS m/z 429.8 [M+H]$^+$.

Preparation 4

Synthesis of 5-bromo-3-(5-(4-(bromomethyl)-2-methoxyphenyl)-1,3,4-oxadiazol-2-yl)pyrazin-2-amine

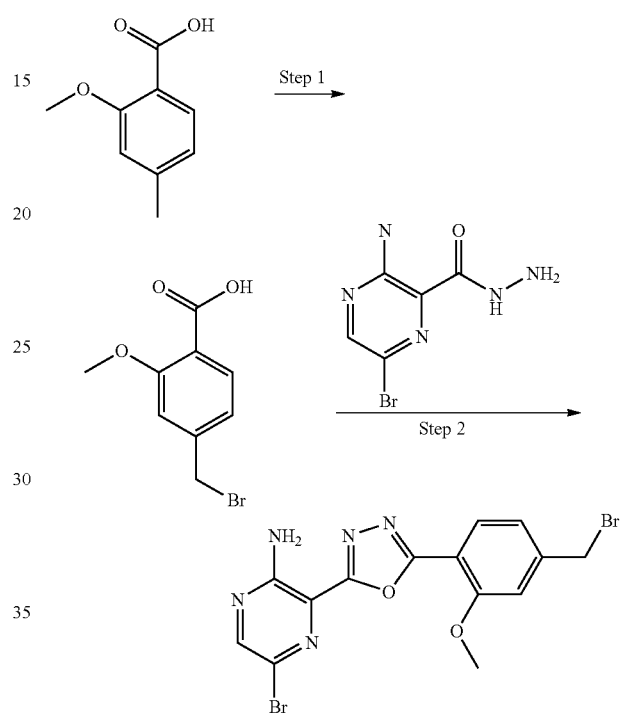

Step 1: 2-Methoxy-4-methylbenzoic acid (8.0 g, 48.1 mmol) in CCl$_4$ (80 mL) was treated with N-bromosuccinimide (9.1 g, 51.0 mmol) followed by AIBN (791 mg, 4.81 mmol) and heated at reflux for 3 h. The reaction mixture was allowed to cool to room temperature. The resulting precipitate was removed by filtration and washed with water to remove the excess succinamide and unreacted starting material. The solid was then washed with acetonitrile, dissolved in DCM, dried over Na$_2$SO$_4$, filtered and concentrated in vacuo to provide 4-(bromomethyl)-2-methoxybenzoic acid (5.15 g, 44% yield) as a white solid. $^1$H NMR (400 MHz, CDCl$_3$) δ 10.57 (s, 1H), 8.16 (d, J=8.1 Hz, 1H), 7.16 (d, J=8.1 Hz, 1 Hz), 7.10 (s, 1 H), 4.48 (s, 2H), 4.11 (s, 3H).

Step 2: Dibromo(triphenyl)phosphorane (19.17 g, 43.61 mmol) was added to a suspension of 3-amino-6-bromo-pyrazine-2-carbohydrazide (2.3 g, 9.91 mmol) and 4-(bromomethyl)-2-methoxybenzoic acid (2.43 g, 9.91 mmol) in acetonitrile (70 mL). The reaction mixture was stirred at room temperature for 2 h and then cooled in an ice water bath upon which DIEA (7.69 g, 10.4 mL, 59.47 mmol) was added dropwise. The ice water bath was removed after the addition of DIEA and the reaction mixture was stirred overnight. Water (20 mL) was added dropwise to the stirring solution and was allowed to stir for an additional 20 min after the water addition. The resulting precipitate was filtered and then washed with a 1:1 water/acetonitrile mixture until the dark color disappeared. The solid was then washed with water and hexane and dried to yield 5-bromo-3-[5-[4-(bromomethyl)-2- methoxy-phenyl]-1,3,4-oxadiazol-2-yl]

pyrazin-2-amine (1.88 g, 43% yield) as a mustard yellow solid. $^1$H NMR (400 MHz, DMSO-$d_6$) δ 8.44 (s, 1H), 7.92 (d, J=8.0 Hz, 1H), 7.42 (s, 1H), 7.27 (d, J=7.9 Hz, 1H), 4.79 (s, 2H), 3.95 (s, 3H).

Preparation 5

Synthesis of 5-bromo-3-(5-(3-(bromomethyl)phenyl)-1,3,4-oxadiazol-2-yl)pyrazin-2-amine

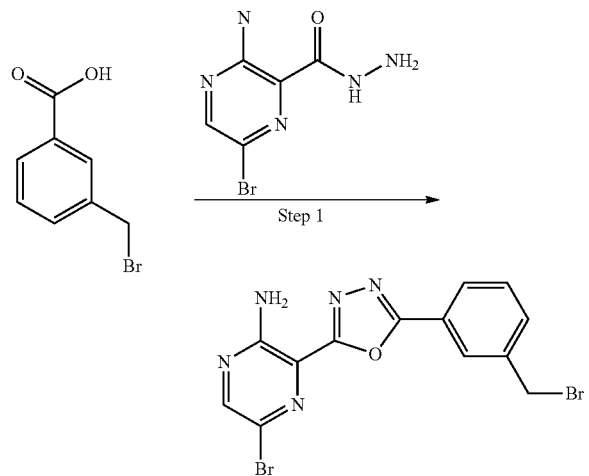

Step 1: Dibromo(triphenyl)phosphorane (9.0 g, 20.46 mmol) was added to a suspension of 3-(bromomethyl)benzoic acid (1.0 g, 4.65 mmol) in anhydrous acetonitrile (31 mL). The reaction mixture was stirred for 1 h at room temperature and then cooled at 0° C. upon which DIEA (8.0 mL, 45.9 mmol) was added dropwise. The reaction mixture was allowed to warm to room temperature and was stirred for 1 h. Water (50 mL) was added dropwise to the stirring solution and was allowed to stir for an additional 20 min. The reaction mixture was filtered and the resulting solid was washed with a 10% water/acetonitrile mixture until the dark color disappeared. The solid was dried to yield 5-bromo-3-(5-(3-(bromomethyl)phenyl)-1,3,4-oxadiazol-2-yl)pyrazin-2-amine as a yellow solid (1.9 g, 99% yield). $^1$NMR (400 MHz, DMSO-$d_6$) δ 8.46 (s, 1H), 8.20 (s, 1H), 8.07 (d, J=7.6 Hz, 1H), 7.76 (d, J=7.7 Hz, 1H), 7.64 (dd, J=19.0, 11.0 Hz, 1H), 4.90 (s, 2H).

Preparation 6

(R)-4-(1-(tert-butoxycarbonylamino)ethyl)benzoic acid was prepare as described in the *Journal of Ocular Pharmacology and Therapeutics*, 2009, 25, 187-194

Preparation 7

3-(1-(tert-butoxycarbonylamino)ethyl)benzoic acid was prepared as described in WO2009/036996.

Scheme B

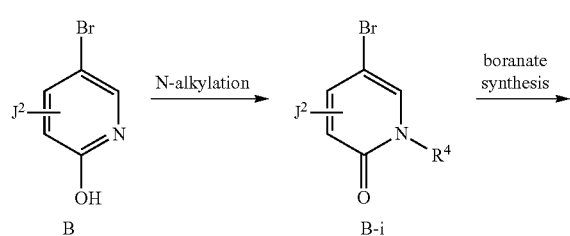

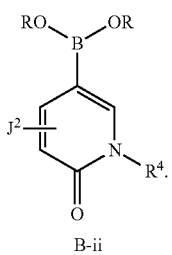

Scheme B depicts a general method for the preparation of intermediates of Formula B-ii. Compound B is reacted with an alcohol R$^4$OH under Mitsunobu conditions to give rise to compounds of the Formula B-i. Suitable Mitsunobu conditions include but are not limited to Bu$_3$P/DEAD in an appropriate solvent such as CHCl$_3$ or THF.

Alternatively, compounds of formula B-i may be obtained from B using alkylation conditions known to those skilled in the art such as, but not limited to, treatment of B with R$^4$-LG and base, wherein LG is an appropriate leaving group such as halogen, mesylate, or triflate. Compounds of Formula B-i are converted to the corresponding boronic acid or ester B-ii utilizing standard conditions known to those skilled in the art such as, but not limited to, treatment with bis(pinacolato)diboron, Pd-catalyst, and base.

Preparation 8

Synthesis of 1-(1-cyclopropylethyl)-5-(4,4,5,5-tetramethyl-1,3,2-dioxaborolan-2-yl)pyridin-2(1H)-one

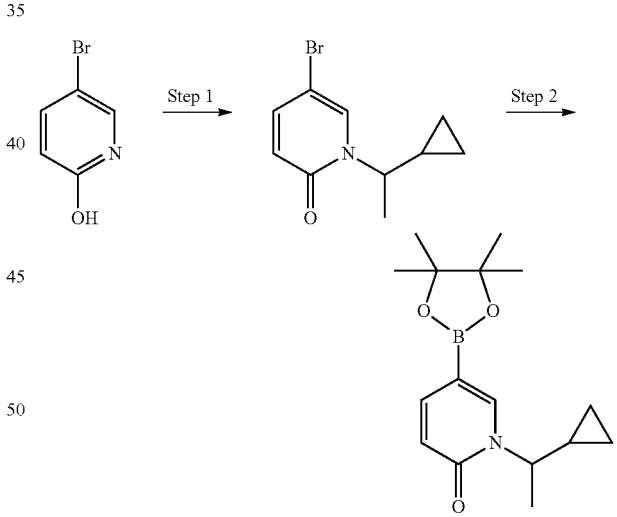

Step 1: To a solution of 2-hydroxy-5-bromopyridine (6.0 g, 34.5 mmol) in THF (60 mL) at 0° C. was added a solution of DEAD (30 mL of 40% w/v, 68.96 mmol) in THF (50 mL) over 20 min. The resulting mixture was then treated dropwise with tributylphosphine (14.0 g, 17 mL, 68.7 mmol) over 10 min. The reaction mixture was stirred for 30 min at 0° C. and then treated with 1-cyclopropylethanol (4.5 g, 51.7 mmol) and stirred at room temperature for 16 h. The reaction mixture was poured onto ice and quenched with HCl. The layers were separated and the organic layer was washed with 1 M HCl and brine. The organic layer was dried over MgSO$_4$, filtered and concentrated in vacuo. Silica gel chromatography (0-60% ethyl acetate/hexanes) provided 5-bromo-1-(1-cyclopropylethyl)pyridin-2-one (2.0 g, 24% yield). $^1$H NMR (400 MHz, CDCl$_3$) δ 7.61 (d, J=2.6 Hz, 1H), 7.33 (dd, J=9.6, 2.7 Hz, 1H), 6.50 (d, J=9.6 Hz, 1H), 4.38-4.26 (m, 1H), 1.40 (d, J=6.7 Hz, 3H), 1.10-0.99 (m, 1H), 0.80-0.68 (m, 1H), 0.59-0.42 (m, 2H), 0.38-0.26 (m, 1H).

Step 2: 5-Bromo-1-(1-cyclopropylethyl)pyridin-2-one (3.5 g, 14.5 mmol), 4,4,5,5-tetramethyl-2-(4,4,5,5-tetramethyl-1,3,2-dioxaborolan-2-yl)-1,3,2-dioxaborolane (5.5 g, 21.7 mmol), Pd(dppf)Cl$_2$ (1.1 g, 1.5 mmol) and potassium acetate (4.3 g, 43.4 mmol) were dissolved in dioxane (37 mL) and heated at 90° C. for 2 h. The reaction mixture was filtered through Celite and washed with dichloromethane. The filtrate was concentrated in vacuo, and purification by silica gel chromatography (0-60% ethyl acetate/hexanes) provided 1-(1-cyclopropylethyl)-5-(4,4,5,5-tetramethyl-1,3,2-dioxaborolan-2-yl)pyridin-2(1H)-one (1.9 g, 45% yield). LC/MS m/z 290.3 [M+H]$^+$.

The following boron pinacol esters were prepared using procedures analogous to that described above:
1-sec-butyl-5-(4,4,5,5-tetramethyl-1,3,2-dioxaborolan-2-yl)pyridin-2(1H)-one. LC/MS m/z 278.1 [M+H]$^+$.
1-(1-methoxypropan-2-yl)-5-(4,4,5,5-tetramethyl-1,3,2-dioxaborolan-2-yl)pyridin-2(1H)-one.
LC/MS m/z 294.5 [M+H]$^+$.

Preparation 9

Synthesis of 1-isopropyl-5-(4,4,5,5-tetramethyl-1,3,2-dioxaborolan-2-yl)pyridin-2(1H)-one

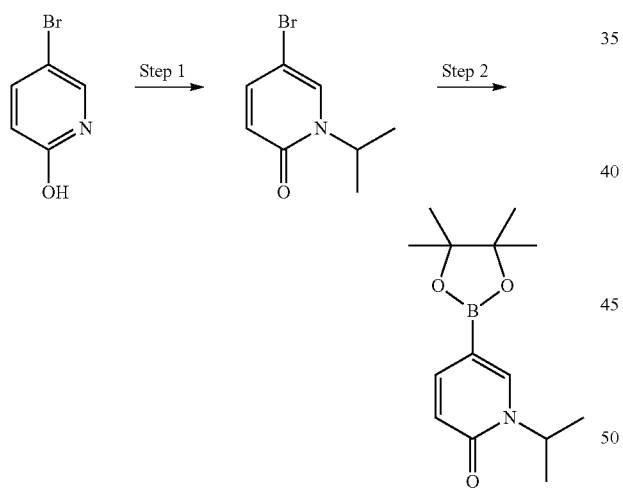

Step 1: Potassium tert-butoxide (16.8 g, 142.2 mmol) was added to a suspension of 5-bromo-1H-pyridin-2-one (25.0 g, 142.2 mmol) in DME (248 mL) and the reaction mixture was stirred for 30 min. To the mixture were added potassium carbonate (13.8 g, 99.5 mmol) and 2-bromopropane (35.0 g, 26.7 mL, 284.4 mmol) and the mixture refluxed for 65 h. The reaction mixture was filtered and concentrated in vacuo. The resulting solid was recrystallized from dichloromethane/hexane to provide 5-bromo-1-isopropyl-pyridin-2-one (19.1 g, 88.40 mmol, 62% yield) as off-white crystals. LC/MS m/z 217.3 [M+H]$^+$. $^1$H NMR (400 MHz, CDCl$_3$) δ 7.41 (d, J=2.7 Hz, 1H), 7.31 (dd, J=9.7, 2.7 Hz, 1H), 6.49 (d, J=9.6 Hz, 1H), 5.22 (dt, J=13.6, 6.8 Hz, 1H), 1.36 (d, J=6.8 Hz, 6H).

Step 2: 5-Bromo-1-isopropyl-pyridin-2-one (9.0 g, 41.7 mmol), bis(dipinacolato)diboron (15.9 g, 62.5 mmol), potassium acetate (10.2 g, 104.2 mmol) and Pd(dppf)Cl$_2$ (915 mg, 1.25 mmol) were suspended in dioxane (30 mL). The reaction mixture was degassed then heated at 100° C. under an atmosphere of nitrogen for 16 h. The reaction mixture was diluted with ethyl acetate, washed with water and brine, dried over anhydrous Na$_2$SO$_4$, filtered, and concentrated in vacuo. Silica gel chromatography (5-60% ethyl acetate/dichloromethane) provided 1-isopropyl-5-(4,4,5,5-tetramethyl-1,3,2-dioxaborolan-2-yl)pyridin-2(1H)-one (7.9 g, 72% yield). LC/MS m/z 264.3 [M+H]$^+$. $^1$H NMR (400 MHz, CDCl$_3$) δ 7.78 (s, 1H), 7.56 (dd, J=9.0, 1.7 Hz, 1H), 6.52 (d, J=9.1 Hz, 1H), 5.26(hept, J=6.9 Hz, 1H), 1.39 (d, J=6.9 Hz, 6H), 1.31 (s, 12H).

The following boron pinacol esters were prepared from corresponding R—X (X=halide or other leaving group) using procedures analogous to that described above:
1-methyl-5-(4,4,5,5-tetramethyl-1,3,2-dioxaborolan-2-yl)pyridin-2(1H)-one. LC/MS m/z 236.2 [M+H]$^+$.
1-isobutyl-5-(4,4,5,5-tetramethyl-1,3,2-dioxaborolan-2-yl)pyridin-2(1H)-one. LC/MS m/z 278.1 [M+H]$^+$.
2-(2-oxo-5-(4,4,5,5-tetramethyl-1,3,2-dioxaborolan-2-yl)pyridin-1(2H)-yl)acetonitrile. LC/MS m/z 261.2 [M+H]$^+$.
1-ethyl-5-(4,4,5,5-tetramethyl-1,3,2-dioxaborolan-2-yl)pyridin-2(1H)-one. LC/MS m/z 250.1 [M+H]$^+$.
1-(2-methoxyethyl)-5-(4,4,5,5-tetramethyl-1,3,2-dioxaborolan-2-yl)pyridin-2(1H)-one. LC/MS m/z 280.4 [M+H]$^+$.
1-(tetrahydrofuran-3-yl)-5-(4,4,5,5-tetramethyl-1,3,2-dioxaborolan-2-yl)pyridin-2(1H)-one. LC/MS m/z 292.2 [M+H]$^+$.
5-(4,4,5,5-tetramethyl-1,3,2-dioxaborolan-2-yl)-1-(1,1,1-trifluoropropan-2-yl)pyridin-2(1H)-one. LC/MS m/z 318.3 [M+H]$^+$.
2-(2-oxo-5-(4,4,5,5-tetramethyl-1,3,2-dioxaborolan-2-yl)pyridin-1(2H)-yl)propanenitrile. LC/MS m/z 275.3 [M+H]$^+$.
1-(2-hydroxyethyl)-5-(4,4,5,5-tetramethyl-1,3,2-dioxaborolan-2-yl)pyridin-2(1H)-one. LC/MS m/z 266.0 [M+H]$^+$.

Preparation 10

Synthesis of 1-(1-fluoropropan-2-yl)-5-(4,4,5,5-tetramethyl-1,3,2-dioxaborolan-2-yl)pyridin-2(1H)-one

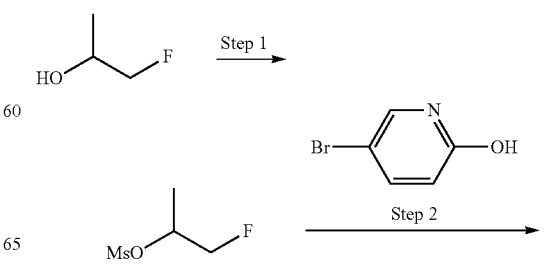

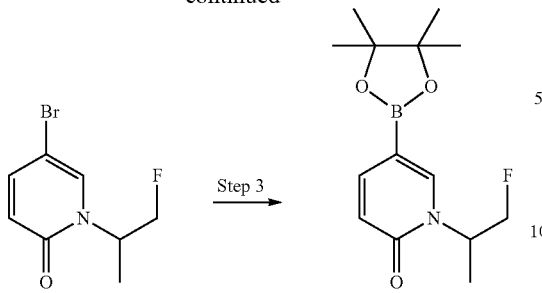

Step 1: 1-Fluoropropan-2-ol (1.2 g, 15.4 mmol) and DMAP (188 mg, 1.54 mmol) in DCM (30 mL) were cooled to 0° C. and treated with TEA (1.7 g, 2.4 mL, 16.9 mmol) followed by MsCl (1.8 g; 1.3 mL, 16.1 mmol). The reaction mixture was warmed gradually to room temperature and stirred for 1 h. The reaction mixture was then washed with saturated NH$_4$Cl solution and brine and dried over Na$_2$SO$_4$. The solvent was removed in vacuo to provide (2-fluoro-1-methyl-ethyl) methanesulfonate which was carried immediately into the next step.

Step 2: 5-Bromo-1H-pyridin-2-one (2.7 g, 15.4 mmol) in DME (30 mL) was treated with KO$^t$Bu (1.7 g, 15.4 mmol) and the reaction was stirred for 30 min. The reaction was then treated with K$_2$CO$_3$ (1.5 g, 10.7 mmol) and a solution of (2-fluoro-1-methyl-ethyl)methanesulfonate (2.4 g, 15.4 mmol) in DME (10 mL). The reaction was stirred at room temperature for 20 min, and then heated at reflux for 16 h. The reaction was cooled, diluted with ethyl acetate and washed with saturated NH$_4$Cl solution, water, and brine. The solvent was removed in vacuo and the residue was purified by silica gel column chromatography (0-90% ethyl acetate/hexanes) to provide 5-bromo-1-(2-fluoro-1-methyl-ethyl)pyridin-2-one as a colorless solid (1.2 g, 33% yield). LC/MS m/z 235.1 [M+H]$^+$. $^1$H NMR (400 MHz, CDCl$_3$) δ 7.52 (d, J=2.5 Hz, 1H), 7.36 (dd, J=9.7, 2.5 Hz, 1H), 6.51 (d, J=9.6 Hz, 1H), 5.38-5.14 (m, 1H), 4.67 (d, J=3.2 Hz, 1H), 4.55 (d, J=3.2 Hz, 1H), 1.51 (d, J=7.2 Hz, 3H).

Step 3: 5-Bromo-1-(2-fluoro-1-methyl-ethyl)pyridin-2-one (550 mg, 2.35 mmol), potassium acetate (692 mg, 7.05 mmol), 4,4,5,5-tetramethyl-2-(4,4,5,5-tetramethyl-1,3,2-dioxaborolan-2-yl)-1,3,2-dioxaborolane (895 mg, 3.53 mmol), and Pd(dppf)Cl$_2$ (172 mg, 0.24 mmol) were combined in dioxane (12 mL) and heated to 90° C. for 2.5 h. The reaction mixture was cooled to room temperature and filtered. The solvent was removed in vacuo and the residue was purified by silica gel column chromatography (0-80% ethyl acetate/hexanes) to provide 1-(1-fluoropropan-2-yl)-5-(4,4,5,5-tetramethyl-1,3,2-dioxaborolan-2-yl)pyridin-2(1H)-one (455 mg, 69% yield). LC/MS m/z 235.1 [M+H]$^+$.

The following boron pinacol esters were prepared from corresponding R$^4$—OMs using procedures analogous to that described above:

5-(4,4,5,5-tetramethyl-1,3,2-dioxaborolan-2-yl)-1-(1,1,1-trifluoropropan-2-yl)pyridin-2(1H)-one. LC/MS m/z 318.3 [M+H]$^+$.

1-(pent-3-yn-2-yl)-5-(4,4,5,5-tetramethyl-1,3,2-dioxaborolan-2-yl)pyridin-2(1H)-one LC/MS m/z 288.5 [M+H]$^+$.

Preparation 11

Synthesis of 5-(4,4,5,5-tetramethyl-1,3,2-dioxaborolan-2-yl)-1-(1-(triisopropylsilyloxy)propan-2-yl)pyridin-2(1H)-one

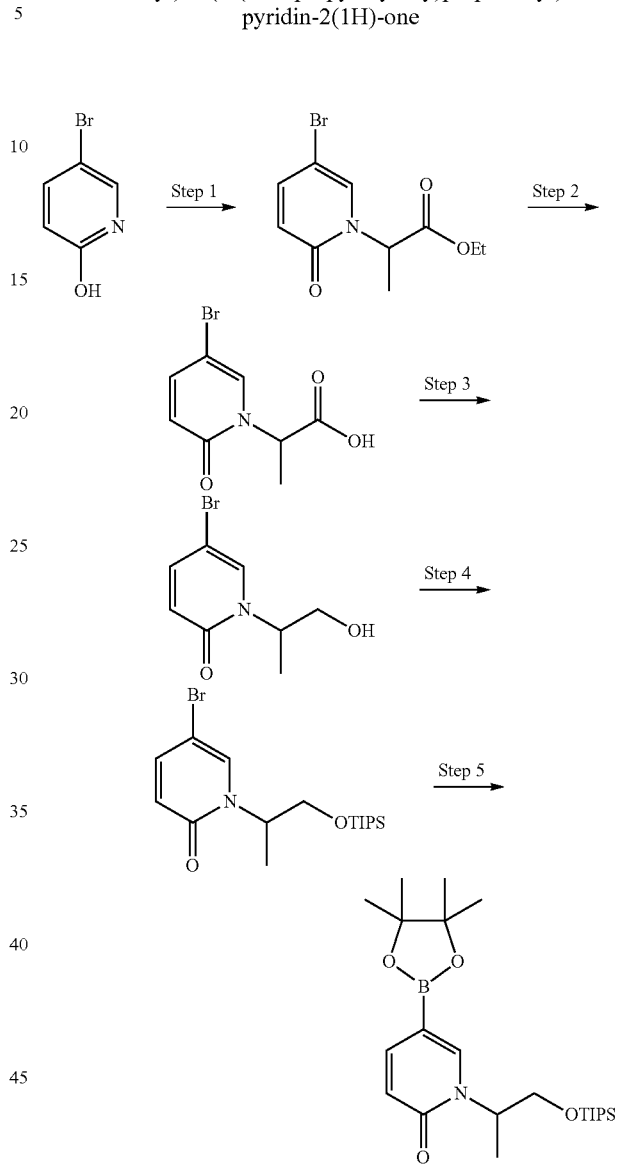

Step 1: Ethyl 2-bromopropanoate (5.0 mL, 38.4 mmol) was dissolved in acetone (60 mL) and sodium iodide (12.67 g, 84.54 mmol) was added. The mixture was stirred for 2 h and the solvents removed under reduced pressure. In a separate flask 5-bromo-1H-pyridin-2-one (3.34 g, 19.21 mmol) was suspended in DME (40 mL) and KO$^t$Bu (2.16 g, 19.21 mmol) added, followed by stirring for 15 min. K$_2$CO$_3$ (1.86 g, 13.45 mmol) and the prepared ethyl 2-iodopropanoate were then added and the mixture heated to 85° C. for 1 h. The reaction was poured into water and extracted with ethyl acetate. The combined organic fractions were dried over Na$_2$SO$_4$, filtered, concentrated to provide ethyl 2-(5-bromo-2-oxopyridin-1(2H)-yl)propanoate (3.68 g, 70% yield). LC/MS m/z 275.9 [M+H]$^+$.

Step 2: To a solution of ethyl 2-(5-bromo-2-oxopyridin-1(2H)-yl)propanoate (3.68 g, 13.43 mmol) in methanol (15 mL) and THF (15 mL) was added aqueous sodium hydroxide (18.8 mL of 1 M, 18.8 mmol) and the solution stirred for 18 h at room temperature. 3 M HCl was then added until the pH reached ~1 and the mixture was extracted with ethyl acetate. The combined organic fractions were dried over MgSO$_4$, filtered and concentrated to provide 2-(5-bromo-2-oxopyridin-1(2H)-yl)propanoic acid (2.61 g, 79% yield). LC/MS m/z 246.9 [M+H]$^+$. $^1$H NMR (400 MHz, DMSO-d$_6$) δ 12.98 (s, 1H), 8.09-7.93 (m, 1H), 7.60-7.49 (m, 1H), 6.39 (dd, J=9.7, 4.2 Hz, 1H), 5.13 (tt, J=11.4, 5.6 Hz, 1H), 1.56 (dd, J=7.2, 4.1 Hz, 3H).

Step 3: To a solution of 2-(5-bromo-2-oxopyridin-1(2H)-yl)propanoic acid (1.33 g, 5.41 mmol) in anhydrous THF (25 mL) was added borane-dimethylsulfide (1.23 g, 1.44 mL, 16.22 mmol) and the mixture heated to 55° C. After 3 h, additional borane-dimethylsulfide (1.23 g, 1.44 mL, 16.22 mmol) was added and the reaction heated at reflux for 2 h. The reaction was quenched with 3 M HCl (30 mL) then diluted with water and extracted with ethyl acetate. The combined organic fractions were dried over MgSO$_4$, filtered, and concentrated to provide 5-bromo-1-(1-hydroxypropan-2-yl)pyridin-2(1H)-one (0.82 g, 65% yield). LC/MS m/z 232.9 [M+H]$^+$.

Step 4: To a solution of 5-bromo-1-(1-hydroxypropan-2-yl)pyridin-2(1H)-one (819 mg, 3.53 mmol) and imidazole (529 mg, 7.76 mmol) in THF (8 mL) was added chloro(triisopropyl)silane (638 mg, 788 µL, 4.24 mmol) and the reaction stirred at room temperature for 1 h. The reaction was poured into water and extracted with ethyl acetate. The combined organic layers were dried over MgSO$_4$, filtered, and concentrated in vacuo. The crude material was purified by silica gel chromatography (0-100% ethyl acetate/hexanes) to provide 5-bromo-1-(1-(triisopropylsilyloxy)propan-2-yl)pyridin-2(1H)-one as a clear oil. LC/MS m/z 247.0 [M+H]$^+$.

Step 5: 5-Bromo-1-(1-(triisopropylsilyloxy)propan-2-yl)pyridin-2(1H)-one (431 mg, 1.24 mmol), 4,4,5,5-tetramethyl-2-(4,4,5,5-tetramethyl-1,3,2-dioxaborolan-2-yl)-1,3,2-dioxaborolane (474 mg, 1.87 mmol), Pd(dppf)Cl$_2$ (91 mg, 0.12 mmol), and potassium acetate (366 mg, 3.73 mmol) were dissolved in dioxane (8 mL) and heated at 90° C. The mixture was filtered through Celite and washed with methylene chloride. The filtrate was concentrated and purified by silica gel chromatography (0-100% ethyl acetate/hexanes) to provide 5-(4,4,5,5-tetramethyl-1,3,2-dioxaborolan-2-yl)-1-(1-(triisopropylsilyloxy) propan-2-yl)pyridin-2(1H)-one (335 mg, 46% yield) as a pale yellow oil. LC/MS m/z 394.1 [M+H]$^+$.

Example 1

Synthesis of 2-[5-[5-amino-6-[5-[2-methoxy-4-(methylaminomethyl)phenyl]-1,3,4-oxadiazol-2-yl]pyrazin-2-yl]-2-oxo-1-pyridyl]propanenitrile Compound I-34

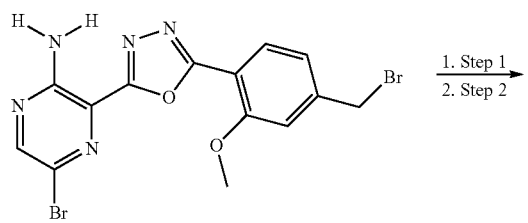

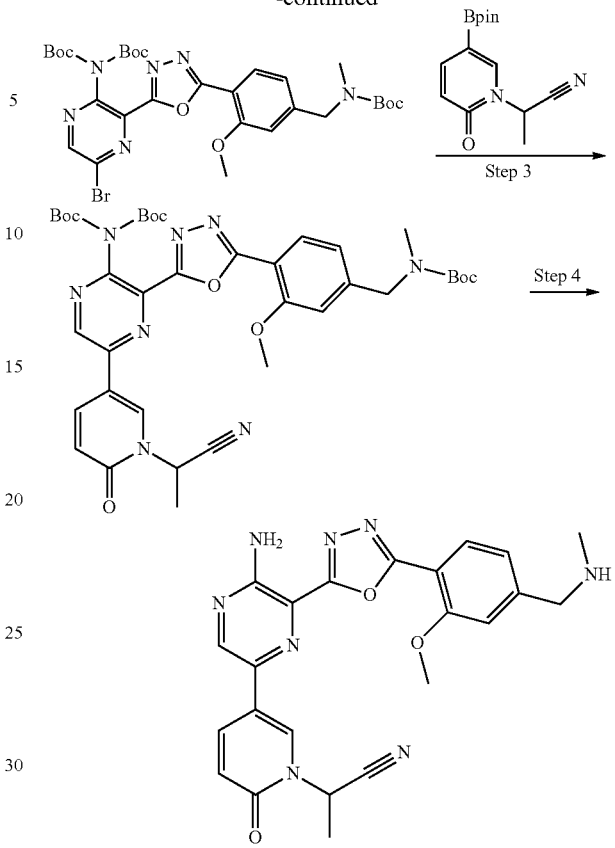

Step 1: To a solution of 5-bromo-3-(5-(4-(bromomethyl)-2-methoxyphenyl)-1,3,4-oxadiazol-2-yl)pyrazin-2-amine (5.0 g, 11.3 mmol) in THF (125 mL) was added sodium carbonate (3.6 g, 34.0 mmol) in one portion. Methylamine (28.3 ml, 2 M in methanol, 56.7 mmol) was then added dropwise over 10 min. The suspension was stirred for 30 min and then heated at 60° C. for 1 h. After cooling, the reaction mixture was diluted with water and extracted with DCM. The combined organics were washed with brine, dried over Na$_2$SO$_4$, filtered and concentrated in vacuo. The solid was then triturated with ether to provide 5-bromo-3-(5-(2-methoxy-4-((methylamino)methyl) phenyl)-1,3,4-oxadiazol-2-yl)pyrazin-2-amine (4.1 g, 92% yield) as a light yellow solid. LC/MS m/z 392.3 [M+H]$^+$.

Step 2: A solution of 5-bromo-3-(5-(2-methoxy-4-((methylamino)methyl)phenyl)-1,3,4-oxadiazol-2-yl)pyrazin-2-amine (1.7 g, 4.35 mmol) in THF (20 mL) was treated with (Boc)$_2$O (4.7 g, 5.0 mL, 21.72 mmol) and DMAP (53 mg, 0.43 mmol). The reaction mixture was stirred for 30 min at room temperature followed by 16 h at 45° C. The solvent was removed in vacuo and the residue was purified by silica gel chromatography (10-50% ethyl acetate/hexanes) to provide tert-butyl N-[[4-[5-[3-[bis(tert-butoxycarbonyl)amino]-6-bromo-pyrazin-2-yl]-1,3,4-oxadiazol-2-yl]-3-methoxy-phenyl]methyl]-N-methyl-carbamate as an off-white foam (1.9 g, 63% yield). LC/MS m/z 692.5 [M+H$^+$.

Step 3: tert-Butyl N-[[44543-[bis(tert-butoxycarbonyl) amino]-6-bromo-pyrazin-2-yl]-1,3,4-oxadiazol-2-yl]-3-methoxy-phenyl]methyl]-N-methyl-carbamate (200 mg, 0.28 mmol), 242-oxo-5-(4,4,5,5-tetramethyl-1,3,2-dioxaborolan-2-yl)-1pyridyl]propanenitrile (101 mg, 0.37 mmol), and Pd(dppf)Cl$_2$ (23 mg, 0.03 mmol) were dissolved in acetonitrile (5 mL) and Na₂CO₃ (2.8 mL of 2 M solution in water, 5.6 mmol). The reaction mixture was heated at 85° C. for 1 h, then cooled and partitioned between ethyl acetate and water. The organic layer washed with brine, dried over Na₂SO4, filtered, and concentrated in vacuo. The crude material was purified by silica gel chromatography (20-100% ethyl acetate/DCM) to provide di-tert-butyl 3-(5-(4-((tert-butoxycarbonyl(methypamino)methyl)-2-methoxyphenyl)-1,3,4-oxadiazol-2-yl)-5-(1-(1-cyanoethyl)-6-oxo-1,6-dihydropyridin-3-yl)pyrazin-2-yliminodicarbonate as a yellow foam (178 mg, 83% yield). LC/MS m/z 759.9 [M+H]⁺

Step 4: Di-tert-butyl 3-(5-(4-((tert-butoxycarbonyl(methyl)amino)methyl)-2-methoxyphenyl)-1,3,4-oxadiazol-2-yl)-5-(1-(1-cyanoethyl)-6-oxo-1,6-dihydropyridin-3-yl)pyrazin-2-yliminodicarbonate (178 mg, 0.24 mmol) was dissolved in DCM (3 mL) and TFA (1 mL) and stirred for 30 min. The reaction was diluted with DCM and washed with 50% saturated sodium carbonate and brine. The organic layer was dried over Na₂SO₄, filtered, and concentrated in vacuo. The resulting residue was purified by HPLC (10-99% CH₃CN/5 mM HCl) and the resulting hydrochloride salt partitioned between DCM and 50% saturated sodium bicarbonate. The organic phase was separated, dried over Na₂SO₄, and concentrated in vacuo to provide 2-[5-[5-amino-6-[5-[2-methoxy-4-(methylaminomethyl)phenyl]-1,3,4-oxadiazol-2-yl]pyrazin-2-yl]-2-oxo-1-pyridyl]propanenitrile Compound I-34 (55 mg, 42% yield). LC/MS m/z 459.5 [M+H]⁺. ¹H NMR (400 MHz, DMSO-d₆) δ 5 (s, 1H), 8.48 (d, J=2.4 Hz, 1H), 8.21 (dd, J=9.6, 2.5 Hz, 1H), 7.93 (d, J=8.0 Hz, 1H), 7.68 (s, 2H), 7.29 (s, 1H), 7.13 (d, J=8.1 Hz, 1H), 6.67 (d, J=9.6 Hz, 1H), 5.90 (q, J=7.1 Hz, 1H), 3.96 (s, 3H), 3.76 (s, 2H), 2.32 (s, 3H), 1.79 (d, J=7.1 Hz, 3H).

Example 2

Synthesis of 2-[5-[5-amino-6-[5-[2-methyl-4-(methylaminomethyl)phenyl]-1,3,4-oxadiazol-2-yl]pyrazin-2-yl]-2-oxo-1-pyridyl]propanoic acid Compound I-38

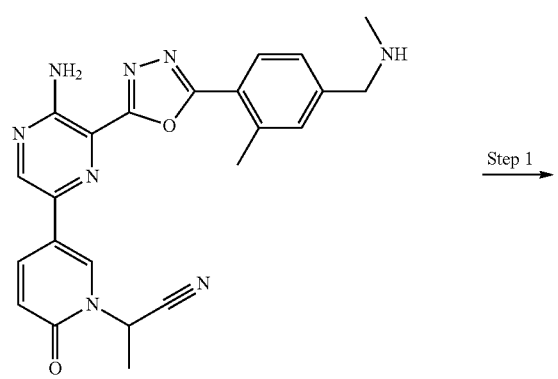

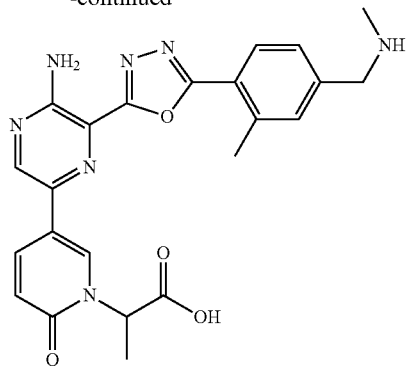

Step 1: 2-[5-[5-amino-6-[5-[2-methyl-4-(methylaminomethyl)phenyl]-1,3,4-oxadiazol-2-yl]pyrazin-2-yl]-2-oxo-1-pyridyl]propanenitrile (25 mg, 0.05 mmol) was suspended in 1 N HCl and heated to 50° C. for 1.5 h, resulting in clean conversion to the acid. The reaction was concentrated in vacuo to provide 2-[5-[5-amino-6-[5-[2-methyl-4-(methylaminomethyl)phenyl]-1,3,4-oxadiazol-2-yl]pyrazin-2-yl]-2-oxo-1-pyridyl]propanoic acid Compound I-38. LC/MS m/z 461.5 [M+H]⁺.

Example 3

Synthesis of 5-[5-amino-6-[5-[2-methyl-4-[[[(3S)-tetrahydrofuran-3-yl]amino]methyl]phenyl]-1,3,4-oxadiazol-2-yl]pyrazin-2-yl]-1-isopropyl-pyridin-2-one Compound I-13,

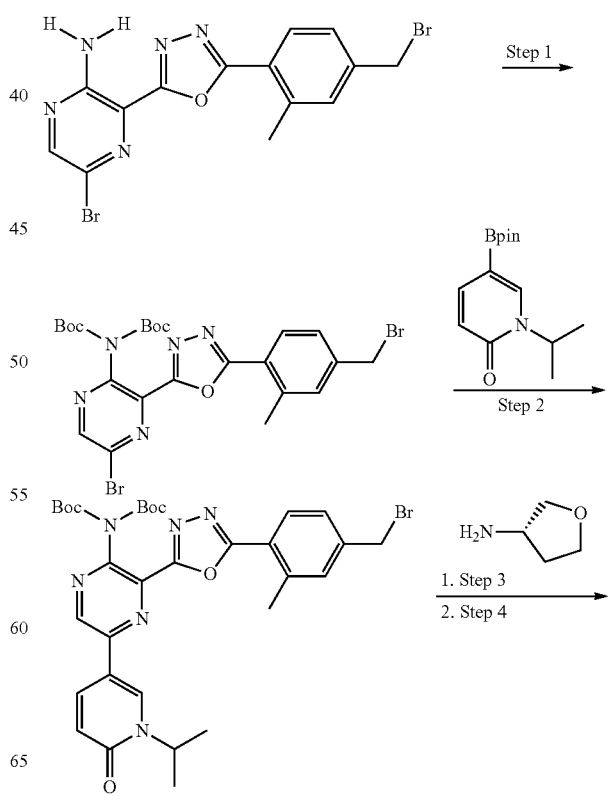

117

-continued

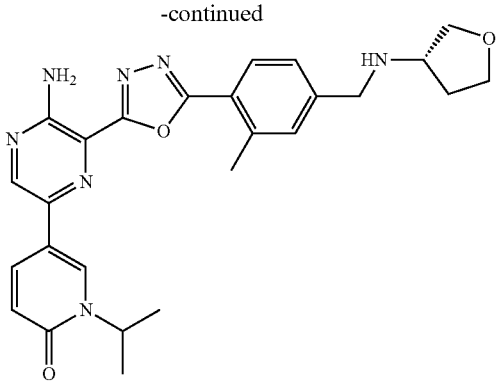

Step 1: To a mixture of 5-bromo-3-[5-[4-(bromomethyl)-2-methyl-phenyl]-1,3,4-oxadiazol-2-yl]pyrazin-2-amine (3.1 g, 7.29 mmol) and DMAP (89 mg, 0.73 mmol) in THF (96 mL) was added (Boc)$_2$O (6.7 g, 29.2 mmol) at room temperature. The reaction mixture was heated at 50° C. for 2 h, then allowed to cool to room temperature and partitioned between ethyl acetate and 1 M HCl. The organic layer was washed with saturated NaHCO$_3$, brine, dried over Na$_2$SO$_4$, filtered and concentrated in vacuo. The residue was purified by silica gel chromatography (0-15% ethyl acetate/hexanes) to provide tert-butyl N-[5-bromo-3-[5-[4-(bromomethyl)-2-methyl-phenyl]-1,3,4-oxadiazol-2-yl]pyrazin-2-yl]-N-tert-butoxycarbonyl-carbamate (3.3 g, 72% yield) as a white solid. $^1$H NMR (400 MHz, DMSO-d$_6$) δ 9.16 (s, 1H), 8.01 (d, J=8.0 Hz, 1H), 7.64-7.45 (m, 2H), 4.77 (s, 2H), 2.70 (s, J=15.7 Hz, 3H), 1.28 (s, 18H).

Step 2: An aqueous solution of Na$_2$CO$_3$ (1.4 mL of 2 M, 2.88 mmol) was added to a mixture of tert-butyl N-[5-bromo-3-[5-[4-(bromomethyl)-2-methyl-phenyl]-1,3,4-oxadiazol-2-yl]pyrazin-2-yl]-N-tert-butoxycarbonyl-carbamate (600 mg, 0.96 mmol), 1-isopropyl-5-(4,4,5,5-tetramethyl-1,3,2-dioxaborolan-2-yl)pyridin-2-one (253 mg, 0.96 mmol) and Pd(PPh$_3$)$_2$ (67 mg, 0.10 mmol) in DME (9 mL). The reaction mixture was degassed with argon, sealed and heated at 80° C. for 1 h. The reaction mixture was allowed to cool to room temperature and was partitioned between ethyl acetate and water. The aqueous layer was extracted once with ethyl acetate and the combined organics were dried over Na$_2$SO$_4$, filtered and concentrated in vacuo. Silica gel chromatography (0-70% ethyl acetate/hexanes) provided tert-butyl N-[3-[5-[4-(bromomethyl)-2-methyl-phenyl]-1,3,4-oxadiazol-2-yl]-5-(1-isopropyl-6-oxo-3-pyridyl)pyrazin-2-yl]-N-tert-butoxycarbonyl-carbamate (300 mg, 46%) as a yellow foam. $^1$H NMR (400 MHz, DMSO-d$_6$) δ 9.43 (s, 1H), 8.72 (d, J=2.3 Hz, 1H), 8.29 (dd, J=9.5, 2.4 Hz, 1H), 8.07 (d, J=8.0 Hz, 1H), 7.60 (s, 1H), 7.56 (d, J=8.2 Hz. 1H), 6.64 (d, J=9.5 Hz, 1H), 5.26-5.04 (m, 1H), 4.81 (s, 2H), 2.72 (s, 3H), 1.44 (d, J=6.9 Hz, 6H), 1.29 (s, 18H).

Step 3 and 4: To tert-butyl N-[3-[5-[4-(bromomethyl)-2-methyl-phenyl]-1,3,4-oxadiazol-2-yl]-5-(1-isopropyl-6-oxo-3-pyridyl)pyrazin-2-yl]-N-tert-butoxycarbonyl-carbamate (200 mg, 0.29 mmol) and (3S)-tetrahydrofuran-3-amine (77 mg, 0.8799 mmol) in DMF (5 mL) was added DIEA (190 mg, 255 µL, 1.47 mmol) and the reaction mixture was heated at 85° C. for 45 min. The reaction was cooled and solvent was removed in vacuo. The residue was treated with 50% TFA/DCM (1 mL) and stirred at room temperature for 20 min. The reaction was concentrated and purified by HPLC (CH$_3$CN/5 mM HCl) to provide 5-[5-amino-6-[5-[2-

118 methyl-4-[[[(3S)-tetrahydrofuran-3-yl]amino]methyl]phenyl]-1,3,4-oxadiazol-2-yl]pyrazin-2-yl]-1-isopropyl-pyridin-2-one Compound I-13. LC/MS m/z 488.2 [M+H]$^+$.

Example 4

Synthesis of 5-[5-amino-6-[5-[3-(methylaminomethyl)phenyl]-1,3,4-oxadiazol-2-yl]pyrazin-2-yl]-1-isopropyl-pyridin-2-one Compound I-47

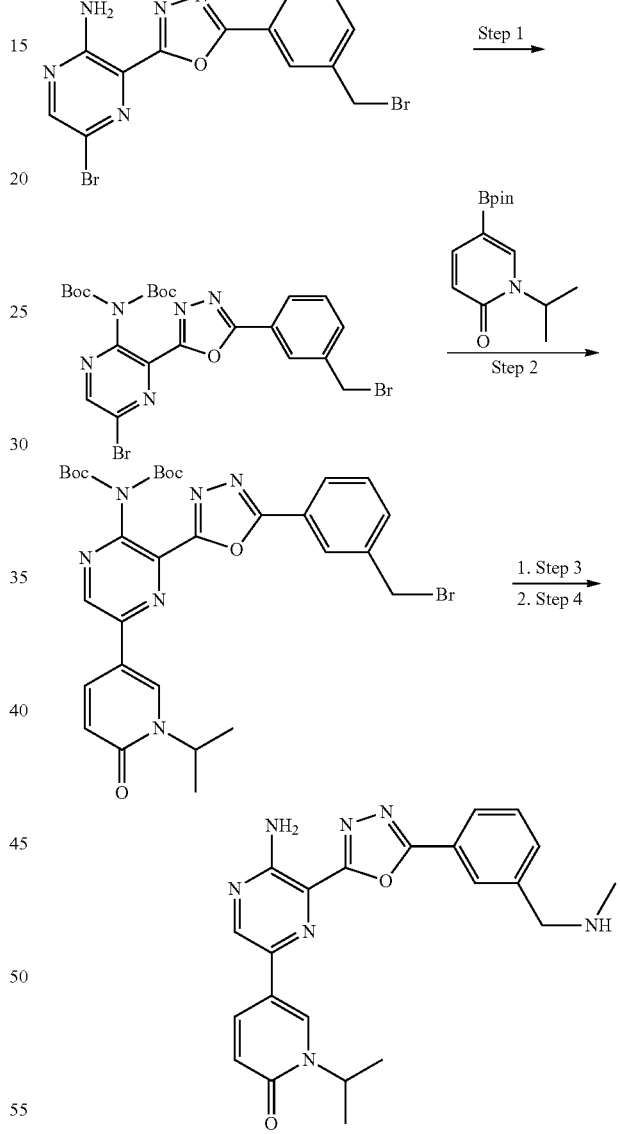

Step 1: To a mixture of 5-bromo-3-[5-[3-(bromomethyl)phenyl]-1,3,4-oxadiazol-2-yl]pyrazin-2-amine (1.0 g, 2.43 mmol) and DMAP (30 mg, 0.24 mmol) in THF (31 mL) was added (Boc)$_2$O (2.2 g, 2.3 mL, 9.73 mmol). The reaction mixture was heated at 50° C. for 3 h, then allowed to cool to room temperature and partitioned between ethyl acetate and 1 M HCl. The organic layer was washed with NaHCO$_3$ solution and brine, dried over MgSO$_4$, filtered and concentrated to dryness under reduced pressure. The residue was purified by silica gel column chromatography (0-10% ethyl acetate/hexanes) to provide Cert-butyl N-[5-bromo-3-[5-[3-(bromomethyl)phenyl]-1,3,4-oxadiazol-2-yl]pyrazin-2-yl]-N-tert-butoxycarbonyl-carbamate (0.7 g, 45%) as a white solid. $^1$H NMR (400 MHz, DMSO-d$_6$) δ9.7 (d, J=5.3 Hz, 1H), 8.22 (s, 1H), 8.07 (d, J=7.7 Hz, 1H), 7.79 (d, J=8.0 Hz, 1H), 7.68 (t, J=7.8 Hz, 1H), 4.88 (s, 2H), 1.29 (s, 18H).

Step 2: A solution of aqueous Na$_2$CO$_3$ (1.2 mL of 2 M, 2.45 mmol) was added to a mixture of 1-isopropyl-5-(4,4,5,5-tetramethyl-1,3,2-dioxaborolan-2-yl)pyridin-2-one (215 mg, 0.82 mmol), tert-butyl N-[5-bromo-3-[5-[3-(bromomethyl)phenyl]-1,3,4-oxadiazol-2-yl]pyrazin-2-yl]-N-tert-butoxycarbonyl-carbamate (500 mg, 0.82 mmol) and Pd(dppf)Cl$_2$ (60 mg, 0.082 mmol) in acetonitrile (7 mL). The reaction mixture was degassed with argon, sealed and heated at 80° C. for 30 min. The reaction mixture was allowed to cool to room temperature and partitioned between ethyl acetate and water. The aqueous layer was extracted once with ethyl acetate and the combined organics dried over Na$_2$SO$_4$, filtered and concentrated in vacuo. Silica gel chromatography (0-60% ethyl acetate/hexanes) provided tert-butyl N-[3-[5-[3-(bromomethyl)phenyl]-1,3,4-oxadiazol-2-yl]-5-(1-isopropyl-6-oxo-3-pyridyl)pyrazin-2-yl]-N-tert-butoxycarbonyl-carbamate (267 mg, 49%) as an orange oil. $^1$H NMR (400 MHz, DMSO-d$_6$) δ 9.45 (s, 1H), 8.73 (s, 1H), 8.32 (dd, J=9.5, 2.6 Hz, 1H), 8.25 (s, 1H), 8.16-8.06 (m, 1H), 7.80 (d, J=1.0 Hz, 1H), 7.73-7.66 (m, 1H), 6.64 (d, J=9.5 Hz, 1H), 5.17-5.08 (m, 1H), 4.87 (s, 2H), 1.45 (d, J=7.2 Hz, 6H), 1.29 (s, 18H).

Step 3: tert-Butyl N-[3-[5-[3-(bromomethyl)phenyl]-1,3,4-oxadiazol-2-yl]-5-(1-isopropyl-6-oxo-3-pyridyl)pyrazin-2-yl]-N-tert-butoxycarbonyl-carbamate (265 mg, 0.40 mmol) was dissolved in dichloromethane (3 mL) followed by the addition of HCl (4.0 mL of 4 M solution in dioxane, 15.88 mmol). The reaction mixture was stirred at room temperature for 2 h. The solvent and excess HCl were removed under reduced pressure to provide 5-[5-amino-6-[5-[3-(bromomethyl)phenyl]-1,3,4-oxadiazol-2-yl]pyrazin-2-yl]-1-isopropyl-pyridin-2-one as a yellow solid which was taken directly to the next step. LC/MS m/z 468.3 [M+H]$^+$.

Step 4: A mixture of 5-[5-amino-6-[5-[3-(bromomethyl)phenyl]-1,3,4-oxadiazol-2-yl]pyrazin-2-yl]-1-isopropyl-pyridin-2-one (70 mg, 0.14 mmol), methylamine (3.0 mL of 2 M solution in THF, 6.0 mmol) and Na$_2$CO$_3$ (44 mg, 0.42 mmol) was stirred for 1 h at 70° C. The reaction mixture was cooled to room temperature, diluted with DMF (1 mL) and purified by HPLC (10-99% CH$_3$CN/5mM HCl) to provide 5-[5-amino-6-[5-[3-(methylamino-methyl)phenyl]-1,3,4-oxadiazol-2-yl]pyrazin-2-yl]-1-isopropyl-pyridin-2-one Compound I-47. $^1$H NMR (400 MHz, DMSO-d$_6$) 9.26 (s, 2H), 8.95 (s, 1H), 8.44-8.29 (m, 2H), 8.24-8.13 (m, 2H), 7.84 (d, J=7.7 Hz, 1H), 7.75 (t, J=7.7 Hz, 1H), 7.66 (s, 1H), 6.57 (d, J=9.5 Hz, 1H), 5.21-5.06 (m, 1H), 4.29 (t, J=5.7 Hz, 2H), 2.60 (t, J=5.2 Hz, 3H), 1.42 (d, J=6.8 Hz, 6H).

Scheme C

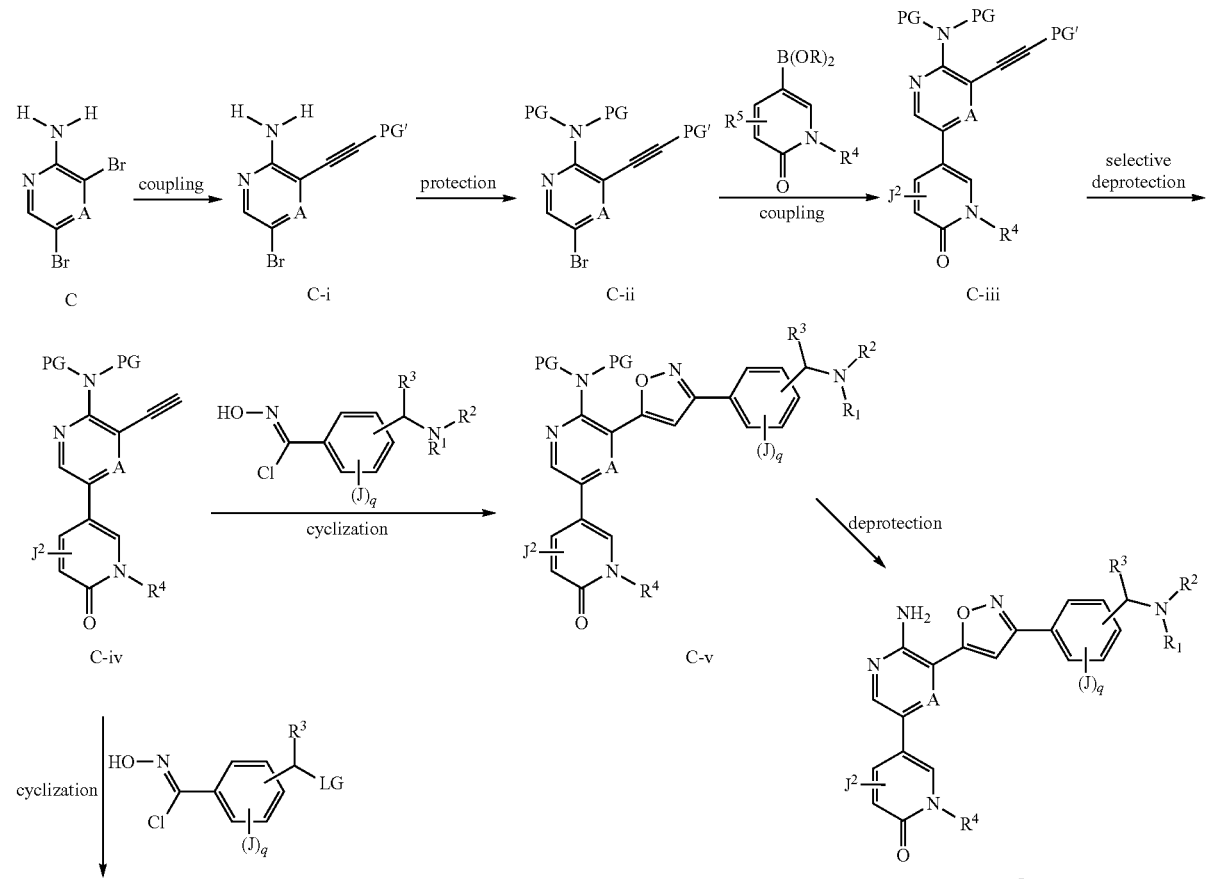

-continued

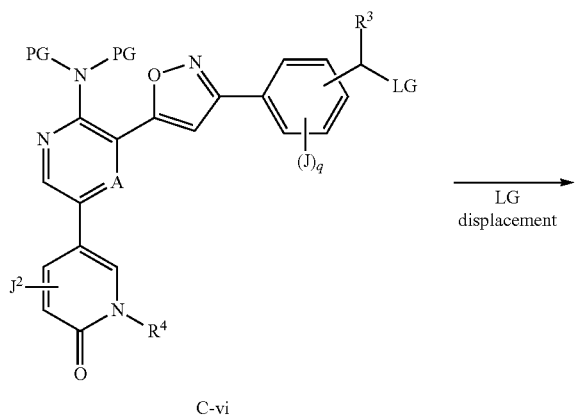

C-vi

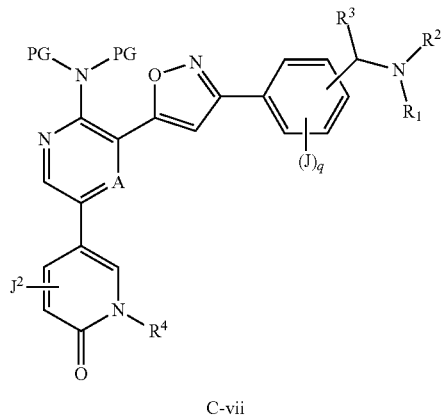

C-vii deprotection

LG displacement

Scheme C depicts a general method for making compounds of Formula I in which Ring D is isoxazole. Compound C is selectively reacted with a suitably protected alkyne under Sonogashira coupling conditions to provide compounds of Formula C-i. Suitable alkyne protecting groups PG' include, but are not limited to, TMS, TES or TIPS. Compounds of Formula C-i are then protected with a suitable amine protecting group PG orthogonal to PG' such as, but not limited to BOC (Butyl Carbamate), to give compounds of Formula C-ii. The pyridone ring system is introduced under metal-mediated coupling conditions, including but not limited to Suzuki coupling of C-ii with an appropriate boronic ester or boronic acid to provide compounds of Formula C-iii. Compounds of Formula C-iii are then selectively deprotected under standard conditions known to those skilled in the art such as, but not limited to, treatment with base such as $K_2CO_3$ or fluoride to remove the alkyne protecting group PG' to yield compounds of Formula C-iv. The assembly of the 3,5-disubstituted isoxazole can be achieved through the 1,3-dipolar cycloaddition of the terminal acetylene of compound C-iv with an appropriate chloro oxime to provide the desired isoxazole. Compounds of Formula C-v are constructed via a route wherein the amine functionality —$NR^1R^2$ (protected as PG if $R^2$=H) is installed on the chloro oxime building block prior to cyclization, while compounds of Formula C-vi are constructed via the cyclization wherein the chloro oxime building block is functionalized with the appropriate leaving group (LG). Isoxazole intermediate C-vi is further functionalized through the nucleophilic displacement of the leaving group (LG) with the amine $NHR^1R^2$ to form compounds of Formula C-vii. Suitable leaving groups include but are not limited to halogens, mesylates, or triflates. Removal of the nitrogen protecting group PG from compounds of Formula C-v and C-vii takes place under standard conditions known to those skilled in the art such as, but not limited to, treatment with HCl or TFA to provide compounds of Formula I in which Ring D is isoxazole. In addition, substituents $R^4$ on Formula I can undergo further functionalization by reactions known to those skilled in the art such as, but not limited to, hydrolysis, nucleophilic displacement reactions, acylation reactions, amide bond formation reactions, or further deprotection to reveal additional functionality.

Preparation 12

Synthesis of tert-butyl N-tert-butoxycarbonyl-N-[5-(1-cyclopentyl-6-oxo-3-pyridyl)-3-ethynyl-pyrazin-2-yl]carbamate

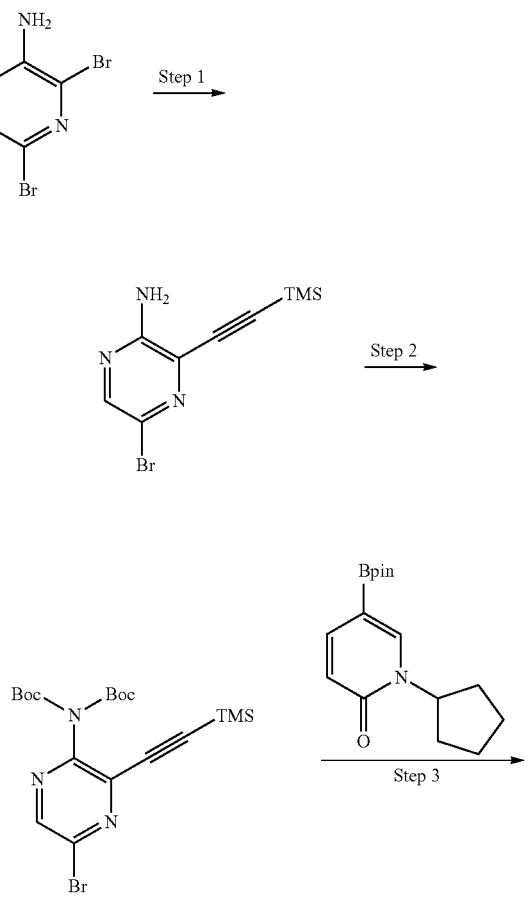

123

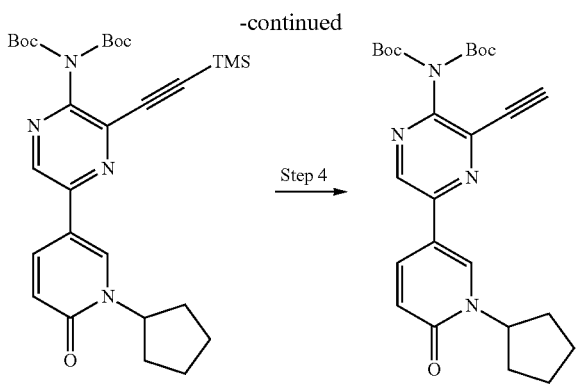

Step 1: (Trimethylsilyl)acetylene (1.9 g, 2.7 mL, 18.8 mmol) was added dropwise to a solution of 3,5-dibromopyrazin-2-amine (5.0 g, 19.8 mmol), triethylamine (10.0 g, 13.8 mL, 98.9 mmol), copper (I) iodide (452 mg, 2.37 mmol) and Pd(PPh$_3$)$_4$(1.14 g, 0.99 mmol) in DMF (25 mL) and the resulting solution stirred at room temperature for 30 min. The reaction was diluted with ethyl acetate and water and the layers separated. The aqueous layer was extracted further with ethyl acetate and the combined organics washed with water, dried over MgSO$_4$, and concentrated in vacuo. The mixture was purified via silica gel chromatography (0-15% ethyl acetate/hexanes) to afford 5-bromo-3-((trimethylsilyl)ethynyl)pyrazin-2-amine as a yellow solid (3.99 g, 75% yield). $^1$H NMR (400 MHz, DMSO-d$_6$) δ 0.30 (s, 9H), 8.06 (s, 1H); MS (ES$^+$) 271.82

Step 2: 5-Bromo-3-(2-trimethylsilylethynyl)pyrazin-2-amine (480 mg, 1.78 mmol) was dissolved in DCM (15 mL) and treated with Boc-anhydride (1.16 g, 1.22 mL, 5.33 mmol), followed by DMAP (22 mg, 0.18 mmol). The mixture was allowed to stir at room temperature overnight. The reaction was washed with NaHCO$_3$, extracted with DCM, dried over MgSO$_4$, filtered and concentrated. The resulting brown oil was purified by silica gel chromatography (0-10% ethyl acetate/hexanes) to afford the product as a colorless oil (641 mg, 77% yield). $^1$H NMR (400 MHz, DMSO-d$_6$) δ 0.00 (s, 9H), 1.11 (s, 18H) and 8.63 (s, 1H).

Step 3: 1-Cyclopentyl-5-(4,4,5,5-tetramethyl-1,3,2-dioxaborolan-2-yl)pyridin-2-one (4.71 g, 16.29 mmol), tert-butyl N-[5-bromo-3-(2-trimethylsilylethynyl)pyrazin-2-yl]-N-tert-butoxycarbonyl-carbamate (5.11 g, 10.86 mmol), and Pd(PPh$_3$)$_2$Cl$_2$ (762 mg, 1.09 mmol) were combined in acetonitrile (50 mL) and treated with aqueous sodium carbonate (16 mL of 2 M, 32 mmol) and heated at 50° C. for 2 h. The reaction was diluted with water and ethyl acetate, passed through a pad of Celite and the layers separated. The organic layer was washed with brine, dried over Na$_2$SO$_4$, and concentrated in vacuo. Silica gel chromatography (10-100% ethyl acetate/hexane) provided tert-butyl N-tert-butoxycarbonyl-N-[5-(1-cyclopentyl-6-oxo-3-pyridyl)-3-(2-trimethylsilylethynyl)pyrazin-2-yl]carbamate as a brown foam (4.36 g, 73% yield). LC/MS m/z 553.5[M+H]$^+$.

Step 4: tert-Butyl N-tert-butoxycarbonyl-N-[5-(1-cyclopentyl-6-oxo-3-pyridyl)-3-(2-trimethylsilylethynyl)pyrazin-2-yl]carbamate (4.36 g, 7.89 mmol) in DMF (20 mL) was treated with sodium carbonate (4.7 mL of 2 M, 9.4 mmol) and heated at 75° C. for 1 h. The reaction was cooled to room temperature, treated with water (60 mL) and sonicated for 1 h. The solution was decanted from the insoluble material, taken up in ethyl acetate and washed with 0.5 N HCl and brine, dried over Na$_2$SO$_4$, filtered and concentrated in vacuo to provide tert-butyl N-tert-butoxycarbonyl-N-[5-(1-cyclopentyl-6-oxo-3-pyridyl)-3-ethynyl-pyrazin-2-yl]carbamate as a brown foam (3.1 g, 82% yield). LC/MS m/z 481 [M+H]$^+$. $^1$H NMR (400 MHz, DMSO-d6) δ 9.15 (s, 1H), 8.52 (d, J=2.5 Hz, 1H), 8.14 (dd, J=9.6, 2.6 Hz, 1H), 6.55 (d, J=9.5 Hz, 1H), 5.16-5.05 (m, 1H), 4.89 (s, 1H), 2.08-2.00 (m, 2H), 1.94-1.81 (m, 4H), 1.73-1.60 (m, 2H), 1.38 (s, 18H).

The following acetylene intermediates if Formula C-iv were prepared in an analogous manner:

tert-ButylN-tert-butoxycarbonyl-N-[5-[1-(1-cyclopropylethyl)-6-oxo-3-pyridyl]-3-ethynyl-pyrazin-2-yl]carbamate. $^1$H NMR (400 MHz, DMSO-d$_6$) δ 9.18 (t, J=4.9 Hz, 1H), 8.83-8.67 (m, 1H), 8.15 (dd, J=12.3, 5.3 Hz, 1H), 6.56 (dd, J=9.4, 5.4 Hz, 1H), 4.21(d, J=6.5 Hz, 1H), 1.56-1.43 (m, 5H), 1.42-1.30 (m, 21H), 0.68 (s, 1H), 0.46 (d, J=5.8 Hz, 2H), 0.20 (d, J=5.1 Hz, 1H).

tert-Butyl N-tert-butoxycarbonyl-N-[3-ethynyl-5-(1-isopropyl-6-oxo-3-pyridyl)pyrazin-2-yl]carbamate. LC/MS m/z 455.5 [M+H]$^+$. $^1$H NMR (400 MHz, CDCl$_3$) δ 8.65 (s, 1H), 8.28 (d, J=2.4 Hz, 1H), 7.93 (dd, J=9.5, 2.6 Hz, 1H), 6.68 (d, J=9.5 Hz, 1H), 5.32 (dt, J=13.6, 6.7 Hz, 1H), 3.46 (s, 1H), 1.46 (d, J=6.8 Hz, 6H), 1.42 (s, 18H).

Preparation 13

Synthesis of tert-butyl 4-(chloro(hydroxyimino)methyl)-3-fluorobenzyl(methyl)carbamate

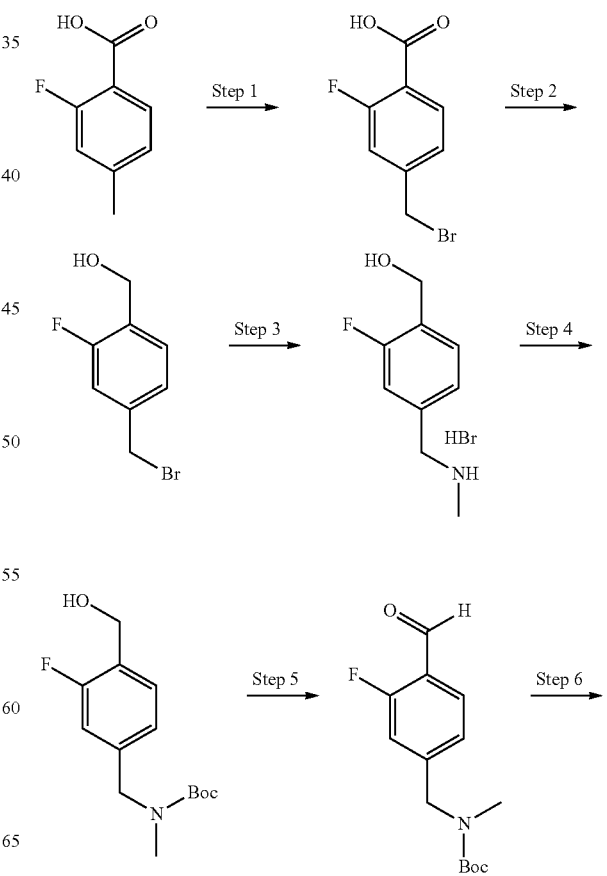

-continued

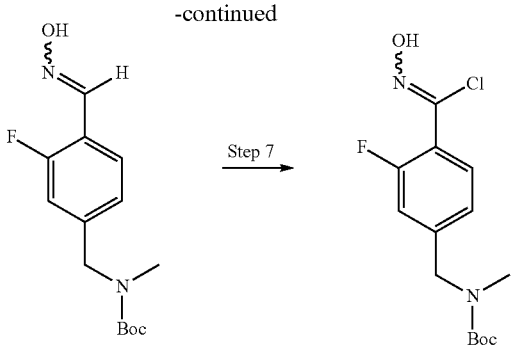

Step 1: AIBN (533 mg, 3.24 mmol) and N-bromosuccinimide (6.35 g, 35.68 mmol) were added to 2-fluoro-4-methyl-benzoic acid (5.0 g, 32.4 mmol) in CCl$_4$ (50 mL) and the reaction mixture heated for 3 h at 90° C. The reaction mixture was cooled, filtered, and the filter cake was washed once with CCl$_4$, then three times with water. The filter cake was then dissolved in a 1:1 mixture of acetonitrile/MeOH, dried over Na$_2$SO$_4$, filtered and concentrated in vacuo to afford 4-(bromomethyl)-2-fluoro-benzoic acid (4.7 g, 62% yield) as an off-white solid. $^1$H NMR (400 MHz, DMSO-d$_6$) δ13.30 (s, 1H), 7.89-7.81 (m, 1H), 7.42 (dd, J=8.9, 4.0 Hz, 1H), 7.38 (dd, J=8.0, 1.5 Hz, 1H), 4.73 (s, 2H).

Step 2: 4-(Bromomethyl)-2-fluoro-benzoic acid (4.65 g, 19.95 mmol) was dissolved in anhydrous THF (70 mL) under a nitrogen atmosphere and cooled in an ice bath. A solution of borane-THF complex (32 mL of 1 M, 32 mmol) in THF was added dropwise and the reaction mixture was allowed to warm to room temperature over 5 h. The reaction mixture was quenched with methanol and concentrated in vacuo. The resulting residue was partitioned between ethyl acetate and 1 M HCl and the aqueous layer was extracted once with ethyl acetate. The combined organics were dried over Na$_2$SO$_4$, filtered and concentrated to provide (4-(bromomethyl)-2-fluorophenyl)methanol as a white solid (4.12 g, 94% yield). $^1$H NMR (400 MHz, DMSO-d$_6$) δ 7.45 (t, J=7.8 Hz, 1H), 7.33-7.22 (m, 2H), 5.29 (s, 1H), 4.70 (s, 2H), 4.53 (s, 2H).

Step 3: [4-(Bromomethyl)-2-fluoro-phenyl]methanol (5.14 g, 23.46 mmol) was dissolved in methylamine (235 mL of 2 M in methanol, 470 mmol) and heated at 45° C. for 1 h. The reaction mixture was allowed to cool to room temperature, and the solvent and excess methyamine removed under reduced pressure. The residue was triturated with Et$_2$O to provide [2-fluoro-4-(methylaminomethyl)phenyl]methanol (4.84 g, 82% yield) as an off-white solid. $^1$H NMR (400 MHz, DMSO-d$_6$) δ 8.55 (s, 1H), 7.53 (t, J=7.7 Hz, 1H), 7.35-7.25 (m, 2H), 5.35 (t, J=5.2 Hz, 1H), 4.56 (d, J=4.8 Hz, 2H), 4.12 (s, 2H), 3.33 (s, 1H), 2.55 (s, 2H), 2.37 (s, 1H).

Step 4: To a mixture of [2-fluoro-4-(methylaminomethyl) phenyl]methanol (4.58 g, 18.31 mmol) and triethylamine (17.9 mL, 128 mmol) in THF (137 mL) was added (Boc)$_2$O (4.80 g, 22.0 mmol) in one portion. Water (7 mL) was added to form a homogeneous solution and the reaction was stirred for 4 h. The reaction mixture was partitioned between ethyl acetate and 1 M HCl. The organic layer was washed with saturated NaHCO$_3$ solution and brine, dried over Na$_2$SO$_4$, filtered and concentrated to an oil under reduced pressure. Silica gel chromatography (0-30% ethyl acetate/hexanes) provided tert-butyl N-[[3-fluoro-4-(hydroxymethyl)phenyl] methyl]-N-methyl-carbamate (3.53 g, 72% yield) as a colorless oil. $^1$H NMR (400 MHz, DMSO-d$_6$) δ 7.44 (t, J=7.7 Hz, 1H), 7.04 (d, J=7.8 Hz, 1H), 6.96 (d, J=11.1 Hz, 1H), 5.23 (t, J=5.7 Hz, 1H), 4.52 (d, J=5.7 Hz, 2H), 4.33 (s, 2H), 2.76 (s, 3H), 1.41 (d, J=16.7 Hz, 9H).

Step 5: To a solution of tert-butyl N-[[3-fluoro-4-(hydroxymethyl)phenyl]methyl]-N-methyl-carbamate (3.51 g, 13.03 mmol) in DCM (30 mL) was added MnO$_2$ (9.06 g, 104.2 mmol) and the reaction stirred at room temperature for 48 h. An additional 9 g of MnO$_2$ was added and the reaction stirred for an additional 24 h. The reaction mixture was filtered through Celite and concentrated in vacuo to provide tert-butyl N-[(3-fluoro-4-formyl-phenyl)methyl]-N-methyl-carbamate (2.56 g, 74% yield) as a clear yellow oil. $^1$H NMR (400 MHz, DMSO-d$_6$) δ 10.19 (s, 1H), 7.85 (t, J=7.5 Hz, 1H), 7.21 (t, J=10.1 Hz, 2H), 4.46 (s, 2H), 2.82 (s, 3H), 1.39 (d, J=36.5 Hz, 9H).

Step 6: To a solution of tert-butyl N-[(3-fluoro-4-formyl-phenyl)methyl]-N-methyl-carbamate (2.5 g, 9.4 mmol) in THF (43 mL) was added sodium acetate (1.92 g, 23.38 mmol). The solution was cooled to 0° C. (ice bath) and hydroxylamine hydrochloride (845 mg, 12.16 mmol) added. The reaction was allowed to warm to room temperature over 2 h. The solvents were removed in vacuo and the residue partitioned between ethyl acetate and water. The organic layer was washed with brine, dried over Na$_2$SO$_4$, filtered and concentrated in vacuo to provide tert-butyl 3-fluoro-4-((hydroxyimino)methyl)benzyl(methyl)carbamate (2.62 g, 99% yield) as a white solid. $^1$H NMR (400 MHz, DMSO-d$_6$) δ 11.56 (s, 1H), 8.19 (s, 1H), 7.72 (t, J=7.8 Hz, 1H), 7.16-7.01 (m, 2H), 4.38 (s, 2H), 2.79 (s, 3H), 1.40 (d, J=23.7 Hz, 9H).

Step 7: To a solution of tert-butyl 3-fluoro-4-((hydroxyimino)methyl)benzyl(methyl)carbamate (2.6 g, 9.2 mmol) in DMF (30 mL) at 0° C. was added N-chlorosuccinimide (1.35g, 10.1 mmol). The reaction was stirred at 0° C. for 1 h then allowed to warm to room temperature and stirred for 3 h. The reaction was concentrated under reduced pressure, diluted with ethyl acetate and washed with 0.5 HCl, water, brine, and dried over Na$_2$SO$_4$. The organics were concentrated in vacuo to provide tert-butyl 4-(chloro(hydroxyimino)methyl)-3-fluorobenzyl(methyl)carbamate as a colorless oil, which was carried forward without purification.

Preparation 14

Synthesis of tert-butyl 1-(3-(chloro(hydroxyimino) methyl)phenyl)ethylcarbamate

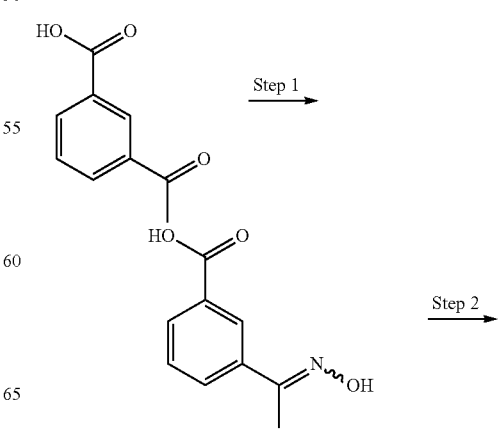

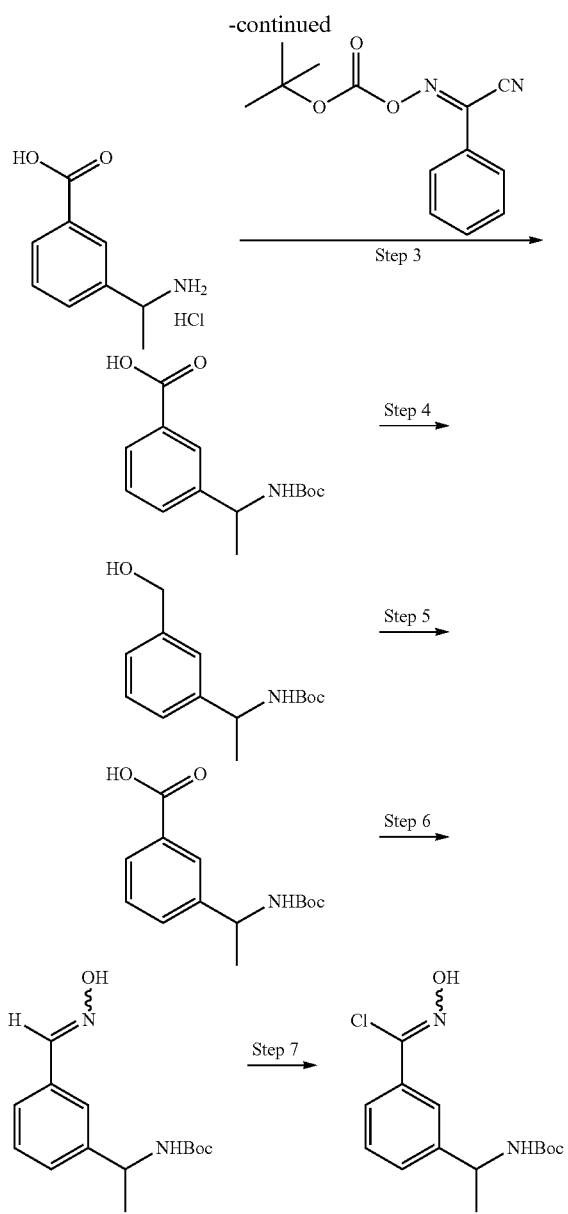

benzoic acid hydrochloride (2.4 g, 94% yield) as a white solid. $^1$H NMR (400 MHz, CD$_3$OD) δ 8.16 (s, 1H), 8.07 (d, J=7.8 Hz, 1H), 7.70 (d, J=7.7 Hz, 1H), 7.58 (t, J=7.7 Hz, 1H), 4.55 (q, J=6.7 Hz, 1H), 1.66 (d, J=6.9 Hz, 3H).

Step 3: To a solution of 3-(1-aminoethyl)benzoic acid (10.2 g, 50.6 mmol) in water (283 mL) and was added a solution of tert-butyl[(cyano-phenyl-methylene)amino]carbonate (13.1 g, 53.1 mmol) in acetone (283 mL) followed by triethylamine (21 mL, 151 mmol). After stirring for 16 h at room temperature, the reaction mixture was concentrated in vacuo and the residue partitioned between ethyl acetate and water and the layers separated. The organic layer was extracted with saturated sodium bicarbonate solution. The combined aqueous layers were acidified to pH 2 with 1 N HCl and extracted with ethyl acetate. The combined organic extracts were dried over Na$_2$SO$_4$, filtered and concentrated in vacuo to yield an off-white solid. The solid was triturated with ethyl acetate/hexanes to provide 3-[1-(tert-butoxycarbonylamino)ethyl]benzoic acid (8.3 g, 62% yield) as a white solid. $^1$H NMR (400 MHz, CDCl$_3$) δ 8.07 (s, 1H), 8.02-7.94 (m, 1H), 7.60-7.51 (m, 1H), 7.43 (t, J=7.7 Hz, 1H), 4.88 (s, 1H), 1.48 (d, J=6.7 Hz, 3H), 1.37 (s, 9H).

Step 4: 3-[1-(tert-butoxycarbonylamino)ethyl]benzoic acid (7.57 g, 28.53 mmol) was dissolved in anhydrous THF (45 mL) followed by the dropwise addition of borane-dimethylsulfide (42.8 mL of 2 M in THF, 85.6 mmol). The reaction was stirred for 3 h at room temperature then cooled to 0° C. and quenched with MeOH. The solvents were removed under reduced pressure and the resulting residue partitioned between 1M HCl and ethyl acetate. The organic layer was washed with saturated sodium bicarbonate and brine, dried over Na$_2$SO$_4$, filtered and concentrated in vacuo. Silica gel chromatography (30% ethyl acetate/hexanes) provided tert-butyl N-[1-[3-(hydroxymethyl)phenyl]ethyl]carbamate (4.91 g, 68% yield). $^1$H NMR (400 MHz, DMSO-d$_6$) δ 7.38 (d, J=8.1 Hz, 1H), 7.23 (d, J=4.3 Hz, 2H), 7.14 (d, J=7.7 Hz, 2H), 5.17 (t, J=5.7 Hz, 1H), 4.64-4.54 (m, 1H), 4.47 (d, J=5.6 Hz, 2H), 1.36 (s, 9H), 1.28 (d, J=7.0 Hz, 3H).

Step 5: To a solution of tert-butyl N-[1-[3-(hydroxymethyl)phenyl]ethyl]carbamate (4.91 g, 19.54 mmol) in DCM (40 mL) was added MnO$_2$ (13.59 g, 156.3 mmol) and the reaction mixture was stirred at room temperature for 48 h at room temperature. An additional 3 g of MnO$_2$ was added and the reaction mixture was stirred for an additional 12 h. The reaction mixture was filtered through a pad of Celite and concentrated in vacuo to provide tert-butyl N-[1-(3-formylphenyl)ethyl]carbamate (4.0 g, 82% yield) as a clear oil. $^1$H NMR (400 MHz, DMSO-d$_6$) δ10.00 (s, 1H), 7.83 (s, 1H), 7.78 (d, J=7.4 Hz, 1H), 7.64 (d, J=7.7 Hz, 1H), 7.55 (dd, J=15.4, 7.8 Hz, 2H), 4.75-4.64 (m, 1H), 1.41-1.30 (m, 12H).

Step 6: To a solution of tert-butyl N-[1-(3-formylphenyl)ethyl]carbamate (4.0 g, 16.0 mmol) and sodium acetate (3.3 g, 40.1 mmol) in THF (69 mL) at 0° C. was added hydroxylamine hydrochloride (1.4 g, 20.9 mmol). The reaction was allowed to warm to room temperature and stirred for 16 h. The reaction was concentrated and the resulting residue partitioned between ethyl acetate and water. The organic layer was washed with brine, dried over Na$_2$SO$_4$, filtered and concentrated in vacuo to provide tert-butyl 1-(3-((hydroxyimino)methyl)phenyl)ethylcarbamate as a colorless gel (4.24 g, quantitative yield). $^1$H NMR (400 MHz, DMSO-d$_6$) δ 11.20 (s, 1H), 8.11 (s, 1H), 7.53 (s, 1H), 7.41 (q, J=8.3 Hz, 2H), 7.38-7.24 (m, 2H), 4.61 (dd, J=14.0, 6.7 Hz, 1H), 1.33 (d, J=21.1 Hz, 9H), 1.30 (d, J=7.0 Hz, 3H).

Step 7: To a solution of tert-butyl 1-(3-((hydroxyimino)methyl)phenyl)ethylcarbamate (4.2 g, 16.0 mmol) in DMF Step 1: 3-Acetylbenzoic acid (10.0 g, 60.9 mmol), hydroxylamine hydrochloride (33.9 g, 487.4 mmol) and sodium acetate (45.0 g, 548.3 mmol) were suspended in ethanol (115 mL) and water (115 mL) and the mixture refluxed for 30 min. The solvents were removed under reduced pressure, and the resulting residue was triturated with water. The resulting solid was filtered and dried to provide 3-(1-(hydroxyimino)ethyl)benzoic acid (10.34 g, 95% yield) a white solid. $^1$H NMR (400 MHz, DMSO-d$_6$) δ 12.86 (s, 1H), 11.36 (s, 1H), 8.22 (s, 1H), 7.95-7.91 (m, 1H), 7.88 (dd, J=4.7, 3.1 Hz, 1H), 7.52 (t, J=7.8 Hz, 1H), 2.18 (s, 3H).

Step 2: 3-(1-(Hydroxyimino)ethyl)benzoic acid (2.28 g, 12.73 mmol) and palladium on carbon (10 wt. %, 1.355 g, 12.73 mmol) in ethanol (170 mL) and aq. HCl (2.1 mL of 12 M, 24.2 mmol) were stirred under an atmosphere of H$_2$ at 40 psi for 6 h. The reaction mixture was sparged with nitrogen for 30 min then filtered through a pad of Celite eluting with methanol. The filtrate was concentrated under reduced pressure and triturated with Et$_2$O to provide 3-(1-aminoethyl)

(69 mL) at 0° C. was added N-chlorosuccinimide (2.4 g, 17.6 mmol) and the reaction stirred for 2 h while allowing to warm to room temperature. The reaction mixture was diluted with ethyl acetate (300 mL) and then washed with saturated brine solution. The organic layer was dried over $Na_2SO_4$, filtered and concentrated to a thick colorless gel. The residue was then triturated with $Et_2O$/hexanes and filtered to provide tert-butyl 1-(3-(chloro(hydroxyimino)methyl)phenyl)ethylcarbamate (4.3 g, 90% yield). $^1H$ NMR (400 MHz, DMSO-$d_6$) δ 12.37 (s, 1H), 7.72 (s, 1H), 7.69-7.60 (m, 1H), 7.45 (dd, J=36.5, 6.2 Hz, 3H), 4.64 (dt, J=12.6, 6.4 Hz, 1H), 1.45-1.25 (m, 12H).

Preparation 15

Synthesis of 4-(chloromethyl)-N-hydroxybenzimidoyl chloride

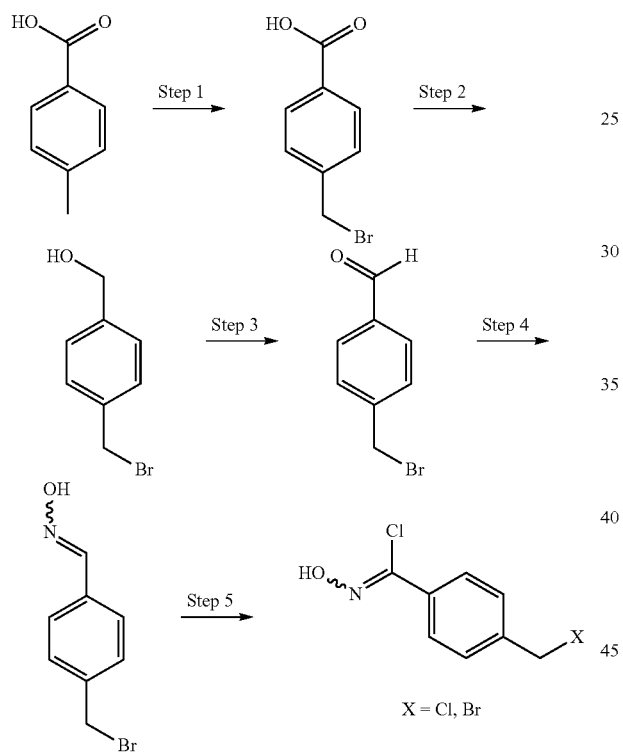

X = Cl, Br

Step 1: A solution of 4-methylbenzoic acid (10.0 g, 73.5 mmol) in ethyl acetate (142 mL) was treated with a solution of $BrO_3Na$ (28.2 g, 220.4 mmol) in water (110 mL). A solution of $NaHSO_3$ (22.9 g, 220.4 mmol) in water (220 mL) was then added dropwise over 20 min to the reaction mixture [Caution: exotherm] and the reaction mixture stirred for 4 h. The aqueous layer was extracted with $Et_2O$. The combined organics were washed with 1 M $Na_2S_2O_3$, dried over $Na_2SO_4$, filtered and concentrated in vacuo. The resulting solid was recrystallized from methanol to provide 4-(bromomethyl)benzoic acid (12.2 g, 77% yield) as a white solid. $^1H$ NMR (400 MHz, DMSO-d6) δ 13.05 (s, 1H), 7.93 (d, J=8.2 Hz, 2H), 7.58 (t, J=9.2 Hz, 2H), 4.76 (s, 2H).

Step 2: A solution of 4-(bromomethyl)benzoic acid (5.5 g, 25.6 mmol) in THF (30 mL) was cooled to 0° C. and treated with borane-THF solution (38.4 mL of 1 M, 38.4 mmol). The reaction mixture was allowed to warm to room temperature and then stirred for 2 h. The reaction was quenched with methanol followed by water and then concentrated under reduced pressure. The residue was partitioned between 1N HCl and ethyl acetate, and the organic layer washed with $NaHCO_3$, water, and brine. The solution was dried over $Na_2SO_4$, filtered, and concentrated in vacuo to provide [4-(bromomethyl)phenyl]methanol as a colorless solid (5.1 g, 99% yield). $^1H$ NMR (400 MHz, CDCl$_3$) δ 7.39 (d, J=8.1 Hz, 2H), 7.34 (d, J=8.2 Hz, 2H), 4.69 (s, 2H), 4.50 (s, 2H), 1.73-1.62 (m, 1H).

Step 3: A solution of [4-(bromomethyl)phenyl]methanol (5.1 g, 25.4 mmol) in DCM (56 mL) was treated with $MnO_2$ (17.7 g, 203.0 mmol) and stirred for 16 h. Additional $MnO_2$ was added (17.7 g, 203.0 mmol) and stirring continued for 48 h. The reaction was filtered through Celite and washed with DCM. The filtrate was concentrated in vacuo and purified by silica gel chromatography (0-50% ethyl acetate/hexanes) to provide 4-(bromomethyl)benzaldehyde as a white solid (3.2 g, 63% yield). $^1H$ NMR (400 MHz, DMSO-$d_6$) δ 10.01 (s, 1H), 7.91 (d, J=8.1 Hz, 2H), 7.67 (d, J=8.1 Hz, 2H), 4.79 (s, 2H).

Step 4: A solution of 4-(bromomethyl)benzaldehyde (5.0 g, 25.1 mmol) in THF (50 mL) at 0° C. was treated with sodium acetate (4.5 g, 55.3 mmol) followed by hydroxylamine hydrochloride (1.9 g, 27.6 mmol). The reaction was allowed to warm to room temperature and then stirred for 16 h. The reaction was concentrated and the resulting residue partitioned between ethyl acetate and water. The organic layer was washed with brine, dried over $Na_2SO_4$, filtered, and concentrated in vacuo to provide 4-(bromomethyl)benzaldehyde oxime as a colorless solid (5.3 g, 98% yield). LC/MS m/z 215.3 [M+H]$^+$.

Step 5: A solution of 4-(bromomethyl)benzaldehyde oxime (521 mg, 2.43 mmol) in DMF (10 mL) at 0° C. was treated with N-chlorosuccinimide (358 mg, 2.68 mmol). The reaction mixture was allowed to warm to room temperature and then stirred for 16 h. The reaction mixture was concentrated and partitioned between ethyl acetate and water. The organic layer was washed with brine, dried over $Na_2SO_4$, filtered, and concentrated in vacuo to provide a mixture of 4-(chloromethyl)-N-hydroxybenzimidoyl chloride and 4-(bromomethyl)-N-hydroxybenzimidoyl chloride as a light yellow oil in quantitative yield. The crude material was taken forward without further purification.

Preparation 16

Synthesis of 3-(chloromethyl)-N-hydroxybenzimidoyl chloride

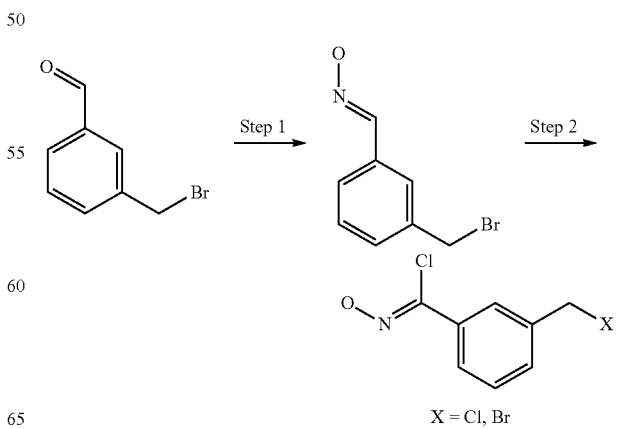

X = Cl, Br

Step 1: To a solution of 3-(bromomethyl)benzaldehyde (2.5 g, 12.6 mmol) in ethanol (13 mL) was added hydroxylamine (830 μL of 50% w/v, 12.6 mmol) at 0° C. The reaction mixture was allowed to warm to room temperature and stirred for 30 min. The solvent was removed under reduced pressure and the resulting residue partitioned between ethyl acetate and water. The organic layer was washed with saturated aq. NaHCO$_3$, dried over MgSO$_4$, filtered and concentrated in vacuo. Silica gel column chromatography (0-5% ethyl acetate/hexanes) provided 3-(bromomethyl)benzaldehyde oxime (2.7 g, 58%). LC/MS m/z 215.3 [M+H]$^+$. $^1$H NMR (400 MHz, DMSO-d6) δ 11.31 (s, 1H), 8.14 (s, 1H), 7.68 (s, 1H), 7.52 (d, J=7.5 Hz, 1H), 7.45 (d, J=7.7 Hz, 1H), 7.39 (t, J=7.6 Hz, 1H), 4.72 (s, 2H).

Step 2: To a solution of 3-(bromomethyl)benzaldehyde oxime (500 mg, 2.34 mmol) in DMF (1.5 mL) was added N-chlorosuccinimide (312 mg, 2.34 mmol) and the reaction mixture stirred at 50° C. for 2 h. Additional N-chlorosuccinimide (150 mg) was added after 2 h and the reaction mixture stirred for another 2 h, after which the reaction was poured onto ice and the aqueous layer was extracted with dichloromethane. The combined organic layers were dried over MgSO$_4$, filtered and concentrated. Silica gel chromatography (0-10% ethyl acetate/hexanes) provided a mixture of 3-(chloromethyl)-N-hydroxybenzimidoyl chloride and 3-(bromomethyl)-N-hydroxybenzimidoyl chloride (348 mg, 60%). The crude material was taken forward without further purification.

Example 5

Synthesis of 5-(5-amino-6-(3-(3-(1-aminoethyl)phenyl)isoxazol-5-yl)pyrazin-2-yl)-1-(1-cyclopropylethyl)pyridin-2(1H)-one Compound I-57

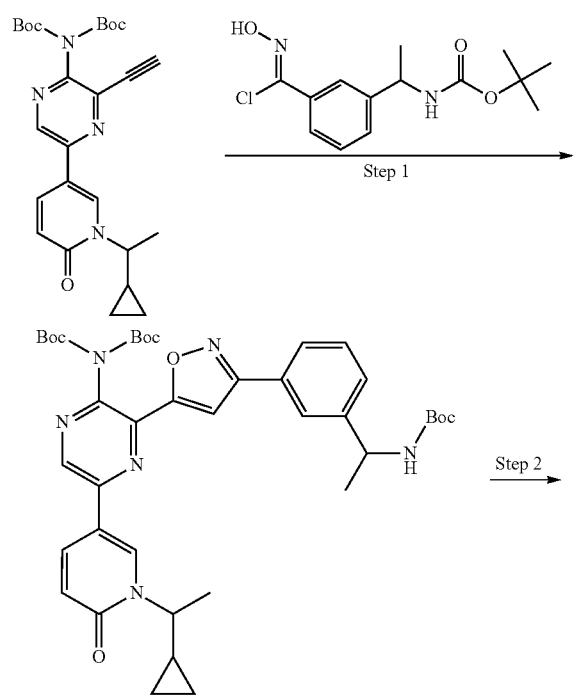

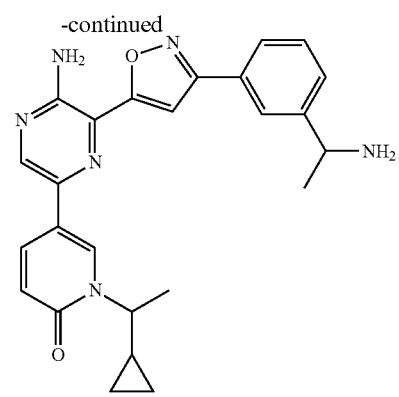

Step 1: To a solution of tert-butyl 1-(3-(chloro(hydroxyimino)methyl)phenyl)ethylcarbamate (942 mg, 3.15 mmol) and tert-butyl N-tert-butoxycarbonyl-N-[5-[1-(1-cyclopropylethyl)-6-oxo-3-pyridyl]-3-ethynyl-pyrazin-2-yl]carbamate (505 mg, 1.05 mmol) in THF (5 mL) was added triethylamine (440 μL, 3.15 mmol) dropwise at room temperature. The reaction was heated at 65° C. for 1 h, then cooled and poured onto ice. The aqueous solution was extracted with ethyl acetate, and the combined organics layers dried over Na$_2$SO$_4$, filtered and concentrated in vacuo. Silica gel chromatography (10-30% ethyl acetate/DCM) provided tert-butyl N-tert-butoxycarbonyl-N-[3-[3-[3-[1-(tert-butoxycarbonylamino)ethyl]phenyl]isoxazol-5-yl]-5-[1-(1-cyclopropylethyl)-6-oxo-3-pyridyl]pyrazin-2-yl]carbamate (273 mg, 35%). $^1$H NMR (400 MHz, DMSO-d$_6$) δ 9.35 (s, 1H), 8.87 (d, J=2.3 Hz, 1H), 8.42 (d, J=12.0 Hz, 1H), 7.94 (d, J=8.6 Hz, 2H), 7.85 (d, J=8.3 Hz, 1H), 7.61-7.42 (m, 3H), 6.62 (d, J=9.6 Hz, 1H), 4.80-4.67 (m, 1H), 4.25 (dd, J=15.7, 8.2 Hz, 1H), 1.62-1.55 (m, 1H), 1.52-1.48 (m, 3H), 1.42-1.29 (m, 30H), 0.78-0.65 (m, 1H), 0.49 (dd, J=11.7, 5.7 Hz, 2H), 0.23 (dd, J=9.3, 3.9 Hz, 1H).

Step 2: To a solution of tert-butyl N-tert-butoxycarbonyl-N-[3-[3-[3-[1-(tert-butoxycarbonylamino)ethyl]phenyl]isoxazol-5-yl]-5-[1-(1-cyclopropylethyl)-6-oxo-3-pyridyl]pyrazin-2-yl]carbamate (273 mg, 0.37 mmol) in anhydrous DCM (3 mL) was added HCl (3.7 mL of 4 M in dioxane, 14.7 mmol) and the reaction stirred for 4 h at room temperature. The solvents and excess HCl were removed under reduced pressure. The resulting solid was triturated with MeOH/Et$_2$O, filtered and dried to provide 5-[5-amino-6-[3-[3-(1-aminoethyl)phenyl]isoxazol-5-yl]pyrazin-2-yl]-1-(1-cyclopropylethyl)pyridin-2-one (140 mg, 78%). $^1$H NMR (400 MHz, DMSO-d$_6$) δ 8.82 (s, 1H), 8.57-8.47 (m, 4H), 8.22 (s, 1H), 8.17 (dd, J=9.5, 2.6 Hz, 1H), 8.02 (t, J=5.1 Hz, 1H), 7.77 (s, 1H), 7.72-7.60 (m, 2H), 6.54 (d, J=9.5 Hz, 1H), 4.59-4.49 (m, 1H), 4.24 (tt, J=13.6, 6.8 Hz, 1H), 1.58 (d, J=6.8 Hz, 3H), 1.56-1.51 (m, 1H), 1.47 (d, J=6.8 Hz, 3H), 0.68 (dd, J=14.3, 7.8 Hz, 1H), 0.52-0.41 (m, 2H), 0.26-0.15 (m, 1H).

Example 6

Synthesis of 5-(5-amino-6-(3-(3-((methylamino)methyl)phenyl)isoxazol-5-yl)pyrazin-2-yl)-1-isopropylpyridin-2(1H)-one (Compound I-49)

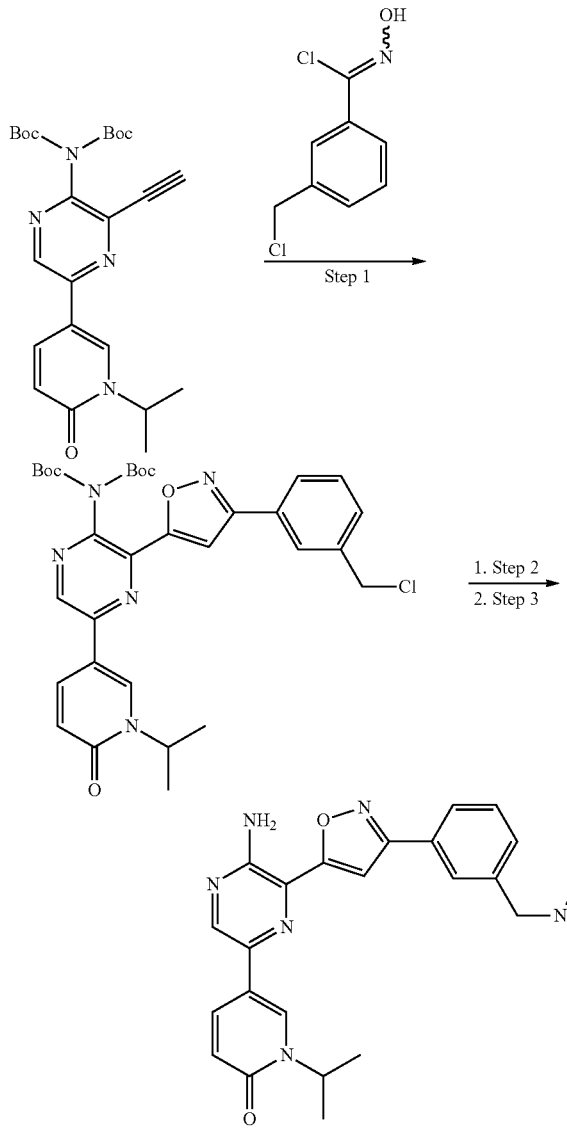

Step 1: To a solution of tert-butyl N-tert-butoxycarbonyl-N-[3-ethynyl-5-(1-isopropyl-6-oxo-3-pyridyl)pyrazin-2-yl]carbamate (300 mg, 0.66 mmol) and 3-(chloromethyl)-N-hydroxybenzimidoyl chloride (135 mg, 0.66 mmol) in THF (1.5 mL) was added triethylamine (110 μL, 0.79 mmol) dropwise. The reaction was heated at 65° C. for 1 h, then cooled and poured onto ice. The aqueous solution was extracted with ethyl acetate, and the combined organic layers dried over $Na_2SO_4$, filtered and concentrated in vacuo. Silica gel chromatography (0-60% ethyl acetate/hexanes) provided tert-butyl N-tert-butoxycarbonyl-N-[3-[3-[3-(chloromethyl)phenyl]isoxazol-5-yl]-5-(1-isopropyl-6-oxo-3-pyridyl)pyrazin-2-yl]carbamate (300 mg, 73%). $^1$H NMR (400 MHz, DMSO-$d_6$) δ 9.45 (s, 1H), 8.73 (s, 1H), 8.30 (dd, J=17.5, 14.8 Hz, 2H), 8.17-8.02 (m, 1H), 7.79 (d, J=7.9 Hz, 1H), 7.74-7.64 (m, 1H), 6.64 (d, J=9.5 Hz, 1H), 5.76 (s, 2H), 4.87 (s, 1H), 1.45 (d, J=7.2 Hz, 6H), 1.29 (s, 18H).

Step 2: To a solution of tert-butyl N-tert-butoxycarbonyl-N-[3-[3-[3-(chloromethyl)phenyl]isoxazol-5-yl]-5-(1-isopropyl-6-oxo-3-pyridyl)pyrazin-2-yl]carbamate (295 mg, 0.47 mmol) in DCM (3 mL) was added HCl (4.7 mL of 4 M in dioxane, 19.0 mmol). The reaction was stirred at room temperature for 3 h, and then heated at 40° C. for 1 h. The solvent and excess HCl were removed under reduced pressure to provide 5-[5-amino-6-[3-[3-(chloromethyl)phenyl]isoxazol-5-yl]pyrazin-2-yl]-1-isopropyl-pyridin-2-one in quantitative yield. $^1$H NMR (400 MHz, DMSO-$d_6$) δ 8.80 (s, 1H), 8.34 (d, J=2.2 Hz, 1H), 8.17 (dd, J=9.5, 2.4 Hz, 1H), 8.10 (s, 1H), 7.99 (d, J=7.0 Hz, 1H), 7.75 (s, 1H), 7.64-7.57 (m, 2H), 6.54 (d, J=9.5 Hz, 1H), 5.12 (m, 1 H), 4.88 (s, 2H), 1.41 (d, J=6.8 Hz, 6H).

Step 3: A mixture of 5-[5-amino-6-[3-[3-(chloromethyl)phenyl]isoxazol-5-yl]pyrazin-2-yl]-1-isopropyl-pyridin-2-one (90 mg, 0.20 mmol), methylamine (5.0 mL of 2 M in THF, 10.0 mmol) and $Na_2CO_3$ (62 mg, 0.59 mmol) was stirred for 16 h at 70° C. HPLC purification (10-99% $CH_3CN$/5 mM HCl) provided 5-[5-amino-6-[3-[3-(methylaminomethyl)phenyl]isoxazol-5-yl]pyrazin-2-yl]-1-isopropyl-pyridin-2-one (Compound I-49). LC/MS m/z 417.5 [M+H]$^+$. $^1$H NMR (400 MHz, DMSO-$d_6$) δ 9.37 (s, 2H), 8.81 (s, 1H), 8.35 (d, J=2.3 Hz, 1H), 8.25 (s, 1H), 8.16 (dd, J=9.5, 2.5 Hz, 1H), 8.06 (d, J=7.6 Hz, 1H), 7.75 (s, 1H), 7.71 (d, J=7.6 Hz, 1H), 7.64 (t, J=7.7 Hz, 1H), 6.54 (d, J=9.5 Hz, 1H), 5.13 (dt, J=13.7, 6.9 Hz, 1H), 4.23 (t, J=5.7 Hz, 2H), 2.58 (t, J=5.3 Hz, 3H), 1.42 (t, J=9.3 Hz, 6H).

Scheme D

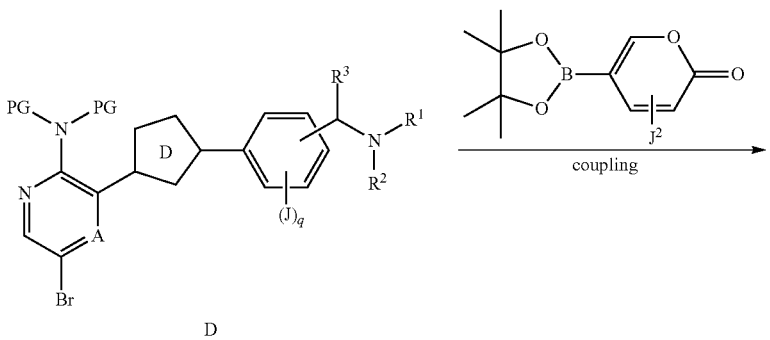

D

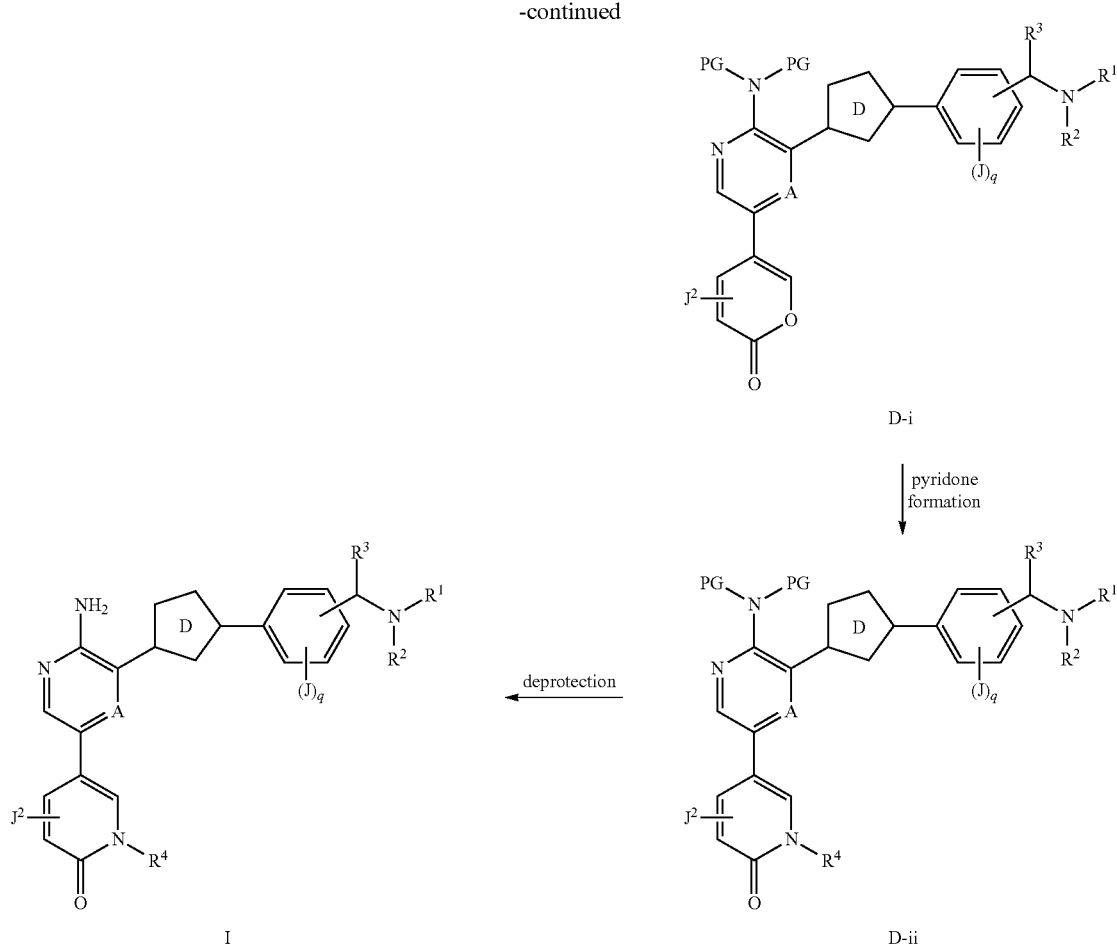

Scheme D depicts a general method for making compounds of Formula I. Compounds of Formula D are protected with a suitable amine protecting group PG such as, but not limited to BOC (Butyl Carbamate), and if $R^2$=H in —$NR^1R^2$, then $R^2$ is protected as PG. The pyrone ring system is introduced under metal-mediated coupling conditions, including but not limited to Suzuki coupling with an appropriate pyrone boronic ester or boronic acid to provide compounds of Formula D-i. The pyrone D-i is converted to the corresponding pyridone D-ii by treatment with either neat amine $NHR^1R^2$ or NHR'$R^2$ in an appropriate solvent such as, but not limited to, methanol (See *Bull. Korean Chem. Soc.* 2001, 22, 234-236). Removal of the nitrogen protecting group PG from compounds of Formula D-ii takes place under standard conditions known to those skilled in the art such as, but not limited to, treatment with HCl or TFA to provide compounds of Formula I. In addition, substituents $R^4$ on Formula I can undergo further functionalization by reactions known to those skilled in the art such as, but not limited to, hydrolysis, nucleophilic displacement reactions, acylation reactions, amide bond formation reactions, or further deprotection to reveal additional functionality. The intermediate 5-(4,4,5,5-tetramethyl-1,3,2-dioxaborolan-2-yl)-2H-pyran-2-one was synthesized as described in *Synlett*, 2003, 2, 253-255.

Example 7

Synthesis of 5-[5-amino-6-[5-[2-methyl-4-(methylaminomethyl)phenyl]-1,3,4-oxadiazol-2-yl]pyrazin-2-yl]-1-(2-dimethylaminoethyl)pyridin-2-one (Compound I-24)

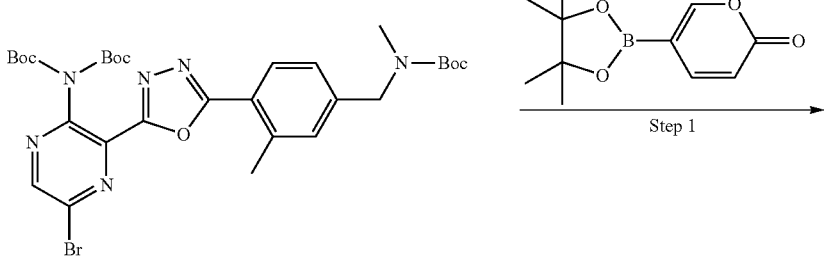

Step 1

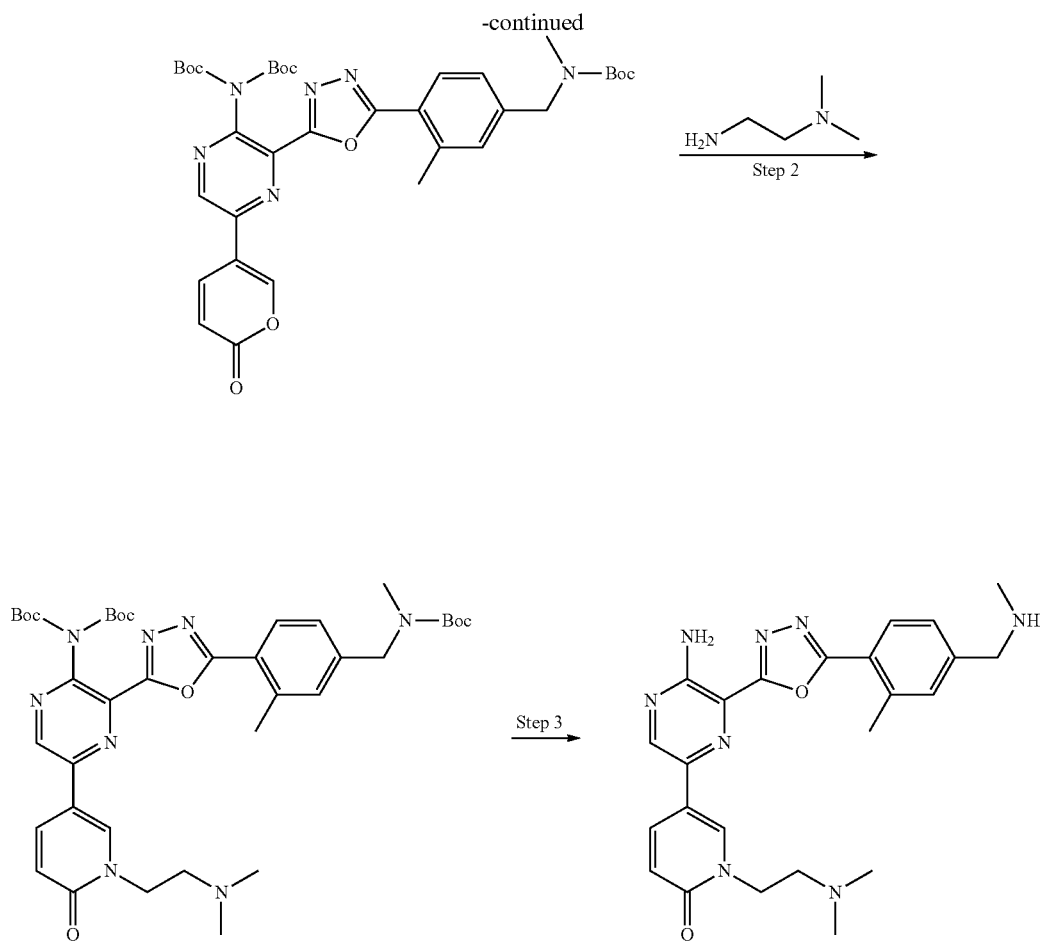

Step 1: Di-tert-butyl 5-bromo-3-(5-(4-((tert-butoxycarbonyl(methyl)amino)methyl)-2-methylphenyl)-1,3,4-oxadiazol-2-yl)pyrazin-2-yliminodicarbonate (545 mg, 0.807 mmol), 5-(4,4,5,5-tetramethyl-1,3,2-dioxaborolan-2-yl)-2H-pyran-2-one (197 mg, 0.887 mmol), and Pd(PPh$_3$)$_2$ (57 mg, 0.08 mmol) were dissolved in DME (4 mL) and aqueous Na$_2$CO$_3$ (800 µL, of 2 M, 1.60 mmol). The mixture was heated at 80° C. for 1 h under nitrogen atmosphere. The mixture was filtered through Celite and washed with ethyl acetate. The filtrate was concentrated and the crude material was partially purified by silica gel chromatography (0-50% ethyl acetate/hexanes) to give an off-white solid (423 mg, 76% yield). LC/MS m/z 691.3 [M+H]$^+$.

Step 2: Di-tert-butyl 3-(5-(4-((tert-butoxycarbonyl(methyl)amino)methyl)-2-methylphenyl)-1,3,4-oxadiazol-2-yl)-5-(2-oxo-2H-pyran-5-yl)pyrazin-2-yliminodicarbonate (85 mg, 0.1231 mmol) was dissolved in methanol (1 mL) and the mixture cooled to 0° C. N,N-dimethylethane-1,2-diamine (24 mg, 30 µL, 0.28 mmol) was added and the mixture stirred for 30 min, then allowed to warm to room temperature and stirred for 3 h. The mixture was concentrated in vacuo and silica gel chromatography (0-10% methanol/DCM) provided the desired product. LC/MS m/z 761.4 [M+H]$^+$.

Step 3: Di-tert-butyl 3-(5-(4-((tert-butoxycarbonyl(methyl)amino)methyl)-2-methylphenyl)-1,3,4-oxadiazol-2-yl)-5-(1-(2-(dimethylamino)ethyl)-6-oxo-1,6-dihydropyridin-3-yl)pyrazin-2-yliminodicarbonate from Step 2 was dissolved in 4 M HCl in dioxane (1 mL) and stirred at room temperature for 2 h. The solvent was removed under reduced pressure and the resulting solid triturated with Et$_2$O and filtered to provide 5-[5-amino-6-[5-[2-methyl-4-(methylaminomethyl)phenyl]-1,3,4-oxadiazol-2-yl]pyrazin-2-yl]-1-(2-dimethylaminoethyl)pyridin-2-one (8 mg, 12% yield from Step 1). LC/MS m/z 461.1 [M+H]$^+$. $^1$H NMR (400 MHz, DMSO-d$_6$) δ 10.38-10.23 (m, 1H), 9.38-9.28 (m, 2H), 8.84 (s, 1H), 8.57 (d, J=2.4 Hz, 1H), 8.27-8.10 (m, 2H), 7.65 (d, J=9.8 Hz, 4H), 6.65 (d, J=9.5 Hz, 1H), 4.41 (t, J=6.3 Hz, 2H), 4.20 (t, J=5.8 Hz, 3H), 3.57-3.45 (m, 4H), 2.87 (d, J=4.7 Hz, 7H), 2.75 (s, 3H), 2.58 (t, J=5.3 Hz, 4H).

Scheme E-1
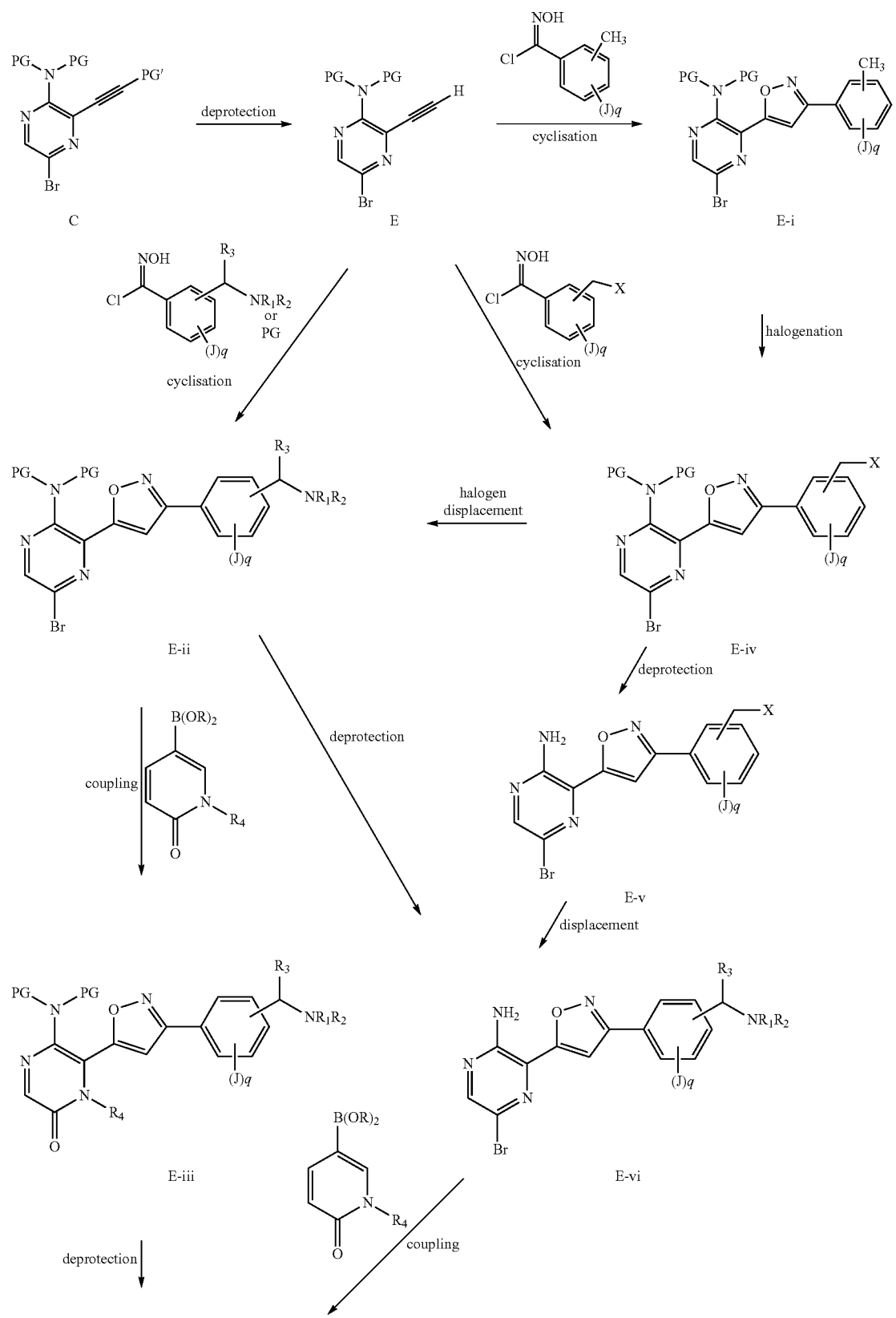

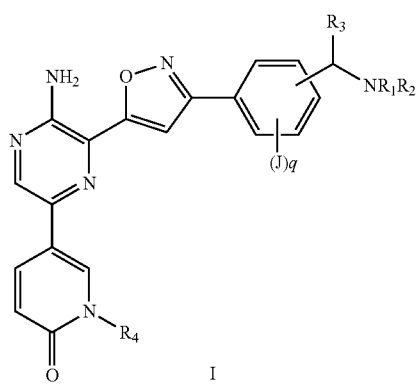

-continued

Scheme E-1 depicts a general method for making compounds of Formula I in which Ring D is isoxazole. Compound C contains amino protecting groups PG, and a alkyne protecting group PG'. Suitable PG include, but are not limited to Boc (tert-butoxycarbonyl); Suitable PG' include, but are not limited to, TMS, TES or TIPS. Compounds of Formula C are selectively deprotected using conditions such as but not limited to $K_2CO_3$ or fluoride to remove the alkyne protecting group PG' to yield compounds of Formula E. The assembly of the 3,5-disubstituted isoxazole can be achieved through 1,3-dipolar cycloaddition of the terminal acetylene of compound E with an appropriate chloro oxime, under basic conditions, to provide the desired isoxazole in compounds of Formula Ei, Eii or Eiv. Suitable conditions include, but are not limited to use of triethylamine.

Compounds of Formula E-i are subjected to halogenation of the benzylic methyl with reagents such as, but not limited to NBS to give compounds of Formula E-iv, where X is a halogen. Compounds of Formula E-iv can also be made directly with the halogen already in place on the chloro oxime prior to cyclisation. The leaving group X on compounds of Formula E-iv may be displaced by an amine of Formula $NHR_1R_2$, leading to compounds of Formula E-ii. Compounds of Formula E-ii can be made directly from 1,3-dipolar cycloaddition with a chloro oxime which contains the appropriate amine substitution. Removal of the amino protecting group PG from compounds of Formula E-ii occurs under standard conditions known to those skilled in the art to generate intermediates E-vi. Alternatively, such a PG deprotection can be performed from compounds of Formula E-iv to provide compounds of Formula E-v, prior to amine displacement which will furnish compounds of Formula E-vi.

From compounds of Formula E-ii, the pyridone ring system is introduced under metal-mediated coupling conditions, including but not limited to Suzuki coupling with an appropriate boronic ester or boronic acid to provide compounds of Formula E-iii. Removal of the amino protecting group PG from compounds of Formula E-iii takes place under standard conditions known to those skilled in the art such as, but not limited to, treatment with HCl or TFA to provide compounds of Formula I in which Ring D is isoxazole.

Alternatively, the pyridone ring system can be introduced on compounds of Formula E-vi using conditions as described above to give directly compounds of Formula I. In addition, compounds of Formula I can undergo further functional group transformations on substituent $R_4$, using reactions known to those skilled in the art such as, but not limited to, hydrolysis, nucleophilic displacement reactions, acylation reactions, amide bond formation reactions, or further deprotection to reveal additional functionality.

Preparations 17-24 and Examples 9-11 Relate to Schemes E-1.

Preparation 17

Synthesis of Di-tert-butyl(5-bromo-3-ethynylpyrazin-2-yl)carbamate

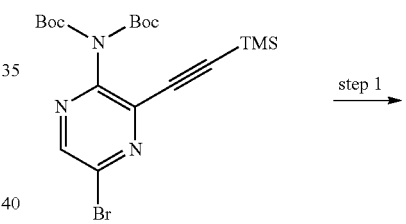

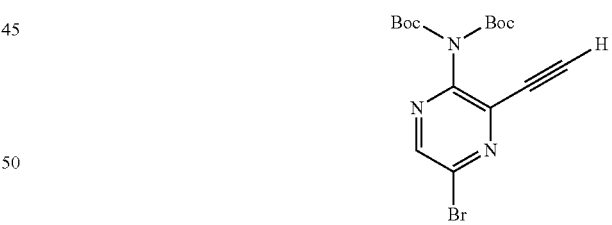

Step 1: Sodium carbonate (77.30 mL of 2 M, 154.6 mmol) was added to a suspension of tert-butyl N-[5-bromo-3-(2-trimethylsilylethynyl)pyrazin-2-yl]-N-tert-butoxycarbonyl-carbamate (60.6 g, 128.8 mmol) in DMF (303.0 mL) and heated at 75° C. for 45 min. The reaction mixture was allowed to cool to room temperature and then diluted with water (900 mL). The precipitate was left to stand for 30 min and was isolated by filtration and washed with water (300 mL). The yellow powder was transferred to a flask and triturated with ethyl acetate (300 mL) to give the sub-titled product as a white powder (48.39 g, 94% yield). $^1$H NMR (400.0 MHz, DMSO-$d_6$) 1.43 (18H, s), 3.53 (1H, s), 8.55 (1H, s); MS (ES$^+$) 243.9, MS (ES$^-$) 334.2.

Preparation 18

Synthesis of Di-tert-butyl(5-bromo-3-(3-(4-(chloromethyl)phenyl)isoxazol-5-yl)pyrazin-2-yl)carbamate

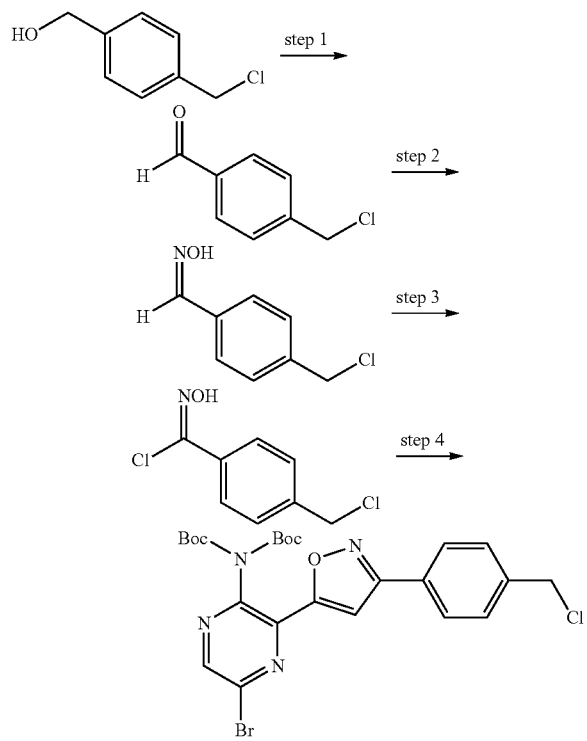

Step 1: MnO₂ (51.08 g, 587.5 mmol) was added to a solution of [4-(chloromethyl)phenyl]methanol (9.2 g, 58.75 mmol) in DCM (608 mL). The mixture was stirred at room temperature for 48 h. The oxidant was removed by filtration, and the filtrate was concentrated in vacuo to give 4-(chloromethyl)benzaldehyde as a white solid (7.5 g, 83% yield). ¹H NMR (400.0 MHz, CDCl₃) 4.65 (2H, s), 7.58 (2H, d), 7.91 (2H, d) and 10.05 (H, s).

Step 2: Hydroxlamine hydrochloride (10.11 g, 145.5 mmol) was added to a solution of 4-(chloromethyl)benzaldehyde (7.5 g, 48.51 mmol) in ethanol. The mixture was heated at 50° C. for 3 h. After this time the reaction mixture was concentrated in vacuo. The residue was partitioned between DCM and water. The organic layer was separated, dried over MgSO₄, filtered and concentrated in vacuo to give (1E)-4-(chloromethyl)benzaldehyde oxime as a white solid (8.1 g, 98% yield). ¹H NMR (400.0 MHz, DMSO-d₆) 4.75 (2H, s), 7.45 (2H, d), 7.60 (2H, d), 8.15 (1H, s), 11.3 (H, s)

Step 3: (1E)-4-(chloromethyl)benzaldehyde oxime (1.662 g, 9.801 mmol) was dissolved in DMF (34.99 mL), N-chlorosuccinimide (1.570 g, 11.76 mmol) was added followed by a solution of HCl in dioxane (15.70 mL of 4 M, 62.82 mmol). The mixture was stirred at room temperature for 30 min. After this time water was added, and the mixture was extracted with ethyl acetate. The organic layer was separated, washed with water, saturated brine, dried over Na₂SO₄, filtered and concentrated in vacuo to give (1Z)-4-(chloromethyl)-N-hydroxy-benzimidoyl chloride as a solid (2.0 g, 100% yield). ¹H NMR (400.0 MHz, CDCl₃) 4.63 (2H, s), 7.45 (2H, d), 7.86 (2H, d) and 8.36 (H, s).

Step 4: Triethylamine (1.128 g, 1.554 mL, 11.15 mmol) was added to a solution of tert-butyl N-(5-bromo-3-ethynyl-pyrazin-2-yl)-N-tert-butoxycarbonyl-carbamate (3.7 g, 9.291 mmol) and (1Z)-4-(chloromethyl)-N-hydroxy-benzimidoyl chloride (1.994 g, 9.774 mmol) in DCM (26.24 mL). The mixture was stirred at room temperature for 18 h. The reaction mixture was partitioned between DCM and water. The organic layer was separated, dried over MgSO₄, filtered and concentrated in vacuo to give the crude product as an oil. Purification by silica chromatography eluting with 10-40% ethyl acetate/petroleum ether gave the sub-titled product as a pale yellow solid (3.19 g, 66% yield). ¹H NMR (400.0 MHz, CDCl₃) 1.41 (18H, s), 4.66 (2H, s), 7.37 (1H, s), 7.54 (2H, d, J=8.2), 7.90 (2H, d, J=8.2 Hz) and 8.66 (1H, s); MS (ES⁺) 410.9, MS (ES⁻) 464.8.

Preparation 19

Synthesis of Di-tert-butyl(5-bromo-3-(3-(4-(bromomethyl)phenyl)isoxazol-5-yl)pyrazin-2-yl)carbamate

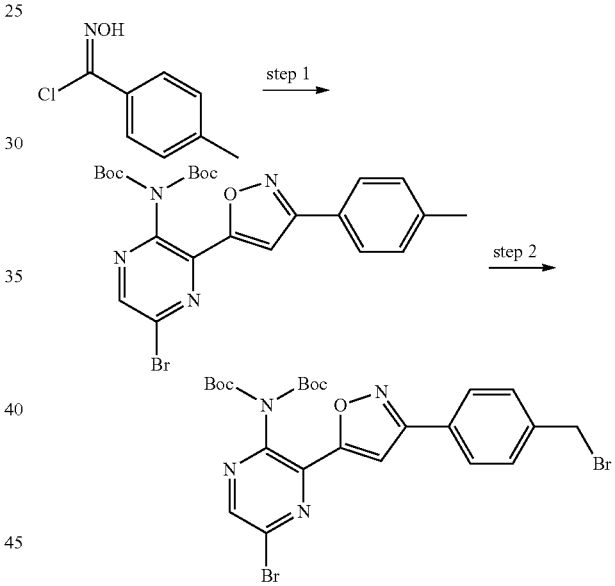

Step 1: N-hydroxy-4-methyl-benzimidoyl chloride (1.548 g, 9.127 mmol) and tert-butyl N-(5-bromo-3-ethynyl-pyrazin-2-yl)-N-tert-butoxycarbonyl-carbamate (4 g, 10.04 mmol) were dissolved in DMF (5.540 mL). Et₃N (1.108 g, 1.526 mL, 10.95 mmol) was added dropwise. The mixture was stirred at room temperature for 45 min followed by heating to 65° C. for 1 h. After this time the reaction mixture was cooled to room temperature and diluted with ethyl acetate (5 mL) and water (5 mL) and the layers separated. The aqueous layer was extracted further with ethyl acetate (2×5 mL) and the combined organic extracts were washed with water (3×10 mL), dried over MgSO₄, filtered and concentrated in vacuo to give the crude product. Purification by silica chromatography eluting with 0-30% ethyl acetate/petroleum ether to give tert-butyl N-[5-bromo-3-[3-(p-tolyl)isoxazol-5-yl]pyrazin-2-yl]-N-tert-butoxycarbonyl-carbamate as a solid (3.5 g, 60% yield). ¹H NMR (400.0 MHz, CDCl₃) 1.4 (18H, s), 2.45 (3H, s), 7.35 (1H, s), 7.35 (2H, d), 7.8 (2H, d) and 8.65 (1H, s); MS (ES⁺) 376.9, 431.0.

Step 2: Tert-butyl N-[5-bromo-3-[3-(p-tolyl)isoxazol-5-yl]pyrazin-2-yl]-N-tert-butoxycarbonyl-carbamate (1.800 g, 3.387 mmol) was dissolved in fluorobenzene (15 mL). 2-(1-cyano-1-methyl-ethyl)azo-2-methyl-propanenitrile (111.2 mg, 0.6774 mmol) and 1-bromopyrrolidine-2,5-dione (723.3 mg, 4.064 mmol) were added. The mixture was heated to 90° C. for 1 h. After this time the solids were removed by filtration and the filtrate was concentrated in vacuo to give the sub-titled product as an oil (2 g, 70% purity, 68% yield). $^1$H NMR (400.0 MHz, CDCl$_3$) 1.5 (18H, s), 4.55 (2H, s), 7.35 (1H, s), 7.55 (2H, d), 7.85 (2H, d) and 8.65 (1H, s), MS (ES$^+$) 454.8, 510.8.

Preparation 20

Synthesis of Di-tert-butyl(5-bromo-3-(3-(4-((isopropylamino)methyl)phenyl)isoxazol-5-yl)pyrazin-2-yl) carbamate

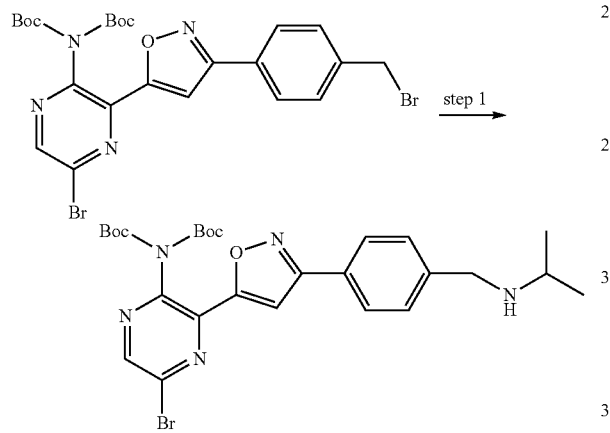

Step 1: Tert-butyl N-[5-bromo-3-[3-[4-(bromomethyl)phenyl]isoxazol-5-yl]pyrazin-2-yl]-N-tert-butoxycarbonyl-carbamate (100 mg, 0.1639 mmol) was added to a solution of propan-2-amine (96.88 mg, 140.8 µL, 1.639 mmol) in DMF (2 mL). The mixture was stirred at room temperature for 1 h. After this time the reaction mixture was diluted with ethyl acetate, washed with water and brine. The organic layer was separated and concentrated in vacuo to give the crude product. Purification by silica chromatography eluting with 20% ether/petroleum ether gave the sub-titled product as a solid. This material was not completely clean and was used as such in the next step (90 mg, 93% yield). MS (ES$^+$) 590.0.

Preparation 21

Synthesis of tert-butyl N-[[4-[5-[3-[bis(tert-butoxycarbonyl)amino]-6-bromo-pyrazin-2-yl]isoxazol-3-yl]phenyl]methyl]-N-cyclopropyl-carbamate

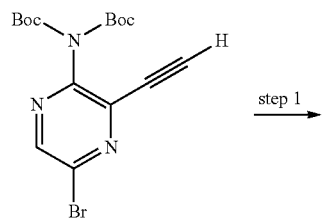

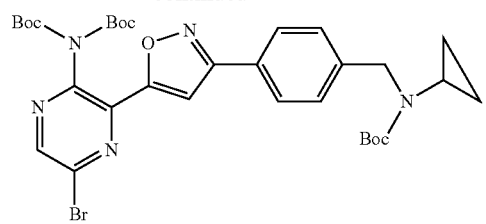

Step I: NCS (204.6 mg, 1.532 mmol) was added to a solution of tert-butyl N-cyclopropyl-N-[[4-[(E)-hydroxyiminomethyl]phenyl]methyl]carbamate in DMF (3 mL) and the mixture heated at 55° C. for 30 min. The reaction mixture was allowed to cool to room temperature, and tert-butyl N-(5-bromo-3-ethynyl-pyrazin-2-yl)-N-tert-butoxycarbonyl-carbamate (610 mg, 1.532 mmol) and TEA (186.0 mg, 256.2 µL.838 mmol) was added dropwise. The mixture was stirred at room temperature for 45 min followed by heating to 65° C. for 2 hr. After this time the reaction mixture was allowed to cool to room temperature and diluted with ethyl acetate (5 mL) and water (5 mL) and the layers separated. The aqueous layer was extracted further with ethyl acetate (2×5 mL) and the combined organic extracts were dried over MgSO$_4$, filtered and concentrated in vacuo to give a solid. Purification by silica chromatography eluting with 10-30% ethyl acetate/petroleum ether gave the sub-titled product (430 mg, 41% yield). $^1$H NMR (400.0 MHz, CDCl$_3$) 0.66-0.77 (4H, m), 1.40 (18H, s), 1.48 (9H, s), 2.51 (1H, m), 3.25-3.31 (2H, m), 4.50 (2H, s), 7.35-7.38 (3H, m), 7.83-7.89 (2H, m) and 8.65 (1H, s); MS (ES$^+$) 532.0, 588.1.

Preparation 22

Synthesis of Di-tert-butyl(3-[3-[4-((cyclopropylamino)methyl)phenyl)isoxazol-5-yl)-5-(6-oxo-1,6-dihydropyridin-3-yl)pyrazin-2-yl)carbamate

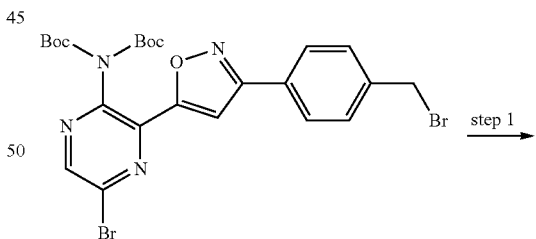

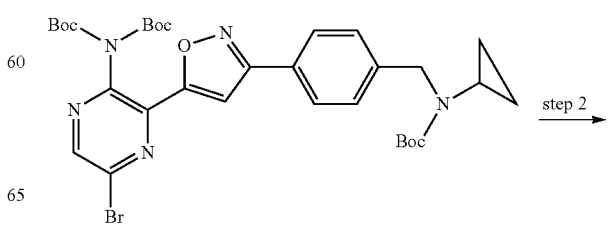

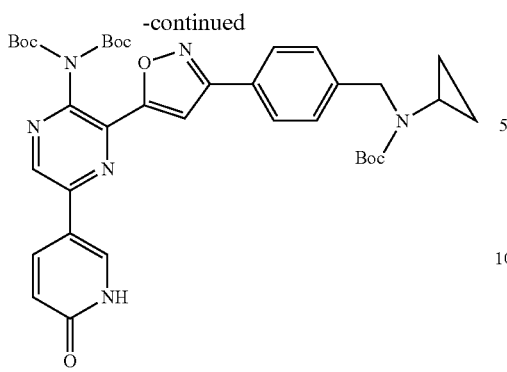

Step 1: Tert-butyl N-[5-bromo-3-[3-[4-(bromomethyl)phenyl]isoxazol-5-yl]pyrazin-2-yl]-N-tert-butoxycarbonyl-carbamate (100 mg, 0.1639 mmol) was added to a solution of cyclopropanamine (93.58 mg, 113.6 µL, 1.639 mmol) in DMF (2 mL). The mixture was stirred at room temperature for 1 hr. After this time the reaction mixture was diluted with ethyl acetate, washed with water and brine and concentrated to a solid in vacuo. The solid was dissolved in DCM (10 mL) and triethylamine (16.59 mg, 22.85 µL, 0.1639 mmol) and di-tert-butyl carbonate (35.77 mg, 37.65 µL, 0.1639 mmol) was added. The resulting mixture was stirred at room temperature for 1 h and then concentrated to an oil in vacuo. Purification by silica chromatography eluting with 20% ether/petroleum gave tert-butyl N[[4-[5-[3-[bis(tert-butoxycarbonyl)amino]-6-bromo-pyrazin-2-yl]isoxazol-3-yl]phenyl]methyl]-N-cyclopropyl-carbamate (80 mg, 71% yield). $^1$H NMR (400.0 MHz, CDCl$_3$) 0.66-0.77 (4H, m), 1.40 (18H, s), 1.48 (9H, s), 2.51 (1H, m), 3.25-3.31 (2H, m), 4.50 (2H, s), 7.35-7.38 (3H, m), 7.83-7.89 (2H, m) and 8.65 (1H, s); MS (ES$^+$) 532.0, 588.1.

Step 2: Tert-butyl N-[[-4-[5-[3-[bis(tert-butoxycarbonyl)amino]-6-bromo-pyrazin-2-yl]isoxazol-3-yl]phenyl]methyl]-N-cyclopropyl-carbamate (800 mg, 1.165 mmol) was dissolved in dioxane (4 mL) and 5-(4,4,5,5-tetramethyl-1,3,2-dioxaborolan-2-yl)pyridin-2-ol (257.5 mg, 1.165 mmol) was added. The reaction mixture was degassed with 3× nitrogen/vacuum cycles. Pd(dppf)Cl$_2$.DCM (23.78 mg, 0.02912 mmol) was added and the reaction was degassed a further 3 times. An aqueous solution of sodium carbonate (1.747 mL of 2 M, 3.495 mmol) was added and the reaction mixture was heated at 80° C. for 4 h. The reaction was cooled to room temperature and diluted with ethyl acetate and water. The aqueous layer was further extracted with ethyl acetate and the combined organic extracts were washed with brine (×2), dried over MgSO$_4$, filtered and concentrated in vacuo. Purification by automated silica chromatography eluting with 0-100% ethyl acetate/petroleum ether gave the sub-titled product as a beige solid (505 mg, 62% yield). $^1$H NMR (400 MHz, CDCl$_3$) 0.69-0.78 (4H, m), 1.42 (18H, s), 1.50 (9H, s), 2.54 (1H, m), 4.52 (2H, s), 6.82-6.85 (H, d), 7.35 (H, s), 7.40-7.42 (2H, d), 7. 88-7.90 (2H, d), 8.29-8.32 (1H, m), 8.42 (1H, s), 8.83 (1H, s) and 12.75 (1H, m); MS (ES$^+$) 545.1, 601.2, 701.2, MS (ES$^-$) 701.2.

Preparation 23

Synthesis of 1-((4-(5-(3-amino-6-bromopyrazin-2-yl)isoxazol-3-yl)benzyl)amino)-2-methylpropan-2-ol

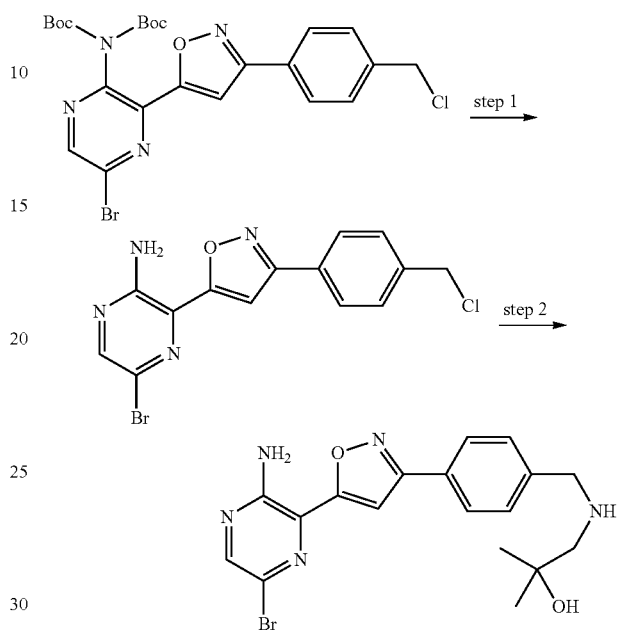

Step 1: Tert-butyl N-[5-bromo-3-[3-[4-(chloromethyl)phenyl]isoxazol-5-yl]pyrazin-2-yl]-N-tert-butoxycarbonyl-carbamate (500 mg, 0.8836 mmol) was dissolved in DCM (25 mL). TFA (2.500 mL) was added and the mixture was stirred at room temperature for 15 min. The reaction mixture was concentrated in vacuo to give 5-bromo-3-[3-[4-(chloromethyl)phenyl]isoxazol-5-yl]pyrazin-2-amine as a yellow solid that was used without further purification (330 mg, 99% yield). MS (ES$^-$) 364.9.

Step 2: 1-amino-2-methyl-propan-2-ol (78.75 mg, 0.8835 mmol), 5-bromo-3-[3-[4-(chloromethyl)phenyl]isoxazol-5-yl]pyrazin-2-amine (32.30 mg, 0.08835 mmol) and DIPEA (22.84 mg, 30.78 µL, 0.1767 mmol) were combined in NMP (1 mL) and the reaction mixture was heated in a microwave reactor at 110° C. for 30 min. The reaction mixture was concentrated in vacuo and the sub-titled product was used crude. MS (ES$^+$) 420.5 (ES$^-$) 418.6.

Preparation 24

Synthesis of 5-bromo-3-(3-(2-fluoro-4-((methylamino)methyl)phenyl)isoxazol-5-yl)pyrazin-2-amine

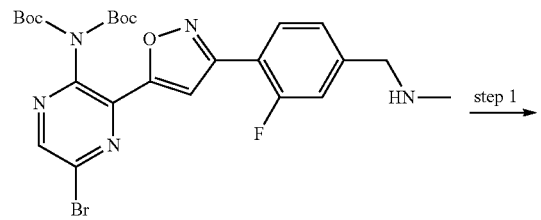

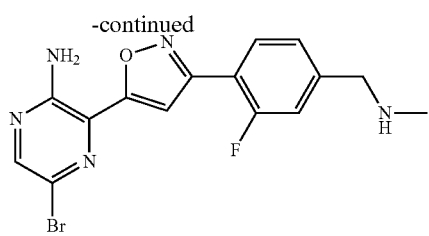

Step 1: Tert-butyl N-[[4-[5-[3-[bis(tert-butoxycarbonyl)amino]-6-bromo-pyrazin-2-yl]isoxazol-3-yl]-3-fluoro-phenyl]methyl]-N-methyl-carbamate (50 mg, 0.07369 mmol) was stirred at room temperature for 2 h in a mixture of DCM (5 mL) and TFA (0.5 mL). The reaction mixture was concentrated in vacuo. The residue was partitioned between DCM and saturated aqueous bicarbonate solution. The combined organic extracts were dried over MgSO$_4$, filtered and concentrated in vacuo to give the sub-titled product as an oil. The product was used without any further purification. MS (ES$^+$) 380.5

Example 9

Synthesis of 5-[5-amino-6-[3-[4-[(cyclopropylamino)methyl]phenyl]isoxazol-5-yl]pyrazin-2-yl]-1H-pyridin-2-one (Compound I-111)

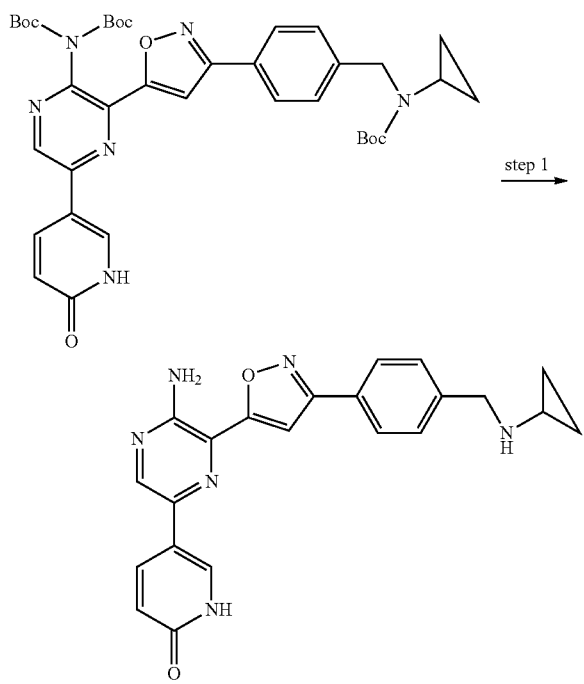

Step 1: Tert-butyl N-[[4-[5-[3-[bis(tert-butoxycarbonyl)amino]-6-(6-oxo-1H-pyridin-3-yl)pyrazin-2-yl]isoxazol-3-yl]phenyl]methyl]-N-cyclopropyl-carbamate (29.99 mg, 0.04280 mmol) was dissolved in DCM (3 mL) followed by the addition of TFA (146.4 mg, 98.92 µL, 1.284 mmol). The mixture was stirred at room temperature for 1 h and then concentrated to an oil. Purification was purified by reverse phase preparative HPLC [Waters Sunfire C18, 10 mM, 100 Å column, gradient 10%-95% B (solvent A: 0.05% TFA in water; solvent B: CH$_3$CN) over 16 minutes at 25 mL/min] gave the sub-titled product (9.5 mg, 44% yield). H$^1$ NMR (400.0 MHz, DMSO-d$_6$) 0.8-0.9 (4H, m), 2.6-2.65 (1H, m), 4.25-4.3 (2H, m), 6.5 (1H, d), 6.9 (2H, s), 7.65 (2H, d), 7.78 (1H, s), 8.05 (2H, d), 8.1-8.12 (1H, m), 8.7 (1H, s), 8.8 (2H, brs); MS (ES$^+$) 401.1, MS (ES$^-$) 399.1

Example 10

Synthesis of 2-[5-[5-amino-6-[3-[4-[(cyclopropylamino)methyl]-2-fluoro-phenyl]isoxazol-5-yl]pyrazin-2-yl]-2-oxo-1-pyridyl]-2-ethyl-butanenitrile (Compound I-135)

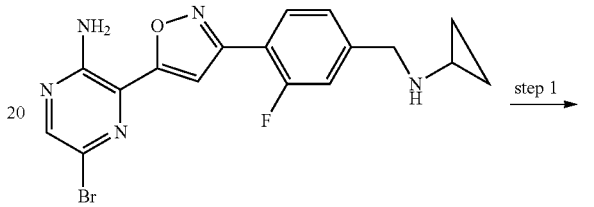

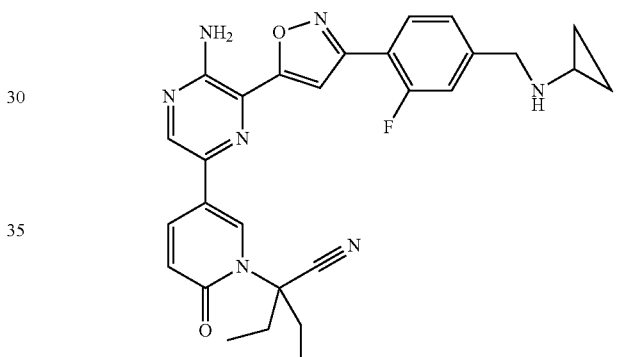

Step 1: 5-bromo-3-[3-[4-[(cyclopropylamino)methyl]-2-fluoro-phenyl]isoxazol-5-yl]pyrazin-2-amine (28.70 mg, 0.071 mmol), 2-ethyl-242-oxo-5-(4,4,5,5-tetramethyl-1,3,2-dioxaborolan-2-yl)-1-pyridyl]butanenitrile (35 mg, 0.1107 mmol), K$_3$PO$_4$ (106.5 µL of 2 M, 0.2130 mmol), Pd(PPh$_3$)$_4$ (8.204 mg, 0.007 mmol) in toluene (2 mL) and EtOH (0.5 mL) was degassed and then heated in a microwave reactor a 80° C. for 20 min. The reaction mixture was concentrated in vacuo. The residue was partitioned between DCM and water. The layers were separated and the organic extract was dried over MgSO$_4$, filtered and concentrated in vacuo to give an oil. Purification was purified by reverse phase preparative HPLC [Waters Sunfire C18, 10 mM, 100 Å column, gradient 10%-95% B (solvent A: 0.05% TFA in water; solvent B: CH$_3$CN) over 16 minutes at 25 mL/min] gave the sub-titled product (3.44 mg, 9.44% yield). H$^1$ NMR (400.0 MHz, CDCl$_3$) 8.44 (d, J=2.2 Hz, 1H), 8.33 (s, 1H), 7.93-7.87 (m, 2H), 7.39 (d, J=3.3 Hz, 1H), 7.18-7.15 (m, 3H), 6.59 (d, J=9.5 Hz, 1H), 5.78 (s, 2H), 3.84 (s, 2H), 2.88 (m, 2H), 2.18 (m, 2H), 2.12 (m, 1H), 1.00 (t, J=7.4 Hz, 6H) and 0.41-0.33 (m, 4H) ppm; MS (ES$^+$) 514.0, MS (ES$^-$) 512.0.

Example 11

Synthesis of 2-(5-(5-amino-6-(3-(4-((methylamino)methyl)phenyl)isoxazol-5-yl)pyrazin-2-yl)-2-oxopyridin-1(2H)-yl)-N,N-diethylpropanamide (Compound I-101)

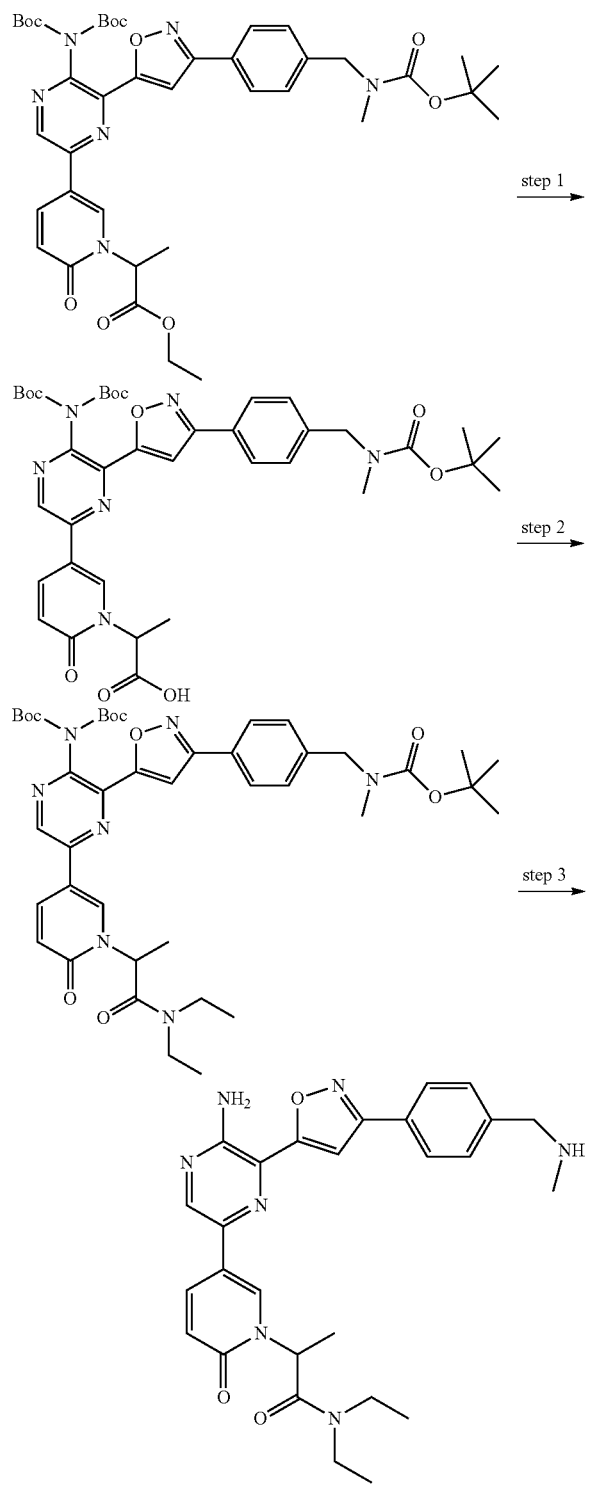

Step 1: To a solution of ethyl 2-[5-[5-[bis(tert-butoxycarbonyl)amino]-6-[3-[4-[[tert-butoxycarbonyl(methyl)amino]methyl]phenyl]isoxazol-5-yl]pyrazin-2-yl]-2-oxo-1-pyridyl]propanoate (2.7 g, 3.485 mmol) in THF (30 mL) was added LiOH (8.710 mL of 2 M, 17.42 mmol). The resulting solution was stirred at 40° C. for 4 hr. After this time the reaction mixture was neutralised with HCl and then extracted with EtOAc. The organics layer was separated, dried over MgSO$_4$, filtered and concentrated in vacuo to give 2-[5-[5-[bis(tert-butoxycarbonyl)amino]-6-[3-[4-[[tert-butoxycarbonyl(methyl)amino]methyl]phenyl]isoxazol-5-yl]pyrazin-2-yl]-2-oxo-1-pyridyl]propanoic acid as a yellow solid (1.2 g, 46% yield).

Step 2: To a solution of 2-[5-[5-[bis(tert-butoxycarbonyl)amino]-6-[3-[4[[tert-butoxycarbonyl(methyl)amino]methyl]phenyl]isoxazol-5-yl]pyrazin-2-yl]-2-oxo-1-pyridyl]propanoic acid (100 mg, 0.1339 mmol), diethoxyphosphorylformonitrile (21.84 mg, 0.1339 mmol), and Et$_3$N (40.65 mg, 55.99 µL, 0.4017 mmol) in 1,2-dimethoxyethane (1 mL) was added N-diethylamine solution in THF (133.9 µL of 2 M, 0.2678 mmol) and the resulting solution was stirred overnight at room temperature. After this time, water was added, followed by DCM (5 mL) and the organic layer separated and the organic solution containing di-tert-butoxycarbonyl(3-(3-(4-(((tert-butoxycarbonyl)(methyl)amino)methyl)phenyl)isoxazol-5-yl)-5-(1-(1-(diethylamino)-1-oxopropan-2-yl)-6-oxo-1,6-dihydropyridin-3-yl)pyrazin-2-yl)carbamate was used directly in the next step.

Step 3: HCl (1 mL of 1M, 1.000 mmol) was added the solution of DCM containing di-tert-butoxycarbonyl(3-(3-(4-(((tert-butoxycarbonyl)(methyl)amino)methyl)phenyl)isoxazol-5-yl)-5-(1-(1-(diethylamino)-1-oxopropan-2-yl)-6-oxo-1,6-dihydropyridin-3-yl)pyrazin-2-yl)carbamate and the resulting solution was stirred for 1 hr. After this time the reaction mixture was passed through an SCX cartridge and the cartridge was washed with MeOH. The product mixture was eluted off with MeOH/NH$_3$. Purification was purified by reverse phase preparative HPLC [Waters Sunfire C18, 10 mM, 100 Å column, gradient 10%-95% B (solvent A: 0.05% TFA in water; solvent B: CH$_3$CN) over 16 minutes at 25 mL/min] gave the sub-titled product (3.89 mg, 6% yield). MS (ES$^+$) 502.0, MS (ES$^-$) 500.0.

Scheme E-2

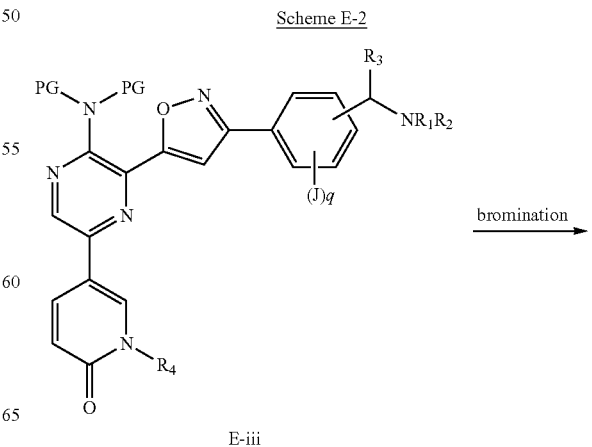

E-iii

153
-continued

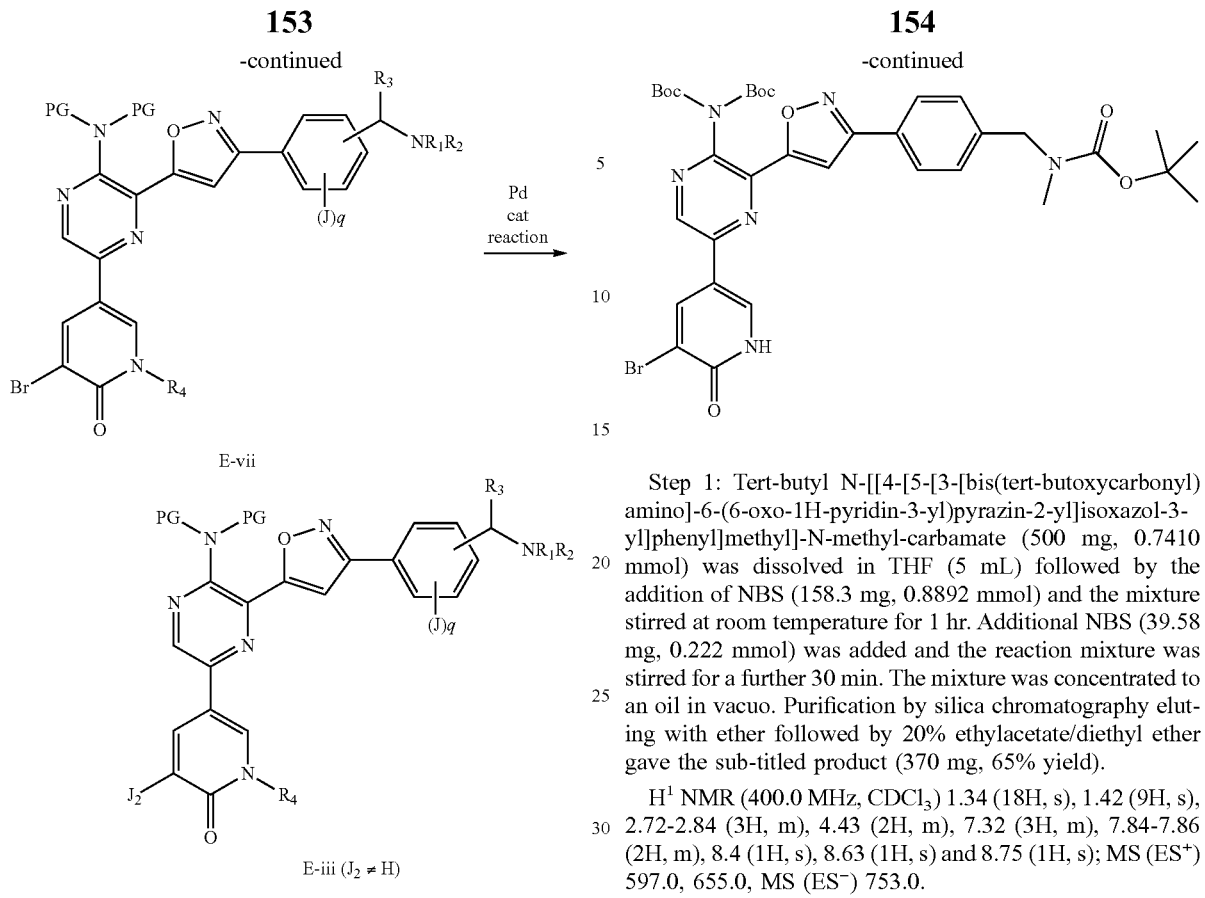

E-vii

E-iii (J₂ ≠ H)

Scheme E-2 depicts a general method for the preparation of compounds of Formula E-iii where the pyridone nucleus is further functionalized by substituent J₂ (with J₂≠H). Compounds of Formula E-iii can be subjected to halogenation with reagent such as, but not limited to NBS to give compounds of Formula E-vii. Compounds of Formula E-vii were used as coupling partners in metal-mediated coupling reactions, including but not limited to Suzuki coupling, with an appropriate boronic ester or boronic acid to provide compounds of Formula E-iii where the pyridone nucleus is further functionalized by substituent J₂ (with H₂≠H). Preparation 25 and Example 12 Relate to Scheme E-2

Preparation 25

Synthesis of tert-butyl(5-(5-bromo-6-oxo-1,6-dihydropyridin-3-yl)-3-(3-(4-(((tert-butoxycarbonyl)(methyl)amino)methyl)phenyl)isoxazol-5-yl)pyrazin-2-yl)(tert-butoxycarbonyl)carbamate 154
-continued Step 1: Tert-butyl N-[[4-[5-[3-[bis(tert-butoxycarbonyl)amino]-6-(6-oxo-1H-pyridin-3-yl)pyrazin-2-yl]isoxazol-3-yl]phenyl]methyl]-N-methyl-carbamate (500 mg, 0.7410 mmol) was dissolved in THF (5 mL) followed by the addition of NBS (158.3 mg, 0.8892 mmol) and the mixture stirred at room temperature for 1 hr. Additional NBS (39.58 mg, 0.222 mmol) was added and the reaction mixture was stirred for a further 30 min. The mixture was concentrated to an oil in vacuo. Purification by silica chromatography eluting with ether followed by 20% ethylacetate/diethyl ether gave the sub-titled product (370 mg, 65% yield).

$H^1$ NMR (400.0 MHz, $CDCl_3$) 1.34 (18H, s), 1.42 (9H, s), 2.72-2.84 (3H, m), 4.43 (2H, m), 7.32 (3H, m), 7.84-7.86 (2H, m), 8.4 (1H, s), 8.63 (1H, s) and 8.75 (1H, s); MS ($ES^+$) 597.0, 655.0, MS ($ES^-$) 753.0.

Example 12

Synthesis of 3-[4-(methylaminomethyl)phenyl]isoxazol-5-yl]pyrazin-2-yl]-3-phenyl-1H-pyridin-2-one (Compound I-123)

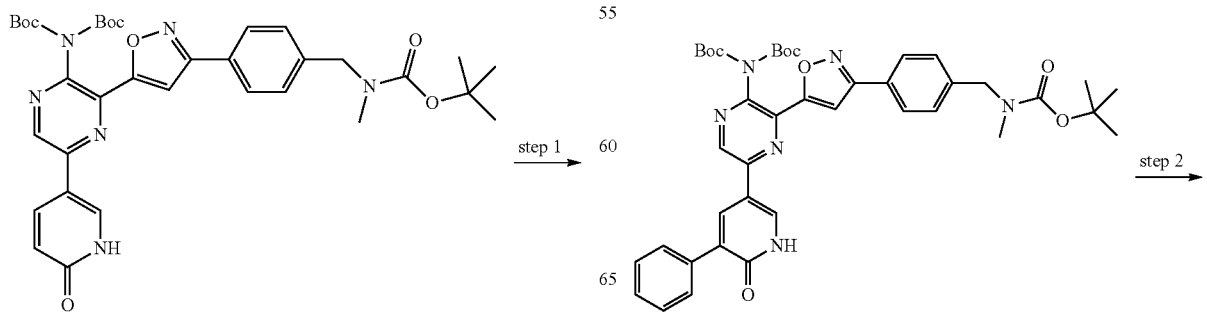

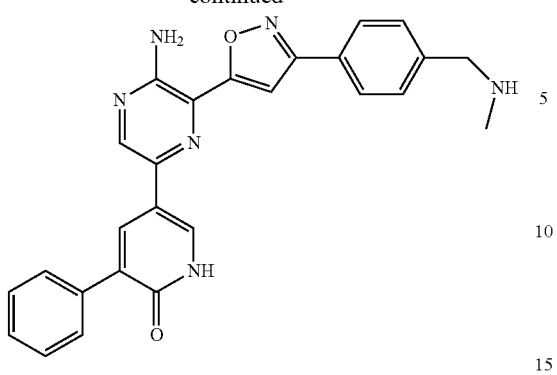

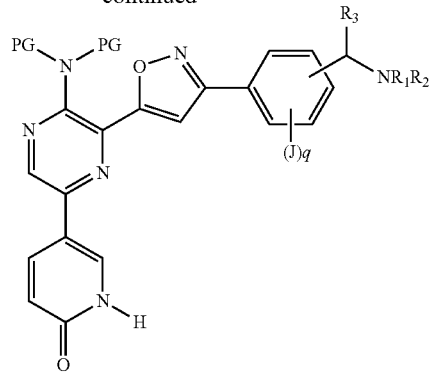

E-iii (R₄ ≠ H)

Scheme E-3 depicts another general method for the preparation of intermediates of Formula E-iii, where R₄≠H. Compounds of Formula E-iii, where R₄═H, are reacted with an alcohol R₄OH under Mitsunobu conditions to give rise to compounds of Formula E-iii, where R₄≠H. Suitable Mitsunobu conditions include, but are not limited to, Bu₃P/DIAD in an appropriate solvent such as CHCl₃ or THF. Alternatively, compounds of Formula E-iii, where R₄≠H, may be obtained from compounds of Formula E-iii, where R₄═H, using alkylation conditions known to those skilled in the art such as, but not limited to, treatment of compounds of Formula E-iii, where R₄═H, with R₄-LG and a base (eg triethylamine), where LG is an appropriate leaving group such as halogen, mesylate, or triflate.

Preparation 26 Relate to Scheme E-3

Preparation 26

Synthesis of tert-butyl N-[[4-[5-[3-[bis(tert-butoxycarbonyl)amino]-6-[1-(3-methylcyclopentyl)-6-oxo-3-pyridyl]pyrazin-2-yl]isoxazol-3-yl]phenyl]methyl]-N-methyl-carbamate Step 1: Tert-butyl N-[[4-[5-[3-[bis(tert-butoxycarbonyl)amino]-6-(5-bromo-6-oxo-1H-pyridin-3-yl)pyrazin-2-yl]isoxazol-3-yl]phenyl]methyl]-N-methyl-carbamate (50 mg, 0.06634 mmol) was added to dioxane (1.334 mL) followed by the addition of cyclopenta-1,4-dien-1-yl(diphenyl)phosphane (3.294 mg, 0.01327 mmol), phenylboronic acid (10.52 mg, 0.08624 mmol) and sodium carbonate (21.09 mg, 0.1990 mmol). The mixture heated to 80° C. for 2 hr. The mixture was filtered through celite and concentrated to an oil in vacuo. Purification by column chromatography eluting with 30% diethyl ether/petroleum ether gave the product (25 mg, 50% yield). MS (ES⁺) 651.3, 751.3, MS (ES⁻) 749.2.

Step 2: Tert-butyl N-[[4-[5-[3-[bis(tert-butoxycarbonyl)amino]-6-(6-oxo-5phenyl-1H-pyridin-3-yl)pyrazin-2-yl]isoxazol-3-yl]phenyl]methyl]-N-methyl-carbamate (25 mg, 0.03330 mmol) was dissolved in DCM (3 mL) followed by the addition of TFA (189.8 mg, 128.2 µL, 1.665 mmol). The mixture was stirred for 1 hr at room temperature and then concentrated to an oil in vacuo. The residue was purified by reverse phase preparative HPLC [Waters Sunfire C18, 10 mM, 100 Å column, gradient 10%-95% B (solvent A: 0.05% TFA in water; solvent B: CH₃CN) over 16 minutes at 25 mL/min] to give sub-titled product (6 mg, 31% yield). H¹ NMR (400.0 MHz, DMSO-d₆) 2.62-2.68 (3H,s), 4.22 (2H, s), 6.9 (2H,s), 7.47 (1H,t), 7.45 (2H,t), 7.68 (2H,d), 7.74 (1H,$), 7.82 (2H,d), 8.08-8.12 (3H,m), 8.31 (1H,d), 8.77-8.83 (3H,m), 12.2 (1H,s). MS (ES⁺) 451.2, MS (ES⁻) 449.2.

Scheme E-3

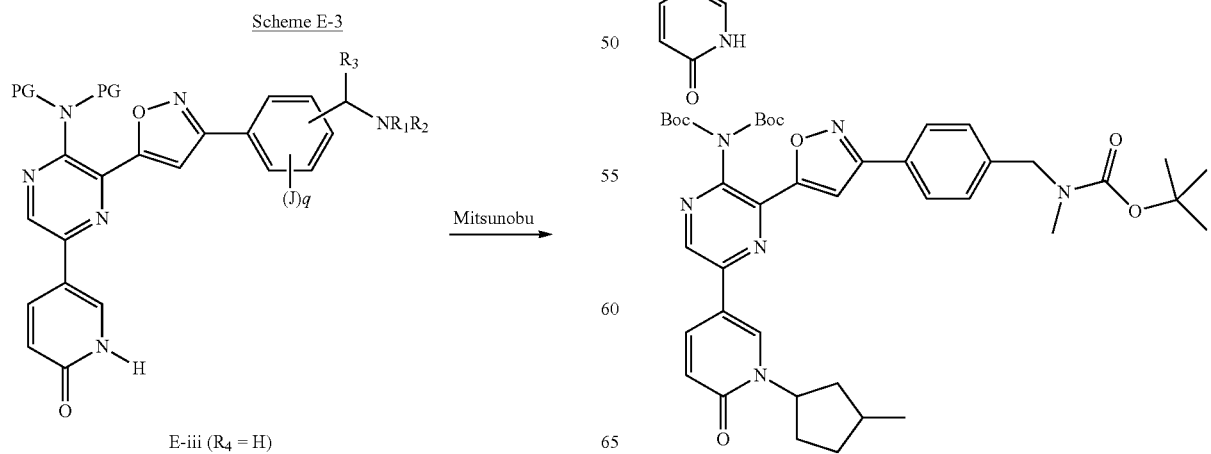

E-iii (R₄ = H)

Step 1: Tert-butyl N-[[4-[5-[3-[bis(tert-butoxycarbonyl)amino]-6-(6-oxo-1H-pyridin-3-yl)pyrazin-2-yl]isoxazol-3-yl]phenyl]methyl]-N-methyl-carbamate (130 mg, 0.1927 mmol) and DIAD (77.93 mg, 75.88 µL, 0.3854 mmol) were dissolved in Chloroform (2 mL) and cooled to 0° C. in an ice bath and tributylphosphane (77.97 mg, 96.02 µL, 0.3854 mmol) was added slowly. The reaction was stirred at room temperature for 30 min then 3-methylcyclopentanol (28.96 mg, 31.82 µL, 0.2891 mmol) was added and the mixture stirred at room temperature for 16 h. The reaction mixture was purified directly by silica chromatography eluting with 0-100% EtOAc/Petroleum Ether to give the sub-titled product as a yellow solid (33.8 mg, 23% yield). $H^1$ NMR (400.0 MHz, DMSO-$d_6$) d 1.18 (d, 3H), 1.30 (s, 18H), 1.35-1.41 (m, 3H), 1.49 (2×s, 9H), 2.02-2.14 (m, 4H), 2.82 (s, 3H), 4.46 (s, 2H), 5.24-5.28 (m, 1H), 6.60 (2×s, 1H), 7.40 (d, 2H), 7.41 (2×s, 8.00 (d, 1H), 8.70 (2×d, 1H) and 9.33 (2×s, 1H); MS (ES$^+$) 757.45.

Analytical Data Table

| Cmpd No. | HNMR | LCMS ES Plus | LCMS (Rt min) |
|---|---|---|---|
| I-1 | — | 390.2 | 1.53 |
| I-2 | — | 434.4 | 1.72 |
| I-3 | — | 418.2 | 1.78 |
| I-4 | — | 420.5 | 1.52 |
| I-5 | — | 433.3 | 0.37 |
| I-6 | 1H NMR (400 MHz, DMSO) d 9.31 (s, 2H), 8.90 (d, J = 2.3 Hz, 1H), 8.36 (s, 1H), 8.15-8.08 (m, 1H), 8.03 (dd, J = 7.9, 2.2 Hz, 1H), 7.61 (s, 2H), 7.30 (d, J = 8.1 Hz, 1H), 6.57 (d, J = 9.3 Hz, 1H), 5.23-5.05 (m, 1H), 4.23 (s, 2H), 2.60 (s, 3H), 1.40 (d, J = 6.8 Hz, 7H). | 448.5 | 1.25 |
| I-7 | — | 415.4 | 1.39 |
| I-8 | — | 476.2 | 2.13 |
| I-9 | — | 446.2 | 2.03 |
| I-10 | 1H NMR (400 MHz, DMSO) d 9.29 (s, 2H), 8.93 (s, 1H), 8.39 (d, J = 2.4 Hz, 1H), 8.25 (t, J = 7.8 Hz, 1H), 8.13 (dd, J = 9.5, 2.5 Hz, 1H), 7.76 (d, J = 11.5 Hz, 1H), 7.63 (d, J = 8.1 Hz, 1H), 6.57 (d, J = 9.5 Hz, 1H), 5.14 (dt, J = 13.8, 6.8 Hz, 1H), 4.27 (s, 2H), 2.60 (s, 3H), 1.40 (d, J = 6.8 Hz, 6H). | 436.5 | 1 |
| I-11 | 1H NMR (400 MHz, DMSO) d 9.30 (d, J = 4.5 Hz, 2H), 8.80 (s, 1H), 8.34 (d, J = 2.3 Hz, 1H), 8.17 (dd, J = 9.5, 2.5 Hz, 1H), 8.09 (d, J = 8.2 Hz, 2H), 7.77 (s, 1H), 7.73 (d, J = 8.2 Hz, 2H), 6.54 (d, J = 9.5 Hz, 1H), 5.13 (m, 1H), 4.20 (t, J = 5.8 Hz, 2H), 2.57 (t, J = 5.3 Hz, 3H), 1.41 (d, J = 6.8 Hz, 6H). | 417.5 | 1.1 |
| I-12 | — | 432.2 | 1.14 |
| I-13 | — | 488.24 | 1.07 |
| I-14 | — | 458.1 | 0.82 |
| I-15 | H NMR (400.0 MHz, DMSO) d 1.80 (d, 3H), 2.89 (s, 3H), 3.72 (s, 2H), 5.86 (q, 1H), 6.65 (d, 1H), 6.97 (br s, 2H), 7.51 (d, 1H), 7.73 (s, 1H), 7.95 (d, 2H), 8.30 (dd, 1H), 8.49 (d, 1H) and 8.73 (s, 1H) ppm | 428.1 | 1.14 |
| I-16 | 1H NMR (400 MHz, CDCl3) d 8.49 (s, 1H), 8.33 (d, J = 2.4 Hz, 1H), 8.15 (d, J = 8.0 Hz, 1H), 8.02 (dd, J = 9.6, 2.5 Hz, 1H), 7.42-7.31 (m, 2H), 6.75 (d, J = 9.6 Hz, 1H), 6.16 (q, J = 7.1 Hz, 1H), 3.83 (s, 2H), 2.82 (s, 3H), 2.50 (s, 3H), 1.82 (d, J = 7.1 Hz, 3H). | 443.5 | 1.05 |
| I-17 | $^1$H NMR (400 MHz, DMSO-$d_6$) δ 9.50-9.34 (m, 2H), 8.87 (s, 1H), 8.36 (d, J = 2.2 Hz, 1H), 8.20-8.07 (m, 2H), 7.72-7.59 (m, 3H), 6.57 (d, J = 9.5 Hz, 1H), 5.27-5.15 (m, J = 5.2 Hz, 1H), 4.20 (t, J = 5.6 Hz, 2H), 3.84-3.72 (m, 1H), 3.57 (dd, J = 10.2, 5.1 Hz, 1H), 3.26 (s, 3H), 2.75 (s, 3H), 2.57 (t, J = 5.3 Hz, 3H), 1.37 (d, J = 7.0 Hz, 3H). | 462 | 0.83 |
| I-18 | $^1$H NMR (400 MHz, DMSO-$d_6$) δ 9.13 (s, 2H), 8.92 (s, 1H), 8.54 (d, J = 2.5 Hz, 1H), 8.22-8.09 (m, 2H), 7.69-7.55 (m, 4H), 6.56 (d, J = 9.5 Hz, 1H), 4.42-4.09 (m, 12H), 2.75 (s, 3H), 2.59 (t, J = 5.3 Hz, 3H), 1.45 (d, J = 6.8 Hz, 4H), 1.18 (d, J = 6.2 Hz, 1H), 0.69 (s, 1H), 0.53-0.42 (m, 2H), 0.22 (d, J = 4.7 Hz, 1H). | 458.1 | 0.87 |
| I-19 | 1H NMR (400 MHz, DMSO) d 9.46 (s, 2H), 8.82 (s, 1H), 8.48 (d, J = 2.5 Hz, 1H), 8.13 (dd, J = 9.5, 2.5 Hz, 1H), 8.04 (d, J = 7.8 Hz, 1H), 7.64 (s, 1H), 7.31 (d, J = 8.1 Hz, 1H), 6.56 (d, J = 9.5 Hz, 1H), 4.23 (t, J = 5.7 Hz, 2H), 4.02 (d, J = 7.1 Hz, 2H), 4.00 (s, 3H), 2.58 (t, J = 5.2 Hz, 3H), 1.30 (t, J = 7.1 Hz, 3H). | 434.5 | 0.96 |
| I-20 | 1H NMR (400 MHz, DMSO) d 9.01 (s, 2H), 8.91 (s, 1H), 8.38 (d, J = 2.5 Hz, 1H), 8.14 (dd, J = 13.9, 5.1 Hz, 2H), 7.67-7.60 (m, 2H), 6.56 (d, J = 9.5 Hz, 1H), 5.22-5.07 (m, 1H), 4.23 (s, 2H), 3.41-3.33 (m, 1H), 2.77 (s, 3H), 1.40 (d, J = 6.8 Hz, 6H), 1.32 (d, J = 6.5 Hz, 6H). | 460.5 | 1.16 |

-continued

Analytical Data Table

| Cmpd No. | HNMR | LCMS ES Plus | LCMS (Rt min) |
|---|---|---|---|
| I-21 | 1H NMR (400 MHz, DMSO) d 9.09 (s, 2H), 8.91 (s, 1H), 8.38 (s, 1H), 8.14 (dd, J = 13.7, 5.2 Hz, 2H), 7.74 (s, 1H), 7.70 (d, J = 8.5 Hz, 1H), 6.57 (d, J = 9.5 Hz, 1H), 5.19-5.08 (m, 1H), 4.19 (s, 2H), 2.77 (s, 3H), 1.41 (s, 11H), 1.39 (s, 4H). | 474.5 | 1.15 |
| I-22 | H NMR (400.0 MHz, DMSO) d 1.05 (d, 1.2H), 1.12 (d, 1.8H), 1.21-1.30 (m, 1H), 1.54-1.72 (m, 2H), 1.85-1.97 (m, 1H), 2.01-2.14 (m, 3H), 2.29 (s, 3H), 3.71 (s, 2H), 5.14-5.30 (m, 1H), 6.52 (d, 1H), 6.89 (br s, 2H), 7.50 (d, 2H), 7.70 (d, 1H), 7.95 (d, 2H), 8.14-8.18 (m, 1H), 8.29 (d, 0.6H), 8.34 (d, 0.4H), 8.76 (s, 0.6H) and 8.78 (s, 0.4H) ppm | 457.2 | 1.19 |
| I-23 | DMSO 1.42 (6H, d), 2.1-2.15 (1H, m), 2.23-2.33 (1H, m), 3.7-3.75 (1H, m), 3.8-3.85 (1H, m), 3.9-4.0 (3H, m), 4.3-4.35 (2H, m), 5.1-5.2 (1H, m), 6.55 (1H, d), 6.9 (2H, brs), 7.7 (2H, d), 7.75 (1H, s), 8.1 (2H, d), 8.15-8.2 (1H, m), 8.35-8.38 (1H, m), 8.72 (1H, s), 9.1 (2H, brs) | 473.1 | 0.64 |
| I-24 | $^1$H NMR (400 MHz, DMSO-$d_6$) δ 10.38-10.23 (m, 1H), 9.38-9.28 (m, 2H), 8.84 (s, 1H), 8.57 (d, J = 2.4 Hz, 1H), 8.27-8.10 (m, 2H), 7.65 (d, J = 9.8 Hz, 4H), 6.65 (d, J = 9.5 Hz, 1H), 4.41 (t, J = 6.3 Hz, 2H), 4.20 (t, J = 5.8 Hz, 3H), 3.57-3.45 (m, 4H), 2.87 (d, J = 4.7 Hz, 7H), 2.75 (s, 3H), 2.58 (t, J = 5.3 Hz, 4H). | 461.1 | 0.56 |
| I-25 | $^1$H NMR (400 MHz, DMSO-$d_6$) δ 9.46 (s, 2H), 8.90 (s, 1H), 8.30 (d, J = 2.3 Hz, 1H), 8.11 (dd, J = 9.5, 2.3 Hz, 1H), 8.03 (d, J = 7.9 Hz, 1H), 7.65 (s, 1H), 7.31 (d, J = 8.0 Hz, 1H), 6.58 (d, J = 9.5 Hz, 1H), 4.96 (dd, J = 14.2, 7.1 Hz, 1H), 4.00 (s, 4H), 2.58 (t, J = 5.2 Hz, 3H), 1.91-1.73 (m, 2H), 1.39 (d, J = 6.8 Hz, 3H), 0.80 (t, J = 7.3 Hz, 3H). | 462.1 | 0.81 |
| I-26 | 1H NMR (400 MHz, DMSO) d 9.44 (s, 2H), 8.81 (s, 1H), 8.40 (d, J = 2.4 Hz, 1H), 8.14 (dd, J = 9.5, 2.4 Hz, 1H), 8.03 (d, J = 8.0 Hz, 1H), 7.64 (s, 1H), 7.31 (d, J = 8.0 Hz, 1H), 6.57 (d, J = 9.5 Hz, 1H), 4.23 (t, J = 5.9 Hz, 2H), 4.00 (s, 3H), 3.83 (d, J = 7.5 Hz, 2H), 2.59 (t, J = 5.3 Hz, 3H), 2.22-2.04 (m, 1H), 0.91 (d, J = 6.7 Hz, 6H). | 462.5 | 1.06 |
| I-27 | 1H NMR (400 MHz, DMSO) d 9.08 (s, 2H), 8.78 (s, 1H), 8.47 (d, J = 1.5 Hz, 1H), 8.24 (dd, J = 9.6, 2.5 Hz, 1H), 8.15 (d, J = 8.0 Hz, 1H), 7.64 (s, 1H), 7.60 (d, J = 9.0 Hz, 1H), 6.68 (d, J = 9.7 Hz, 1H), 4.99 (q, J = 9.3 Hz, 2H), 4.21 (t, J = 5.8 Hz, 2H), 2.75 (s, 3H), 2.60 (t, J = 5.3 Hz, 3H). | 472.5 | 1.15 |
| I-28 | 1H NMR (400 MHz, DMSO) d 9.10 (s, 2H), 8.77 (s, 1H), 8.44 (s, 1H), 8.22 (d, J = 9.6 Hz, 1H), 8.05 (d, J = 7.9 Hz, 1H), 7.69 (s, 2H), 7.55 (s, 1H), 7.29 (d, J = 7.9 Hz, 1H), 6.68 (d, J = 9.6 Hz, 1H), 5.07-4.89 (m, 2H), 4.24 (t, J = 4.1 Hz, 2H), 3.99 (s, 3H), 2.61 (s, 3H). | 488.5 | 1.08 |
| I-29 | 1H NMR (400 MHz, DMSO) d 9.43 (bs, 2H), 8.80 (s, 1H), 8.34 (d, J = 2.4 Hz, 1H), 8.14 (dd, J = 9.5, 2.4 Hz, 1H), 8.08 (t, J = 7.8 Hz, 1H), 7.70 (d, J = 11.6 Hz, 1H), 7.61-7.53 (m, 2H), 6.53 (d, J = 9.5 Hz, 1H), 5.14-5.08 (m, 1H), 4.23 (t, J = 5.8 Hz, 2H), 2.58 (t, J = 5.4 Hz, 3H), 1.40 (d, J = 6.8 Hz, 6H). | 435.5 | 1.08 |
| I-30 | 1H NMR (400 MHz, DMSO) d 9.12 (s, 2H), 8.87 (s, 1H), 8.59 (d, J = 2.1 Hz, 1H), 8.26-8.07 (m, 2H), 7.63 (dd, J = 23.0, 10.5 Hz, 4H), 6.59 (d, J = 9.4 Hz, 1H), 5.82 (s, 1H), 4.21 (s, 2H), 2.76 (s, 3H), 2.59 (t, J = 5.0 Hz, 3H), 1.87 (d, J = 1.8 Hz, 3H), 1.54 (d, J = 6.8 Hz, 3H). | 456.1 | 0.88 |
| I-31 | 1H NMR (400 MHz, DMSO) d 9.12 (s, 2H), 8.87 (s, 1H), 8.59 (d, J = 2.1 Hz, 1H), 8.26-8.07 (m, 2H), 7.63 (dd, J = 23.0, 10.5 Hz, 4H), 6.59 (d, J = 9.4 Hz, 1H), 5.82 (s, 1H), 4.21 (s, 2H), 2.76 (s, 3H), 2.59 (t, J = 5.0 Hz, 3H), 1.87 (d, J = 1.8 Hz, 3H), 1.54 (d, J = 6.8 Hz, 3H). | 450.1 | 0.77 |
| I-32 | 1H NMR (400 MHz, DMSO) d 9.30 (s, 2H), 8.87 (s, 1H), 8.33 (s, 1H), 8.13 (s, 0H), 8.07 (dd, J = 36.3, 8.1 Hz, 2H), 7.60 (s, 3H), 7.30 (d, J = 7.6 Hz, 1H), 6.55 (d, J = 9.4 Hz, 1H), 5.17 (s, 2H), 4.24 (s, 2H), 3.99 (s, 3H), 2.60 (s, 3H), 2.33-2.14 (m, 0H), 1.93 (dd, J = 113.0, 39.6 Hz, 8H). | 474.1 | 0.79 |

-continued

Analytical Data Table

| Cmpd No. | HNMR | LCMS ES Plus | LCMS (Rt min) |
|---|---|---|---|
| I-33 | 1H NMR (400 MHz, DMSO) d 9.11 (s, 2H), 8.94 (s, 1H), 8.45 (s, 1H), 8.15 (d, J = 8.3 Hz, 3H), 7.94-7.50 (m, 6H), 6.53 (d, J = 9.6 Hz, 1H), 5.30-4.99 (m, 2H), 4.21 (s, 6H), 2.77 (s, 4H), 2.59 (t, J = 5.3 Hz, 7H), 2.39 (t, J = 9.0 Hz, 5H), 1.83 (s, 3H). | 444.1 | 0.76 |
| I-34 | 1H NMR (400 MHz, DMSO) d 8.83 (s, 1H), 8.48 (d, J = 2.4 Hz, 1H), 8.21 (dd, J = 9.6, 2.5 Hz, 1H), 7.93 (d, J = 8.0 Hz, 1H), 7.68 (s, 2H), 7.29 (s, 1H), 7.13 (d, J = 8.1 Hz, 1H), 6.67 (d, J = 9.6 Hz, 1H), 5.90 (q, J = 7.1 Hz, 1H), 3.96 (s, 3H), 3.76 (s, 2H), 2.32 (s, 3H), 1.79 (d, J = 7.1 Hz, 3H). | 459.5 | 0.98 |
| I-35 | 1H NMR (400 MHz, DMSO) d 9.08 (s, 2H), 8.90 (s, 1H), 8.36 (d, J = 2.4 Hz, 1H), 8.11 (dd, J = 9.5, 2.5 Hz, 1H), 8.07 (d, J = 7.9 Hz, 1H), 7.67 (s, 1H), 7.37 (d, J = 8.1 Hz, 1H), 6.57 (d, J = 9.4 Hz, 1H), 5.18-5.09 (m, 1H), 4.24 (d, J = 12.5 Hz, 2H), 4.01 (s, 3H), 1.54-0.96 (m, 15H). | 490.5 | 1.04 |
| I-36 | — | 464 | 0.63 |
| I-37 | 1H NMR (400 MHz, DMSO) d 9.42 (s, 2H), 8.91 (s, 1H), 8.52 (s, 1H), 8.20-8.08 (m, 1H), 8.02 (d, J = 8.0 Hz, 1H), 7.63 (s, 1H), 7.31 (d, J = 6.9 Hz, 1H), 6.56 (d, J = 9.5 Hz, 1H), 4.23 (s, 3H), 3.99 (s, 3H), 2.59 (s, 3H), 1.45 (d, J = 6.7 Hz, 3H), 0.68 (m, 1H), 0.47 (m, 2H), 0.22 (m, 1H). | 474.3 | 1.1 |
| I-38 | 1H NMR (400 MHz, DMSO) d 9.36 (s, 2H), 8.86 (d, J = 2.1 Hz, 1H), 8.43 (d, J = 2.3 Hz, 0.6H), 8.37 (d, J = 2.4 Hz, 0.4H), 8.26-8.10 (m, 2H), 7.67 (m, 3H), 7.37 (s, 1H), 7.27 (d, J = 16.8 Hz, 1H), 7.12 (s, 1H), 6.58 (t, J = 9.9 Hz, 1H), 5.50 (m, 0.4H), 5.29 (m, 0.6H), 4.20 (t, J = 5.7 Hz, 2H), 2.75 (s, 3H), 2.57 (t, J = 5.3 Hz, 3H), 1.74-1.56 (m, 3H). | 462.5 | 0.98 |
| I-39 | — | 443.7 | 1.09 |
| I-40 | — | 485.4 | 1.07 |
| I-41 | 1H NMR (400 MHz, DMSO) d 9.50 (s, 2H), 8.90 (s, 1H), 8.32 (s, 1H), 8.21 (dd, J = 9.6, 2.4 Hz, 1H), 8.02 (d, J = 7.9 Hz, 1H), 7.66 (s, 1H), 7.32 (d, J = 8.0 Hz, 1H), 6.71 (d, J = 9.6 Hz, 1H), 6.21-5.67 (m, 1H), 4.23 (t, J = 5.8 Hz, 2H), 3.99 (s, 3H), 2.58 (t, J = 5.3 Hz, 3H), 1.73 (d, J = 7.3 Hz, 3H). | 502.1 | 0.74 |
| I-42 | 1H NMR (400 MHz, DMSO) d 8.97-8.92 (m, 1H), 8.47 (dd, J = 4.8, 4.4 Hz, 3H), 8.42-8.37 (m, 1H), 8.35-8.28 (m, 1H), 8.22-8.11 (m, 2H), 7.86-7.81 (m, 1H), 7.79-7.73 (m, 1H), 6.61-6.54 (m, 1H), 5.20-5.10 (m, 1H), 4.63 (td, J = 11.0, 5.4 Hz, 1H), 1.58 (d, J = 6.7 Hz, 3H), 1.41 (d, J = 6.8 Hz, 6H). | 418.5 | 1.26 |
| I-43 | 1H NMR (400 MHz, DMSO) d 9.42 (s, 2H), 8.78 (s, 1H), 8.31 (d, J = 2.2 Hz, 1H), 8.17 (dd, J = 9.6, 2.1 Hz, 1H), 8.08 (d, J = 8.0 Hz, 3H), 7.81-7.68 (m, 5H), 6.53 (d, J = 9.4 Hz, 1H), 4.20 (t, J = 5.7 Hz, 2H), 3.57 (s, 2H), 2.56 (t, J = 5.2 Hz, 4H), 2.22-1.94 (m, 2H), 1.94-1.54 (m, 6H). | 443.7 | 1.11 |
| I-44 | 1H NMR (400 MHz, DMSO) d 9.18 (s, 2H), 8.81 (s, 1H), 8.35 (d, J = 2.3 Hz, 1H), 8.18 (dd, J = 9.5, 2.5 Hz, 1H), 8.09 (d, J = 8.2 Hz, 2H), 7.87-7.76 (m, 3H), 6.54 (d, J = 9.5 Hz, 1H), 5.13 (dt, J = 13.4, 6.7 Hz, 1H), 4.19 (d, J = 6.2 Hz, 2H), 1.40 (d, J = 4.6 Hz, 16H). | 459.7 | 1.36 |
| I-45 | 1H NMR (400 MHz, DMSO) d 8.94 (s, 1H), 8.62 (s, 3H), 8.39 (d, J = 2.3 Hz, 1H), 8.19 (m, 3H), 7.81 (d, J = 8.2 Hz, 2H), 7.65 (s, 1H), 6.58 (d, J = 9.5 Hz, 1H), 5.14 (dt, J = 13.5, 6.8 Hz, 1H), 4.64-4.48 (m, 1H), 1.57 (d, J = 6.7 Hz, 3H), 1.41 (d, J = 6.8 Hz, 6H). | 418.5 | 0.92 |
| I-46 | 1H NMR (400 MHz, DMSO) d 9.08 (s, 2H), 8.95 (s, 1H), 8.40 (s, 2H), 8.23-8.14 (m, 2H), 7.90 (d, J = 7.5 Hz, 1H), 7.76 (t, J = 7.8 Hz, 1H), 7.67 (s, 1H), 6.57 (d, J = 9.5 Hz, 1H), 5.21-5.07 (m, 1H), 4.30 (s, 2H), 1.42 (t, J = 3.1 Hz, 15H). | 460.5 | 0.98 |
| I-47 | 1H NMR (400 MHz, DMSO) d 9.26 (s, 2H), 8.95 (s, 1H), 8.44-8.29 (m, 2H), 8.24-8.13 (m, 2H), 7.84 (d, J = 7.7 Hz, 1H), 7.75 (t, J = 7.7 Hz, 1H), 7.66 (s, 1H), 6.57 (d, J = 9.5 Hz, 1H), 5.21-5.06 (m, 1H), 4.29 (t, J = 5.7 Hz, 2H), 2.60 (t, J = 5.2 Hz, 3H), 1.42 (d, J = 6.8 Hz, 6H). | 418.5 | 0.92 |

-continued

Analytical Data Table

| Cmpd No. | HNMR | LCMS ES Plus | LCMS (Rt min) |
|---|---|---|---|
| I-48 | 1H NMR (400 MHz, DMSO) d 9.27 (s, 2H), 8.81 (s, 1H), 8.36 (s, 2H), 8.17 (dd, J = 9.5, 2.4 Hz, 1H), 8.05 (d, J = 7.8 Hz, 1H), 7.81 (d, J = 8.1 Hz, 2H), 7.64 (t, J = 7.7 Hz, 1H), 6.54 (d, J = 9.5 Hz, 1H), 5.18-5.08 (m, 1H), 4.22 (s, 2H), 1.46-1.37 (m, 15H). | 459.7 | 1.05 |
| I-49 | 1H NMR (400 MHz, DMSO) d 9.37 (s, 2H), 8.81 (s, 1H), 8.35 (d, J = 2.3 Hz, 1H), 8.25 (s, 1H), 8.16 (dd, J = 9.5, 2.5 Hz, 1H), 8.06 (d, J = 7.6 Hz, 1H), 7.75 (s, 1H), 7.71 (d, J = 7.6 Hz, 1H), 7.64 (t, J = 7.7 Hz, 1H), 6.54 (d, J = 9.5 Hz, 1H), 5.13 (dt, J = 13.7, 6.9 Hz, 1H), 4.23 (t, J = 5.7 Hz, 2H), 2.58 (t, J = 5.3 Hz, 3H), 1.42 (t, J = 9.3 Hz, 6H). | 417.5 | 1 |
| I-50 | 1H NMR (400 MHz, MeOD) d 8.58 (d, J = 7.6 Hz, 8H), 8.42-8.26 (m, 12H), 8.12 (s, 1H), 8.09 (d, J = 8.2 Hz, 14H), 7.75-7.60 (m, 20H), 6.74 (d, J = 9.3 Hz, 7H), 5.35-5.21 (m, 6H), 4.28 (s, 17H), 2.22 (s, 12H), 1.90 (d, J = 75.9 Hz, 38H), 1.50 (s, 65H). | 485.2 | 0.86 |
| I-51 | 1H NMR (400 MHz, DMSO) d 8.78 (s, 1H), 8.31 (d, J = 2.5 Hz, 1H), 8.16 (dd, J = 9.5, 2.5 Hz, 1H), 8.10 (d, J = 8.3 Hz, 2H), 7.79 (s, 1H), 7.77 (s, 2H), 6.89 (s, 2H), 6.53 (d, J = 9.5 Hz, 1H), 5.18-5.09 (m, 1H), 4.43 (d, J = 5.8 Hz, 2H), 3.14-3.05 (m, 5H), 2.10-1.99 (m, 4H), 1.92-1.86 (m, 5H), 1.72-1.64 (m, 2H). | 483.5 | 1.12 |
| I-52 | 1H NMR (400 MHz, DMSO) d 8.86 (s, 2H), 8.78 (s, 1H), 8.31 (d, J = 2.4 Hz, 1H), 8.17 (dd, J = 9.5, 2.5 Hz, 1H), 8.08 (d, J = 8.3 Hz, 2H), 7.78-7.72 (m, 3H), 6.53 (d, J = 9.5 Hz, 1H), 5.18-5.06 (m, 1H), 4.19 (s, 2H), 3.56 (s, 2H), 2.09-1.98 (m, 2H), 1.96-1.79 (m, 4H), 1.77-1.60 (m, 2H), 1.33 (s, 6H). | 501.5 | 1.31 |
| I-53 | 1H NMR (400 MHz, DMSO) d 8.79 (s, 1H), 8.55 (s, 3H), 8.32 (d, J = 2.3 Hz, 1H), 8.22 (s, 1H), 8.16 (dd, J = 9.5, 2.5 Hz, 1H), 8.02 (d, J = 7.5 Hz, 1H), 7.76 (s, 1H), 7.66 (dt, J = 15.2, 7.7 Hz, 2H), 6.54 (d, J = 9.5 Hz, 1H), 5.18-5.06 (m, 1H), 4.57-4.47 (m, 1H), 2.08-1.97 (m, 2H), 1.94-1.83 (m, 4H), 1.73-1.64 (m, 2H), 1.58 (d, J = 6.7 Hz, 3H). | 443.7 | 1.09 |
| I-54 | 1H NMR (400 MHz, DMSO) d 9.39 (s, 2H), 8.80 (s, 1H), 8.50 (d, J = 2.5 Hz, 1H), 8.19-8.04 (m, 2H), 7.69 (dd, J = 11.7, 1.3 Hz, 1H), 7.61-7.53 (m, 2H), 6.53 (d, J = 9.5 Hz, 1H), 4.43-4.17 (m, 3H), 2.58 (t, J = 5.4 Hz, 3H), 1.45 (d, J = 6.8 Hz, 3H), 0.67 (dd, J = 8.1, 5.8 Hz, 1H), 0.63-0.29 (m, 2H), 0.21 (dd, J = 9.4, 4.2 Hz, 1H). | 461.1 | 0.78 |
| I-55 | 1H NMR (400 MHz, DMSO) d 8.81 (s, 1H), 8.52 (d, J = 3.0 Hz, 3H), 8.35 (d, J = 2.5 Hz, 1H), 8.22 (s, 1H), 8.16 (dd, J = 9.5, 2.6 Hz, 1H), 8.03 (d, J = 7.4 Hz, 1H), 7.76 (s, 1H), 7.66 (dt, J = 15.1, 7.7 Hz, 2H), 6.54 (d, J = 9.5 Hz, 1H), 5.20-5.07 (m, 1H), 4.54 (dt, J = 9.3, 4.7 Hz, 1H), 1.58 (d, J = 6.8 Hz, 3H), 1.41 (d, J = 6.8 Hz, 6H). | 417.2 | 0.94 |
| I-56 | 1H NMR (400 MHz, DMSO) d 9.36 (s, 4H), 8.77 (s, 2H), 8.30 (s, 2H), 8.19-7.99 (m, 3H), 7.69 (d, J = 11.8 Hz, 2H), 7.56 (d, J = 2.2 Hz, 3H), 6.52 (d, J = 9.5 Hz, 2H), 5.40-4.86 (m, 3H), 4.22 (d, J = 5.7 Hz, 4H), 2.58 (t, J = 5.2 Hz, 5H), 2.24-1.86 (m, 9H), 1.68 (s, 6H). | 461.2 | 0.82 |
| I-57 | 1H NMR (400 MHz, DMSO) d 8.82 (s, 1H), 8.57-8.47 (m, 4H), 8.22 (s, 1H), 8.17 (dd, J = 9.5, 2.6 Hz, 1H), 8.02 (t, J = 5.1 Hz, 1H), 7.77 (s, 1H), 7.72-7.60 (m, 2H), 6.54 (d, J = 9.5 Hz, 1H), 4.59-4.49 (m, 1H), 4.24 (tt, J = 13.6, 6.8 Hz, 1H), 1.58 (d, J = 6.8 Hz, 3H), 1.56-1.51 (m, 1H), 1.47 (d, J = 6.8 Hz, 3H), 0.68 (dd, J = 14.3, 7.8 Hz, 1H), 0.52-0.41 (m, 2H), 0.26-0.15 (m, 1H). | 443.1 | 1.04 |
| I-58 | DMSO 1.42 (6H, d), 2.1-2.15 (1H, m), 2.23-2.33 (1H, m), 3.7-3.75 (1H, m), 3.8-3.85 (1H, m), 3.9-4.0 (3H, m), 4.3-4.35 (2H, m), 5.1-5.2 (1H, m), 6.55 (1H, d), 6.9 (2H, brs), 7.7 (2H, d), 7.75 (1H, s), 8.1 (2H, d), 8.15-8.2 (1H, m), 8.35-8.38 (1H, m), 8.72 (1H, s), 9.1 (2H, brs) | 473.1 | 0.64 |
| I-59 | H NMR (400.0 MHz, DMSO) d 1.41 (d, 6H), 4.67-4.77 (m, 1H), 4.82-4.89 (m, 2H), 5.13 (sept, 1H), 6.54 (d, 1H), 6.91 (s, 2H), 7.70 (d, 2H), 7.78 (s, 1H), 8.13 (d, 2H), 8.17 (dd, 1H), 8.35 (d, 1H), 8.73 (s, 3H) and 8.82 (s, 1H) ppm | 435.1 | 0.65 |

Analytical Data Table

| Cmpd No. | HNMR | LCMS ES Plus | LCMS (Rt min) |
|---|---|---|---|
| I-60 | DMSO 1.36 (6H, d), 1.42 (6H, d), 3.37-3.42 (1H, m), 4.25-4.3 (2H, m), 5.1-5.2 (1H, m), 6.55 (1H, d), 6.9 (2H, brs), 7.7 (2H, d), 7.8 (1H, s), 8.12 (2H, d), 8.15-8.2 (1H, m), 8.35-8.38 (1H, m), 8.75 (2H, brs), 8.82 (1H, s) | 445.2 | 0.61 |
| I-61 | DMSO 0.6-0.7 (4H, m), 1.3 (6H, d), 2.6-2.7 (1H, m), 4.1 (2H, s), 4.95-5.0 (1H, m), 6.4 (1H, d), 6.75 (2H, brs), 7.55 (2H, d), 7.65 (1H, s), 7.95 (2H, d), 8.05-8.1 (1H, m), 8.18-8.22 (1H, m), 8.68 (1H, s), 8.9 (2H, brs) | 443.2 | 0.7 |
| I-62 | H NMR (400.0 MHz, DMSO) d 0.44-0.53 (m, 4H), 1.28-1.36 (m, 1H), 2.29 (s, 3H), 3.72 (s, 2H), 3.86 (d, 2H), 6.54 (d, 1H), 6.89 (br s, 2H), 7.52 (d, 2H), 7.73 (s, 1H), 7.95 (d, 2H), 8.21 (dd, 1H), 8.48 (d, 1H) and 8.70 (s, 1H) ppm [1] | 428.196 | 1.15 |
| I-63 | DMSO 1.25 (3H, t), 1.42 (6H, d), 3.0-3.1 (2H, m), 4.2-4.25 (2H, m), 5.1-5.2 (1H, m), 6.55 (1H, d), 6.9 (2H, brs), 7.7 (2H, d), 7.8 (1H, s), 8.12 (2H, d), 8.15-8.2 (1H, m), 8.35-8.38 (1H, m), 8.8-8.85 (3H, m), [1] | 430.212 | 0.58 |
| I-64 | (DMSO) 1.24 (6H, m), 2.47 (3H, t), 3.79 (3H, s), 4.06 (2H, m), 4.97 (1H, m), 6.37 (1H, d), 6.72 (2H, br s), 7.04 (1H, m), 7.24 (1H, d), 7.34 (1H, s), 7.73 (1H, d), 7.95 (1H, dd), 8.18 (1H, d), 8.62 (1H, s) and 8.70 (2H, br s) ppm [1] | 446.207 | 0.57 |
| I-65 | DMSO 1.42 (6H, m), 4.37 (2H, s), 5.1-5.2 (1H, m), 6.5-6.55 (2H, m), 6.6 (2H, d), 6.85-6.9 (2H, brs), 7.05 (2H, t), 7.55 (2H, d), 7.7 (1H, s), 7.97 (2H, d), 8.08-8.2 (2H, m), 8.37-8.4 (1H, m), 8.8 (1H, s), [1] | 478.212 | 0.92 |
| I-66 | H NMR (400.0 MHz, DMSO) d 1.68-1.72 (m, 2H), 2.05-2.16 (m, 2H), 2.25 (s, 3H), 3.48 (t, 2H), 3.68 (s, 2H), 4.00 (dd, 2H), 4.93-5.00 (m, 1H), 6.54 (d, 1H), 6.86 (s, 2H), 7.47 (d, 2H), 7.69 (s, 1H), 7.92 (d, 2H), 8.18 (dd, 1H), 8.33 (d, 1H) and 8.80 (s, 1H) ppm [1] | 458.207 | 1.08 |
| I-67 | DMSO 1.42 (6H, d), 2.63 (3H, s), 4.18 (2H, s), 5.17-5.21 (1H, m), 5.25-5.3 (1H, m), 6.0-6.1 (1H, m), 6.3-6.38 (2H, m), 7.48 (1H, s), 7.55 (2H, d), 8.0 (2H, d), 8.17-8.22 (2H, m), 8.53 (1H, s) [1] | 442.212 | 0.66 |
| I-68 | H NMR (400.0 MHz, DMSO) d 0.09-0.12 (m, 2H), 0.50-0.52 (m, 2H), 0.78 (s, 3H), 2.05 (s, 3H), 3.48 (s, 2H), 3.72 (s, 2H), 6.31 (d, 1H), 6.66 (br s, 2H), 7.27 (d, 2H), 7.48 (s, 1H), 7.71 (d, 2H), 7.96 (dd, 1H), 8.18 (d, 1H) and 8.45 (s, 1H) ppm [1] | 442.212 | 1.18 |
| I-69 | H NMR (400.0 MHz, DMSO) d 2.29 (s, 3H), 3.72 (s, 2H), 5.04 (s, 2H), 6.55-6.57 (m, 2H), 6.91 (br s, 2H), 7.51 (d, 2H), 7.63 (t, 1H), 7.72 (s, 1H), 7.75 (s, 1H), 7.95 (d, 2H), 8.21 (dd, 1H), 8.55 (d, 1H) and 8.68 (s, 1H) ppm [1] | 454.175 | 1.15 |
| I-70 | H NMR (400.0 MHz, DMSO) d 1.85-1.92 (m, 2H), 2.10 (t, 2H), 2.29 (s, 3H), 3.42 (t, 2H), 3.55 (t, 2H), 3.71 (s, 2H), 4.14 (t, 2H), 6.50 (d, 1H), 6.89 (br s, 2H), 7.51 (d, 2H), 7.73 (s, 1H), 7.95 (d, 2H), 8.17 (dd, 1H), 8.35 (d, 1H) and 8.67 (s, 1H) ppm [1] | 485.218 | 1.11 |
| I-71 | — | 494.107 | 0.63 |
| I-72 | H NMR (400.0 MHz, DMSO) d −0.01-0.03 (m, 1H), 0.35-0.43 (m, 1H), 0.59-0.66 (m, 2H), 0.75 (d, 3H), 2.04 (s, 3H), 3.47 (s, 2H), 3.54 (dd, 1H), 3.68 (dd, 1H), 6.29 (d, 1H), 6.63 (br s, 2H), 7.26 (d, 2H), 7.47 (s, 1H), 7.70 (d, 2H), 7.96 (dd, 1H), 8.22 (d, 1H) and 8.44 (s, 1H) ppm [1] | 442.212 | 1.17 |
| I-73 | H NMR (400.0 MHz, DMSO) d 2.29 (s, 3H), 3.07 (t, 2H), 3.72 (s, 2H), 4.28 (t, 2H), 6.59 (d, 1H), 6.93 (br s, 2H), 7.51 (d, 2H), 7.73 (s, 1H), 7.95 (d, 2H), 8.25 (dd, 1H), 8.52 (d, 1H) and 8.67 (s, 1H) ppm [1] | 427.176 | 1.08 |
| I-74 | H NMR (400.0 MHz, DMSO) d 0.94 (t, 3H), 1.48-1.54 (m, 2H), 2.29 (s, 3H), 3.21 (s, 3H), 3.48-3.53 (m, 1H), 3.71 (s, 2H), 3.90 (dd, 1H), 4.19 (dd, 1H), 6.54 (d, 1H), 6.89 (br s, 2H), 7.51 (d, 2H), 7.72 (s, 1H), 7.95 (d, 2H), 8.21 (dd, 1H), 8.35 (d, 1H) and 8.67 (s, 1H) ppm [1] | 460.222 | 1.15 |
| I-75 | DMSO 1.2 (3H, t), 1.4 (6H, d), 2.6-2.7 (2H, m), 4.2-4.3 (2H, m), 5.1-5.2 (1H, m), 6.85-6.9 (2H, brs), 7.65 (2H, d), 7.7 (1H, s), 7.97-8.0 (1H, m), 8.12 (2H, d), 8.1-8.12 (1H, m), 8.87-8.92 (2H, m), [1] | 444.227 | 0.65 |

-continued

Analytical Data Table

| Cmpd No. | HNMR | LCMS ES Plus | LCMS (Rt min) |
|---|---|---|---|
| I-76 | H NMR (400.0 MHz, DMSO) d 2.34 (s, 3H), 3.19 (s, 2H), 6.47 (d, 1H), 6.85 (br s, 2H), 7.53 (d, 2H), 7.73 (s, 1H), 7.99 (d, 2H), 8.11 (d, 1H), 8.23 (dd, 1H), 8.69 (s, 1H) and 11.91 (br s, 1H) ppm [1] | 374.149 | 1.09 |
| I-77 | H NMR (400.0 MHz, DMSO) d 0.87 (t, 3H), 0.94 (d, 3H), 1.17-1.24 (m, 1H), 1.35-1.45 (m, 2H), 1.48-1.57 (m, 1H), 1.68-1.75 (m, 1H), 2.29 (s, 3H), 3.71 (s, 2H), 4.01 (t, 2H), 6.52 (d, 1H), 6.88 (br s, 2H), 7.50 (d, 2H), 7.73 (s, 1H), 7.95 (d, 2H), 8.19 (dd, 1H), 8.46 (d, 1H) and 8.70 (s, 1H) ppm [1] | 458.243 | 1.28 |
| I-78 | MEOH 2.8 (3H, s), 4.35 (2H, s), 7.6 (1H, s), 7.71 (2H, d), 8.1 (2H, d), 8.13-8.15 (1H, m), 8.45 (1H, s), 8.73 (1H, d) [1] | 452.06 | 0.52 |
| I-79 | H NMR (400.0 MHz, DMSO) d 0.10-0.20 (m, 1H), 0.35-0.50 (m, 2H), 0.60-0.70 (m, 1H), 1.26 (d, J = 6.8 Hz, 1H), 1.40-1.50 (m, 4H), 2.29 (s, 2H), 3.13 (d, J = 9.4 Hz, 1H), 3.65 (s, 2H), 4.15-4.25 (m, 1H), 6.49-6.50 (d, 1H), 6.90 (s, 2H), 7.49-7.50 (d, 2H), 7.75 (d, J = 8.2 Hz, 1H), 7.90-8.00 (m, 2H), 8.15 (d, 1H) and 8.75 (s, 1H) ppm [1], H NMR (400.0 MHz, DMSO) d 0.00 (m, 1H), 0.05-0.30 (m, 2H), 0.40-0.50 (m, 1H), 1.00-1.10 (m, 1H), 1.25 (d, J = 6.9 Hz, 3H), 1.30-1.35 (m, 1H), 2.40 (d, J = 5.3 Hz, 3H), 4.02 (s, 4H), 6.33 (d, J = 9.5 Hz, 1H), 6.70 (br s, 2H), 7.46 (d, J = 8.2 Hz, 2H), 7.56 (s, 1H), 7.89 (d, J = 8.2 Hz, 2H), 7.95 (d, 1H), 8.30 (s, 1H) and 8.61 (s, 2H) ppm [2] | 442.212 | 0.61, 0.61 [2] |
| I-80 | H NMR (400.0 MHz, DMSO) d 0.43-0.46 (m, 2H), 0.71-0.73 (m, 2H), 2.29 (s, 3H), 3.22 (d, 2H), 3.71 (s, 2H), 4.06 (s, 2H), 4.81 (t, 1H), 6.57 (d, 1H), 6.91 (br s, 2H), 7.51 (d, 2H), 7.71 (s, 1H), 7.94 (d, 2H), 8.21 (dd, 1H), 8.41 (d, 1H) and 8.66 (s, 1H) ppm [1] | 458.207 | 1.12 |
| I-81 | dmso d6 1.30 (3H, t), 2.29 (3H, s), 3.72 (2H, s), 4.03 (2H, q), 6.52 (2H, d), 6.89 (2H, d), 7.50 (2H, d), 7.75 (1H, s), 7.96 (2H, d), 8.20 (1H, dd), 8.48 (1H, d), 8.70 (1H, s) [1] | 402.18 | 2.51 |
| I-82 | dmso d6 0.80 (3H, t), 1.39 (3H, d), 2.24 (3H, s), 3.73 (2H, s), 4.90-4.98 (1H, m), 6.54 (1H, d), 6.90 (2H, s), 7.50 (1H, d), 7.72 (1H, s), 7.96 (2H, d), 8.18 (1H, dd), 8.28 (1H, d), 8.79 (1H, s) [1] | 430.212 | 2.66 |
| I-83 | dmso d6 0.76 (6H, t), 1.75-1-85 (4H, m), 2.30 (3H, s), 3.73 (2H, s), 4.75-4.86 (1H, m), 6.55 (1H, d), 6.89 (2H, s), 7.50 (2H, d), 7.72 (1H, s), 7.96 (2H, d), 8.17-8.21 (2H, m), 8.78 (1H, s) [1] | 444.227 | 2.72 |
| I-84 | H NMR (400.0 MHz, DMSO) d 2.28 (s, 3H), 3.71 (s, 2H), 5.53 (s, 2H), 6.61 (d, 1H), 6.93 (br s, 2H), 7.51 (d, 2H), 7.72 (d, 1H), 7.74 (s, 1H), 7.78 (d, 1H), 7.94 (d, 2H), 8.28 (dd, 1H), 8.67 (d, 1H) and 8.68 (s, 1H) ppm [1] | 471.148 | 0.98 |
| I-85 | H NMR (400.0 MHz, DMSO) d 2.28 (s, 3H), 3.71 (s, 2H), 3.76 (s, 3H), 5.24 (s, 2H), 6.53 (d, 1H), 6.80 (d, 1H), 6.91 (br s, 2H), 7.12 (d, 1H), 7.51 (d, 2H), 7.70 (s, 1H), 7.94 (d, 2H), 8.22 (dd, 1H), 8.55 (d, 1H) and 8.66 (s, 1H) ppm [1] | 468.202 | 1.08 |
| I-86 | H NMR (400.0 MHz, DMSO) d 1.58-1.63 (m, 1H), 1.80-2.01 (m, 3H), 2.29 (s, 3H), 3.65 (q, 1H), 3.71 (s, 2H), 3.82 (q, 1H), 3.91 (q, 1H), 4.16-4.20 (m, 2H), 6.54 (d, 1H), 6.89 (br s, 2H), 7.50 (d, 2H), 7.72 (s, 1H), 7.95 (d, 2H), 8.20 (dd, 1H), 8.38 (d, 1H) and 8.66 (s, 1H) ppm [1] | 458.207 | 1.13 |
| I-87 | H NMR (400.0 MHz, DMSO) d 1.23-1.31 (m, 1H), 1.46 (br s, 3H), 1.62 (br d, 1H), 1.77-1.84 (m, 1H), 2.29 (s, 3H), 3.23-3.34 (m, 1H), 3.63-3.71 (m, 1H), 3.71 (s, 2H), 3.82-3.88 (m, 2H), 4.16 (dd, 1H), 6.53 (d, 1H), 6.89 (br s, 2H), 7.50 (d, 2H), 7.73 (s, 1H), 7.95 (d, 2H), 8.20 (dd, 1H), 8.33 (d, 1H) and 8.66 (s, 1H) ppm [1] | 472.222 | 1.18 |
| I-88 | MeOH 2.6-2.7 (3H, m), 4.1-4.2 (2H, m), 4.6 (2H, s), 7.6-7.65 (3H, m), 8.0-8.1 (3H, m), 8.4-8.42 (1H, m), 8.58 (1H, s) [1] | 404.16 | 0.43 |
| I-89 | DMSO 1.2 (3H, t), 2.6-2.65 (3H, m), 4.2-4.25 (2H, m), 6.85 (1H, s), 7.68 (2H, d), 7.75 (1H, s), 7.95-8.0 (1H, m), 8.05-8.08 (1H, m), 8.1 (2H, d), 8.7 (1H, s), 8.8 (2H, brs) [1] | 402.18 | 0.54 |

-continued

Analytical Data Table

| Cmpd No. | HNMR | LCMS ES Plus | LCMS (Rt min) |
|---|---|---|---|
| I-90 | DMSO 2.6-2.65 (3H, m), 4.2-4.25 (2H, m), 6.9 (1H, s), 7.68 (2H, d), 7.78 (1H, s), 8.08 (2H, d), 8.1-8.12 (1H, m), 8.5-8.52 (1H, m), 8.7 (1H, s), 8.8 (2H, brs) [1] | 408.11 | 0.5 |
| I-91 | H NMR (400.0 MHz, DMSO) d 8.85 (s, 2H), 8.75 (s, 1H), 8.35 (d, J = 2.5 Hz, 1H), 8.22 (dd, J = 2.6, 9.5 Hz, 2H), 8.10 (d, J = 8.3 Hz, 2H), 7.77 (s, 1H), 7.67 (d, J = 8.2 Hz, 2H), 6.92 (s, 1H), 6.55 (d, J = 9.5 Hz, 1H), 5.47 (q, J = 7.2 Hz, 1H), 4.24-4.21 (m, 2H), 2.63-2.61 (m, 6H) and 1.63 (d, J = 7.4 Hz, 3H) ppm [1] | 459.202 | 2.11 |
| I-92 | dmso d6 0.25-0.28 (2H, m), 0.33-0.39 (2H, m), 1.61-1.71 (2H, m), 1.81-1.91 (4H, m), 1.96-2.06 (3H, m), 3.80 (2H, s), 5.58-5.68 (1H, m), 6.53 (1H, d), 6.89 (2H, s), 7.51 (2H, d), 7.71 (1H, s), 7.95 (2H, d), 8.17 (1H, dd), 8.31 (1H, s), 8.77 (1H, s) [1] | 468.227 | 2.52 |
| I-93 | dmso d6 0.23-0.27 (2H, m), 0.32-0.38 (2H, m), 0.76 (6H, t), 1.80-1.85 (4H, m), 2.05-2.07 (1H, m), 3.80 (2H, s), 4.75-4.86 (1H, m), 6.55 (1H, d), 6.89 (2H, s), 7.51 (2H, d), 7.72 (1H, s), 7.95 (2H, d), 8.17-8.21 (2H, m), 8.78 (1H, s) [1] | 470.243 | 2.53 |
| I-94 | (DMSO) 0.76 (6H, t), 1.57 (3H, d), 1.83 (4H, m), 4.56 (1H, m), 4.83 (1H, m), 6.56 (1H, m), 6.93 (2H, br s), 7.66 (2H, m), 7.73 (1H, s), 8.03 (1H, m), 8.15-8.18 (2H, m), 8.23 (1H, m), 8.32 (3H, br s) and 8.82 (1H, s) ppm [1], (DMSO) d 0.76 (6H, t), 1.56 (3H, d), 1.84 (4H, m), 4.54 (1H, m), 4.82 (1H, m), 6.56 (1H, d), 6.93 (2H, br s), 7.65 (2H, m), 7.27 (1H, s), 8.04 (1H, m), 8.15-8.23 (3H, m), 8.32 (3H, br s) and 8.82 (1H, s) ppm [2] | 444.227 | 0.65, 0.65 [2] |
| I-95 | H NMR (400.0 MHz, DMSO) d 2.62 (s, 3H), 3.27 (s, 3H), 3.65 (t, 2H), 4.18 (t, 2H), 4.22 (s, 2H), 6.54 (d, 1H), 6.92 (br s, 2H), 7.67 (d, 2H), 7.78 (s, 1H), 8.11 (d, 2H), 8.21 (dd, 1H), 8.40 (d, 1H), 8.69 (s, 1H) and 8.77 (br s, 2H) ppm [1] | 432.191 | 0.95 |
| I-96 | H NMR (400.0 MHz, DMSO) d −0.01 (d, J = 4.6 Hz, 2H), 0.36 (d, J = 6.8 Hz, 2H), 0.72-0.74 (m, 1H), 1.56 (d, J = 7.1 Hz, 2H), 2.24 (s, 3H), 3.66 (s, 2H), 4.02 (s, 2H), 6.47 (d, J = 9.5 Hz, 1H), 6.83 (s, 2H), 7.46 (d, J = 8.0 Hz, 2H), 7.68 (s, 1H), 7.90 (d, J = 8.0 Hz, 2H), 8.42 (d, J = 2.3 Hz, 1H), 8.64 (s, 1H) and 8.71 (s, 1H) ppm [1] | 442.212 | 0.61 |
| I-97 | H NMR (400.0 MHz, DMSO) d 0.85-0.92 (m, 6H), 1.12-1.24 (m, 1H), 1.33-1.45 (m, 2H), 1.45-1.99 (m, 1H), 2.29 (s, 3H), 3.72 (s, 2H), 3.76-3.81 (m, 1H), 3.92-3.96 (m, 1H), 6.53 (d, J = 9.5 Hz, 1H), 6.89 (s, 2H), 7.51 (d, J = 8.2 Hz, 2H), 7.73 (s, 1H), 7.95 (d, J = 8.1 Hz, 2H), 8.21 (d, 1H), 8.40 (d, 1H) and 8.69 (s, 1H) ppm [1] | 444.227 | 0.65 |
| I-98 | H NMR (400.0 MHz, DMSO) d 2.25 (s, 2H), 2.63 (s, 1H), 3.67 (s, 2H), 4.58 (s, 2H), 6.48 (d, J = 9.5 Hz, 1H), 6.85 (s, 2H), 7.23 (s, 1H), 7.47 (d, J = 8.2 Hz, 2H), 7.70 (s, 2H), 7.91 (d, J = 8.2 Hz, 2H), 8.37 (s, 1H), 8.40 (s, 1H) and 8.61 (s, 1H) ppm [1] | 431.171 | 0.43 |
| I-99 | dmso d6 0.32-0.37 (2H, m), 1.81 (3H, d), 2.01-2.08 (1H, m), 3.80 (2H, s), 5.80-5.88 (1H, m), 6.65 (1H, d), 6.97 (2H, s), 7.51 (2H, d), 7.73 (1H, s) 7.94 (2H, d), 8.27 (1H, d), 8.49 (1H, s), 8.74 (1H, s) [1] | 453.191 | 0.57 |
| I-100 | MeOH 1.2 (6H, d), 2.6-2.65 (3H, m), 4.2-4.25 (2H, m), 7.45 (1H, s), 7.55 (2H, d), 7.85 (1H, d), 7.92-8.0 (3H, m), 8.45 (1H, s), [1] | 416.196 | 0.57 |
| I-101 |  | 501.249 | 0.59 |
| I-102 |  | 499.233 | 0.55 |
| I-103 | (DMSO) 1.57 (3H, d), 4.56 (1H, m), 6.48 (1H, d), 6.89 (2H, br s), 7.65 (2H, m), 7.72 (1H, s), 8.03 (1H, m), 8.12 (1H, br s), 8.15 (1H, s), 8.20 (1H, dd), 8.32 (3H, br s), 8.72 (1H, s) and 12.03 (1H, br s) ppm [1] | 374.149 | 0.48 |
| I-104 | (DMSO) 1.41 (3H, d), 1.50 (3H, d), 4.41 (1H, m), 5.33 (1H, m), 6.40 (1H, d), 6.78 (2H, br s), 7.16 (1H, s), 7.50 (1H, m), 7.57 (2H, m), 7.88 (1H, m), 7.90 (1H, m), 8.04 (1H, dd), 8.06 (4H, m) and 8.62 (1H, s) ppm [1] | 445.186 | 0.49 |

Analytical Data Table

| Cmpd No. | HNMR | LCMS ES Plus | LCMS (Rt min) |
|---|---|---|---|
| I-105 | (DMSO) d 0.35 (2H, m), 0.75 (2H, m), 1.03 (3H, s), 1.33 (3H, d), 3.96 (2H, s), 4.14 (1H, m), 6.55 (1H, d), 6.90 (2H, br s), 7.48-7.56 (2H, m), 7.71 (1H, s), 7.84 (1H, d), 8.02 (1H, m), 8.18-8.21 (1H, dd), 8.42 (1H, m) and 8.69 (1H, s) ppm [1] | 442.212 | 0.64 |
| I-106 | (DMSO) d 0.02 (1H, m), 0.39 (1H, m), 0.62 (1H, m), 0.75 (3H, d), 0.81 (1H, m), 1.33 (3H, m), 3.52 (masked signal), 3.69 (1H, m), 4.31 (1H, m), 6.30 (1H, m), 6.68 (2H, br s), 7.41 (2H, m), 7.48 (1H, m), 7.77-7.80 (1H, m), 7.91 (1H, s), 7.94 (1H, dd), 8.08 (3H, br s), 8.24 (1H, m) and 8.47 (1H, s) ppm [1] | 442.212 | 0.65 |
| I-107 | DMSO 1.6-1.7 (4H, m), 1.75-1.8 (2H, m), 1.95-2.0 (2H, m), 2.6-2.65 (3H, m), 3.05-3.15 (1H, m), 4.2-4.25 (2H, m), 6.85 (2H, s), 7.68 (2H, d), 7.73 (1H, s), 7.95-8.02 (2H, m), 8.12 (2H, d), 8.7 (1H, s), 8.85 (2H, brs) [1] | 442.212 | 0.63 |
| I-108 | H NMR (400.0 MHz, DMSO d 2.62 (t, 3H), 3.56 (s, 3H), 4.23 (t, 2H), 6.54 (d, 1H), 6.91 (br s, 2H), 7.67 (d, 2H), 7.80 (s, 1H), 8.10 (d, 2H), 8.21 (dd, 1H), 8.51 (d, 1H), 8.70 (s, 1H) and 8.81 (br s, 2H) ppm [1] | 388.165 | 0.93 |
| I-109 | H NMR (400.0 MHz, DMSO) d 0.92 (t, 3H), 1.74 (sept, 2H), 2.62 (t, 3H), 3.95 (t, 2H), 4.23 (t, 2H), 6.54 (d, 1H), 6.91 (br s, 2H), 7.67 (d, 2H), 7.79 (s, 1H), 8.10 (d, 2H), 8.20 (dd, 1H), 8.46 (d, 1H), 8.71 (s, 1H) and 8.80 (br s, 2H) ppm [1] | 416.196 | 1 |
| I-110 | H NMR (400.0 MHz, DMSO) d 2.62 (t, 3H), 3.70 (t, 2H), 4.07 (t, 2H), 4.23 (t, 2H), 4.96 (br s, 1H), 6.54 (d, 1H), 6.90 (br s, 2H), 7.67 (d, 2H), 7.78 (s, 1H), 8.10 (d, 2H), 8.20 (dd, 1H), 8.39 (d, 1H), 8.68 (s, 1H) and 8.81 (br s, 2H) ppm [1] | 418.175 | 0.89 |
| I-111 | DMSO 0.8-0.9 (4H, m), 2.6-2.65 (1H, m), 4.25-4.3 (2H, m), 6.5 (1H, d), 6.9 (2H, s), 7.65 (2H, d), 7.78 (1H, s), 8.05 (2H, d), 8.1-8.12 (1H, m), 8.7 (1H, s), 8.8 (2H, brs) [1] | 400.165 | 0.57 |
| I-112 | DMSO 0.8-0.9 (4H, m), 2.6-2.65 (1H, m), 4.25-4.3 (2H, m), 6.9 (1H, s), 7.68 (2H, d), 7.78 (1H, s), 8.08 (2H, d), 8.1-8.12 (1H, m), 8.5-8.52 (1H, m), 8.7 (1H, s), 8.95 (2H, brs) [1] | 434.126 | 0.63 |
| I-113 | H NMR (400.0 MHz, MeOH) d 1.21 (s, 3H), 2.45 (s, 3H), 3.64 (s, 2H), 3.83 (s, 2H), 4.48-4.53 (m, 2H), 4.71-4.74 (m, 2H), 7.54-7.59 (m, 3H), 7.72 (s, 1H), 7.98 (d, 2H), 8.78 (s, 1H) and 8.99-9.02 (m, 2H) ppm [1] | 458.207 | 0.82 |
| I-114 | MeOH 1.6-1.65 (2H, m), 1.67-1.7 (2H, m), 2.1-2.15 (2H, m), 2.3-2.35 (2H, m), 2.7 (3H, s), 3.4-3.5 (1H, m), 4.2 (2H, s), 6.2-6.22 (1H, m), 7.42 (1H, s), 7.55 (2H, d), 7.9 (1H, d), 8.0-8.1 (3H, m), 8.42 (1H, s), [1] | 454.212 | 0.65 |
| I-115 | DMSO 1.2-1.4 (4H, m), 1.65-1.85 (6H, m), 2.6-2.7 (3H, m), 4.2-4.25 (2H, m), 6.85 (2H, m), 7.6 (2H, d), 7.7 (1H, s), 7.85-7.95 (2H, m), 8.15 (2H, d), 8.65 (1H, s), 8.8 (2H, brs) [1] | 456.227 | 0.66 |
| I-116 | DMSO 0.78 (3H, t), 0.85 (3H, t), 1.18-1.22 (2H, m), 1.6-1.72 (4H, m), 2.6-2.65 (3H, m), 2.78-2.83 (1H, m), 4.20-4.22 (2H, m), 6.85 (2H, s), 7.67 (2H, d), 7.7 (1H, s), 7.8-7.91 (1H, m), 7.92-7.95 (1H, m), 8.1 (2H, d), 8.7 (1H, s), 8.8 (2H, brs) [1] | 458.243 | 0.68 |
| I-117 | H NMR (400.0 MHz, DMSO) d 2.31 (s, 3H), 3.75-3.86 (m, 6H), 4.98 (t, J = 5.4 Hz, 3H), 6.54 (d, J = 9.5 Hz, 1H), 6.85 (s, 2H), 7.52 (d, J = 8.1 Hz, 2H), 7.68 (s, 1H), 7.96 (d, J = 8.1 Hz, 2H), 8.17 (dd, J = 2.5, 9.4 Hz, 1H), 8.29 (d, J = 2.4 Hz, 1H) and 8.69 (s, 1H) ppm [1] | 448.186 | 0.43 |
| I-118 | (DMSO) d 1.38-1.42 (12H, m), 2.63 (3H, t), 4.20 (2H, t), 4.78 (1H, m), 5.14 (1H, m), 6.52 (1H, d), 6.85 (2H, br s), 7.16 (1H, d), 7.38 (1H, s), 7.53 (1H, s), 7.92 (1H, d), 8.07 (1H, dd), 8.03 (1H, d), 8.75 (1H, s) and 8.81 (2H, br s) ppm [1] | 474.238 | 0.63 |
| I-119 | MeOH 0.9-1.0 (4H, m), 1.7-1.8 (5H, m), 1.87-1.92 (2H, m), 2.08-2.13 (1H, m), 2.8-2.88 (1H, m), 4.42 (2H, s), 7.55 (1H, s), 7.7 (2H, d), 7.95 (1H, d), 8.1 (2H, d), 8.12-8.14 (1H, m), 8.55 (1H, s) [1] | 468.227 | 0.75 |
| I-120 | MeOH 0.83-1.0 (10H, m), 1.28-1.33 (2H, m), 1.7-1.8 (4H, m), 2.8-2.85 (1H, m), 2.92-2.98 (1H, m), 4.42 (2H, s), 7.55 (1H, s), 7.7 (2H, d), 7.97 (1H, d), 8.08 (1H, d), 8.12 (2H, d), 8.55 (1H, s) [1] | 484.259 | 0.82 |

-continued

Analytical Data Table

| Cmpd No. | HNMR | LCMS ES Plus | LCMS (Rt min) |
|---|---|---|---|
| I-121 | MeOH 1.55 (6H, d), 2.77 (3H, s), 4.3 (2H, s), 7.65 (2H, d), 7.67-7.7 (1H, m), 8.1-8.2 (2H, m), 8.18-8.21 (1H, m), 8.67 (1H, s) [1] | 434.187 | 0.59 |
| I-122 | H NMR (400.0 MHz, DMSO) d 1.10-1.20 (br s, 1H), 1.45-1.65 (m, 5H), 1.70-1.85 (m, 5H), 2.29 (s, 3H), 3.72 (s, 2H), 3.95-4.05 (m, 2H), 6.50 (d, 1H), 6.85 (br s, 2H), 7.49-7.55 (m, 2H), 7.72 (s, 1H), 7.75 (s, 1H), 7.95-8.00 (m, 2H), 8.15-8.25 (m, 1H), 8.45 (d, 1H) and 8.70 (s, 1H) ppm [1] | 470.243 | 0.7 |
| I-123 | DMSO 2.62-2.68 (3H, s), 4.22 (2H, s), 6.9 (2H, s), 7.47 (1H, t), 7.45 (2H, t), 7.68 (2H, d), 7.74 (1H, s), 7.82 (2H, d), 8.08-8.12 (3H, m), 8.31 (1H, d), 8.77-8.83 (1H, m), 12.2 (1H, s) [1] | 450.18 | 0.6 |
| I-124 | (DMSO) d 1.04 (3H, d), 1.12 (1H, d), 1.19 (1H, d), 1.53-1.58 (5H, m), 1.76 (1H, m), 1.90-2.14 (4H, m), 2.42 (1H, m), 4.56 (1H, m), 5.26 (1H, m), 6.53 (1H, d), 6.92 (2H, br s), 7.66 (2H, m), 7.71 (1H, m), 8.03 (1H, m), 8.14 (2H, m), 8.30-8.35 (5H, m) and 8.79 (1H, d) ppm [1] | 456.227 | 0.68 |
| I-125 | H NMR (400.0 MHz, DMSO) d 2.03 (s, 6H), 2.35 (s, 3H), 3.81 (s, 2H), 6.66 (d, J = 9.4 Hz, 1H), 6.93 (s, 2H), 7.54 (d, J = 8.1 Hz, 2H), 7.73 (s, 1H), 7.98 (d, J = 8.1 Hz, 2H), 8.24-8.29 (m, 2H) and 8.76 (s, 1H) ppm [1] | 441.191 | 1.76, 1.75 [2] |
| I-126 | CDCl3 0.78-0.86 (6H, m), 1.68-1.86 (4H, m), 2.90 (2H, dt), 3.87 (2H, s), 4.53 (2H, dt), 4.92-5.02 (1H, m), 5.74 (2H, br s), 6.66 (1H, d), 7.20 (1H, s), 7.43 (2H, d), 7.74-7.88 (4H, m), 8.30 (1H, s) [1] | 476.234 | 0.74 |
| I-127 | CDCl3 0.86 (6H, t), 1.59-1.70 (2H, m), 1.75-1.88 (2H, m), 2.18-2.32 (2H, m), 2.67-2.80 (2H, m), 3.17-3.27 (1H, m), 3.74 (1H, s), 4.91-5.01 (1H, m), 5.75 (2H, br s), 6.65 (1H, d), 7.19 (1H, s), 7.40 (1H, d), 7.73-7.88 (4H, m), 8.30 (1H, s) [1] | 520.24 | 0.88 |
| I-128 | DMSO 0.77-0.9 (10H, m), 1.8-1.9 (4H, m), 2.75-2.8 (1H, m), 4.37 (2H, s), 4.8-4.85 (1H, m), 6.55 (1H, d), 6.95 (2H, brs), 7.5-7.7 (4H, m), 8.08-8.18 (2H, m), 8.22 (1H, d), 8.8 (1H, s), 9.1 (2H, brs) [1] | 488.234 | 0.83 |
| I-129 | DMSO 0.85-0.95 (6H, m), 1.8-1.9 (4H, m), 2.62 (3H, s), 4.35 (2H, s), 5.85-5.95 (1H, m), 6.6 (1H, d), 7.9-8.0 (2H, m), 7.5-7.7 (3H, m), 8.15-8.3 (3H, m), 8.8 (1H, s), 8.9-9.0 (2H, m), [1] | 462.218 | 0.64 |
| I-130 | dmso d 0.77 (6H, d), 1.45-2.25 (11H, m), 3.82 (2H, s), 4.77-4.90 (1H, m), 5.20 (1H, d), 6.55 (1H, d), 6.90 (2H, br s), 7.55 (2H, d), 7.73 (1H, s), 7.98 (2H, d), 8.17-8.21 (2H, m), 8.79 (1H, s) [1] | 516.265 | 2.63 |
| I-131 | H NMR (400.0 MHz, DMSO) d 0.76 (t, 6H), 1.83 (quin, 4H), 4.20-4.27 (m, 1H), 4.36-4.45 (m, 1H), 4.48-4.57 (m, 1H), 4.82 (br, s, 1H), 6.56 (d, 1H), 6.91 (br s, 2H), 7.53 (t, 1H), 7.59 (d, 1H), 7.73 (s, 1H), 7.91 (d, 1H), 8.06 (s, 1H), 8.17-8.22 (m, 2H) and 8.79 (s, 1H) ppm [1] | 462.218 | 1.08 |
| I-132 | DMSO 0.8 (3H, t), 1.58-1.75 (4H, m) 2.6-2.65 (3H, m), 2.7-2.78 (1H, m), 4.22-4.26 (2H, m), 6.8-6.83 (2H, m), 7.48-7.52 (2H, m), 7.55-7.65 (1H, m), 7.85-7.88 (1H, m), 7.93-7.98 (1H, m), 8.12 (1H, t), 8.72 (1H, s), 8.88 (2H, brs), 11.85 (1H, s) [1] | 462.218 | 0.65 |
| I-133 | (DMSO) d 0.76 (6H, t), 0.82 (3H, t), 1.81-2.02 (6H, m), 4.30 (1H, m), 4.84 (1H, m), 6.56 (1H, d), 6.93 (2H, br s), 7.62-7.69 (2H, m), 7.72 (1H, s), 8.05 (1H, m), 8.14-8.16 (2H, m), 8.23 (1H, m), 8.34 (3H, br s) and 8.82 (1H, s) ppm [1] | 458.243 | 0.68 |
| I-134 | H NMR (400.0 MHz, DMSO) d 8.74 (s, 1H), 8.27 (dd, J = 2.3, 9.5 Hz, 1H), 8.22 (d, J = 2.1 Hz, 1H), 7.94 (d, J = 8.2 Hz, 2H), 7.69 (s, 1H), 7.50 (d, J = 8.2 Hz, 2H), 6.97 (s, 2H), 6.65 (d, J = 9.5 Hz, 2H), 3.71 (s, 2H), 2.55-2.47 (m, 2H), 2.32-2.27 (m, 2H), 2.30 (s, 3H) and 0.98 (t, J = 7.3 Hz, 6H) ppm [1] | 469.223 | 2.06 |
| I-135 | H NMR (400.0 MHz, CDCl3) d 8.52 (d, J = 2.3 Hz, 1H), 8.41 (s, 1H), 8.02-7.96 (m, 2H), 7.48 (d, J = 3.4 Hz, 1H), 7.28-7.25 (m, 2H), 6.68 (d, J = 9.5 Hz, 1H), 5.89 (s, 2H), 3.84 (s, 2H), 2.96 (qn, J = 7.3 Hz, 2H), 2.50 (s, 3H), 2.26 (td, J = 14.6, 7.3 Hz, 2H) and 1.09 (t, J = 7.4 Hz, 6H) ppm [1] | 487.213 | 2.09 |

-continued

Analytical Data Table

| Cmpd No. | HNMR | LCMS ES Plus | LCMS (Rt min) |
|---|---|---|---|
| I-136 | H NMR (400.0 MHz, CDCl3) d 8.44 (d, J = 2.2 Hz, 1H), 8.33 (s, 1H), 7.93-7.87 (m, 2H), 7.39 (d, J = 3.3 Hz, 1H), 7.18-7.15 (m, 3H), 6.59 (d, J = 9.5 Hz, 1H), 5.78 (s, 2H), 3.84 (s, 2H), 2.88 (m, 2H), 2.18 (m, 2H), 2.12 (m, 1H), 1.00 (t, J = 7.4 Hz, 6H) and 0.41-0.33 (m, 4H) ppm [1] | 513.229 | 2.74 |
| I-137 | (DMSO) d 0.61 (6H, t), 1.21 (4H, m), 1.68 (4H, t), 4.67 (1H, m), 6.41 (1H, d), 6.78 (2H, br s), 7.42 (1H, m), 7.49 (1H, t), 7.61 (1H, s), 7.86 (1H, m), 7.90 (1H, m), 8.00 (1H, dd), 8.08 (1H, m), 8.54 (3H, br s) and 8.66 (1H, s) ppm [1] | 456.227 | 0.75 |
| I-138 | H NMR (400.0 MHz, MeOH) d 8.54 (s, 1H), 8.49 (s, 1H), 8.22 (d, J = 9.4 Hz, 1H), 7.92 (s, 1H), 7.79 (d, J = 7.1 Hz, 1H), 7.53-7.46 (m, 3H), 6.67 (d, J = 9.4 Hz, 1H), 4.16-4.13 (m, 1H), 2.79 (m, 2H), 2.33 (m, 2H), 1.47 (d, J = 6.6 Hz, 3H) and 1.10 (t, J = 7.3 Hz, 6H) ppm [1] | 469.223 | 2.13 |
| I-139 | H NMR (400.0 MHz, MeOH) d 8.52 (d, J = 2.1 Hz, 1H), 8.48 (s, 1H), 8.21 (dd, J = 2.2, 9.4 Hz, 1H), 7.91 (s, 1H), 7.78 (d, J = 7.3 Hz, 1H), 7.53-7.44 (m, 3H), 6.66 (d, J = 9.4 Hz, 1H), 4.15 (d, J = 6.6 Hz, 1H), 2.76 (qn, J = 7.3 Hz, 2H), 2.33 (td, J = 14.7, 7.3 Hz, 2H), 1.47 (d, J = 6.7 Hz, 3H) and 1.10 (t, J = 7.4 Hz, 6H) ppm [1] | 469.223 | 2.13 |
| I-140 | DMSO D6 0.29-0.32 (2H, m), 0.48-0.52 (2H, m), 1.24 (3H, s), 1.74-1.84 (4H, m), 3.80 (2H, s), 4.72-4.85 (1H, m), 6.53 (1H, d), 6.84 (2H, br s), 7.48 (2H, d), 7.68 (1H, s), 7.91 (2H, d), 8.12-8.20 (2H, m), 8.76 (1H, s) [1] | 484.259 | 0.79 |
| I-141 | H NMR (400.0 MHz, DMSO) d 8.79 (s, 1H), 8.23-8.16 (m, 3H), 7.89 (s, 1H), 7.71 (s, 1H), 7.32 (s, 1H), 6.89 (s, 2H), 6.56 (d, J = 9.4 Hz, 1H), 4.85 (br s, 1H), 4.32 (d, J = 6.5 Hz, 1H), 2.15 (br s, 1H), 1.82 (t, J = 7.0 Hz, 4H), 1.32 (d, J = 6.5 Hz, 3H) and 0.76 (t, J = 7.2 Hz, 6H) ppm [1] | 462.218 | 0.69 |
| I-142 | H NMR (400.0 MHz, DMSO) d 8.79 (s, 1H), 8.20 (d, J = 2.4 Hz, 1H), 8.11 (d, J = 9.4 Hz, 1H), 7.89-7.75 (m, 2H), 7.50 (s, 1H), 7.37 (d, J = 2.4 Hz, 1H), 6.94 (s, 2H), 6.50 (s, 1H), 4.80 (br s, 1H), 4.51-4.41 (m, 1H), 1.64 (t, J = 7.2 Hz, 4H), 1.35 (d, J = 6.6 Hz, 3H) and 0.58 (t, J = 7.3 Hz, 7H) ppm [1] | 462.218 | 0.66 |
| I-143 | H NMR (400.0 MHz, DMSO) d 8.75 (s, 1H), 8.29 (d, 1H), 8.21 (d, J = 2.1 Hz, 1H), 7.95 (d, J = 8.1 Hz, 1H), 7.72 (s, 2H), 7.51 (d, J = 8.1 Hz, 2H), 6.95 (s, 2H), 6.66 (d, J = 9.5 Hz, 1H), 3.71 (s, 2H), 2.87 (m, 2H), 2.29 (s, 3H) and 1.90 (s, 4H) ppm [1] | 467.207 | 1.93 |
| I-144 | H NMR (400.0 MHz, CDCl3) d 8.38 (s, 1H), 8.25 (d, J = 2.3 Hz, 1H), 7.96 (dd, J = 2.4, 9.5 Hz, 1H), 7.85 (d, J = 8.1 Hz, 2H), 7.46 (d, J = 8.1 Hz, 2H), 7.30 (s, 1H), 6.74 (d, J = 9.5 Hz, 1H), 5.87 (s, 2H), 3.93 (s, 2H), 2.18 (m, 1H), 2.14 (s, 6H) and 0.48-0.41 (m, 4H) ppm [1] | 467.207 | 2.23 |
| I-145 | H NMR (400.0 MHz, CDCl3) d 8.39 (s, 1H), 8.25 (d, J = 2.0 Hz, 1H), 7.98 (dd, J = 2.1, 9.5 Hz, 1H), 7.87 (d, J = 8.1 Hz, 2H), 7.50 (d, J = 8.0 Hz, 2H), 7.25 (s, 1H), 6.75 (d, J = 9.5 Hz, 1H), 5.90 (s, 2H), 3.98 (d, J = 7.2 Hz, 1H), 3.88 (s, 2H), 3.80 (m, 2H), 3.68 (dd, J = 3.8, 8.9 Hz, 1H), 3.50-3.48 (m, 1H), 2.14 (s, 6H), 2.11 (m, 1H) and 1.82 (m, 1H) ppm [1] | 497.218 | 2.07 |
| I-146 | (DMSO) d 0.58 (6H, t), 1.53 (6H, s), 1.65 (4H, m), 4.64 (1H, m), 6.38 (1H, d), 6.74 (2H, br s), 7.47-7.54 (2H, m), 7.57 (1H, s), 7.84 (1H, m), 7.97-7.99 (2H, m), 8.04 (1H, m), 8.31 (3H, br s) and 8.63 (1H, s) [1] | 458.243 | 0.67 |
| I-147 | — | 485.218 | 6.97 |
| I-148 | — | 375.144 | 1.45 |
| I-149 | — | 442.187 | 1.29 |
| I-150 | — | 445.223 | 1.1 |
| I-151 | — | 456.202 | 1.32 |

Example 2

Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media from a final concentration of 25 µM in 3-fold serial dilutions and the cells are incubated at 37° C. in 5% $CO_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 h at room temperature in primary antibody (mouse monoclonal anti-phosphorylated histone H2AX Ser139 antibody; Upstate 05-636) diluted 1:250 in block buffer. The cells are then washed five times in wash buffer before incubation for 1h at room temperature in the dark in a mixture of secondary antibody (goat anti-mouse Alexa Fluor 488 conjugated antibody; lnvitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50s for intracellular ATR inhibition are determined using Prism software (GraphPad Prism version 3.0cx for Macintosh, GraphPad Software, San Diego Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry*, 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 3

ATR Inhibition Assay

Compounds were screened for their ability to inhibit ATR kinase using a radioactive-phosphate incorporation assay. Assays were carried out in a mixture of 50 mM Tris/HCl (pH 7.5), 10 mM $MgCl_2$ and 1 mM DTT. Final substrate concentrations were 10 µM [γ-33P]ATP (3 mCi 33P ATP/mmol ATP, Perkin Elmer) and 800 µM target peptide (ASEL-PASQPQPFSAKKK).

Assays were carried out at 25° C. in the presence of 5 nM full-length ATR. An assay stock buffer solution was prepared containing all of the reagents listed above, with the exception of ATP and the test compound of interest. 13.5 µL of the stock solution was placed in a 96 well plate followed by addition of 2 µL of DMSO stock containing serial dilutions of the test compound (typically starting from a final concentration of 15 µM with 3-fold serial dilutions) in duplicate (final DMSO concentration 7%). The plate was pre-incubated for 10 minutes at 25° C. and the reaction initiated by addition of 15 µL [γ-33P]ATP (final concentration 10 µM).

The reaction was stopped after 24 hours by the addition of 30 µL 0.1 M phosphoric acid containing 2 mM ATP. A multiscreen phosphocellulose filter 96-well plate (Millipore, Cat no. MAPHNOB50) was pretreated with 100 µL 0.2M phosphoric acid prior to the addition of 45 µL of the stopped assay mixture. The plate was washed with 5×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Below is a chart showing the ATR Inhibition Ki values of compounds of the disclosure. Compounds with a Ki value of ≤5 nM are marked with "+++." Compounds with a Ki value>5 nM but ≤50 nM are marked with "++." Compounds with a Ki value>50 nM but <100 nM are marked with "+."

| Cmpd No. | Ki Value |
|---|---|
| I-1 | ++ |
| I-2 | ++ |
| I-3 | ++ |
| I-4 | ++ |
| I-5 | + |
| I-6 | +++ |
| I-7 | ++ |
| I-8 | ++ |
| I-9 | ++ |
| I-10 | +++ |
| I-11 | +++ |
| I-12 | +++ |
| I-13 | +++ |
| I-14 | +++ |
| I-15 | +++ |
| I-16 | +++ |
| I-17 | +++ |
| I-18 | +++ |
| I-19 | +++ |
| I-20 | +++ |

| Cmpd No. | Ki Value |
|---|---|
| I-21 | +++ |
| I-22 | +++ |
| I-23 | +++ |
| I-24 | ++ |
| I-25 | +++ |
| I-26 | +++ |
| I-27 | +++ |
| I-28 | +++ |
| I-29 | +++ |
| I-30 | +++ |
| I-31 | ++ |
| I-32 | +++ |
| I-33 | +++ |
| I-34 | +++ |
| I-35 | +++ |
| I-36 | +++ |
| I-37 | +++ |
| I-38 | ++ |
| I-39 | ++ |
| I-40 | ++ |
| I-41 | +++ |
| I-42 | +++ |
| I-43 | +++ |
| I-44 | ++ |
| I-45 | ++ |
| I-46 | + |
| I-47 | ++ |
| I-48 | + |
| I-49 | ++ |
| I-50 | +++ |
| I-51 | ++ |
| I-52 | ++ |
| I-53 | +++ |
| I-54 | +++ |
| I-55 | +++ |
| I-56 | +++ |
| I-57 | +++ |
| I-58 | +++ |
| I-59 | ++ |
| I-60 | +++ |
| I-61 | +++ |
| I-62 | +++ |
| I-63 | +++ |
| I-64 | +++ |
| I-65 | + |
| I-66 | +++ |
| I-67 | + |
| I-68 | +++ |
| I-69 | +++ |
| I-70 | +++ |
| I-71 | ++ |
| I-72 | +++ |
| I-73 | +++ |
| I-74 | +++ |
| I-75 | + |
| I-76 | ++ |
| I-77 | +++ |
| I-78 | +++ |
| I-79 | +++ |
| I-80 | +++ |
| I-81 | +++ |
| I-82 | +++ |
| I-83 | +++ |
| I-84 | +++ |
| I-85 | +++ |
| I-86 | +++ |
| I-87 | +++ |
| I-88 | +++ |
| I-89 | +++ |
| I-90 | +++ |
| I-91 | +++ |
| I-92 | +++ |
| I-93 | +++ |
| I-94 | +++ |
| I-95 | +++ |
| I-96 | +++ |
| I-97 | +++ |
| I-98 | +++ |
| I-99 | +++ |
| I-100 | +++ |
| I-101 | ++ |
| I-102 | +++ |
| I-103 | +++ |
| I-104 | +++ |
| I-105 | +++ |
| I-106 | +++ |
| I-107 | +++ |
| I-108 | +++ |
| I-109 | +++ |
| I-110 | +++ |
| I-111 | +++ |
| I-112 | +++ |
| I-113 | +++ |
| I-114 | +++ |
| I-115 | +++ |
| I-116 | +++ |
| I-117 | +++ |
| I-118 | +++ |
| I-119 | +++ |
| I-120 | +++ |
| I-121 | ++ |
| I-122 | +++ |
| I-123 | +++ |
| I-124 | +++ |
| I-125 | +++ |
| I-126 | +++ |
| I-127 | +++ |
| I-128 | +++ |
| I-129 | +++ |
| I-130 | +++ |
| I-131 | +++ |
| I-132 | +++ |
| I-133 | +++ |
| I-134 | +++ |
| I-135 | +++ |
| I-136 | +++ |
| I-137 | ++ |
| I-138 | +++ |
| I-139 | +++ |
| I-140 | +++ |
| I-141 | +++ |
| I-142 | +++ |
| I-143 | +++ |
| I-144 | +++ |
| I-145 | +++ |
| I-146 | +++ |
| I-147 | +++ |
| I-148 | +++ |
| I-149 | ++ |
| I-150 | + |
| I-151 | ++ |

Example 4

Cisplatin Sensitization Assay

Compounds can be screened for their ability to sensitize HCT116 colorectal cancer cells to Cisplatin using a 96h cell viability (MTS) assay. HCT116 cells, which possess a defect in ATM signaling to Cisplatin (see, Kim et al.; *Oncogene* 21:3864 (2002); see also, Takemura et al.; *JBC* 281:30814 (2006)) are plated at 470 cells per well in 96well polystyrene plates (Costar 3596) in 150 µl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin are then both added simultaneously to the cell media in 2-fold serial dilutions from a top final concentration of 10 μM as a full matrix of concentrations in a final cell volume of 200 μl, and the cells are then incubated at 37° C. in 5% $CO_2$. After 96h, 40 μl of M (Promega G358a) is added to each well and the cells are incubated for 1 h at 37° C. in 5% $CO_2$. Finally, absorbance is measured at 490 nm using a SpectraMax Plus 384 reader (Molecular Devices) and the concentration of compound required to reduce the IC50 of Cisplatin alone by at least 3-fold (to 1 decimal place) can be reported (CP3 shift).

| Cmpd | CP3 shift (uM) |
|---|---|
| I-3 | 0.234 |
| I-6 | 0.156 |
| I-15 | 0.039 |
| I-11 | 0.156 |
| I-22 | 0.02 |
| I-23 | 0.312 |
| I-32 | 0.079 |
| I-37 | 0.078 |
| I-42 | 0.156 |
| I-43 | 0.078 |
| I-44 | 0.312 |
| I-49 | 0.625 |
| I-50 | 0.312 |
| I-53 | 0.039 |
| I-54 | 0.039 |
| I-55 | 0.039 |
| I-57 | 0.02 |
| I-58 | 0.312 |
| I-60 | 0.312 |
| I-61 | 0.078 |
| I-62 | 0.078 |
| I-63 | 0.156 |
| I-64 | 0.078 |
| I-68 | 0.039 |
| I-72 | 0.078 |
| I-73 | 0.156 |
| I-74 | 0.078 |
| I-77 | 0.039 |
| I-78 | 0.625 |
| I-80 | 0.078 |
| I-81 | 0.156 |
| I-82 | 0.079 |
| I-83 | 0.02 |
| I-87 | 0.078 |
| I-89 | 0.312 |
| I-90 | 0.625 |
| I-92 | 0.078 |
| I-93 | 0.02 |
| I-94 | 0.007 |
| I-96 | 0.078 |
| I-97 | 0.078 |
| I-102 | 0.078 |
| I-105 | 0.02 |
| I-106 | 0.039 |
| I-107 | 0.039 |
| I-116 | 0.02 |
| I-119 | 0.156 |
| I-120 | 0.078 |
| I-122 | 0.078 |
| I-123 | 0.078 |
| I-124 | 0.039 |
| I-125 | 0.015 |
| I-126 | 0.625 |
| I-127 | 0.312 |
| I-128 | 0.078 |
| I-129 | 0.02 |
| I-130 | 0.078 |
| I-131 | 0.02 |
| I-132 | 0.01 |
| I-133 | 0.039 |
| I-134 | 0.02 |
| I-135 | 0.01 |
| I-138 | 0.01 |
| I-139 | 0.01 |
| I-140 | 0.156 |

-continued

| Cmpd | CP3 shift (uM) |
|---|---|
| I-143 | 0.01 |
| I-145 | 0.01 |

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

The invention claimed is:

1. A compound of formula I:

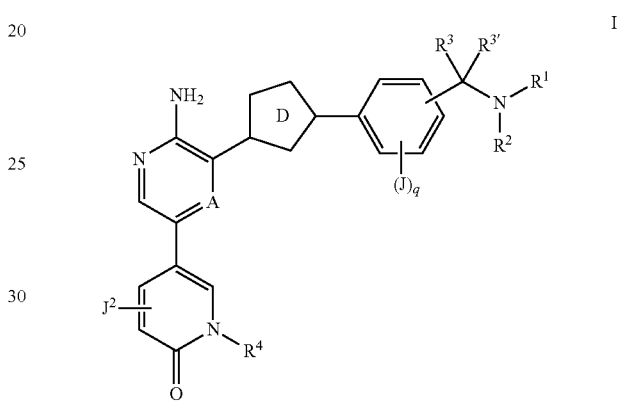

or a pharmaceutically acceptable salt thereof, wherein
A is CH or N;
Ring D is isoxazolyl or oxadiazolyl;
J is —$C_{1-3}$alkyl, —O($C_{1-3}$alkyl), halo, or CN;
q is 0 or 1;
$R^1$ is H, $C_{1-6}$aliphatic, phenyl, or tetrahydrofuranyl, wherein said $C_{1-6}$aliphatic is optionally substituted with one occurrence of OH and up to two occurrences of F;
$R^2$ is H or $C_{1-3}$alkyl;
or $R^1$ and $R^2$, together with the nitrogen atom to which they are attached, optionally form a 4-6 membered monocyclic heterocyclyl ring having 1-2 heteroatoms selected from the group consisting of O, N, and S;
$R^3$ is H or $C_{1-3}$alkyl, wherein said alkyl is optionally substituted with up to three occurrences of F;
$R^{3'}$ is H or $C_{1-3}$alkyl;
or $R^3$ and $R^{3'}$, together with the carbon atom to which they are attached, form a 3-4 membered monocyclic saturated carbocyclic ring;
$R^4$ is Q, —($C_{1-2}$alkyl)-Q, or a $C_{1-10}$aliphatic, wherein up to two methylene units of said $C_{1-10}$aliphatic are optionally replaced with O, NR', S, or CO; and wherein one methylene unit of the $C_{1-2}$alkyl can optionally be replaced with C(=O);
$R^4$ is optionally substituted with 1-3 occurrences of halo, CN, NRR', OR, or $C_{1-3}$aliphatic, wherein said $C_{1-3}$aliphatic is optionally substituted with up to 1 occurrence of CN and up to 4 occurrences of F;
Q is 3-6 membered saturated, partially unsaturated, or aromatic monocyclic ring having 0-2 heteroatoms selected from the group consisting of oxygen, nitrogen, and sulfur; Q is optionally substituted with 1-3 occurrences of halo, CN, NRR', OR, or $C_{1-3}$aliphatic, wherein said $C_{1-3}$aliphatic is optionally substituted with up to 4 occurrences of F;

R' is H or $C_{1-4}$alkyl;

R is H or $C_{1-4}$alkyl;

or R and R', together with the nitrogen to which they are attached, optionally form a 3-6 membered heterocyclic ring having 1-2 heteroatoms selected from the group consisting of O, N, and S;

$J^2$ is H, $C_{1-6}$aliphatic, halo, phenyl, or CN, wherein said $C_{1-6}$aliphatic is optionally substituted with 1-2 occurrences of halo, OH, CN, or OR.

2. The compound of claim 1, wherein $R^1$ is H, $C_{1-6}$aliphatic, or tetrahydrofuranyl, wherein said $C_{1-6}$aliphatic is optionally substituted with one occurrence of OH and up to two occurrences of F;

$R^{3'}$ is H;

$R^4$ is Q, —($C_{1-2}$alkyl)-Q, or a $C_{1-10}$aliphatic, wherein up to two methylene units of said $C_{1-10}$aliphatic are optionally replaced with O, NR', S, or CO;

Q is 3-6 membered saturated or partially unsaturated monocyclic ring having 0-2 heteroatoms selected from the group consisting of oxygen, nitrogen, and sulfur; Q is optionally substituted with 1-3 occurrences of halo, CN, NRR', OR, or $C_{1-3}$aliphatic, wherein said $C_{1-3}$aliphatic is optionally substituted with up to 4 occurrences of F;

$J^2$ is H.

3. The compound of claim 1, wherein A is N.

4. The compound of claim 1, wherein $R^2$ is H.

5. The compound of claim 4, wherein Ring D is isoxazolyl.

6. The compound of claim 4, wherein Ring D is oxadiazolyl.

7. The compound of claim 5,
wherein

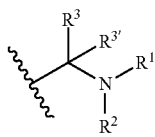

is bonded at the meta or para position of the phenyl ring as shown in Formula Ia and Ib below:

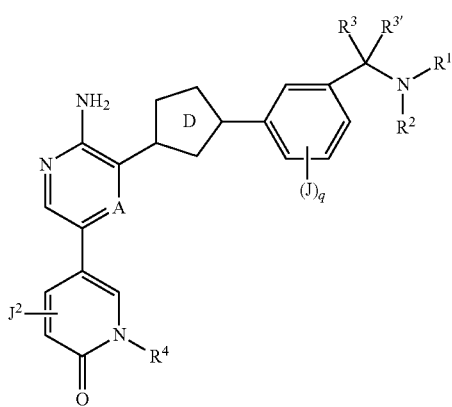

Ia

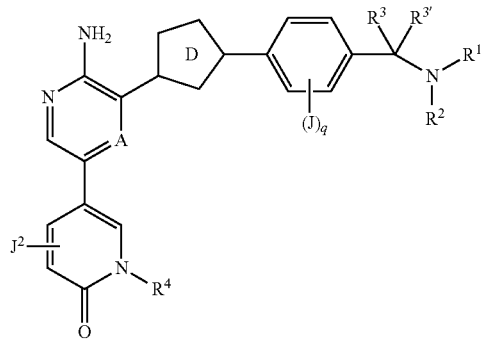

Ib or a pharmaceutically acceptable salt thereof; or
or a pharmaceutically acceptable salt thereof.

8. The compound of claim 7 having Formula Ib or a pharmaceutically acceptable salt thereof.

9. The compound of claim 8, wherein $R^3$ is H or methyl.

10. The compound of claim 9, wherein $R^3$ is H.

11. The compound of claim 1, wherein $R^1$ is $C_{1-6}$aliphatic, phenyl, or tetrahydrofuranyl.

12. The compound of claim 11 wherein $R^1$ is $C_{1-6}$aliphatic or tetrahydrofuranyl.

13. The compound of claim 12, wherein $R^1$ is $C_{1-4}$alkyl or tetrahydrofuranyl.

14. The compound of claim 13, wherein $R^1$ is $C_{1-4}$alkyl.

15. The compound of claim 13, wherein $R^1$ is methyl, isopropyl, tert-butyl, or tetrahydrofuranyl.

16. The compound of claim 11, wherein $R^1$ is $C_{1-6}$aliphatic and wherein $R^1$ is optionally substituted with one occurrence of OH or 1-2 occurrences of fluoro.

17. The compound of claim 1, wherein q is 1.

18. The compound of claim 17, wherein J is bonded at the ortho position of the phenyl ring as shown in Formula Ic:

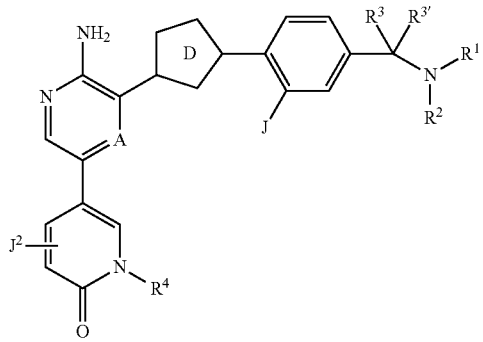

Ic or a pharmaceutically acceptable salt thereof.

19. The compound of claim 18, wherein J is fluoro, $C_{1-3}$alkyl, O($C_{1-3}$alkyl), or CN.

20. The compound of claim 19, wherein J is methyl or isopropyl.

21. The compound of claim 18, wherein J is fluoro, $CH_3$, $OCH_3$, or CN.

22. The compound of claim 1, wherein q is 0.

23. The compound according to claim 1, wherein $R^4$ is Q, —($C_{1-2}$alkyl)-Q, or $C_{1-10}$aliphatic, wherein up to two methylene units of said $C_{1-10}$aliphatic are optionally replaced with O, NR', or CO; and wherein one methylene unit of the $C_{1-2}$alkyl can optionally be replaced with C(═O).

24. The compound of claim 23, wherein Q is a 5 membered heteroaryl having 1-2 heteroatoms selected from the group consisting of O, N, and S; 4-6 membered heterocyclyl having 1 heteroatoms selected from the group consisting of O and N; or a 3-6 membered cycloalkyl.

25. The compound of claim 24, wherein Q is furanyl, thiazoyl, imidazolyl, oxetanyl, tetrahydrofuranyl, tetrahydropyranyl, or 3-6 membered cycloalkyl.

26. The compound of claim 23, wherein $R^4$ is $C_{1-10}$aliphatic, —($C_{1-4}$alkyl)-$CF_3$, —($C_{1-2}$alkyl)-($C_3$-$C_6$cycloaliphatic), —($C_{1-4}$alkyl)-N($C_{1-3}$alkyl)$_2$, —($C_{1-4}$alkyl)-O($C_{1-3}$alkyl), $C_3$-$C_6$cycloaliphatic, or tetrahydrofuranyl, wherein said alkyl group is optionally substituted.

27. The compound of claim 26, wherein $R^4$ is $C_{1-6}$alkyl, —($C_{1-4}$alkyl)-$CF_3$, —($C_{1-2}$alkyl)-($C_3$-$C_6$cycloaliphatic), $C_3$-$C_6$cycloaliphatic, or tetrahydrofuranyl.

28. The compound of claim 1, wherein $R^4$ is methyl, ethyl, isopropyl, sec-butyl, isobutyl, $CH(CH_3)C\equiv CCH_3$, $CH(CH_3)COOH$, $CH_2CONH_2$, $CH(CH_3)CONH_2$, $CH(CH_3)CONHCH_3$, $CH(CH_3)CON(CH_2CH_3)_2$, cyclobutyl, cyclopentyl, methylcyclopentyl, $CH(CH_3)$(cyclopropyl), $CH_2$(cyclopropyl), $CH_2CH_2$(cyclopropyl), $CH_2CH_2$(cyclopentyl), $CH(CH_3)CH_2F$, $CH(CH_3)CF_3$, $CH_2CF_3$, $C(CH_3)_2CN$, $C(CH_2CH_3)_2CN$, $CH(CH_3)CN$, $CH_2CN$, $CH_2CH(CH_3)CH_2CH_3$, $CH(CH_2CH_3)_2$ $CH(CH_2OH)_2$ $CH(CH_3)CH_2OH$, $CH(CH_3)CH_2OCH_3$, $CH_2CH_2OH$, $CH_2CH_2OCH_3$, $CH_2CH_2N(CH_3)_2$, $CH_2CH_2CH_2NH_2$, tetrahydrofuranyl, tetrahydropyranyl, $CH_2$(furanyl), $CH_2$(thiazolyl), $CH_2$(imidazolyl), $CH_2CH_2CN$, $CH_2CH(OCH_3)CH_2CH_3$, $CH_2CH_2CH(CH_3)CH_2CH_3$,

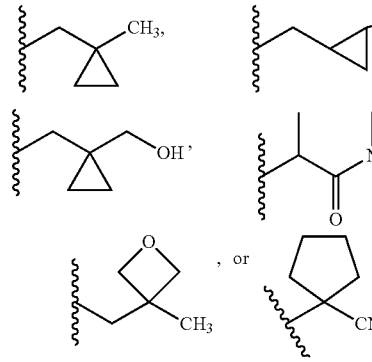

29. The compound of claim 26, wherein $R^4$ is methyl, ethyl, isopropyl, sec-butyl, isobutyl, $CH(CH_3)C\equiv CCH_3$, $CH(CH_3)COOH$, cyclobutyl, cyclopentyl, $CH(CH_3)$(cyclopropyl), $CH(CH_3)CH_2F$, $CH(CH_3)CF_3$, $CH_2CF_3$, $CH(CH_3)CN$, $CH_2CN$, $CH(CH_3)CH_2OH$, $CH_2CH_2OH$, $CH_2CH_2OCH_3$, $CH_2CH_2N(CH_3)_2$, $CH_2CH_2CH_2NH_2$, $CH(CH_3)CH_2OCH_3$, or tetrahydrofuranyl.

30. The compound of claim 28, wherein $R^4$ is methyl, ethyl, isopropyl, sec-butyl, isobutyl, $CH(CH_3)C\equiv CCH_3$, cyclobutyl, cyclopentyl, $CH(CH_3)$(cyclopropyl), $CH(CH_3)CH_2F$, $CH(CH_3)CF_3$, $CH_2CF_3$, $CH(CH_3)CN$, $CH_2CN$, or tetrahydrofuranyl.

31. The compound of claim 1, wherein $J^2$ is H, CN, F, Cl, Br, $CH=CH_2$, methyl, ethyl, isopropyl, $CH_2OH$, $CH(CH_2CH_3)CH_2CH_2CH_3$, $CH(CH_2CH_3)_2$, cyclopentyl, cyclohexyl, cyclohexenyl, or phenyl.

32. The compound of claim 1, wherein
A is N;
$J^2$ is H;
$R^1$ is methyl;
$R^2$ is H;
$R^3$ is H; and
$R^4$ is $C_{1-10}$aliphatic, —($C_{1-4}$alkyl)-$CF_3$, —($C_{1-2}$alkyl)-($C_3$-$C_6$cycloaliphatic), —($C_{1-4}$alkyl)-N($C_{1-3}$alkyl)$_2$, —($C_{1-4}$alkyl)-O($C_{1-3}$alkyl), $C_3$-$C_6$cycloaliphatic, or tetrahydrofuranyl, wherein said alkyl group is optionally substituted.

33. The compound of claim 32, wherein $R^4$ is $C_{1-10}$aliphatic, —($C_{1-4}$alkyl)-$CF_3$, —($C_{1-2}$alkyl)-($C_3$-$C_6$cycloaliphatic), $C_3$-$C_6$cycloaliphatic, or tetrahydrofuranyl.

34. The compound of claim 33, wherein said alkyl group of $R^4$ is optionally substituted with $CH_3$, OH, $OCH_3$, $NH_2$, CN, or tetrahydrofuranyl.

35. A compound selected from the group consisting of:

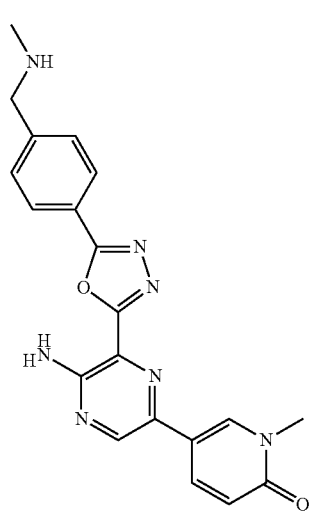

I-1

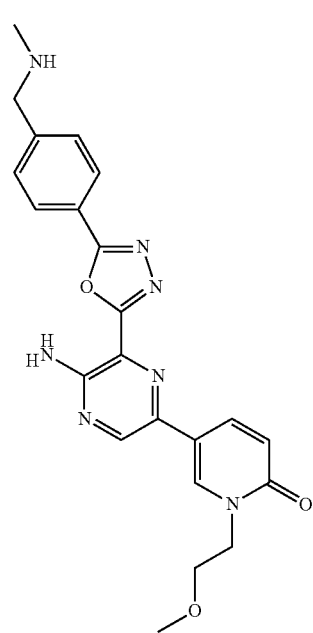

I-2

I-3
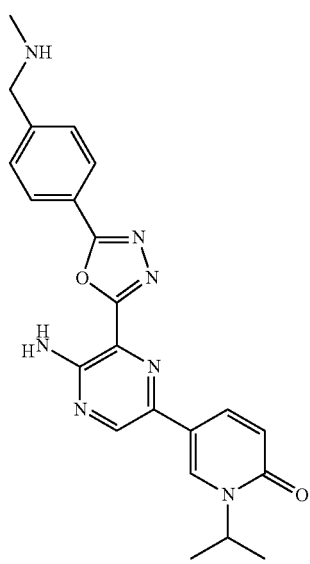
I-4
I-5
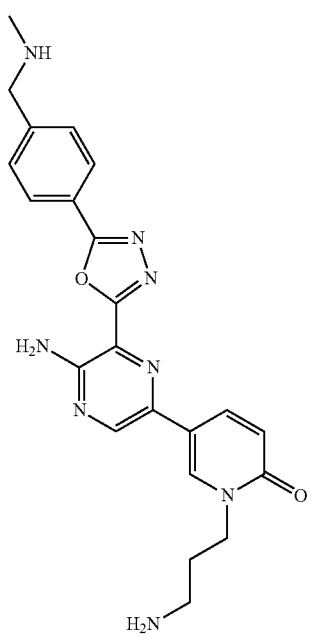
I-6
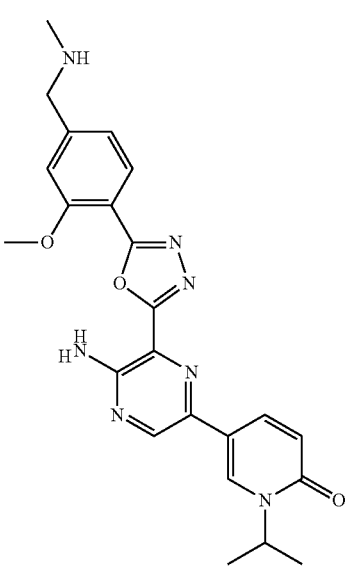

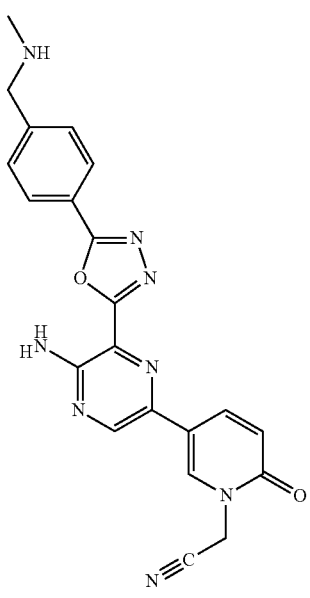
I-7
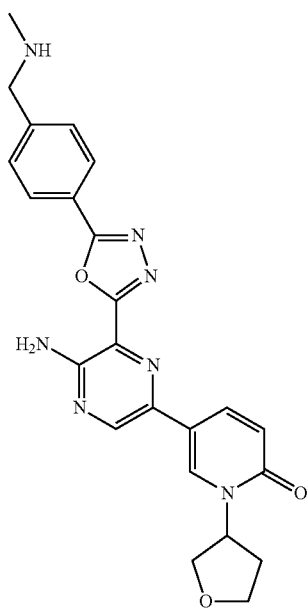
I-9
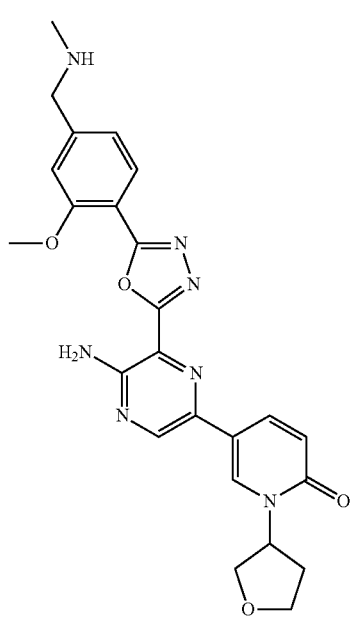
I-8
I-10

I-11
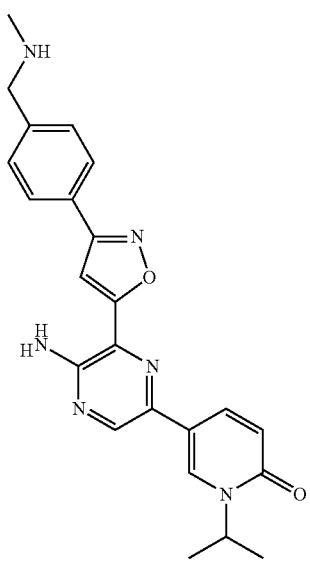
I-12
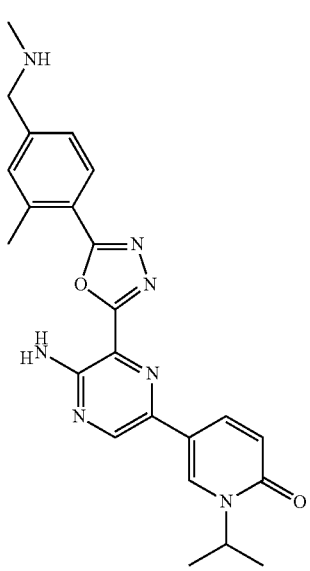
I-13
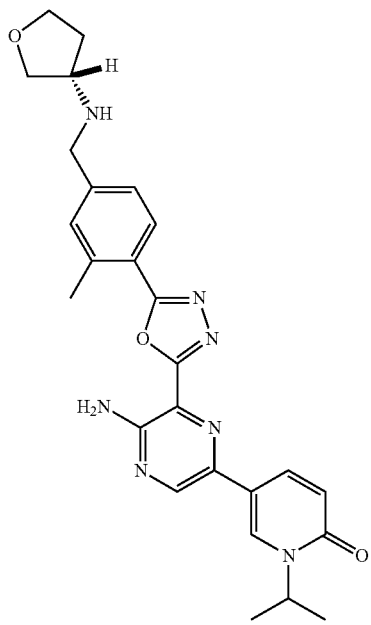
I-14
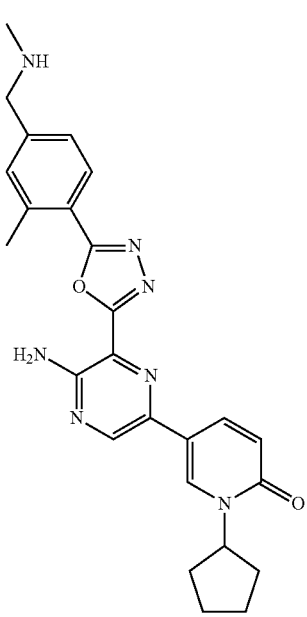

I-15
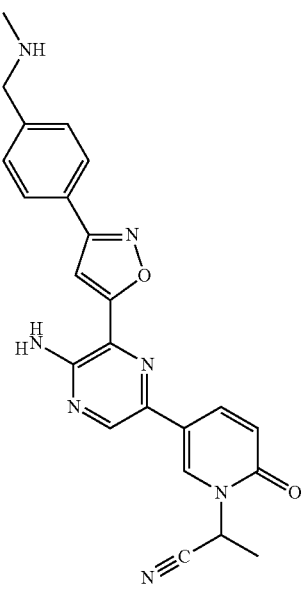
I-16
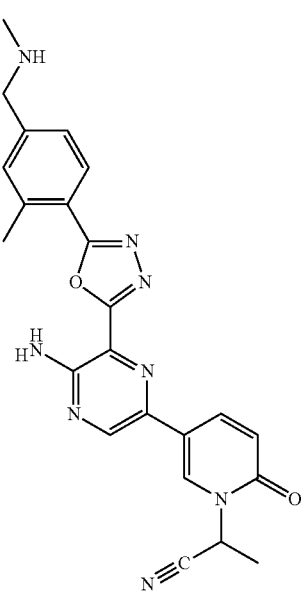
I-17
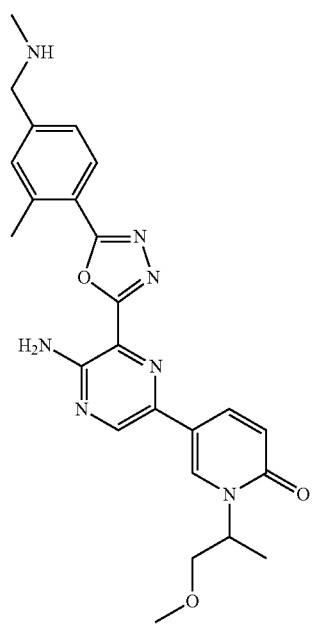
I-18
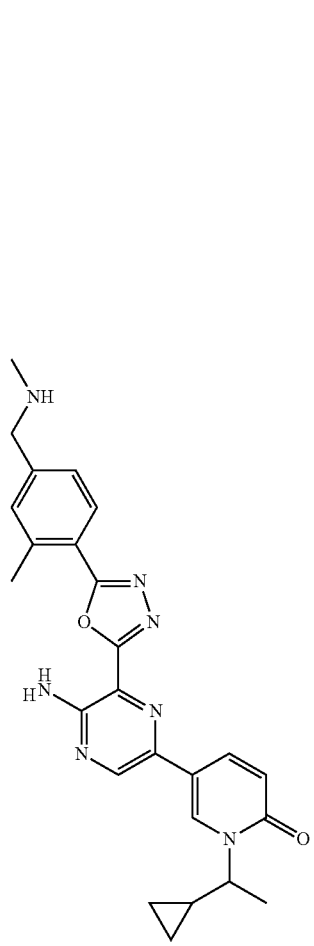

I-19
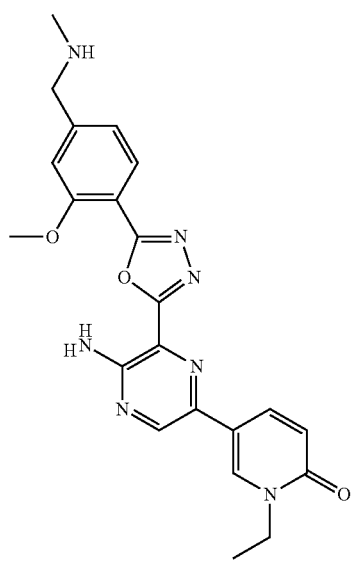
I-20
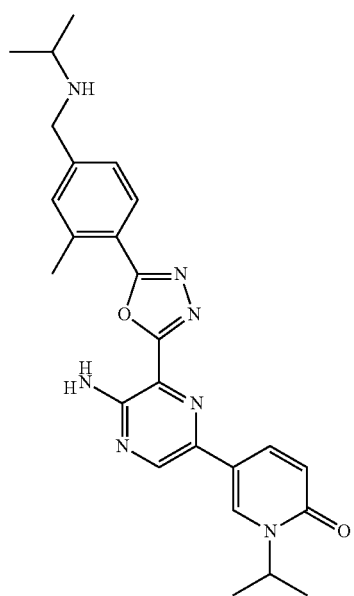
I-21
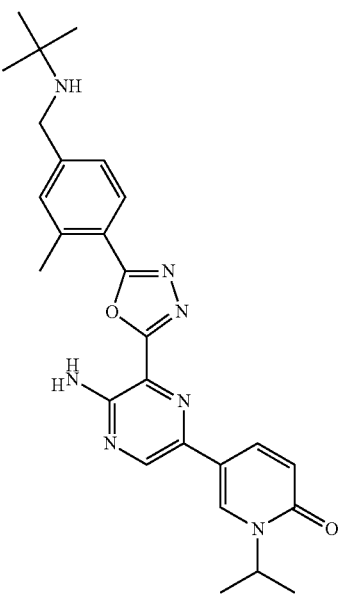
I-22
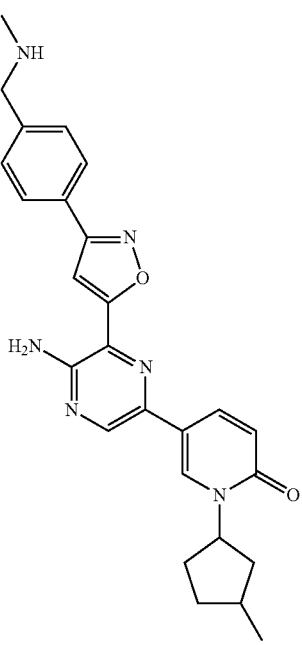

I-23
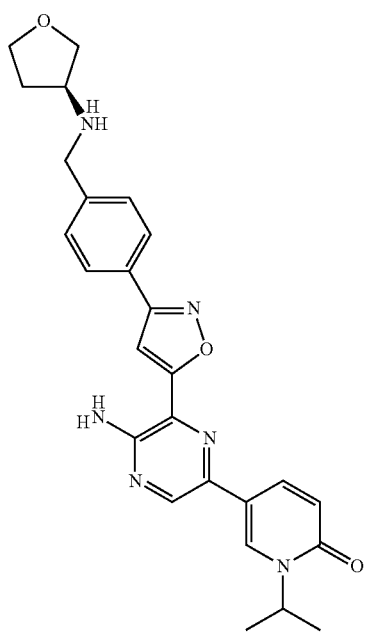
I-24
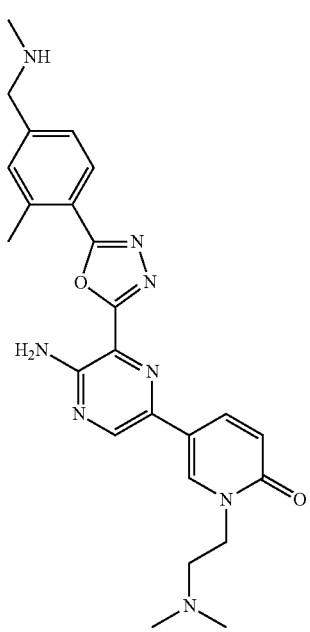
I-25
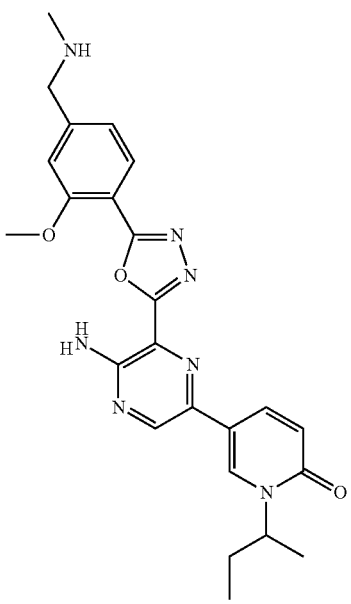
I-26
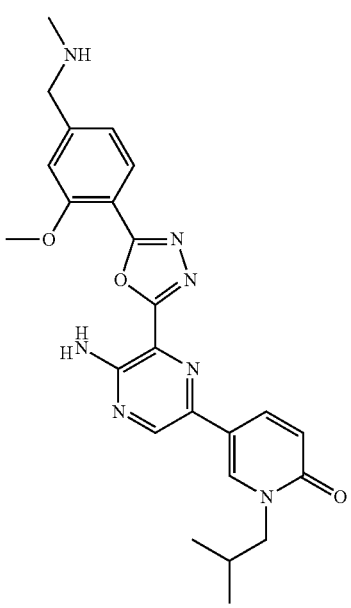

I-27
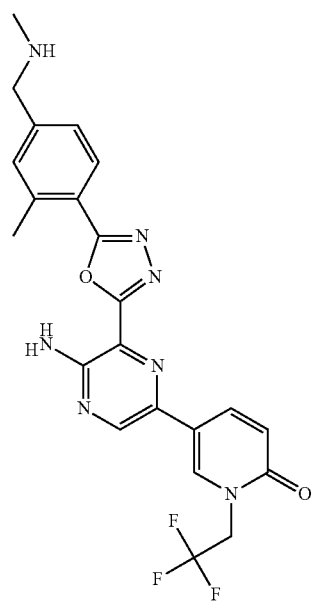
I-29
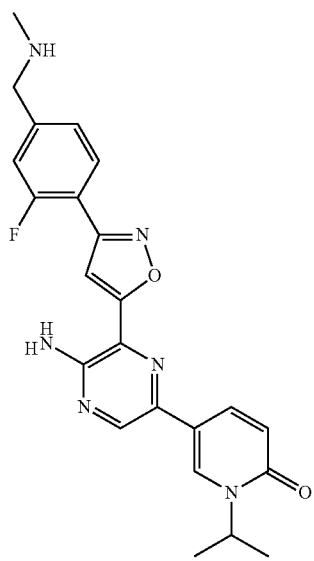
I-28
I-30
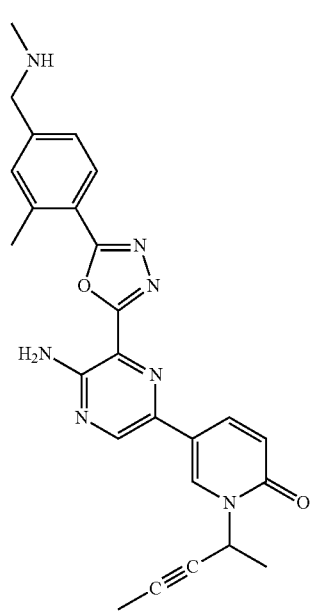

-continued
I-31
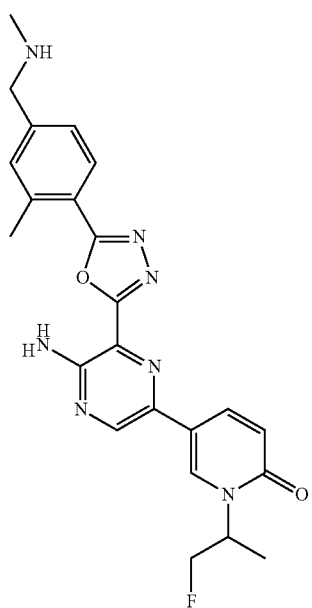
I-33
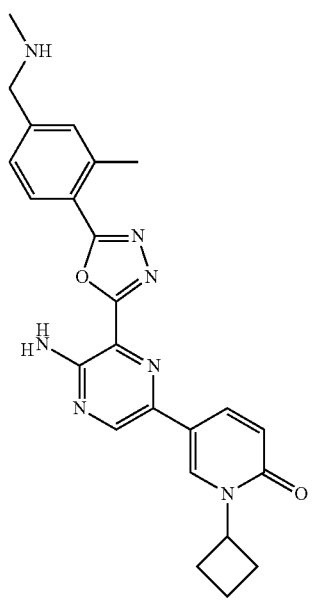
I-32
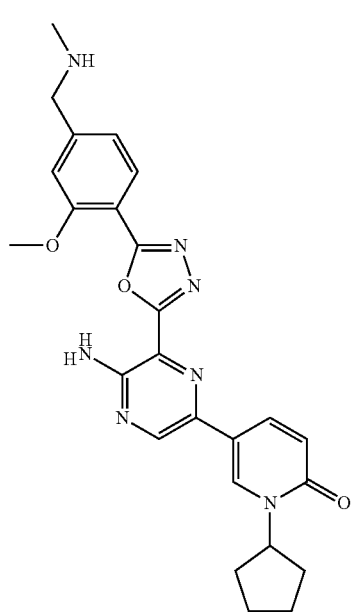
I-34
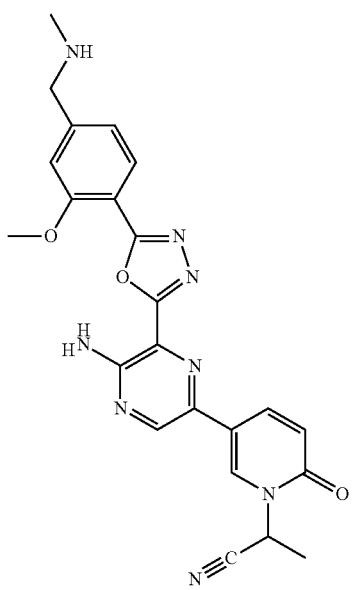

I-35
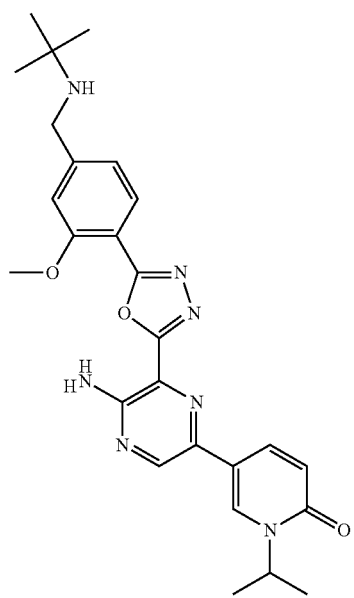
I-36
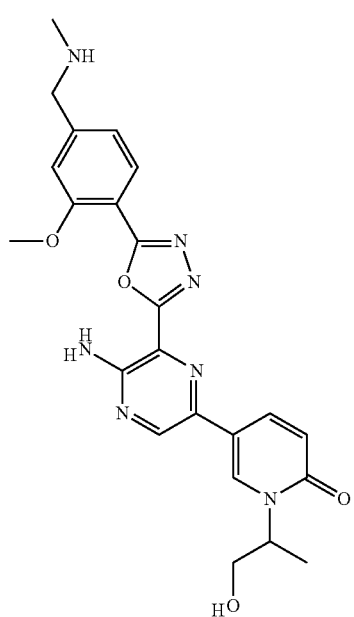
I-37
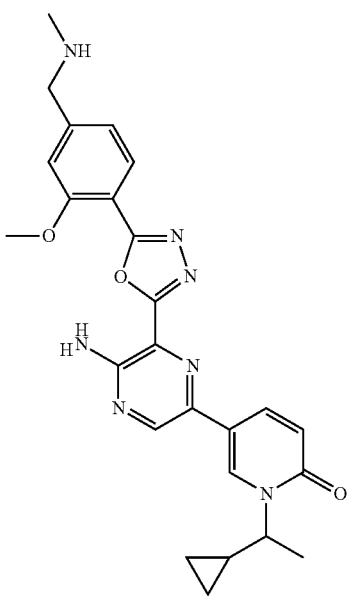
I-38
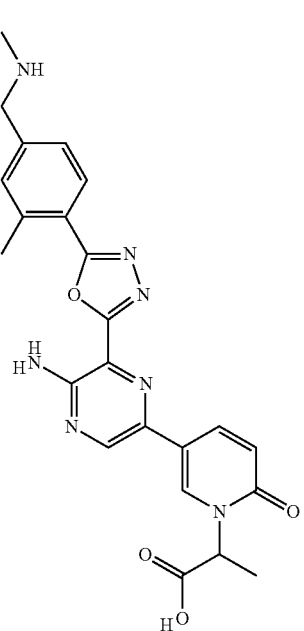

I-39
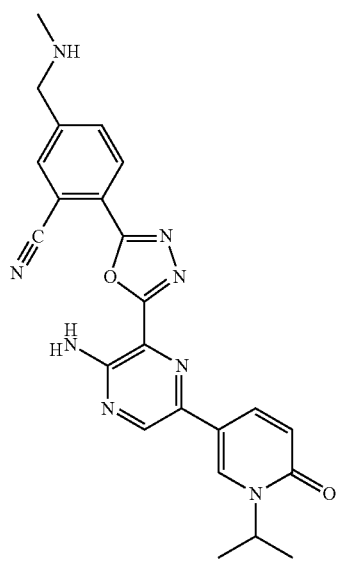
I-40
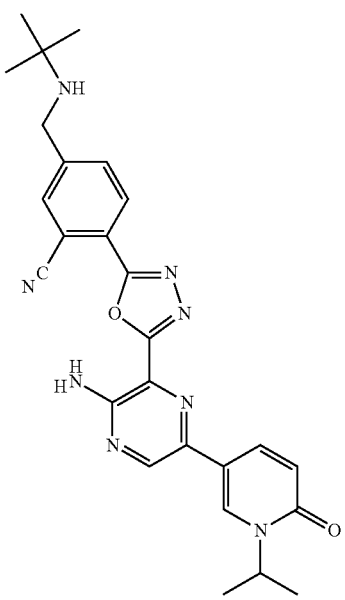
I-41
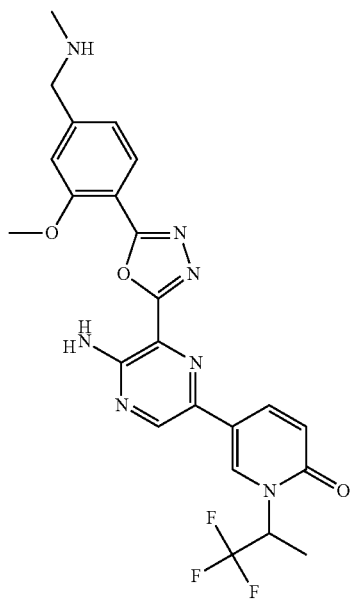
I-42
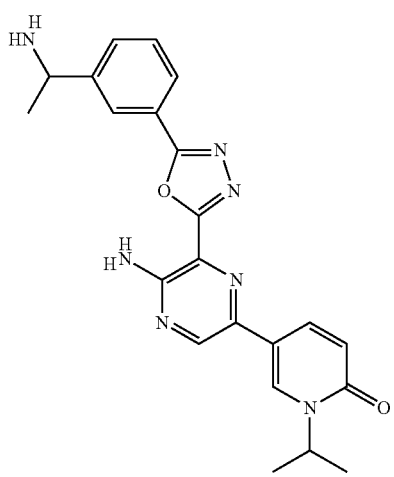
I-43
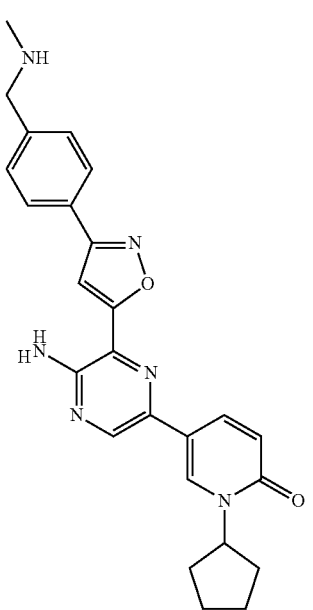

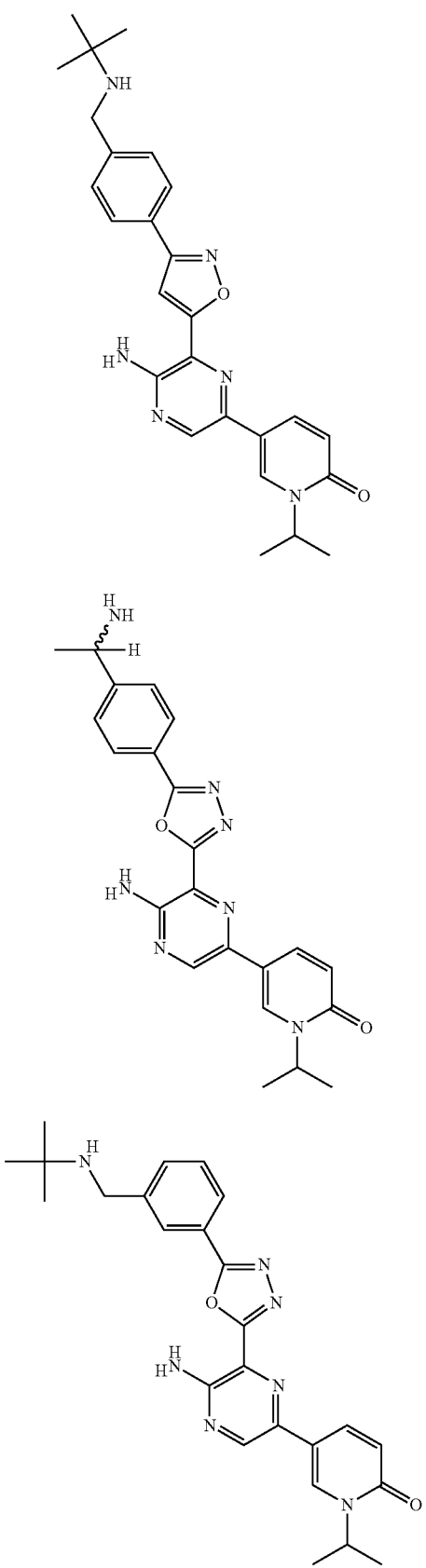
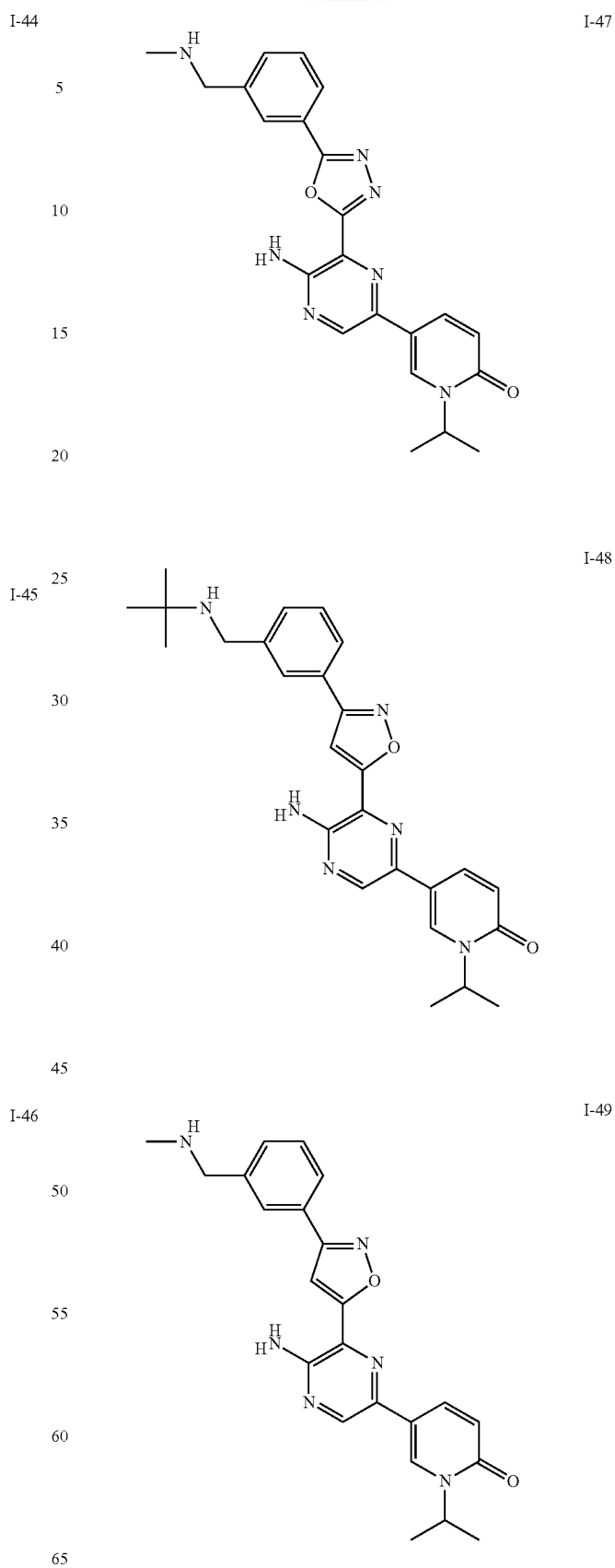

I-50
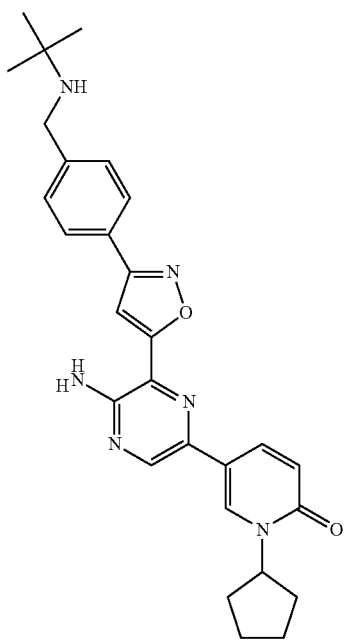
I-52
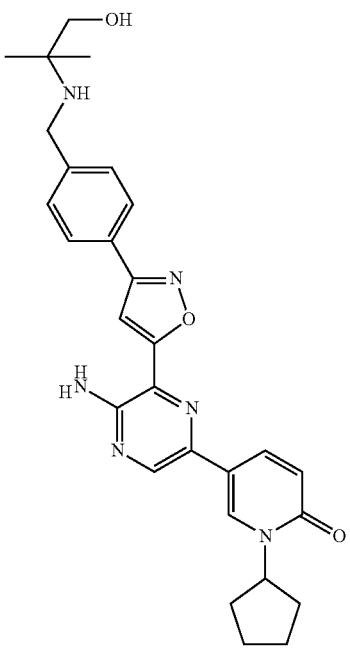
I-51
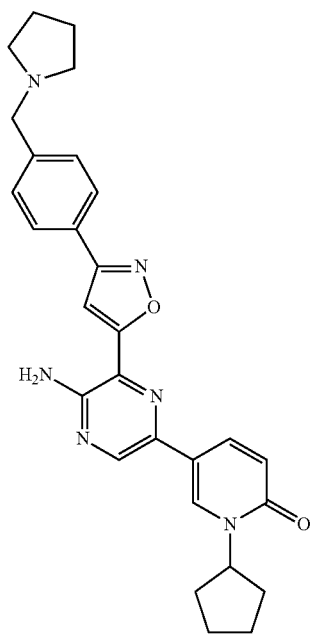
I-53
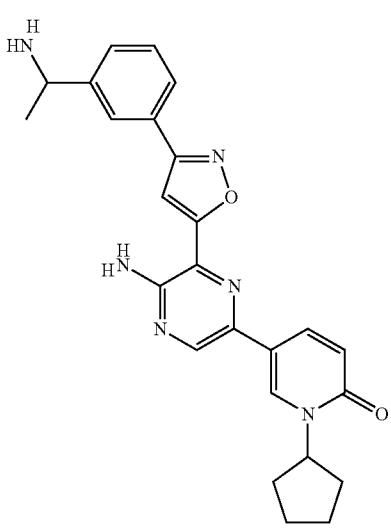

I-54
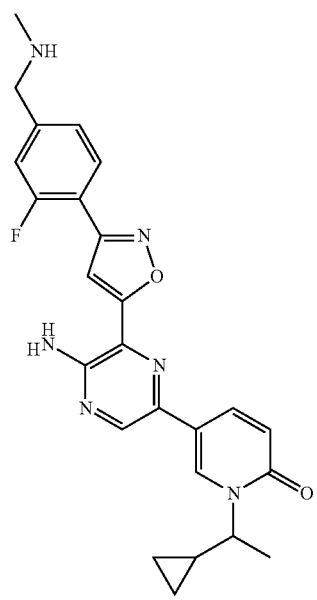
I-55
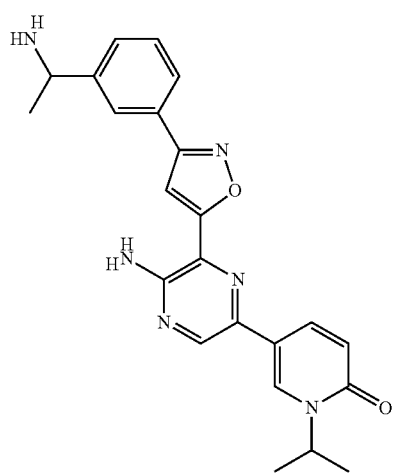
I-56
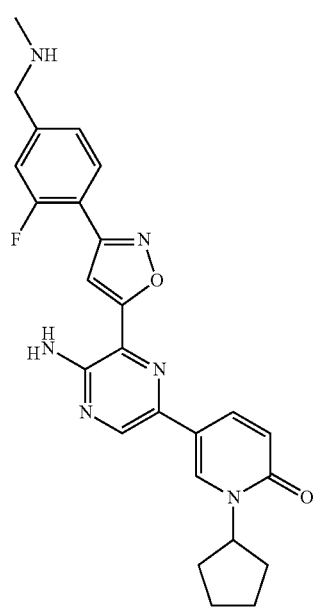
I-57
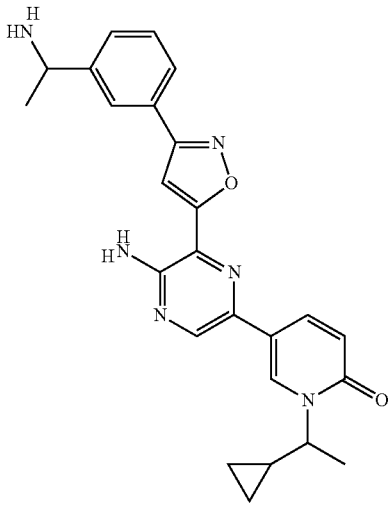
I-58
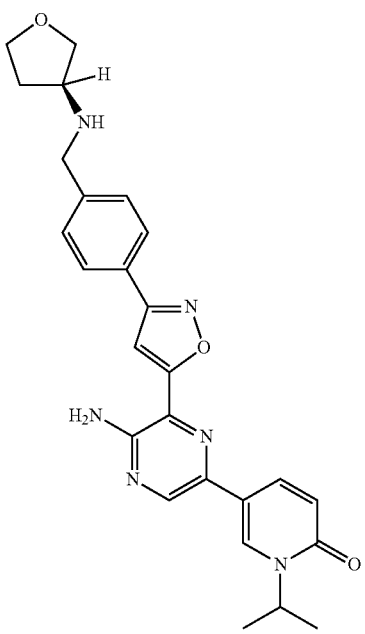

I-59
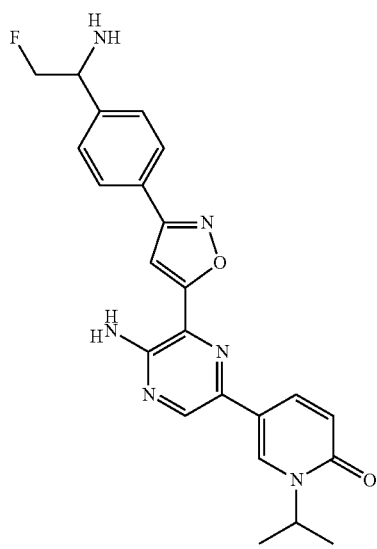
I-60
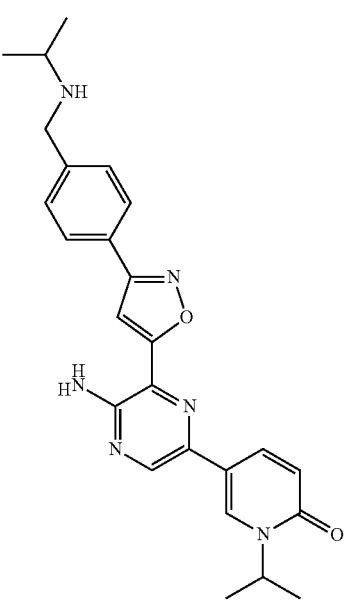
I-61
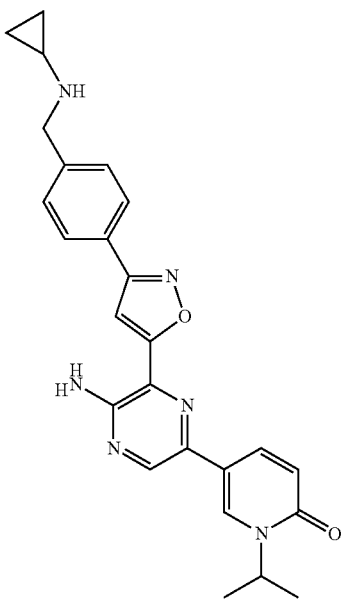
I-62
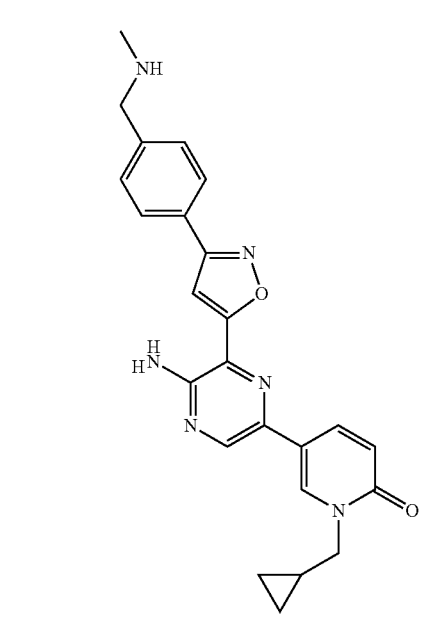

215
-continued
I-63
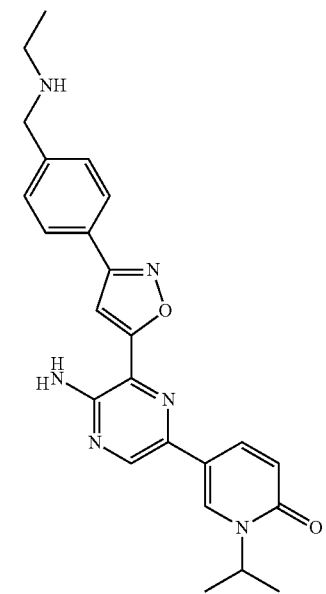
I-64
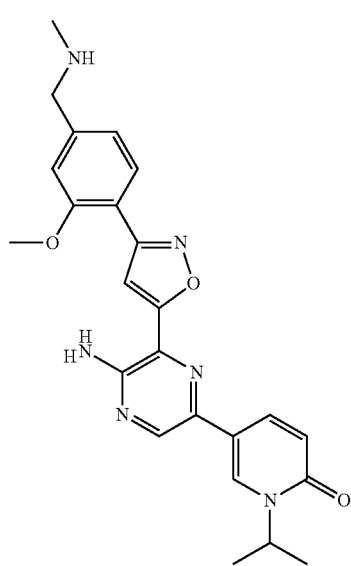
216
-continued
I-65
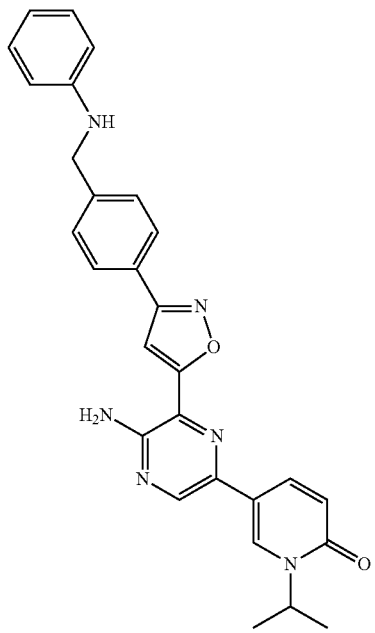
I-66
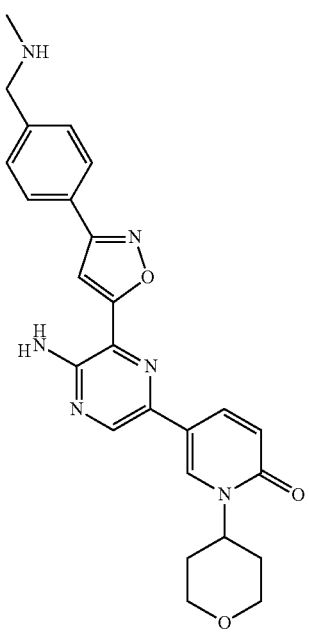
I-67
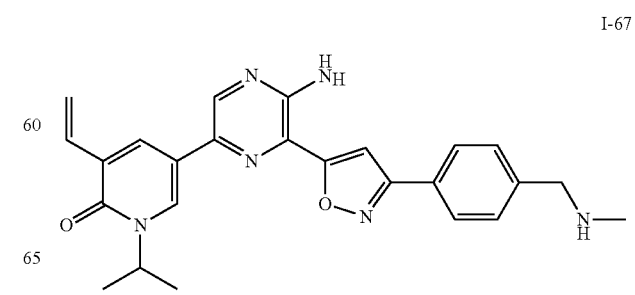

I-68
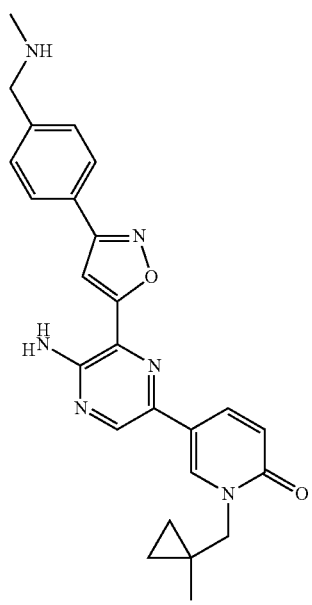
I-69
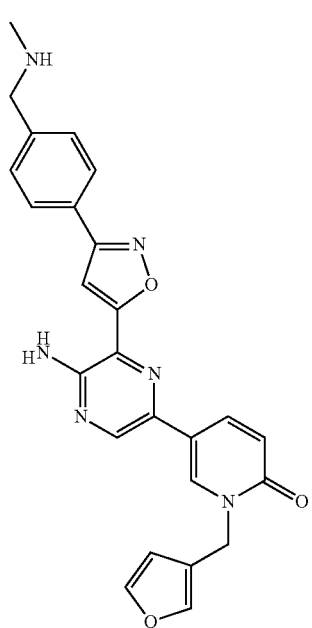
I-70
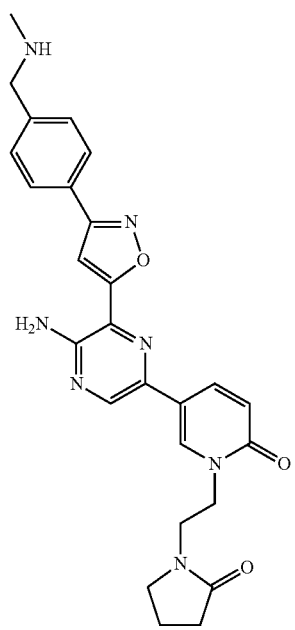
I-71
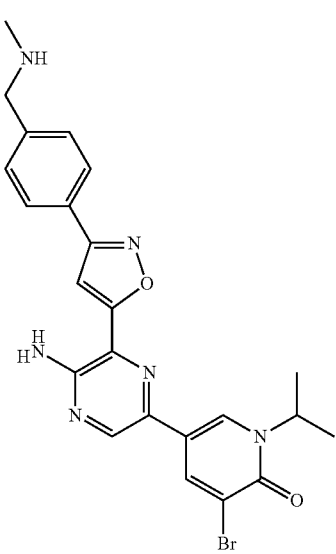

-continued
I-72
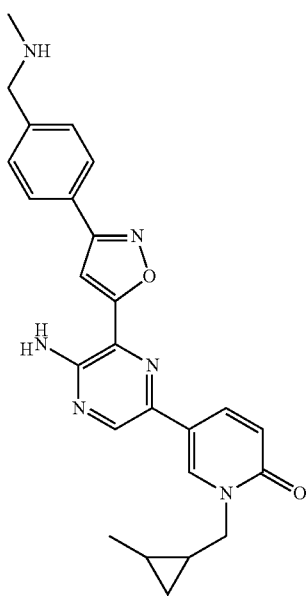
I-73
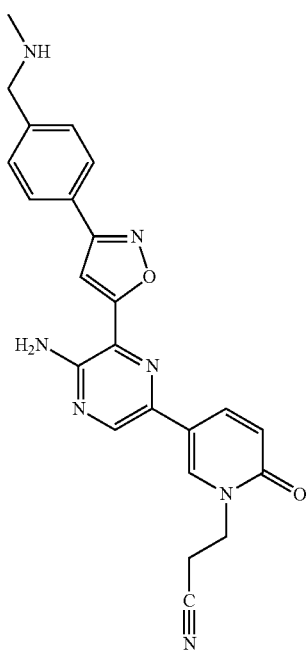
-continued
I-74
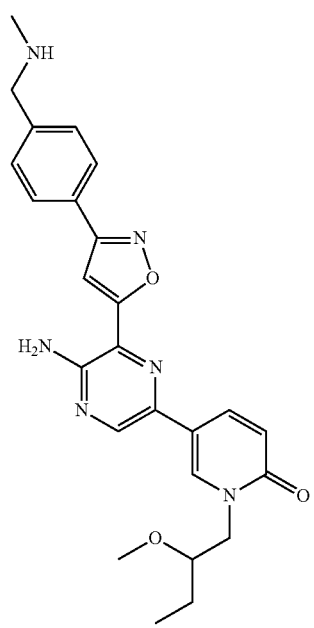
I-75
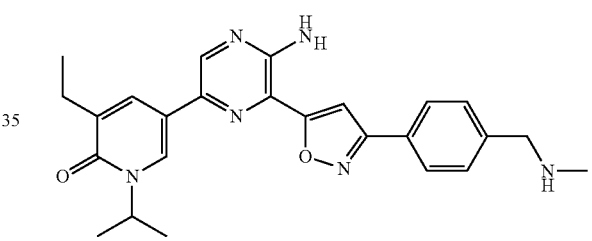
I-76
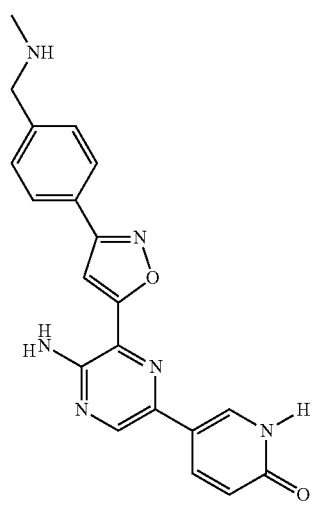

I-77
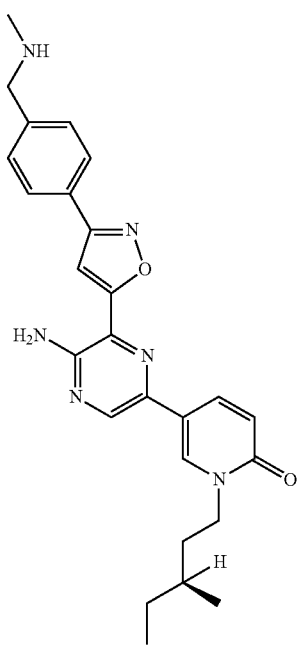
I-78
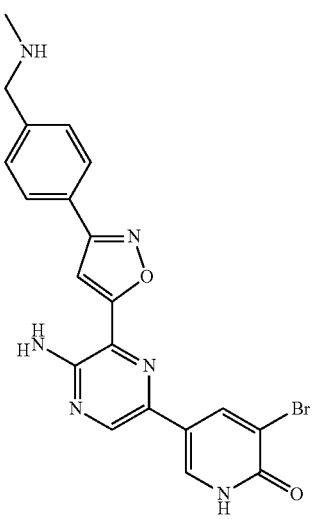
I-79
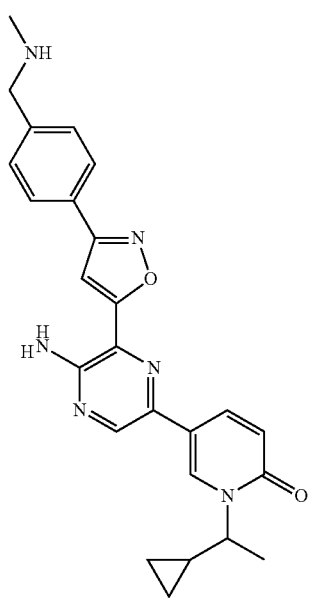
I-80
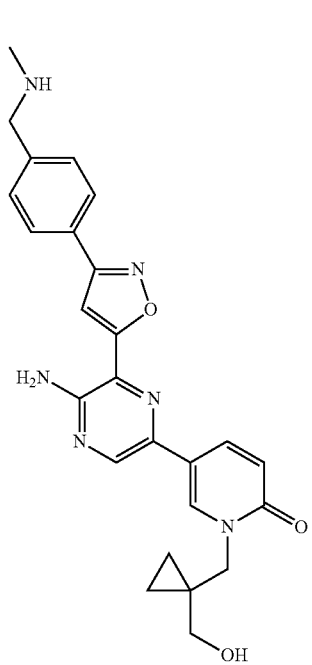

I-81
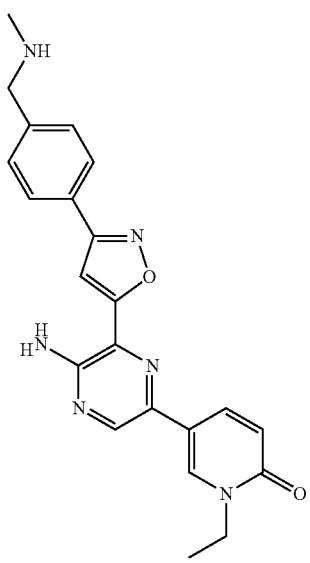
I-82
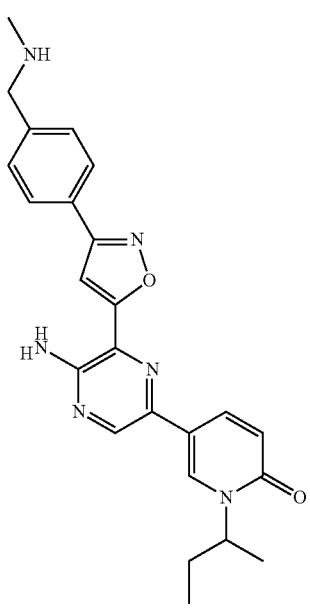
I-83
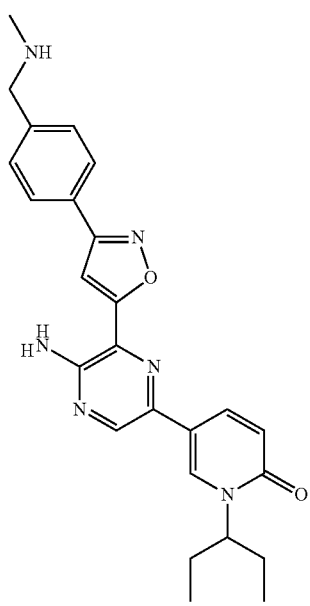
I-84
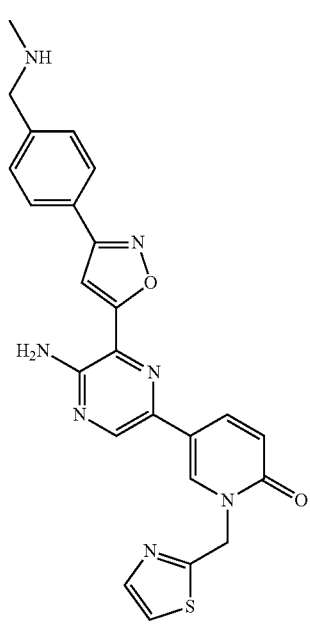

-continued
I-85
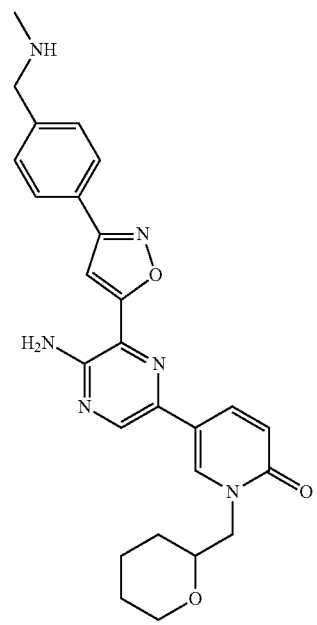
I-87
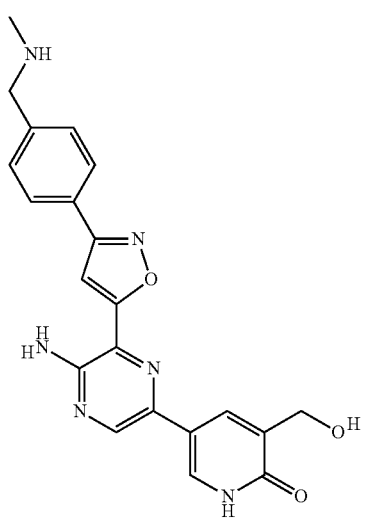
I-88
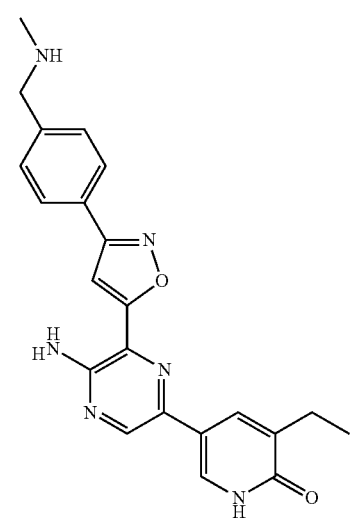
I-89
I-86

I-90
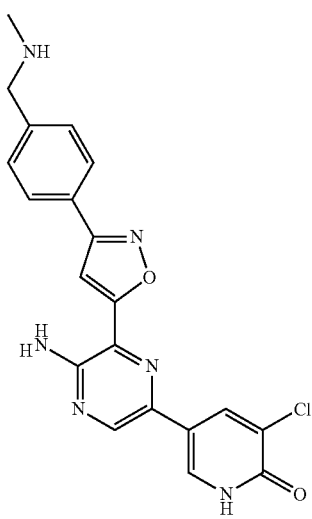
I-91
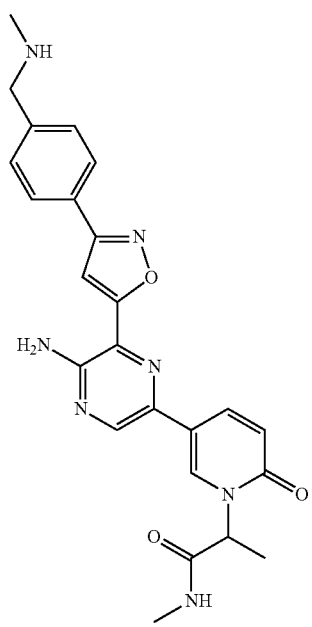
I-92
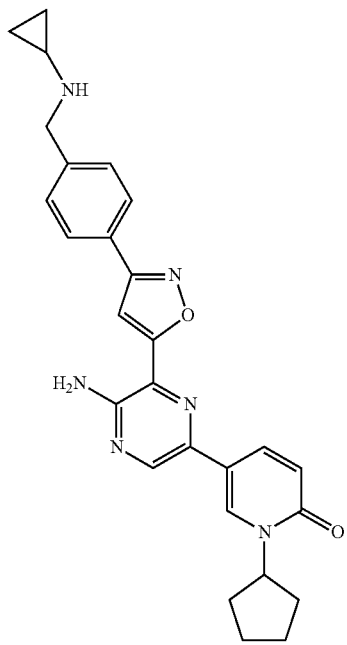
I-93
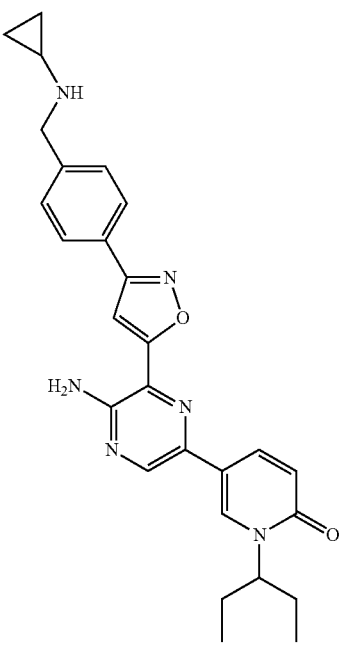

I-94
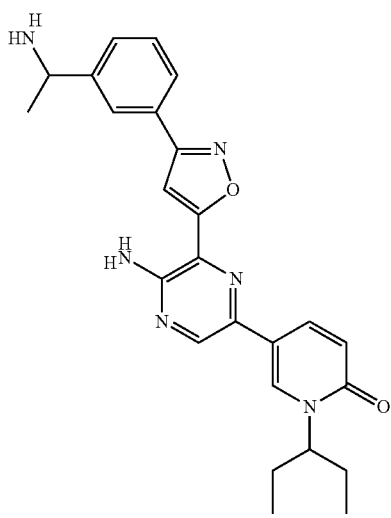
I-95
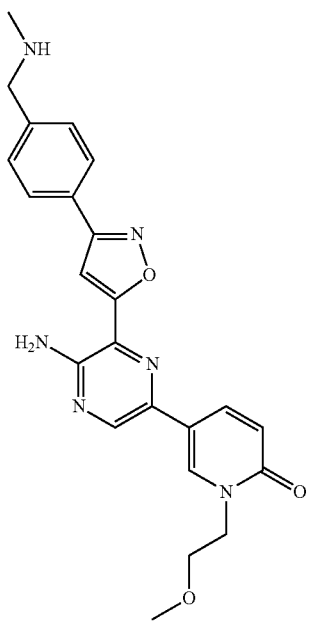
I-96
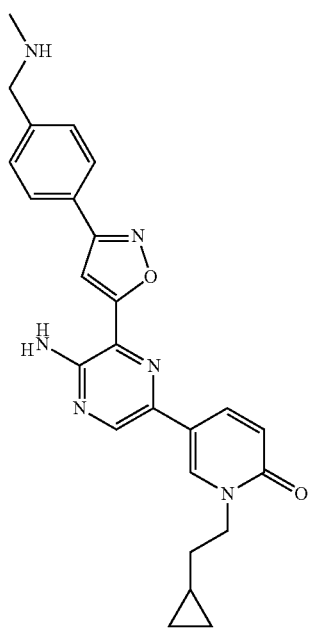
I-97
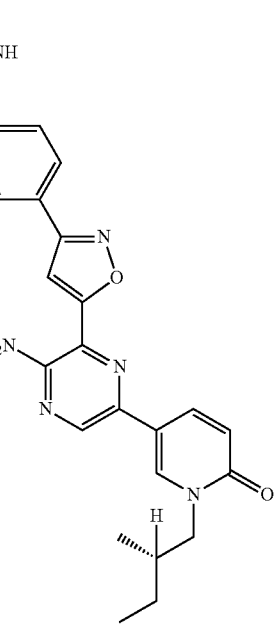

-continued
I-98
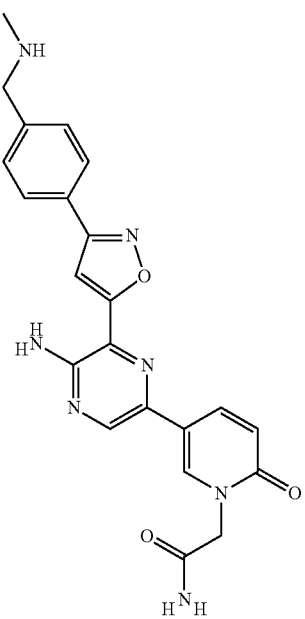
I-99
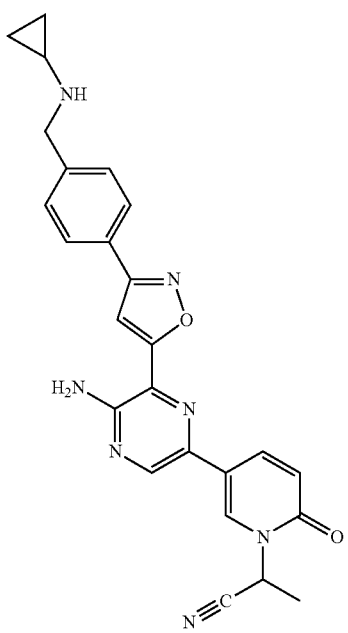
-continued
I-100
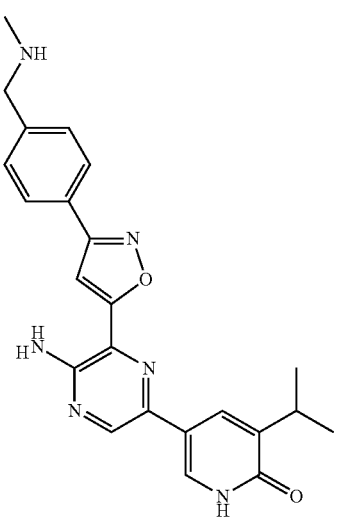
I-101
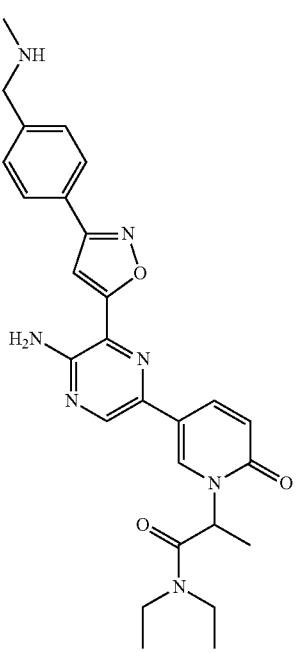

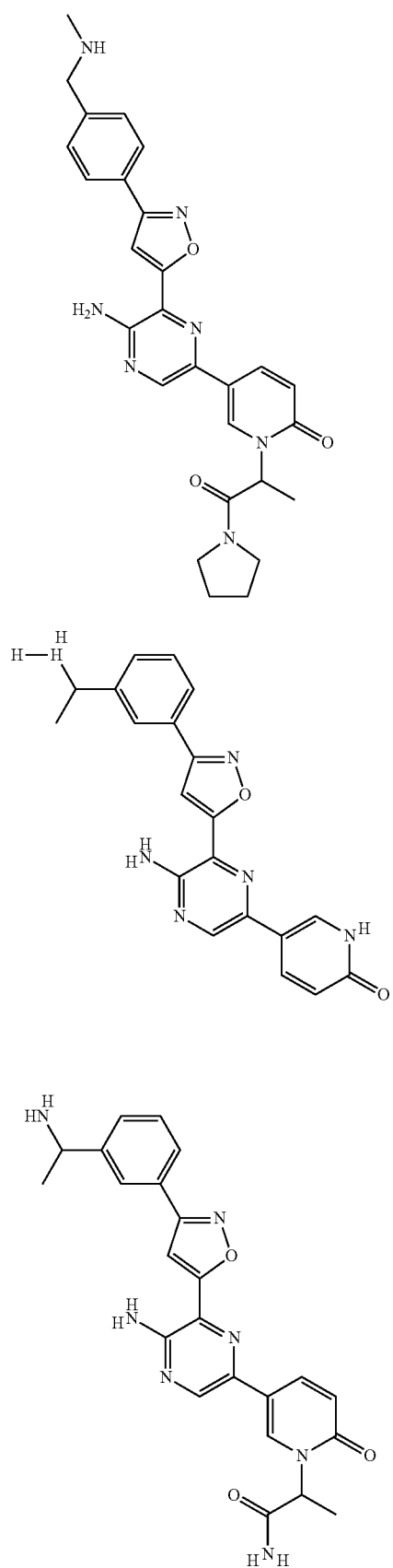
I-102
I-103
I-104
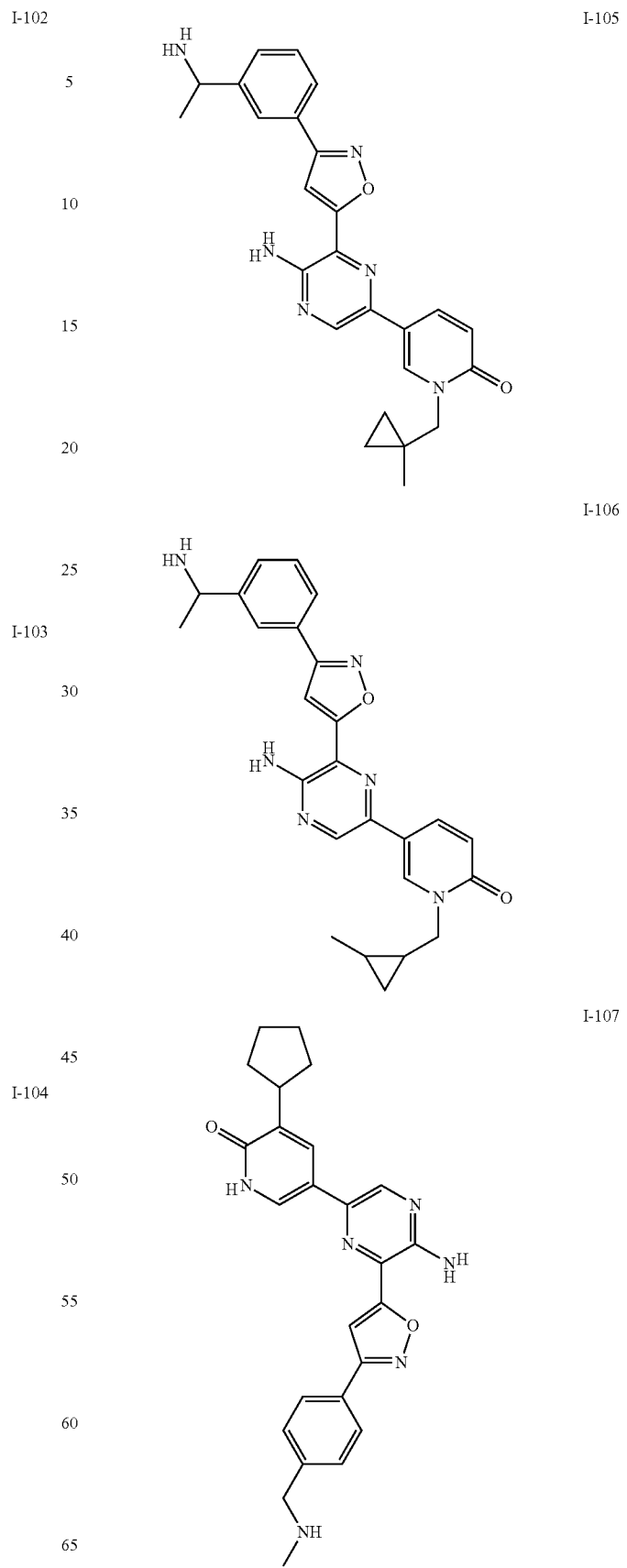
I-105
I-106
I-107

I-108
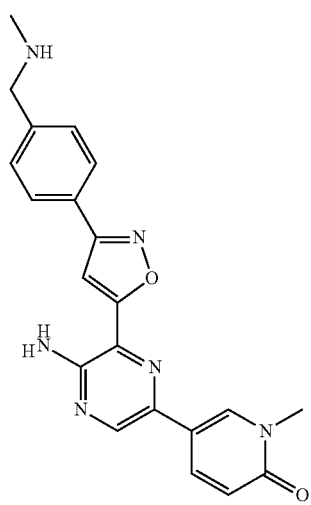
I-109
I-110
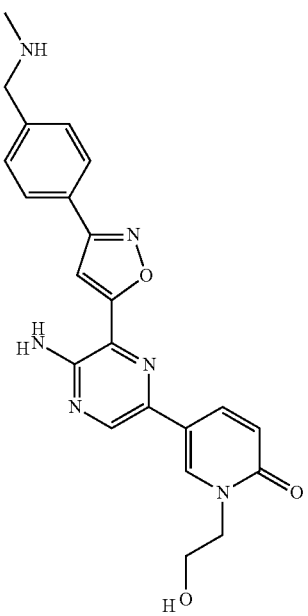
I-111
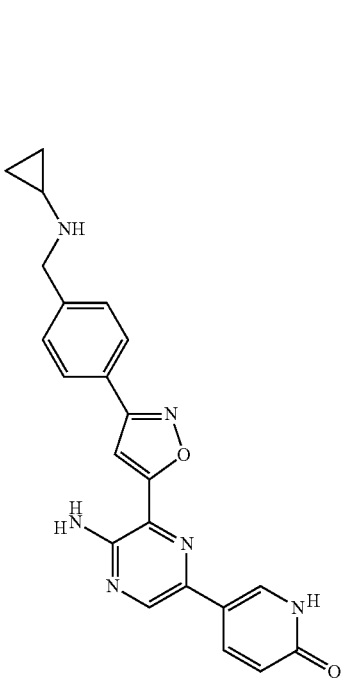

I-112
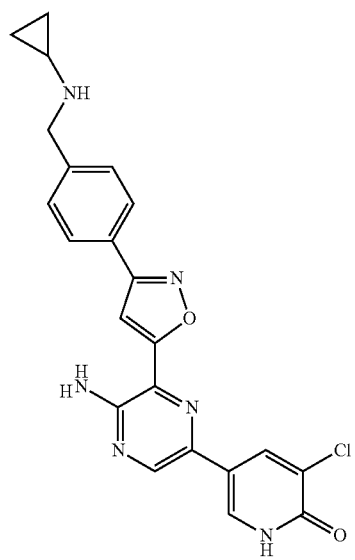
I-113
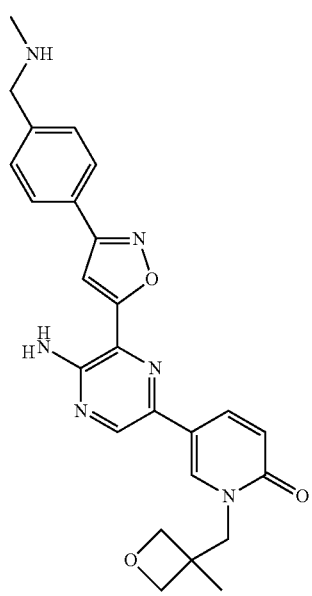
I-114
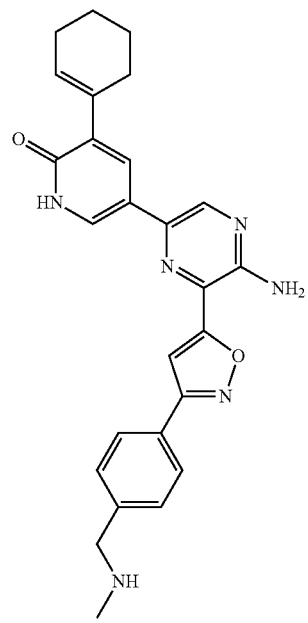
I-115
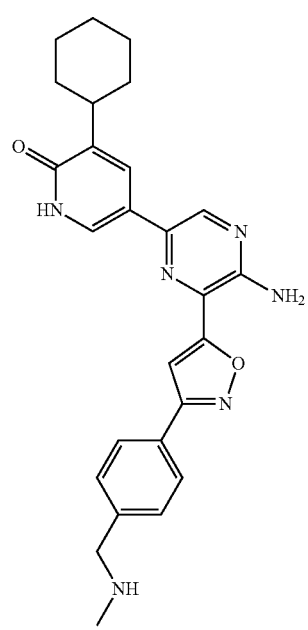

I-116
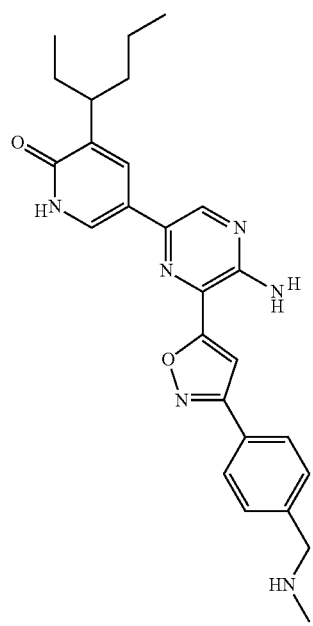
I-117
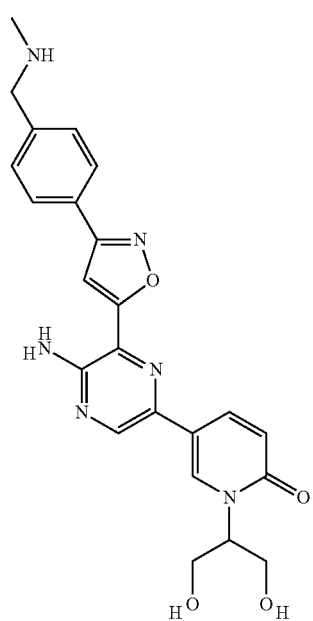
I-118
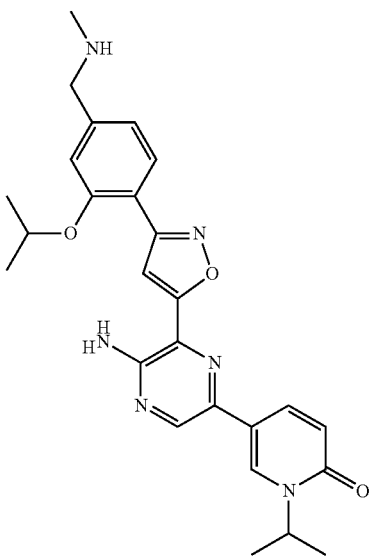
I-119
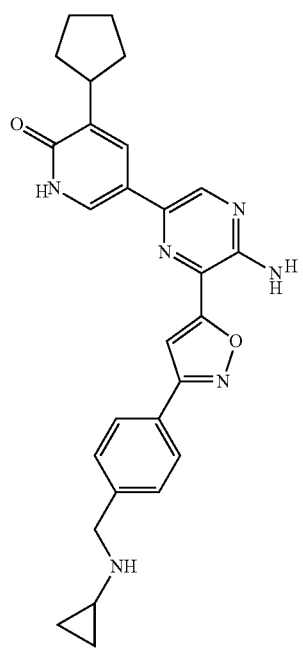

I-120
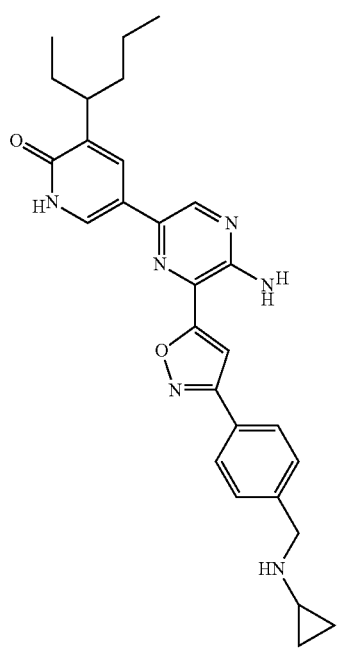
I-121
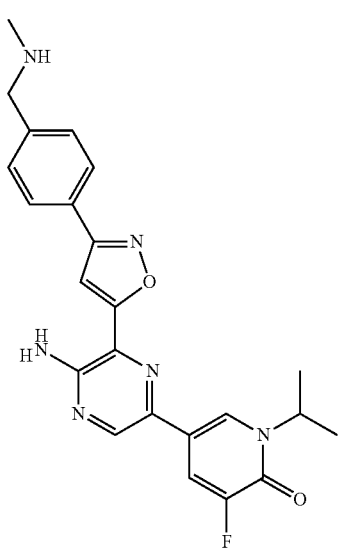
I-122
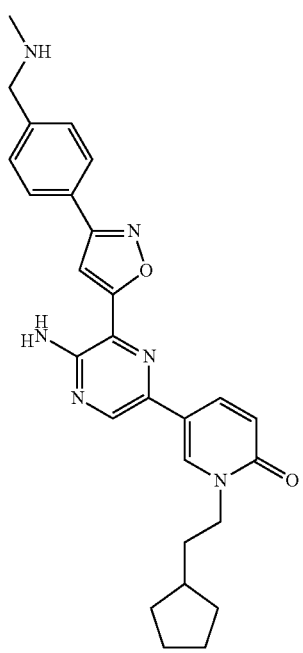
I-123
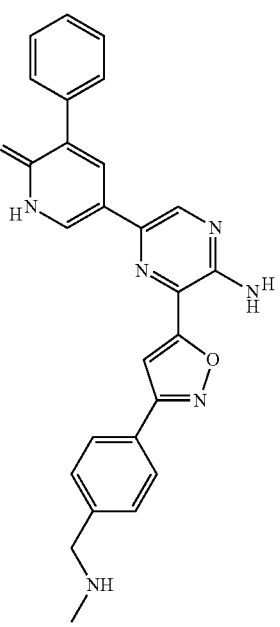

I-124
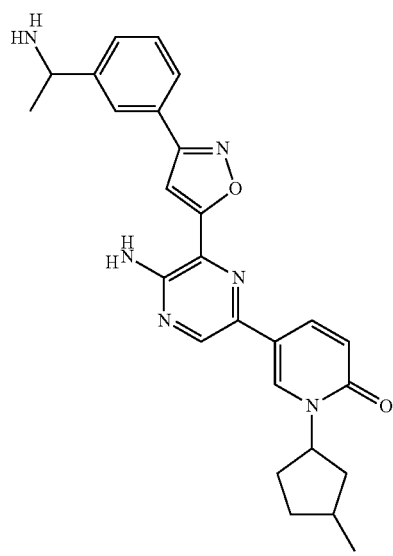
I-125
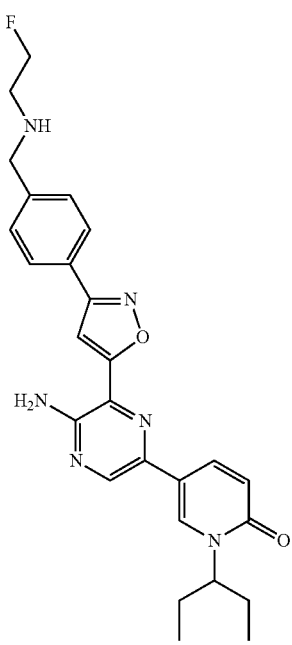
I-126
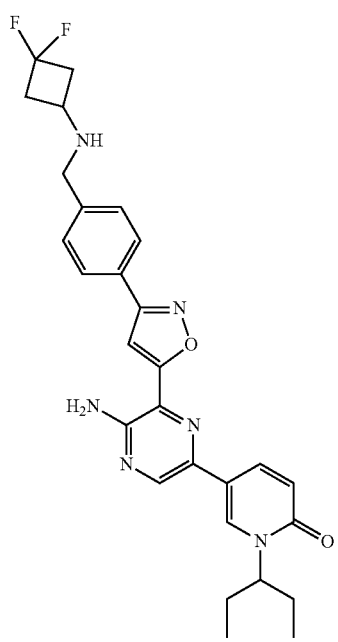
I-127

-continued
I-128
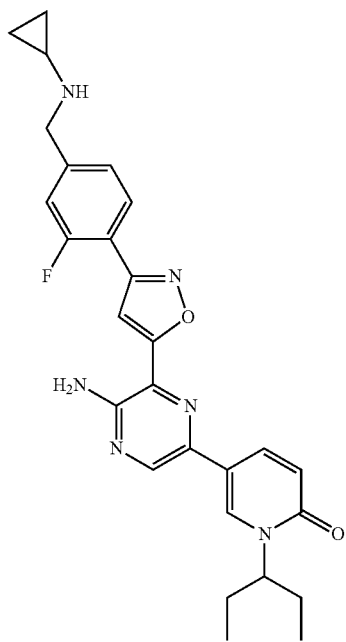
I-129
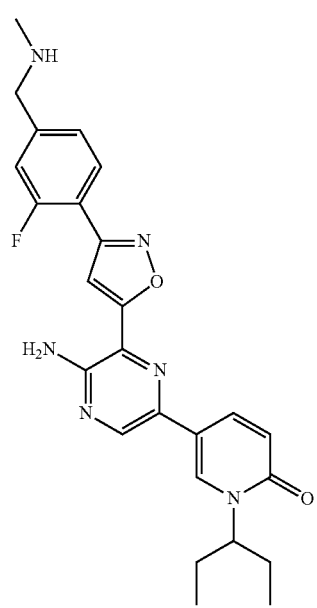
-continued
I-130
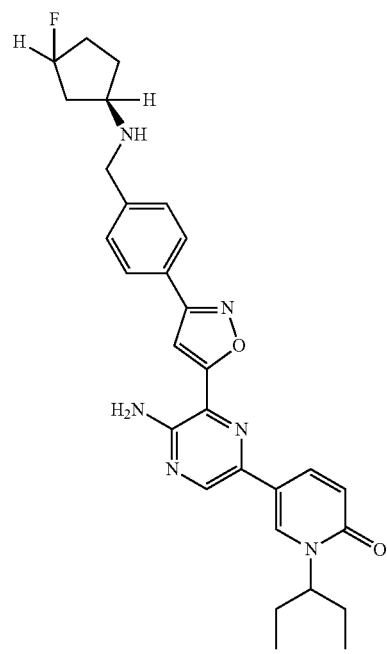
I-131
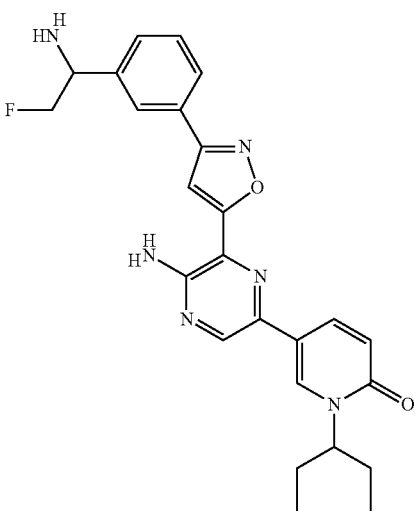
I-132
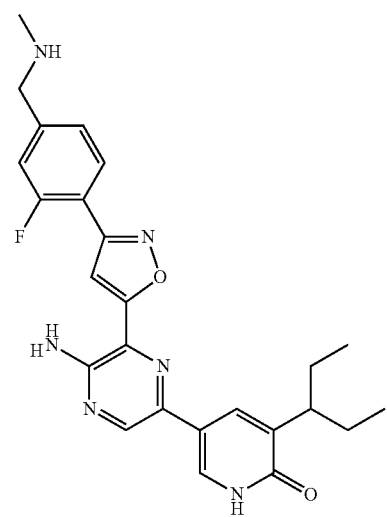

I-133
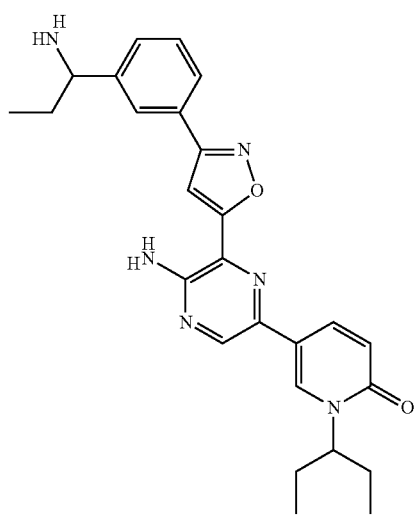
I-134
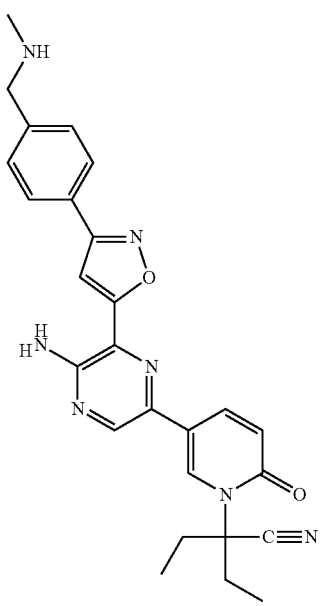
I-135
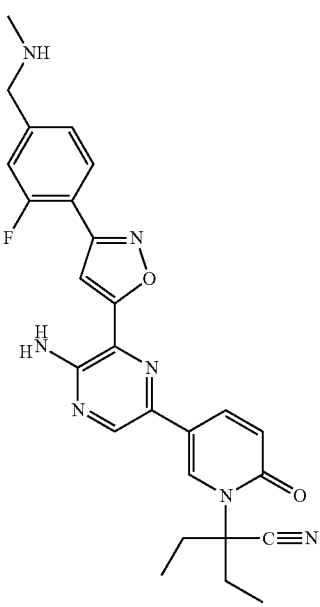
I-136
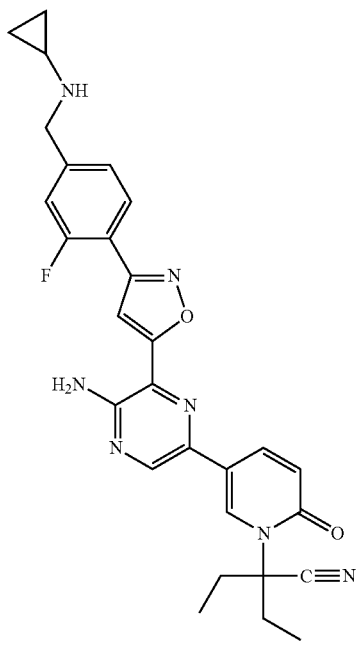

249
-continued
I-137
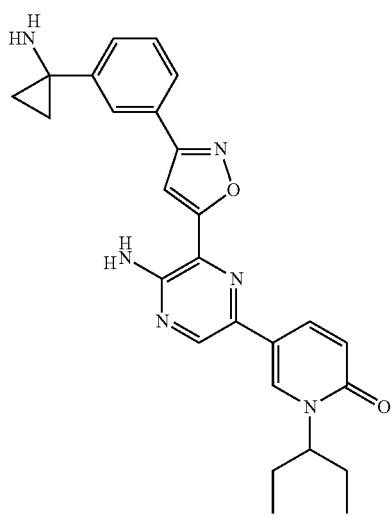
I-138
I-139
250
-continued
I-140
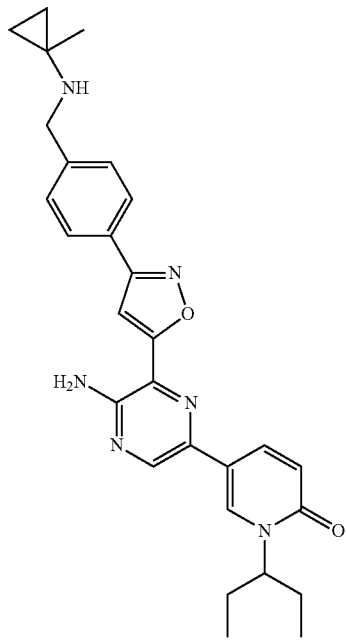
I-141
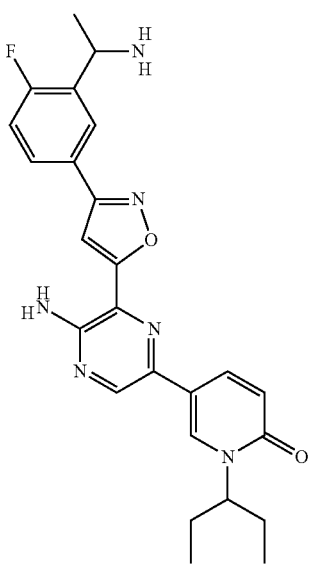

I-142
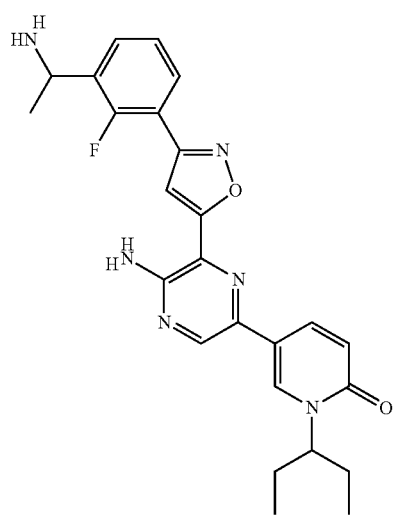
I-144
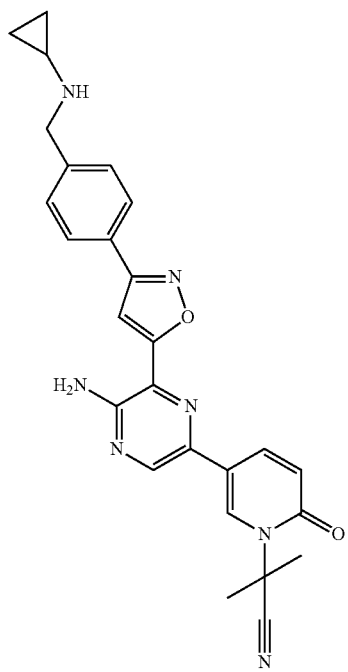
I-143
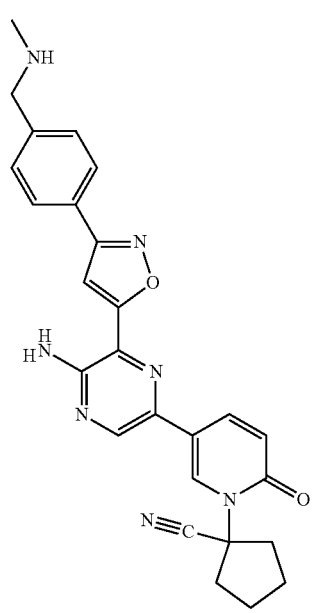
I-145
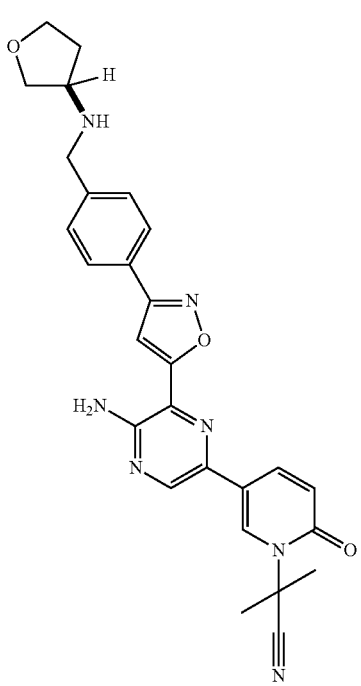

I-146
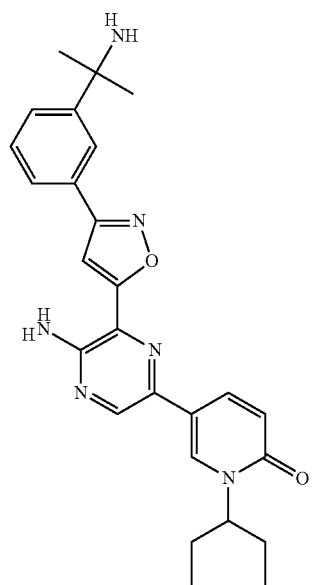
I-147
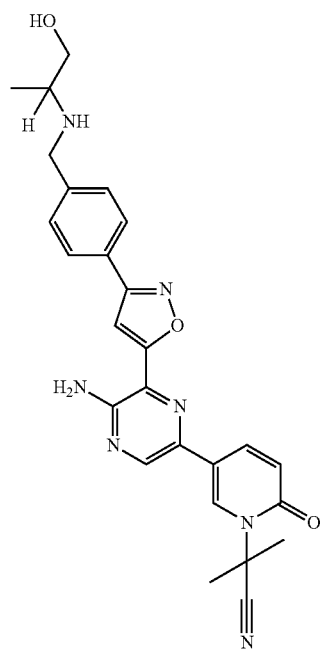
I-146
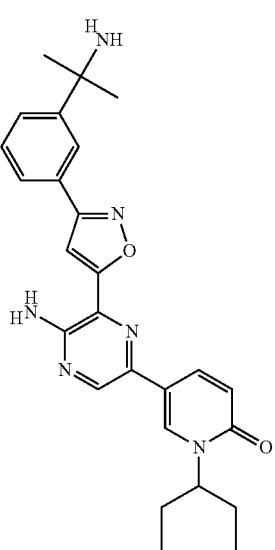
I-148
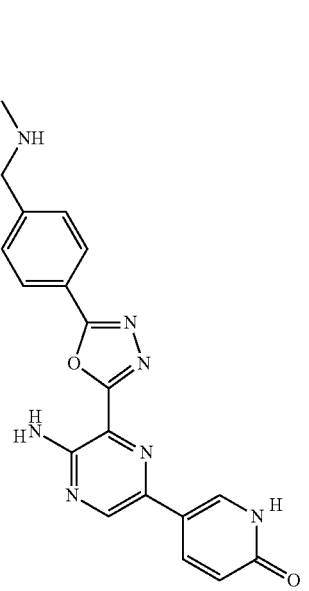

I-149

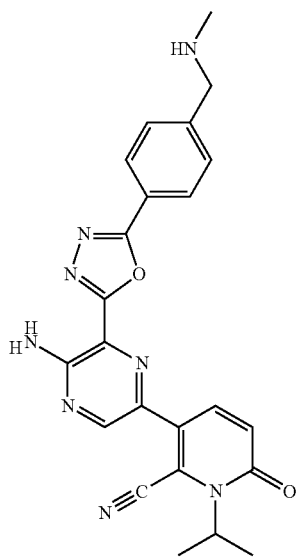

I-150

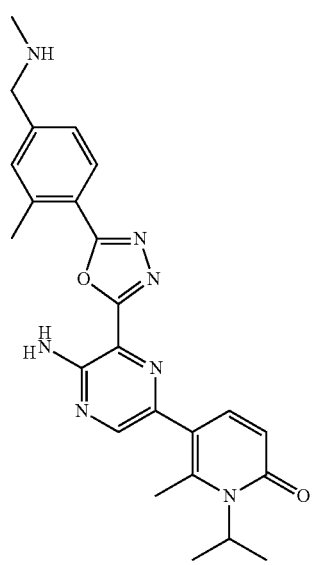

I-151

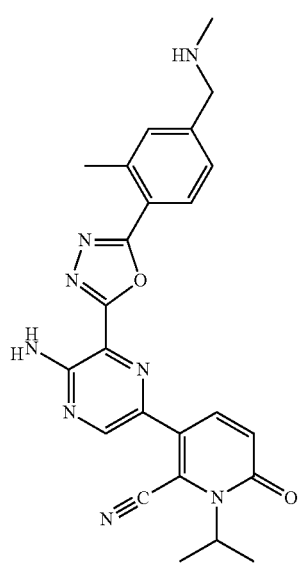

and a pharmaceutically acceptable salt thereof.

36. A pharmaceutical composition comprising a compound of formula I:

![Formula I]

or a pharmaceutically acceptable salt thereof, wherein
A is CH or N;
Ring D is isoxazolyl or oxadiazolyl;
J is —$C_{1-3}$alkyl, —O($C_{1-3}$alkyl), halo, or CN;
q is 0 or 1;
$R^1$ is H, $C_{1-6}$aliphatic, phenyl, or tetrahydrofuranyl, wherein said $C_{1-6}$aliphatic is optionally substituted with one occurrence of OH and up to two occurrences of F;
$R^2$ is H or $C_{1-3}$alkyl;
or $R^1$ and $R^2$, together with the nitrogen atom to which they are attached, optionally form a 4-6 membered monocyclic heterocyclyl ring having 1-2 heteroatoms selected from the group consisting of O, N, and S;
$R^3$ is H or $C_{1-3}$alkyl, wherein said alkyl is optionally substituted with up to three occurrences of F;
$R^{3'}$ is H or $C_{1-3}$alkyl;
or $R^3$ and $R^{3'}$, together with the carbon atom to which they are attached, form a 3-4 membered monocyclic saturated carbocyclic ring;
$R^4$ is Q, —($C_{1-2}$alkyl)-Q, or a $C_{1-10}$aliphatic, wherein up to two methylene units of said $C_{1-10}$aliphatic are optionally replaced with O, NR', S, or CO; and wherein one methylene unit of the $C_{1-2}$alkyl can optionally be replaced with C(=O);

$R^4$ is optionally substituted with 1-3 occurrences of halo, CN, NRR', OR, or $C_{1-3}$aliphatic, wherein said $C_{1-3}$aliphatic is optionally substituted with up to 1 occurrence of CN and up to 4 occurrences of F;

Q is 3-6 membered saturated, partially unsaturated, or aromatic monocyclic ring having 0-2 heteroatoms selected from the group consisting of oxygen, nitrogen, and sulfur; Q is optionally substituted with 1-3 occurrences of halo, CN, NRR', OR, or $C_{1-3}$aliphatic, wherein said $C_{1-3}$aliphatic is optionally substituted with up to 4 occurrences of F;

R' is H or $C_{1-4}$alkyl;

R is H or $C_{1-4}$alkyl;

or R and R', together with the nitrogen to which they are attached, optionally form a 3-6 membered heterocyclic ring having 1-2 heteroatoms selected from the group consisting of O, N, and S;

$J^2$ is H, $C_{1-6}$aliphatic, halo, phenyl, or CN, wherein said $C_{1-6}$aliphatic is optionally substituted with 1-2 occurrences of halo, OH, CN, or OR;

and a pharmaceutically acceptable carrier.

* * * * *